US012221637B2

(12) United States Patent
Sun et al.

(10) Patent No.: US 12,221,637 B2
(45) Date of Patent: Feb. 11, 2025

(54) POLYPEPTIDES HAVING NUCLEASE ACTIVITY

(71) Applicant: Novozymes A/S, Bagsvaerd (DK)

(72) Inventors: Tianqi Sun, Beijing (CN); Jesper Salomon, Holte (DK); Klaus Gori, Dyssegaard (DK); Morten Gjermansen, Greve (DK); Marc Dominique Morant, Frederiksberg (DK); Mary Ann Stringer, Soborg (DK)

(73) Assignee: Novozymes A/S, Bagsvaerd (DK)

( * ) Notice: Subject to any disclaimer, the term of this patent is extended or adjusted under 35 U.S.C. 154(b) by 822 days.

(21) Appl. No.: 17/276,436

(22) PCT Filed: Oct. 3, 2019

(86) PCT No.: PCT/CN2019/109813

§ 371 (c)(1),
(2) Date: Mar. 15, 2021

(87) PCT Pub. No.: WO2020/069670

PCT Pub. Date: Apr. 9, 2020

(65) Prior Publication Data

US 2022/0033738 A1 Feb. 3, 2022

(30) Foreign Application Priority Data

Oct. 4, 2018 (WO) ................ PCT/CN2018/109243

(51) Int. Cl.
*C12N 9/22* (2006.01)
*C11D 3/386* (2006.01)

(52) U.S. Cl.
CPC ............ *C12N 9/22* (2013.01); *C11D 3/38636* (2013.01); *C11D 2111/12* (2024.01)

(58) Field of Classification Search
CPC ........................................................ C12N 9/22
See application file for complete search history.

(56) References Cited

FOREIGN PATENT DOCUMENTS

| | | |
|---|---|---|
| WO | 2011/098579 A1 | 8/2011 |
| WO | 2017/060493 A1 | 4/2017 |
| WO | 2017/060505 A1 | 4/2017 |

OTHER PUBLICATIONS

A0A024S685_HYPJR. UniProtKB/TrEMBL. Aug. 30, 2017.*
Ho. Purification, characterization and complete amino acid sequence of nuclease C1 from *Cunninghamella echinulata* var. *echinulata*. Eur J Biochem. Aug. 15, 1998;256(1):112-8.*
Fransceus. J Ind Microbiol Biotechnol. May 2017;44(4-5):687-695.*
Sanavia. Computational and Structural Biotechnology Journal, vol. 18, 2020, pp. 1968-1979.*
NCBI Blast Search Result. Feb. 27, 2024.*
Studer. Residue mutations and their impact on protein structure and function: detecting beneficial and pathogenic changes. Biochem. J. (2013) 449, 581-594.*
Baroncelli, GenBank Accession No. POS71281.1 (2018).
De Vries et al., GenBank Accession No. OKP14558 (2016).
Guldener et al., GenBank Accession No. CZR63493.1 (2016).
Kuo et al., GenBank Accession No. ETR99726.1 (2015).
Morales-Cruz et al., GenBank Accession No. KKY29506.1 (2015).
Zhu et al., NCBI Reference No. XP_007288705.1 (2014).
Finn et al, 2015, Nucleic Acids Research 44, D279-D285.
Proctor et al., 2018, GenBank Accession No. RFU76918.1.

* cited by examiner

*Primary Examiner* — Yong D Pak
(74) *Attorney, Agent, or Firm* — Elias Lambiris

(57) ABSTRACT

The present invention relates to polypeptides having nuclease activity, and polynucleotides encoding the polypeptides. The invention also relates to nucleic acid constructs, vectors, and recombinant host cells comprising the polynucleotides as well as methods of producing, recovering and using the polypeptides. The invention further relates to cleaning compositions comprising one or more of the polypeptides having nuclease activity, as well as a cleaning method and use of the polypeptides.

20 Claims, No Drawings

Specification includes a Sequence Listing.

SEQUENCE LISTING

```
<160> NUMBER OF SEQ ID NOS: 117

<210> SEQ ID NO 1
<211> LENGTH: 1098
<212> TYPE: DNA
<213> ORGANISM: Trichoderma hamatum
<220> FEATURE:
<221> NAME/KEY: CDS
<222> LOCATION: (1)..(64)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1095)
<220> FEATURE:
<221> NAME/KEY: CDS
<222> LOCATION: (136)..(795)
<220> FEATURE:
<221> NAME/KEY: CDS
<222> LOCATION: (857)..(1095)

<400> SEQUENCE: 1

atg aag ctc tca aat gct gtg gcc gta agc ctc gtc tcc cta cca ggg       48
Met Lys Leu Ser Asn Ala Val Ala Val Ser Leu Val Ser Leu Pro Gly
            -15                 -10                 -5

gcc atg gct tgg gga g gtgtgtattg actccctcgt gatgcgccat cattatcact    104
Ala Met Ala Trp Gly
        -1  1

tgccttctaa catcagctct cttcgaatca g gt  ctg gga cac gta acg aca       155
                                  Gly Leu Gly His Val Thr Thr
                                          5

gcc ttt gtt gca agc aac ttt atc gcc aat acg aca gaa gcc tac cta      203
Ala Phe Val Ala Ser Asn Phe Ile Ala Asn Thr Thr Glu Ala Tyr Leu
10                  15                  20                  25

aag cag ctc ctt ggt agc caa gat gcc gac tac atg gcc aag gta gcc      251
Lys Gln Leu Leu Gly Ser Gln Asp Ala Asp Tyr Met Ala Lys Val Ala
            30                  35                  40

tcc tgg gcc gac tcg atc aga tac aca aaa tgg ggt aga ttc aca agc      299
Ser Trp Ala Asp Ser Ile Arg Tyr Thr Lys Trp Gly Arg Phe Thr Ser
```

```
            45                  50                  55

acg ttt cat ttc atc gat gcg cac gac agt cct ccc gag gac tgc aat      347
Thr Phe His Phe Ile Asp Ala His Asp Ser Pro Pro Glu Asp Cys Asn
        60                  65                  70

gtc gac ttt gag cgc gat tgt aaa gag acc ggc tgc gtc atc acc gct      395
Val Asp Phe Glu Arg Asp Cys Lys Glu Thr Gly Cys Val Ile Thr Ala
    75                  80                  85

ctg gcc aac tac aca caa cag tcc gtc gac ccg tcc cta ccg gca tgg      443
Leu Ala Asn Tyr Thr Gln Gln Ser Val Asp Pro Ser Leu Pro Ala Trp
90                  95                  100                 105

cgc cga gcg cag gca gcc aag ttt gtc att cac ttt gtc ggc gat ctg      491
Arg Arg Ala Gln Ala Ala Lys Phe Val Ile His Phe Val Gly Asp Leu
                110                 115                 120

cac cag ccg cta cat aac gag gat gtt gca aga ggt gga aac ggt att      539
His Gln Pro Leu His Asn Glu Asp Val Ala Arg Gly Gly Asn Gly Ile
            125                 130                 135

cac gtg ctg tgg aat gga aaa gaa ttc aac ctg cat cac gtc tgg gat      587
His Val Leu Trp Asn Gly Lys Glu Phe Asn Leu His His Val Trp Asp
        140                 145                 150

agc tcc att aca gag aaa tgg ctt ggc atg cgt ggt aga aaa cca tat      635
Ser Ser Ile Thr Glu Lys Trp Leu Gly Met Arg Gly Arg Lys Pro Tyr
    155                 160                 165

agc tgg gcg gag aag tgg tcc aaa gat ctc aca cag aag atc aac agc      683
Ser Trp Ala Glu Lys Trp Ser Lys Asp Leu Thr Gln Lys Ile Asn Ser
170                 175                 180                 185

ggc ata tac gca gac gag aag gac gat tgg ttg aag gac ttg gac ttt      731
Gly Ile Tyr Ala Asp Glu Lys Asp Asp Trp Leu Lys Asp Leu Asp Phe
                190                 195                 200

agc aac ccc gaa gag acg gca ttg gct tgg tca cga gaa tgt aac aaa      779
Ser Asn Pro Glu Glu Thr Ala Leu Ala Trp Ser Arg Glu Cys Asn Lys
            205                 210                 215

ctt gtg tgc gag tat g gtaagtcaag cccaaatctg cgccagaccc tagctttgtc    835
Leu Val Cys Glu Tyr
        220

actaacctgg tgaatttata g ta  ttc ccc gag ggt ccc aag gcc att gct      885
                        Val Phe Pro Glu Gly Pro Lys Ala Ile Ala
                                225                 230

ggc caa gag ttg agc ggc gag tac tac gaa aag gcg gct cct gtg ctc      933
Gly Gln Glu Leu Ser Gly Glu Tyr Tyr Glu Lys Ala Ala Pro Val Leu
        235                 240                 245

gaa aag caa gtc gcc cgt gcc gga tac cga atg gca gct tgg ttg gac      981
Glu Lys Gln Val Ala Arg Ala Gly Tyr Arg Met Ala Ala Trp Leu Asp
    250                 255                 260

aag gtt gtc gac caa tac cta aag ttg gaa gca agc tac aca gga gag     1029
Lys Val Val Asp Gln Tyr Leu Lys Leu Glu Ala Ser Tyr Thr Gly Glu
265                 270                 275                 280

ctg ccc acc gaa gac tat atg gaa gag cct ttg gat gaa ttt atg gag     1077
Leu Pro Thr Glu Asp Tyr Met Glu Glu Pro Leu Asp Glu Phe Met Glu
                285                 290                 295

gag cca att gga gag tta taa                                         1098
Glu Pro Ile Gly Glu Leu
            300


<210> SEQ ID NO 2
<211> LENGTH: 321
<212> TYPE: PRT
<213> ORGANISM: Trichoderma hamatum

<400> SEQUENCE: 2

Met Lys Leu Ser Asn Ala Val Ala Val Ser Leu Val Ser Leu Pro Gly
```

```
                -15                 -10                 -5

Ala Met Ala Trp Gly Gly Leu Gly His Val Thr Thr Ala Phe Val Ala
        -1  1               5                   10

Ser Asn Phe Ile Ala Asn Thr Thr Glu Ala Tyr Leu Lys Gln Leu Leu
    15                  20                  25

Gly Ser Gln Asp Ala Asp Tyr Met Ala Lys Val Ala Ser Trp Ala Asp
30                  35                  40                  45

Ser Ile Arg Tyr Thr Lys Trp Gly Arg Phe Thr Ser Thr Phe His Phe
                50                  55                  60

Ile Asp Ala His Asp Ser Pro Pro Glu Asp Cys Asn Val Asp Phe Glu
            65                  70                  75

Arg Asp Cys Lys Glu Thr Gly Cys Val Ile Thr Ala Leu Ala Asn Tyr
        80                  85                  90

Thr Gln Gln Ser Val Asp Pro Ser Leu Pro Ala Trp Arg Arg Ala Gln
    95                  100                 105

Ala Ala Lys Phe Val Ile His Phe Val Gly Asp Leu His Gln Pro Leu
110                 115                 120                 125

His Asn Glu Asp Val Ala Arg Gly Gly Asn Gly Ile His Val Leu Trp
                130                 135                 140

Asn Gly Lys Glu Phe Asn Leu His His Val Trp Asp Ser Ser Ile Thr
            145                 150                 155

Glu Lys Trp Leu Gly Met Arg Gly Arg Lys Pro Tyr Ser Trp Ala Glu
        160                 165                 170

Lys Trp Ser Lys Asp Leu Thr Gln Lys Ile Asn Ser Gly Ile Tyr Ala
    175                 180                 185

Asp Glu Lys Asp Asp Trp Leu Lys Asp Leu Asp Phe Ser Asn Pro Glu
190                 195                 200                 205

Glu Thr Ala Leu Ala Trp Ser Arg Glu Cys Asn Lys Leu Val Cys Glu
                210                 215                 220

Tyr Val Phe Pro Glu Gly Pro Lys Ala Ile Ala Gly Gln Glu Leu Ser
            225                 230                 235

Gly Glu Tyr Tyr Glu Lys Ala Ala Pro Val Leu Glu Lys Gln Val Ala
        240                 245                 250

Arg Ala Gly Tyr Arg Met Ala Ala Trp Leu Asp Lys Val Val Asp Gln
    255                 260                 265

Tyr Leu Lys Leu Glu Ala Ser Tyr Thr Gly Glu Leu Pro Thr Glu Asp
270                 275                 280                 285

Tyr Met Glu Glu Pro Leu Asp Glu Phe Met Glu Glu Pro Ile Gly Glu
                290                 295                 300

Leu


<210> SEQ ID NO 3
<211> LENGTH: 302
<212> TYPE: PRT
<213> ORGANISM: Trichoderma hamatum

<400> SEQUENCE: 3

Trp Gly Gly Leu Gly His Val Thr Thr Ala Phe Val Ala Ser Asn Phe
1               5                   10                  15

Ile Ala Asn Thr Thr Glu Ala Tyr Leu Lys Gln Leu Leu Gly Ser Gln
            20                  25                  30

Asp Ala Asp Tyr Met Ala Lys Val Ala Ser Trp Ala Asp Ser Ile Arg
        35                  40                  45

Tyr Thr Lys Trp Gly Arg Phe Thr Ser Thr Phe His Phe Ile Asp Ala
```

```
    50                  55                  60

His Asp Ser Pro Pro Glu Asp Cys Asn Val Asp Phe Glu Arg Asp Cys
65                  70                  75                  80

Lys Glu Thr Gly Cys Val Ile Thr Ala Leu Ala Asn Tyr Thr Gln Gln
                85                  90                  95

Ser Val Asp Pro Ser Leu Pro Ala Trp Arg Arg Ala Gln Ala Ala Lys
            100                 105                 110

Phe Val Ile His Phe Val Gly Asp Leu His Gln Pro Leu His Asn Glu
        115                 120                 125

Asp Val Ala Arg Gly Gly Asn Gly Ile His Val Leu Trp Asn Gly Lys
    130                 135                 140

Glu Phe Asn Leu His His Val Trp Asp Ser Ser Ile Thr Glu Lys Trp
145                 150                 155                 160

Leu Gly Met Arg Gly Arg Lys Pro Tyr Ser Trp Ala Glu Lys Trp Ser
                165                 170                 175

Lys Asp Leu Thr Gln Lys Ile Asn Ser Gly Ile Tyr Ala Asp Glu Lys
            180                 185                 190

Asp Asp Trp Leu Lys Asp Leu Asp Phe Ser Asn Pro Glu Glu Thr Ala
        195                 200                 205

Leu Ala Trp Ser Arg Glu Cys Asn Lys Leu Val Cys Glu Tyr Val Phe
    210                 215                 220

Pro Glu Gly Pro Lys Ala Ile Ala Gly Gln Glu Leu Ser Gly Glu Tyr
225                 230                 235                 240

Tyr Glu Lys Ala Ala Pro Val Leu Glu Lys Gln Val Ala Arg Ala Gly
                245                 250                 255

Tyr Arg Met Ala Ala Trp Leu Asp Lys Val Val Asp Gln Tyr Leu Lys
            260                 265                 270

Leu Glu Ala Ser Tyr Thr Gly Glu Leu Pro Thr Glu Asp Tyr Met Glu
        275                 280                 285

Glu Pro Leu Asp Glu Phe Met Glu Glu Pro Ile Gly Glu Leu
    290                 295                 300


<210> SEQ ID NO 4
<211> LENGTH: 1138
<212> TYPE: DNA
<213> ORGANISM: Morchella costata
<220> FEATURE:
<221> NAME/KEY: CDS
<222> LOCATION: (1)..(339)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1135)
<220> FEATURE:
<221> NAME/KEY: CDS
<222> LOCATION: (404)..(1135)

<400> SEQUENCE: 4

atg cat acc agc acc ctc ccc ctc ctc ctc ctc ccc gcc gtc ttc gcc       48
Met His Thr Ser Thr Leu Pro Leu Leu Leu Leu Pro Ala Val Phe Ala
    -20                 -15                 -10

ccc tcc gcc tcg gcc tgg ggc atg ctc ggc cac cgc acc gtc gcc ctc       96
Pro Ser Ala Ser Ala Trp Gly Met Leu Gly His Arg Thr Val Ala Leu
-5              -1  1               5                   10

ctg tcg acg cgc tat ctc ctc ccc gag acc gca gtc ttc gta aag tcc      144
Leu Ser Thr Arg Tyr Leu Leu Pro Glu Thr Ala Val Phe Val Lys Ser
            15                  20                  25
```

```
ctc ctc cca aag ccc cag acc atc gtc tcg gcc tcc acc tgg ccc gac      192
Leu Leu Pro Lys Pro Gln Thr Ile Val Ser Ala Ser Thr Trp Pro Asp
        30                  35                  40

tac tac gca cac acg ccc gac ggc cgc tac tcc gcg ccc tgg cac tgg      240
Tyr Tyr Ala His Thr Pro Asp Gly Arg Tyr Ser Ala Pro Trp His Trp
    45                  50                  55

atc gac tcc cac gat aac ccg ccg cac acc tgc gag gtc aac tac cgc      288
Ile Asp Ser His Asp Asn Pro Pro His Thr Cys Glu Val Asn Tyr Arg
60                  65                  70                  75

cgt gac tgc agc ggc gac gag ggc tgc atc gtc agt gcc atc gcc aac      336
Arg Asp Cys Ser Gly Asp Glu Gly Cys Ile Val Ser Ala Ile Ala Asn
                80                  85                  90

atg gtacgtctca gggttagggt tggtcgtgga attatggata tggatatgct           389
Met

aacacgcaca acag aca tcg cgg gtg acg gac gag gag ctc ccg ttc tac      439
                Thr Ser Arg Val Thr Asp Glu Glu Leu Pro Phe Tyr
                        95                  100

gag cgc cag atg gcg cta aag ttc atc atc cac ttt gtc ggc gac atc      487
Glu Arg Gln Met Ala Leu Lys Phe Ile Ile His Phe Val Gly Asp Ile
105                 110                 115                 120

cac cag ccg ctg cac acg gag gac ctt ctg cgc ggc ggc aac cag atc      535
His Gln Pro Leu His Thr Glu Asp Leu Leu Arg Gly Gly Asn Gln Ile
                125                 130                 135

ccc gtg ctg tgg ggc aag cag cac acg aac ctg cac cac gtg tgg gac      583
Pro Val Leu Trp Gly Lys Gln His Thr Asn Leu His His Val Trp Asp
            140                 145                 150

tcg agc atc gcc gag aag cac cgc ggc ggg agc gcg gtg cgc cac gcg      631
Ser Ser Ile Ala Glu Lys His Arg Gly Gly Ser Ala Val Arg His Ala
        155                 160                 165

gtc ggc tgg gcg gac gag ctg cac gcc gag ctt gag cac ggg agg tac      679
Val Gly Trp Ala Asp Glu Leu His Ala Glu Leu Glu His Gly Arg Tyr
    170                 175                 180

agc gag ctg cgc gcc ggg tgg ggc tcg tgc gtc gac ccg cgc acg gcc      727
Ser Glu Leu Arg Ala Gly Trp Gly Ser Cys Val Asp Pro Arg Thr Ala
185                 190                 195                 200

gag gag tgc gcg ctc gcg tgg gcg ggc gag gcc aac cgc tgg atg tgc      775
Glu Glu Cys Ala Leu Ala Trp Ala Gly Glu Ala Asn Arg Trp Met Cys
                205                 210                 215

gac tat gtg ctc ccg cag acg tac ccc gag ggc ctg gag ggc gtg gat      823
Asp Tyr Val Leu Pro Gln Thr Tyr Pro Glu Gly Leu Glu Gly Val Asp
            220                 225                 230

gtc agt ggc gag tac tac gag ggg gcg agg gag gtc gtg gac gtg ttg      871
Val Ser Gly Glu Tyr Tyr Glu Gly Ala Arg Glu Val Val Asp Val Leu
        235                 240                 245

gtt gcg aag gcg ggg tgg agg ctc gcc ggc tac ctg aac atg att gtg      919
Val Ala Lys Ala Gly Trp Arg Leu Ala Gly Tyr Leu Asn Met Ile Val
    250                 255                 260

acg ggg agc acg ggg ctg gag gat ggc gag agg gca gcg acg gcc gcg      967
Thr Gly Ser Thr Gly Leu Glu Asp Gly Glu Arg Ala Ala Thr Ala Ala
265                 270                 275                 280

gtg gag gag gat tgg gtg agc ttt gac aga gag gag gag agg aag tat     1015
Val Glu Glu Asp Trp Val Ser Phe Asp Arg Glu Glu Glu Arg Lys Tyr
                285                 290                 295

gca gtg gca gca gca gcg gag gag gag gag gag gag gca gct tca gga     1063
Ala Val Ala Ala Ala Ala Glu Glu Glu Glu Glu Glu Ala Ala Ser Gly
            300                 305                 310

cac gag ctg aag aag agg gtg atg aac aag gcc aat agc ggc tgg tgg     1111
His Glu Leu Lys Lys Arg Val Met Asn Lys Ala Asn Ser Gly Trp Trp
        315                 320                 325
```

```
ggc aat gtt aga act aac ggc aac tga                                  1138
Gly Asn Val Arg Thr Asn Gly Asn
    330                 335


<210> SEQ ID NO 5
<211> LENGTH: 357
<212> TYPE: PRT
<213> ORGANISM: Morchella costata

<400> SEQUENCE: 5

Met His Thr Ser Thr Leu Pro Leu Leu Leu Leu Pro Ala Val Phe Ala
    -20                 -15                 -10

Pro Ser Ala Ser Ala Trp Gly Met Leu Gly His Arg Thr Val Ala Leu
-5              -1  1               5                   10

Leu Ser Thr Arg Tyr Leu Leu Pro Glu Thr Ala Val Phe Val Lys Ser
            15                  20                  25

Leu Leu Pro Lys Pro Gln Thr Ile Val Ser Ala Ser Thr Trp Pro Asp
        30                  35                  40

Tyr Tyr Ala His Thr Pro Asp Gly Arg Tyr Ser Ala Pro Trp His Trp
    45                  50                  55

Ile Asp Ser His Asp Asn Pro Pro His Thr Cys Glu Val Asn Tyr Arg
60                  65                  70                  75

Arg Asp Cys Ser Gly Asp Glu Gly Cys Ile Val Ser Ala Ile Ala Asn
                80                  85                  90

Met Thr Ser Arg Val Thr Asp Glu Glu Leu Pro Phe Tyr Glu Arg Gln
            95                  100                 105

Met Ala Leu Lys Phe Ile Ile His Phe Val Gly Asp Ile His Gln Pro
        110                 115                 120

Leu His Thr Glu Asp Leu Leu Arg Gly Gly Asn Gln Ile Pro Val Leu
    125                 130                 135

Trp Gly Lys Gln His Thr Asn Leu His His Val Trp Asp Ser Ser Ile
140                 145                 150                 155

Ala Glu Lys His Arg Gly Gly Ser Ala Val Arg His Ala Val Gly Trp
                160                 165                 170

Ala Asp Glu Leu His Ala Glu Leu Glu His Gly Arg Tyr Ser Glu Leu
            175                 180                 185

Arg Ala Gly Trp Gly Ser Cys Val Asp Pro Arg Thr Ala Glu Glu Cys
        190                 195                 200

Ala Leu Ala Trp Ala Gly Glu Ala Asn Arg Trp Met Cys Asp Tyr Val
    205                 210                 215

Leu Pro Gln Thr Tyr Pro Glu Gly Leu Glu Gly Val Asp Val Ser Gly
220                 225                 230                 235

Glu Tyr Tyr Glu Gly Ala Arg Glu Val Val Asp Val Leu Val Ala Lys
                240                 245                 250

Ala Gly Trp Arg Leu Ala Gly Tyr Leu Asn Met Ile Val Thr Gly Ser
            255                 260                 265

Thr Gly Leu Glu Asp Gly Glu Arg Ala Ala Thr Ala Ala Val Glu Glu
        270                 275                 280

Asp Trp Val Ser Phe Asp Arg Glu Glu Glu Arg Lys Tyr Ala Val Ala
    285                 290                 295

Ala Ala Ala Glu Glu Glu Glu Glu Glu Ala Ala Ser Gly His Glu Leu
300                 305                 310                 315

Lys Lys Arg Val Met Asn Lys Ala Asn Ser Gly Trp Trp Gly Asn Val
                320                 325                 330

Arg Thr Asn Gly Asn
```

335

<210> SEQ ID NO 6
<211> LENGTH: 336
<212> TYPE: PRT
<213> ORGANISM: Morchella costata

<400> SEQUENCE: 6

```
Trp Gly Met Leu Gly His Arg Thr Val Ala Leu Leu Ser Thr Arg Tyr
1               5                   10                  15

Leu Leu Pro Glu Thr Ala Val Phe Val Lys Ser Leu Leu Pro Lys Pro
            20                  25                  30

Gln Thr Ile Val Ser Ala Ser Thr Trp Pro Asp Tyr Tyr Ala His Thr
        35                  40                  45

Pro Asp Gly Arg Tyr Ser Ala Pro Trp His Trp Ile Asp Ser His Asp
    50                  55                  60

Asn Pro Pro His Thr Cys Glu Val Asn Tyr Arg Arg Asp Cys Ser Gly
65                  70                  75                  80

Asp Glu Gly Cys Ile Val Ser Ala Ile Ala Asn Met Thr Ser Arg Val
                85                  90                  95

Thr Asp Glu Glu Leu Pro Phe Tyr Glu Arg Gln Met Ala Leu Lys Phe
            100                 105                 110

Ile Ile His Phe Val Gly Asp Ile His Gln Pro Leu His Thr Glu Asp
        115                 120                 125

Leu Leu Arg Gly Gly Asn Gln Ile Pro Val Leu Trp Gly Lys Gln His
    130                 135                 140

Thr Asn Leu His His Val Trp Asp Ser Ser Ile Ala Glu Lys His Arg
145                 150                 155                 160

Gly Gly Ser Ala Val Arg His Ala Val Gly Trp Ala Asp Glu Leu His
                165                 170                 175

Ala Glu Leu Glu His Gly Arg Tyr Ser Glu Leu Arg Ala Gly Trp Gly
            180                 185                 190

Ser Cys Val Asp Pro Arg Thr Ala Glu Glu Cys Ala Leu Ala Trp Ala
        195                 200                 205

Gly Glu Ala Asn Arg Trp Met Cys Asp Tyr Val Leu Pro Gln Thr Tyr
    210                 215                 220

Pro Glu Gly Leu Glu Gly Val Asp Val Ser Gly Glu Tyr Tyr Glu Gly
225                 230                 235                 240

Ala Arg Glu Val Val Asp Val Leu Val Ala Lys Ala Gly Trp Arg Leu
                245                 250                 255

Ala Gly Tyr Leu Asn Met Ile Val Thr Gly Ser Thr Gly Leu Glu Asp
            260                 265                 270

Gly Glu Arg Ala Ala Thr Ala Ala Val Glu Glu Asp Trp Val Ser Phe
        275                 280                 285

Asp Arg Glu Glu Glu Arg Lys Tyr Ala Val Ala Ala Ala Ala Glu Glu
    290                 295                 300

Glu Glu Glu Glu Ala Ala Ser Gly His Glu Leu Lys Lys Arg Val Met
305                 310                 315                 320

Asn Lys Ala Asn Ser Gly Trp Trp Gly Asn Val Arg Thr Asn Gly Asn
                325                 330                 335
```

<210> SEQ ID NO 7
<211> LENGTH: 1116
<212> TYPE: DNA
<213> ORGANISM: Trichoderma reesei
<220> FEATURE:

```
<221> NAME/KEY: CDS
<222> LOCATION: (1)..(131)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1113)
<220> FEATURE:
<221> NAME/KEY: CDS
<222> LOCATION: (213)..(1113)

<400> SEQUENCE: 7

atg cct tcc atg tca aag att gcc ttg gcg act ctg gcc acg ctc cag       48
Met Pro Ser Met Ser Lys Ile Ala Leu Ala Thr Leu Ala Thr Leu Gln
-20                 -15                 -10                 -5

ggc gcc cac gcc tgg gga gtc ctg ggc cac gca acc gtc gcc tac gtg       96
Gly Ala His Ala Trp Gly Val Leu Gly His Ala Thr Val Ala Tyr Val
            -1  1               5                   10

gcc cag cac tat ctc aac gca gcc acg gcc tca tg  gtgagcagac           141
Ala Gln His Tyr Leu Asn Ala Ala Thr Ala Ser Trp
        15                  20

tgacacttat tcatcactga tgatgatgaa gatgacgaca agttcatcca ctgacaatct    201

taatacttca g g gcc cag gga gtc ctc aac gac acg tcc agc tcg tac       249
               Ala Gln Gly Val Leu Asn Asp Thr Ser Ser Ser Tyr
               25                  30                  35

ctg gcc agc atc gcc tcc tgg gcc gac acc tac cgc acc acc gcg gcc      297
Leu Ala Ser Ile Ala Ser Trp Ala Asp Thr Tyr Arg Thr Thr Ala Ala
            40                  45                  50

ggc aag ttc tcg gcg ccc ttc cac ttc atc gac gcc cag gac agc ccg      345
Gly Lys Phe Ser Ala Pro Phe His Phe Ile Asp Ala Gln Asp Ser Pro
        55                  60                  65

ccc agc tcg tgc aac gtc gac tac gac cgc gac tgc ggc agc gcc ggc      393
Pro Ser Ser Cys Asn Val Asp Tyr Asp Arg Asp Cys Gly Ser Ala Gly
    70                  75                  80

tgc tcc atc tcc gcc atg gcc aac tac acc cag cgc gtg ggc gac ggc      441
Cys Ser Ile Ser Ala Met Ala Asn Tyr Thr Gln Arg Val Gly Asp Gly
85                  90                  95                  100

cgg ctg tcc gcc gcc aac gtc gcc gag gcg ctc aag ttc ctg gtg cac      489
Arg Leu Ser Ala Ala Asn Val Ala Glu Ala Leu Lys Phe Leu Val His
               105                 110                 115

ttt gtc ggc gac atg acg cag ccg ctg cac gac gag gcg tac gag gtc      537
Phe Val Gly Asp Met Thr Gln Pro Leu His Asp Glu Ala Tyr Glu Val
            120                 125                 130

ggc ggc aac gac att gcc gtc aag ttc cag ggc tac aac gac aac ctg      585
Gly Gly Asn Asp Ile Ala Val Lys Phe Gln Gly Tyr Asn Asp Asn Leu
        135                 140                 145

cac gcc gac tgg gac acg tac atc ccc gag gcg ctc atc ggc ggc gac      633
His Ala Asp Trp Asp Thr Tyr Ile Pro Glu Ala Leu Ile Gly Gly Asp
    150                 155                 160

tcg ctg gcg gat gcc cag tcc tgg gcc agc tcg ctc gtc agc gac atc      681
Ser Leu Ala Asp Ala Gln Ser Trp Ala Ser Ser Leu Val Ser Asp Ile
165                 170                 175                 180

gcc tcg ggc gcg tac aag tcg cag gcc gcg ggc tgg atc aag ggc gac      729
Ala Ser Gly Ala Tyr Lys Ser Gln Ala Ala Gly Trp Ile Lys Gly Asp
               185                 190                 195

acc ctc ggc gat gtc atc ggc acg gcc acg cgc tgg gcc agc gac gca      777
Thr Leu Gly Asp Val Ile Gly Thr Ala Thr Arg Trp Ala Ser Asp Ala
            200                 205                 210

aac gcc ctc gtc tgc acc gtc gtc atg ccc aac ggc gtg gcg gcc ctg      825
Asn Ala Leu Val Cys Thr Val Val Met Pro Asn Gly Val Ala Ala Leu
        215                 220                 225
```

```
cag cag ggc gac ctg tac ccg acc tac tac gac gcc gtc atc ggc acc      873
Gln Gln Gly Asp Leu Tyr Pro Thr Tyr Tyr Asp Ala Val Ile Gly Thr
    230                 235                 240

gtc gag ctg cag att gca aag ggc ggc tac cgc ctg gcc aac tgg ctc      921
Val Glu Leu Gln Ile Ala Lys Gly Gly Tyr Arg Leu Ala Asn Trp Leu
245                 250                 255                 260

aac atg gtg tac gcg tcc aac att gcg aag cgc gag gcg ggc tct gtc      969
Asn Met Val Tyr Ala Ser Asn Ile Ala Lys Arg Glu Ala Gly Ser Val
                265                 270                 275

gac gct cgg gat gct tcg cct ctg cct gac ctc ttg ggg cga gac ttg     1017
Asp Ala Arg Asp Ala Ser Pro Leu Pro Asp Leu Leu Gly Arg Asp Leu
            280                 285                 290

ctg ccg gct gct cgc cct gct acc cgc gct cag ctt gcg agg gcg gcc     1065
Leu Pro Ala Ala Arg Pro Ala Thr Arg Ala Gln Leu Ala Arg Ala Ala
        295                 300                 305

atg gag ggt tcg tgt tgc gga agt ggt cgg gag cac gag cac aag cac     1113
Met Glu Gly Ser Cys Cys Gly Ser Gly Arg Glu His Glu His Lys His
    310                 315                 320

tag                                                                 1116


<210> SEQ ID NO 8
<211> LENGTH: 344
<212> TYPE: PRT
<213> ORGANISM: Trichoderma reesei

<400> SEQUENCE: 8

Met Pro Ser Met Ser Lys Ile Ala Leu Ala Thr Leu Ala Thr Leu Gln
-20                 -15                 -10                 -5

Gly Ala His Ala Trp Gly Val Leu Gly His Ala Thr Val Ala Tyr Val
            -1  1               5                   10

Ala Gln His Tyr Leu Asn Ala Ala Thr Ala Ser Trp Ala Gln Gly Val
        15                  20                  25

Leu Asn Asp Thr Ser Ser Ser Tyr Leu Ala Ser Ile Ala Ser Trp Ala
    30                  35                  40

Asp Thr Tyr Arg Thr Thr Ala Ala Gly Lys Phe Ser Ala Pro Phe His
45                  50                  55                  60

Phe Ile Asp Ala Gln Asp Ser Pro Pro Ser Ser Cys Asn Val Asp Tyr
                65                  70                  75

Asp Arg Asp Cys Gly Ser Ala Gly Cys Ser Ile Ser Ala Met Ala Asn
            80                  85                  90

Tyr Thr Gln Arg Val Gly Asp Gly Arg Leu Ser Ala Ala Asn Val Ala
        95                  100                 105

Glu Ala Leu Lys Phe Leu Val His Phe Val Gly Asp Met Thr Gln Pro
    110                 115                 120

Leu His Asp Glu Ala Tyr Glu Val Gly Gly Asn Asp Ile Ala Val Lys
125                 130                 135                 140

Phe Gln Gly Tyr Asn Asp Asn Leu His Ala Asp Trp Asp Thr Tyr Ile
                145                 150                 155

Pro Glu Ala Leu Ile Gly Gly Asp Ser Leu Ala Asp Ala Gln Ser Trp
            160                 165                 170

Ala Ser Ser Leu Val Ser Asp Ile Ala Ser Gly Ala Tyr Lys Ser Gln
        175                 180                 185

Ala Ala Gly Trp Ile Lys Gly Asp Thr Leu Gly Asp Val Ile Gly Thr
    190                 195                 200

Ala Thr Arg Trp Ala Ser Asp Ala Asn Ala Leu Val Cys Thr Val Val
205                 210                 215                 220
```

```
Met Pro Asn Gly Val Ala Ala Leu Gln Gln Gly Asp Leu Tyr Pro Thr
                225                 230                 235

Tyr Tyr Asp Ala Val Ile Gly Thr Val Glu Leu Gln Ile Ala Lys Gly
            240                 245                 250

Gly Tyr Arg Leu Ala Asn Trp Leu Asn Met Val Tyr Ala Ser Asn Ile
        255                 260                 265

Ala Lys Arg Glu Ala Gly Ser Val Asp Ala Arg Asp Ala Ser Pro Leu
    270                 275                 280

Pro Asp Leu Leu Gly Arg Asp Leu Leu Pro Ala Ala Arg Pro Ala Thr
285                 290                 295                 300

Arg Ala Gln Leu Ala Arg Ala Ala Met Glu Gly Ser Cys Cys Gly Ser
                305                 310                 315

Gly Arg Glu His Glu His Lys His
            320


<210> SEQ ID NO 9
<211> LENGTH: 324
<212> TYPE: PRT
<213> ORGANISM: Trichoderma reesei

<400> SEQUENCE: 9

Trp Gly Val Leu Gly His Ala Thr Val Ala Tyr Val Ala Gln His Tyr
1               5                   10                  15

Leu Asn Ala Ala Thr Ala Ser Trp Ala Gln Gly Val Leu Asn Asp Thr
            20                  25                  30

Ser Ser Ser Tyr Leu Ala Ser Ile Ala Ser Trp Ala Asp Thr Tyr Arg
        35                  40                  45

Thr Thr Ala Ala Gly Lys Phe Ser Ala Pro Phe His Phe Ile Asp Ala
    50                  55                  60

Gln Asp Ser Pro Pro Ser Ser Cys Asn Val Asp Tyr Asp Arg Asp Cys
65                  70                  75                  80

Gly Ser Ala Gly Cys Ser Ile Ser Ala Met Ala Asn Tyr Thr Gln Arg
                85                  90                  95

Val Gly Asp Gly Arg Leu Ser Ala Ala Asn Val Ala Glu Ala Leu Lys
            100                 105                 110

Phe Leu Val His Phe Val Gly Asp Met Thr Gln Pro Leu His Asp Glu
        115                 120                 125

Ala Tyr Glu Val Gly Gly Asn Asp Ile Ala Val Lys Phe Gln Gly Tyr
    130                 135                 140

Asn Asp Asn Leu His Ala Asp Trp Asp Thr Tyr Ile Pro Glu Ala Leu
145                 150                 155                 160

Ile Gly Gly Asp Ser Leu Ala Asp Ala Gln Ser Trp Ala Ser Ser Leu
                165                 170                 175

Val Ser Asp Ile Ala Ser Gly Ala Tyr Lys Ser Gln Ala Ala Gly Trp
            180                 185                 190

Ile Lys Gly Asp Thr Leu Gly Asp Val Ile Gly Thr Ala Thr Arg Trp
        195                 200                 205

Ala Ser Asp Ala Asn Ala Leu Val Cys Thr Val Val Met Pro Asn Gly
    210                 215                 220

Val Ala Ala Leu Gln Gln Gly Asp Leu Tyr Pro Thr Tyr Tyr Asp Ala
225                 230                 235                 240

Val Ile Gly Thr Val Glu Leu Gln Ile Ala Lys Gly Gly Tyr Arg Leu
                245                 250                 255

Ala Asn Trp Leu Asn Met Val Tyr Ala Ser Asn Ile Ala Lys Arg Glu
```

```
            260                 265                 270

Ala Gly Ser Val Asp Ala Arg Asp Ala Ser Pro Leu Pro Asp Leu Leu
        275                 280                 285

Gly Arg Asp Leu Leu Pro Ala Ala Arg Pro Ala Thr Arg Ala Gln Leu
    290                 295                 300

Ala Arg Ala Ala Met Glu Gly Ser Cys Cys Gly Ser Gly Arg Glu His
305                 310                 315                 320

Glu His Lys His


<210> SEQ ID NO 10
<211> LENGTH: 1081
<212> TYPE: DNA
<213> ORGANISM: Penicillium cremeogriseum
<220> FEATURE:
<221> NAME/KEY: CDS
<222> LOCATION: (1)..(131)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1078)
<220> FEATURE:
<221> NAME/KEY: CDS
<222> LOCATION: (184)..(1078)

<400> SEQUENCE: 10

atg gca cct ctg tcc aag gtt gct ctc gtc acc ctt ggc tcc ttg agc       48
Met Ala Pro Leu Ser Lys Val Ala Leu Val Thr Leu Gly Ser Leu Ser
-20                 -15                 -10                 -5

gga gta aat gca tgg ggt gtg ctt ggc cac gca acc gtt gcc tac gtc       96
Gly Val Asn Ala Trp Gly Val Leu Gly His Ala Thr Val Ala Tyr Val
            -1  1               5                   10

gcg cag aac tac ctt tcg tct ggc act gca tca tg  gtgagggtga           141
Ala Gln Asn Tyr Leu Ser Ser Gly Thr Ala Ser Trp
        15                  20

aagaaatccc cgaggccgcg atggatacta atgattttca ag g gcg caa ggc gtt     196
                                                 Ala Gln Gly Val
                                                 25

ctt gga gac act tcc agc tcg tac cta gcc aac atc gcc tct tgg gct      244
Leu Gly Asp Thr Ser Ser Ser Tyr Leu Ala Asn Ile Ala Ser Trp Ala
    30                  35                  40

gac cag tac cgt gcg aca acc gct ggc aag tgg tcc gcg ccg ctt cac      292
Asp Gln Tyr Arg Ala Thr Thr Ala Gly Lys Trp Ser Ala Pro Leu His
45                  50                  55                  60

ttc atc gac gcc gag gac aat cct ccc acc agc tgc aac gtg gat tac      340
Phe Ile Asp Ala Glu Asp Asn Pro Pro Thr Ser Cys Asn Val Asp Tyr
                65                  70                  75

act cgc gac tgc ggt agc tcc ggc tgc tcc atc tct gca att gca aac      388
Thr Arg Asp Cys Gly Ser Ser Gly Cys Ser Ile Ser Ala Ile Ala Asn
            80                  85                  90

tac act caa cgt gca ggt gat gcc cgg ctc agc act gct caa atc gct      436
Tyr Thr Gln Arg Ala Gly Asp Ala Arg Leu Ser Thr Ala Gln Ile Ala
        95                  100                 105

gaa gct gtc aag ttc ctg gtc cac ttc ctg gga gac gtt act cag ccc      484
Glu Ala Val Lys Phe Leu Val His Phe Leu Gly Asp Val Thr Gln Pro
    110                 115                 120

ctg cac gat gag gcg tac gag gtt ggc gga aac agc atc aag gtc act      532
Leu His Asp Glu Ala Tyr Glu Val Gly Gly Asn Ser Ile Lys Val Thr
125                 130                 135                 140

ttc gat ggt tat agc gac aac ctc cat gcc gac tgg gat acc tac atg      580
Phe Asp Gly Tyr Ser Asp Asn Leu His Ala Asp Trp Asp Thr Tyr Met
```

```
                145                 150                 155

ccc cag aaa ctg atc ggc ggc agc acg ctc tcc gat gca cag tct tgg      628
Pro Gln Lys Leu Ile Gly Gly Ser Thr Leu Ser Asp Ala Gln Ser Trp
            160                 165                 170

gct aag acg ctc gtc ggt gag atc gac tcg gga agc tac aag tct caa      676
Ala Lys Thr Leu Val Gly Glu Ile Asp Ser Gly Ser Tyr Lys Ser Gln
        175                 180                 185

gca gca agc tgg att cag gga gac act atc agt gat cct att act acc      724
Ala Ala Ser Trp Ile Gln Gly Asp Thr Ile Ser Asp Pro Ile Thr Thr
    190                 195                 200

gcc acc cga tgg gcg tct gat gcg aat gcc ttt gtc tgc act gtt gtc      772
Ala Thr Arg Trp Ala Ser Asp Ala Asn Ala Phe Val Cys Thr Val Val
205                 210                 215                 220

atg cca gat gga gct tct gcc ttg gag act ggt gat ctt tac cct acc      820
Met Pro Asp Gly Ala Ser Ala Leu Glu Thr Gly Asp Leu Tyr Pro Thr
                225                 230                 235

tac tac aat tct gct att ggt acc atc gag ctg cag att gca aag ggt      868
Tyr Tyr Asn Ser Ala Ile Gly Thr Ile Glu Leu Gln Ile Ala Lys Gly
            240                 245                 250

gga tac cgc ctg gcc aac tgg ctc aac atg atc tac aac aat gat atc      916
Gly Tyr Arg Leu Ala Asn Trp Leu Asn Met Ile Tyr Asn Asn Asp Ile
        255                 260                 265

gcc aag cga gac ctg gag ggc ttt gtc aac gag gct cga agt gaa ggt      964
Ala Lys Arg Asp Leu Glu Gly Phe Val Asn Glu Ala Arg Ser Glu Gly
    270                 275                 280

ctg ccg gat ctc atg ggt cgc gac ctg ctg ccc gag cct cgc gaa ttg     1012
Leu Pro Asp Leu Met Gly Arg Asp Leu Leu Pro Glu Pro Arg Glu Leu
285                 290                 295                 300

agc cgc gct cag ttg gcc aga gag gct atg gga gga gat tgc tgc ggc     1060
Ser Arg Ala Gln Leu Ala Arg Glu Ala Met Gly Gly Asp Cys Cys Gly
                305                 310                 315

tcc tcg aga cat gct cac tga                                         1081
Ser Ser Arg His Ala His
            320


<210> SEQ ID NO 11
<211> LENGTH: 342
<212> TYPE: PRT
<213> ORGANISM: Penicillium cremeogriseum

<400> SEQUENCE: 11

Met Ala Pro Leu Ser Lys Val Ala Leu Val Thr Leu Gly Ser Leu Ser
-20                 -15                 -10                 -5

Gly Val Asn Ala Trp Gly Val Leu Gly His Ala Thr Val Ala Tyr Val
            -1  1               5                   10

Ala Gln Asn Tyr Leu Ser Ser Gly Thr Ala Ser Trp Ala Gln Gly Val
        15                  20                  25

Leu Gly Asp Thr Ser Ser Ser Tyr Leu Ala Asn Ile Ala Ser Trp Ala
    30                  35                  40

Asp Gln Tyr Arg Ala Thr Thr Ala Gly Lys Trp Ser Ala Pro Leu His
45                  50                  55                  60

Phe Ile Asp Ala Glu Asp Asn Pro Pro Thr Ser Cys Asn Val Asp Tyr
                65                  70                  75

Thr Arg Asp Cys Gly Ser Ser Gly Cys Ser Ile Ser Ala Ile Ala Asn
            80                  85                  90

Tyr Thr Gln Arg Ala Gly Asp Ala Arg Leu Ser Thr Ala Gln Ile Ala
        95                  100                 105

Glu Ala Val Lys Phe Leu Val His Phe Leu Gly Asp Val Thr Gln Pro
```

```
    110                 115                 120

Leu His Asp Glu Ala Tyr Glu Val Gly Gly Asn Ser Ile Lys Val Thr
125                 130                 135                 140

Phe Asp Gly Tyr Ser Asp Asn Leu His Ala Asp Trp Asp Thr Tyr Met
                145                 150                 155

Pro Gln Lys Leu Ile Gly Gly Ser Thr Leu Ser Asp Ala Gln Ser Trp
            160                 165                 170

Ala Lys Thr Leu Val Gly Glu Ile Asp Ser Gly Ser Tyr Lys Ser Gln
        175                 180                 185

Ala Ala Ser Trp Ile Gln Gly Asp Thr Ile Ser Asp Pro Ile Thr Thr
    190                 195                 200

Ala Thr Arg Trp Ala Ser Asp Ala Asn Ala Phe Val Cys Thr Val Val
205                 210                 215                 220

Met Pro Asp Gly Ala Ser Ala Leu Glu Thr Gly Asp Leu Tyr Pro Thr
                225                 230                 235

Tyr Tyr Asn Ser Ala Ile Gly Thr Ile Glu Leu Gln Ile Ala Lys Gly
            240                 245                 250

Gly Tyr Arg Leu Ala Asn Trp Leu Asn Met Ile Tyr Asn Asn Asp Ile
        255                 260                 265

Ala Lys Arg Asp Leu Glu Gly Phe Val Asn Glu Ala Arg Ser Glu Gly
    270                 275                 280

Leu Pro Asp Leu Met Gly Arg Asp Leu Leu Pro Glu Pro Arg Glu Leu
285                 290                 295                 300

Ser Arg Ala Gln Leu Ala Arg Glu Ala Met Gly Gly Asp Cys Cys Gly
                305                 310                 315

Ser Ser Arg His Ala His
            320


<210> SEQ ID NO 12
<211> LENGTH: 322
<212> TYPE: PRT
<213> ORGANISM: Penicillium cremeogriseum

<400> SEQUENCE: 12

Trp Gly Val Leu Gly His Ala Thr Val Ala Tyr Val Ala Gln Asn Tyr
1               5                   10                  15

Leu Ser Ser Gly Thr Ala Ser Trp Ala Gln Gly Val Leu Gly Asp Thr
            20                  25                  30

Ser Ser Ser Tyr Leu Ala Asn Ile Ala Ser Trp Ala Asp Gln Tyr Arg
        35                  40                  45

Ala Thr Thr Ala Gly Lys Trp Ser Ala Pro Leu His Phe Ile Asp Ala
    50                  55                  60

Glu Asp Asn Pro Pro Thr Ser Cys Asn Val Asp Tyr Thr Arg Asp Cys
65                  70                  75                  80

Gly Ser Ser Gly Cys Ser Ile Ser Ala Ile Ala Asn Tyr Thr Gln Arg
                85                  90                  95

Ala Gly Asp Ala Arg Leu Ser Thr Ala Gln Ile Ala Glu Ala Val Lys
            100                 105                 110

Phe Leu Val His Phe Leu Gly Asp Val Thr Gln Pro Leu His Asp Glu
        115                 120                 125

Ala Tyr Glu Val Gly Gly Asn Ser Ile Lys Val Thr Phe Asp Gly Tyr
    130                 135                 140

Ser Asp Asn Leu His Ala Asp Trp Asp Thr Tyr Met Pro Gln Lys Leu
145                 150                 155                 160
```

```
Ile Gly Gly Ser Thr Leu Ser Asp Ala Gln Ser Trp Ala Lys Thr Leu
                165                 170                 175

Val Gly Glu Ile Asp Ser Gly Ser Tyr Lys Ser Gln Ala Ala Ser Trp
            180                 185                 190

Ile Gln Gly Asp Thr Ile Ser Asp Pro Ile Thr Thr Ala Thr Arg Trp
        195                 200                 205

Ala Ser Asp Ala Asn Ala Phe Val Cys Thr Val Val Met Pro Asp Gly
    210                 215                 220

Ala Ser Ala Leu Glu Thr Gly Asp Leu Tyr Pro Thr Tyr Tyr Asn Ser
225                 230                 235                 240

Ala Ile Gly Thr Ile Glu Leu Gln Ile Ala Lys Gly Gly Tyr Arg Leu
                245                 250                 255

Ala Asn Trp Leu Asn Met Ile Tyr Asn Asn Asp Ile Ala Lys Arg Asp
            260                 265                 270

Leu Glu Gly Phe Val Asn Glu Ala Arg Ser Glu Gly Leu Pro Asp Leu
        275                 280                 285

Met Gly Arg Asp Leu Leu Pro Glu Pro Arg Glu Leu Ser Arg Ala Gln
    290                 295                 300

Leu Ala Arg Glu Ala Met Gly Gly Asp Cys Cys Gly Ser Ser Arg His
305                 310                 315                 320

Ala His


<210> SEQ ID NO 13
<211> LENGTH: 1127
<212> TYPE: DNA
<213> ORGANISM: Stenocarpella maydis
<220> FEATURE:
<221> NAME/KEY: CDS
<222> LOCATION: (1)..(64)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1124)
<220> FEATURE:
<221> NAME/KEY: CDS
<222> LOCATION: (142)..(801)
<220> FEATURE:
<221> NAME/KEY: CDS
<222> LOCATION: (964)..(1124)

<400> SEQUENCE: 13

atg aag ctg tct ggt gtc gcc gcg ttg ggc ctt gta gct gtc ccg gaa       48
Met Lys Leu Ser Gly Val Ala Ala Leu Gly Leu Val Ala Val Pro Glu
                -15                 -10                 -5

gtg ctg gca tgg gga g gtgagcagcc gtcccgcgct gtgccccagc accaagacag    104
Val Leu Ala Trp Gly
        -1  1

gtgcatcgtt cgccctttat taacgttagc tgcccag gc  ttt ggg cac atc acg     158
                                         Gly Phe Gly His Ile Thr
                                                 5

atc gca tac gtt gct agc aac ttt gtc cag ccg cag acg aca gcc tac      206
Ile Ala Tyr Val Ala Ser Asn Phe Val Gln Pro Gln Thr Thr Ala Tyr
    10                  15                  20

ttc caa acc ctc ctc cgg aat gac aca gcc gac tac ctc gcc aac gtg      254
Phe Gln Thr Leu Leu Arg Asn Asp Thr Ala Asp Tyr Leu Ala Asn Val
25                  30                  35                  40

gct acg tgg gcc gac tcg atc cgc tat acg aaa tgg ggc cac tat act      302
Ala Thr Trp Ala Asp Ser Ile Arg Tyr Thr Lys Trp Gly His Tyr Thr
                45                  50                  55
```

```
ggc gtg ttc cac ttc atc gac gcc aaa gac gaa ccg ccc aac aac tgc      350
Gly Val Phe His Phe Ile Asp Ala Lys Asp Glu Pro Pro Asn Asn Cys
            60                  65                  70

tcc gtc gag ctc gac cgc gac tgc aag gag gag ggc tgc gtc gta acg      398
Ser Val Glu Leu Asp Arg Asp Cys Lys Glu Glu Gly Cys Val Val Thr
        75                  80                  85

gcg atc caa aac tac acc tcg cag atc ctc gac ccc tcc att cca gtc      446
Ala Ile Gln Asn Tyr Thr Ser Gln Ile Leu Asp Pro Ser Ile Pro Val
    90                  95                  100

tgg ctc cgc gcg cag gcc gcc aaa ttt gtg gtg cac ttt gtc ggc gac      494
Trp Leu Arg Ala Gln Ala Ala Lys Phe Val Val His Phe Val Gly Asp
105                 110                 115                 120

atc cac cag ccc ctg cac gac gaa aac gtg tcc agg ggc ggg aat ggg      542
Ile His Gln Pro Leu His Asp Glu Asn Val Ser Arg Gly Gly Asn Gly
                125                 130                 135

atc cac gtg ctg tgg gag ggg cgg gag ctg aac ctc cac cac gtc tgg      590
Ile His Val Leu Trp Glu Gly Arg Glu Leu Asn Leu His His Val Trp
            140                 145                 150

gac agc tct atc gcg gag aag tgg gtg ggc ggc gtc agg agg aag cca      638
Asp Ser Ser Ile Ala Glu Lys Trp Val Gly Gly Val Arg Arg Lys Pro
        155                 160                 165

tac cat ggg gcg cat gag tgg gct cag gaa ctc acg ggc aag atc aaa      686
Tyr His Gly Ala His Glu Trp Ala Gln Glu Leu Thr Gly Lys Ile Lys
    170                 175                 180

gac ggc caa ttc aag gcc cac agc aag act tgg ctg gac ggc gtg gac      734
Asp Gly Gln Phe Lys Ala His Ser Lys Thr Trp Leu Asp Gly Val Asp
185                 190                 195                 200

ttt gct gat ccc atc aag acc gcc ctg ggt tgg gcg agg gaa gga aat      782
Phe Ala Asp Pro Ile Lys Thr Ala Leu Gly Trp Ala Arg Glu Gly Asn
                205                 210                 215

tca ttt gtc tgt tcg cac g gtgagcgtct ctcgtttccg ctcgttattt           831
Ser Phe Val Cys Ser His
            220

tctgttttct gactggatct cgggccgtcg ttggtctgga gatccagcac gggcctcaat    891

ccacacttgt tcctaccctt catttcgtgg ggctctgtcg accgttcgag caatttgcta    951

acgcatgtct ag tg  ctt ccc gag ggg cca gaa gcc atc gtg gga cag gaa   1001
              Val Leu Pro Glu Gly Pro Glu Ala Ile Val Gly Gln Glu
                      225                 230                 235

cta ggc ggg gag tac tat gaa aag gct gcg ccg gtg att gag ctc cag     1049
Leu Gly Gly Glu Tyr Tyr Glu Lys Ala Ala Pro Val Ile Glu Leu Gln
                240                 245                 250

gtc gcc cgt gcg gga ttc cgt ctt gcg gcg tgg ctc gac ttg atc gtg     1097
Val Ala Arg Ala Gly Phe Arg Leu Ala Ala Trp Leu Asp Leu Ile Val
            255                 260                 265

gcg gcg ctc aag gtc gag tct gag tta tga                             1127
Ala Ala Leu Lys Val Glu Ser Glu Leu
        270                 275
```

<210> SEQ ID NO 14
<211> LENGTH: 295
<212> TYPE: PRT
<213> ORGANISM: Stenocarpella maydis

<400> SEQUENCE: 14

```
Met Lys Leu Ser Gly Val Ala Ala Leu Gly Leu Val Ala Val Pro Glu
                -15                 -10                 -5

Val Leu Ala Trp Gly Gly Phe Gly His Ile Thr Ile Ala Tyr Val Ala
        -1  1               5                   10

Ser Asn Phe Val Gln Pro Gln Thr Thr Ala Tyr Phe Gln Thr Leu Leu
```

```
    15                  20                  25

Arg Asn Asp Thr Ala Asp Tyr Leu Ala Asn Val Ala Thr Trp Ala Asp
30                  35                  40                  45

Ser Ile Arg Tyr Thr Lys Trp Gly His Tyr Thr Gly Val Phe His Phe
                50                  55                  60

Ile Asp Ala Lys Asp Glu Pro Pro Asn Asn Cys Ser Val Glu Leu Asp
            65                  70                  75

Arg Asp Cys Lys Glu Glu Gly Cys Val Val Thr Ala Ile Gln Asn Tyr
        80                  85                  90

Thr Ser Gln Ile Leu Asp Pro Ser Ile Pro Val Trp Leu Arg Ala Gln
    95                  100                 105

Ala Ala Lys Phe Val Val His Phe Val Gly Asp Ile His Gln Pro Leu
110                 115                 120                 125

His Asp Glu Asn Val Ser Arg Gly Gly Asn Gly Ile His Val Leu Trp
                130                 135                 140

Glu Gly Arg Glu Leu Asn Leu His His Val Trp Asp Ser Ser Ile Ala
            145                 150                 155

Glu Lys Trp Val Gly Gly Val Arg Arg Lys Pro Tyr His Gly Ala His
        160                 165                 170

Glu Trp Ala Gln Glu Leu Thr Gly Lys Ile Lys Asp Gly Gln Phe Lys
    175                 180                 185

Ala His Ser Lys Thr Trp Leu Asp Gly Val Asp Phe Ala Asp Pro Ile
190                 195                 200                 205

Lys Thr Ala Leu Gly Trp Ala Arg Glu Gly Asn Ser Phe Val Cys Ser
                210                 215                 220

His Val Leu Pro Glu Gly Pro Glu Ala Ile Val Gly Gln Glu Leu Gly
            225                 230                 235

Gly Glu Tyr Tyr Glu Lys Ala Ala Pro Val Ile Glu Leu Gln Val Ala
        240                 245                 250

Arg Ala Gly Phe Arg Leu Ala Ala Trp Leu Asp Leu Ile Val Ala Ala
    255                 260                 265

Leu Lys Val Glu Ser Glu Leu
270                 275


<210> SEQ ID NO 15
<211> LENGTH: 276
<212> TYPE: PRT
<213> ORGANISM: Stenocarpella maydis

<400> SEQUENCE: 15

Trp Gly Gly Phe Gly His Ile Thr Ile Ala Tyr Val Ala Ser Asn Phe
1               5                   10                  15

Val Gln Pro Gln Thr Thr Ala Tyr Phe Gln Thr Leu Leu Arg Asn Asp
            20                  25                  30

Thr Ala Asp Tyr Leu Ala Asn Val Ala Thr Trp Ala Asp Ser Ile Arg
        35                  40                  45

Tyr Thr Lys Trp Gly His Tyr Thr Gly Val Phe His Phe Ile Asp Ala
    50                  55                  60

Lys Asp Glu Pro Pro Asn Asn Cys Ser Val Glu Leu Asp Arg Asp Cys
65                  70                  75                  80

Lys Glu Glu Gly Cys Val Val Thr Ala Ile Gln Asn Tyr Thr Ser Gln
                85                  90                  95

Ile Leu Asp Pro Ser Ile Pro Val Trp Leu Arg Ala Gln Ala Ala Lys
            100                 105                 110
```

```
Phe Val Val His Phe Val Gly Asp Ile His Gln Pro Leu His Asp Glu
        115                 120                 125

Asn Val Ser Arg Gly Gly Asn Gly Ile His Val Leu Trp Glu Gly Arg
    130                 135                 140

Glu Leu Asn Leu His His Val Trp Asp Ser Ser Ile Ala Glu Lys Trp
145                 150                 155                 160

Val Gly Gly Val Arg Arg Lys Pro Tyr His Gly Ala His Glu Trp Ala
                165                 170                 175

Gln Glu Leu Thr Gly Lys Ile Lys Asp Gly Gln Phe Lys Ala His Ser
            180                 185                 190

Lys Thr Trp Leu Asp Gly Val Asp Phe Ala Asp Pro Ile Lys Thr Ala
        195                 200                 205

Leu Gly Trp Ala Arg Glu Gly Asn Ser Phe Val Cys Ser His Val Leu
    210                 215                 220

Pro Glu Gly Pro Glu Ala Ile Val Gly Gln Glu Leu Gly Gly Glu Tyr
225                 230                 235                 240

Tyr Glu Lys Ala Ala Pro Val Ile Glu Leu Gln Val Ala Arg Ala Gly
                245                 250                 255

Phe Arg Leu Ala Ala Trp Leu Asp Leu Ile Val Ala Ala Leu Lys Val
            260                 265                 270

Glu Ser Glu Leu
        275


<210> SEQ ID NO 16
<211> LENGTH: 1086
<212> TYPE: DNA
<213> ORGANISM: Stenocarpella maydis
<220> FEATURE:
<221> NAME/KEY: CDS
<222> LOCATION: (1)..(122)
<220> FEATURE:
<221> NAME/KEY: sig_peptide
<222> LOCATION: (1)..(51)
<220> FEATURE:
<221> NAME/KEY: mat_peptide
<222> LOCATION: (52)..(1083)
<220> FEATURE:
<221> NAME/KEY: CDS
<222> LOCATION: (192)..(1083)

<400> SEQUENCE: 16

atg gcc tcg aat ctc ctc cta aca ctt gcc gcc ttg caa ggc gtg agg       48
Met Ala Ser Asn Leu Leu Leu Thr Leu Ala Ala Leu Gln Gly Val Arg
        -15                 -10                 -5

gca tgg ggc act ctc ggg cat gcc acc atc gcc tat atc gca cag aac       96
Ala Trp Gly Thr Leu Gly His Ala Thr Ile Ala Tyr Ile Ala Gln Asn
-1  1               5                   10                  15

tac gtt aca gac gaa gta gct tcc tg  gtacgtctga tttacaaaga          142
Tyr Val Thr Asp Glu Val Ala Ser Trp
                20

tgcctcacca gcgtgcaagt acacgaactt accagctttg tcaccgcag g gct caa      198
                                                        Ala Gln
                                                        25

ggt gtg ctc agt gac agc tcc gat tcc tac ctg gcc aac atc gcc tcg      246
Gly Val Leu Ser Asp Ser Ser Asp Ser Tyr Leu Ala Asn Ile Ala Ser
            30                  35                  40

tgg gct gac agc tac cgc aca acg act gcc ggc gca tgg tct gcc cct      294
Trp Ala Asp Ser Tyr Arg Thr Thr Thr Ala Gly Ala Trp Ser Ala Pro
        45                  50                  55

ctg cat ttc att gac gcc gaa gac agc ccg cct agt gac tgc aac gtg      342
Leu His Phe Ile Asp Ala Glu Asp Ser Pro Pro Ser Asp Cys Asn Val
```

```
    60                  65                  70

gat tat gac cgg gac tgt gga tcg acg ggc tgc tcc gtc tcc gcc att      390
Asp Tyr Asp Arg Asp Cys Gly Ser Thr Gly Cys Ser Val Ser Ala Ile
75                  80                  85                  90

gcc aac tac acc cag cgt gtc ggt gat ggc cgc ctt tcc gct gca aac      438
Ala Asn Tyr Thr Gln Arg Val Gly Asp Gly Arg Leu Ser Ala Ala Asn
                95                  100                 105

gtt gcc gaa gcc ctc aag ttc ctg gtc cac ttc act gga gac atc acg      486
Val Ala Glu Ala Leu Lys Phe Leu Val His Phe Thr Gly Asp Ile Thr
            110                 115                 120

cag ccc ctg cat gat gag gct tac gag aag gga gcc aac ggt gtc gac      534
Gln Pro Leu His Asp Glu Ala Tyr Glu Lys Gly Ala Asn Gly Val Asp
        125                 130                 135

gtc act tat cag ggc tac tcc gac aac ctc cat gcc gac tgg gac aca      582
Val Thr Tyr Gln Gly Tyr Ser Asp Asn Leu His Ala Asp Trp Asp Thr
    140                 145                 150

tac ctc ccc gcg acg ctc gtc ggt ggt tcc acc ctt gct gat gcc aag      630
Tyr Leu Pro Ala Thr Leu Val Gly Gly Ser Thr Leu Ala Asp Ala Lys
155                 160                 165                 170

gcc tgg gca acc aac ctc acc gct gag atc aac tcg ggc atc tac aag      678
Ala Trp Ala Thr Asn Leu Thr Ala Glu Ile Asn Ser Gly Ile Tyr Lys
                175                 180                 185

tcc cag gcg gca ggc tgg att gcg ggc gat agc ctg agc gag ccc ata      726
Ser Gln Ala Ala Gly Trp Ile Ala Gly Asp Ser Leu Ser Glu Pro Ile
            190                 195                 200

gat acc gcc atg gcc tgg gcc acc gac gcc aac gcc tac gtc tgc acc      774
Asp Thr Ala Met Ala Trp Ala Thr Asp Ala Asn Ala Tyr Val Cys Thr
        205                 210                 215

gtc gtg atg ccc aac ggc gct gcg gcc ctg acg gcc atg aag gat ctg      822
Val Val Met Pro Asn Gly Ala Ala Ala Leu Thr Ala Met Lys Asp Leu
    220                 225                 230

tac cct aca tac tac gag tcg gtc atc ccc act atc gag ctt cag ata      870
Tyr Pro Thr Tyr Tyr Glu Ser Val Ile Pro Thr Ile Glu Leu Gln Ile
235                 240                 245                 250

gcc aag ggt ggc tat cgc ctt ggg aac tgg ttg aac ctg atc tat aat      918
Ala Lys Gly Gly Tyr Arg Leu Gly Asn Trp Leu Asn Leu Ile Tyr Asn
                255                 260                 265

gcc agc att aag cgg cga gat ctt gtt tct ggc gaa ggc atc aag agg      966
Ala Ser Ile Lys Arg Arg Asp Leu Val Ser Gly Glu Gly Ile Lys Arg
            270                 275                 280

gcc gag aag aag ccg ctg ccg gat ctg atg ggc cgt gac ctc ctt ccg     1014
Ala Glu Lys Lys Pro Leu Pro Asp Leu Met Gly Arg Asp Leu Leu Pro
        285                 290                 295

gcg ccg agg cca ttg agc aag gcg aag ctt gcc agg gct gct ttc ggc     1062
Ala Pro Arg Pro Leu Ser Lys Ala Lys Leu Ala Arg Ala Ala Phe Gly
    300                 305                 310

tat ggc tgt aac cat gag cac tag                                     1086
Tyr Gly Cys Asn His Glu His
315                 320


<210> SEQ ID NO 17
<211> LENGTH: 338
<212> TYPE: PRT
<213> ORGANISM: Stenocarpella maydis

<400> SEQUENCE: 17

Met Ala Ser Asn Leu Leu Leu Thr Leu Ala Ala Leu Gln Gly Val Arg
        -15                 -10                 -5

Ala Trp Gly Thr Leu Gly His Ala Thr Ile Ala Tyr Ile Ala Gln Asn
-1  1               5                   10                  15
```

```
Tyr Val Thr Asp Glu Val Ala Ser Trp Ala Gln Gly Val Leu Ser Asp
                20                  25                  30

Ser Ser Asp Ser Tyr Leu Ala Asn Ile Ala Ser Trp Ala Asp Ser Tyr
            35                  40                  45

Arg Thr Thr Thr Ala Gly Ala Trp Ser Ala Pro Leu His Phe Ile Asp
        50                  55                  60

Ala Glu Asp Ser Pro Pro Ser Asp Cys Asn Val Asp Tyr Asp Arg Asp
    65                  70                  75

Cys Gly Ser Thr Gly Cys Ser Val Ser Ala Ile Ala Asn Tyr Thr Gln
80                  85                  90                  95

Arg Val Gly Asp Gly Arg Leu Ser Ala Ala Asn Val Ala Glu Ala Leu
                100                 105                 110

Lys Phe Leu Val His Phe Thr Gly Asp Ile Thr Gln Pro Leu His Asp
            115                 120                 125

Glu Ala Tyr Glu Lys Gly Ala Asn Gly Val Asp Val Thr Tyr Gln Gly
        130                 135                 140

Tyr Ser Asp Asn Leu His Ala Asp Trp Asp Thr Tyr Leu Pro Ala Thr
    145                 150                 155

Leu Val Gly Gly Ser Thr Leu Ala Asp Ala Lys Ala Trp Ala Thr Asn
160                 165                 170                 175

Leu Thr Ala Glu Ile Asn Ser Gly Ile Tyr Lys Ser Gln Ala Ala Gly
                180                 185                 190

Trp Ile Ala Gly Asp Ser Leu Ser Glu Pro Ile Asp Thr Ala Met Ala
            195                 200                 205

Trp Ala Thr Asp Ala Asn Ala Tyr Val Cys Thr Val Val Met Pro Asn
        210                 215                 220

Gly Ala Ala Ala Leu Thr Ala Met Lys Asp Leu Tyr Pro Thr Tyr Tyr
    225                 230                 235

Glu Ser Val Ile Pro Thr Ile Glu Leu Gln Ile Ala Lys Gly Gly Tyr
240                 245                 250                 255

Arg Leu Gly Asn Trp Leu Asn Leu Ile Tyr Asn Ala Ser Ile Lys Arg
                260                 265                 270

Arg Asp Leu Val Ser Gly Glu Gly Ile Lys Arg Ala Glu Lys Lys Pro
            275                 280                 285

Leu Pro Asp Leu Met Gly Arg Asp Leu Leu Pro Ala Pro Arg Pro Leu
        290                 295                 300

Ser Lys Ala Lys Leu Ala Arg Ala Ala Phe Gly Tyr Gly Cys Asn His
    305                 310                 315

Glu His
320


<210> SEQ ID NO 18
<211> LENGTH: 321
<212> TYPE: PRT
<213> ORGANISM: Stenocarpella maydis

<400> SEQUENCE: 18

Trp Gly Thr Leu Gly His Ala Thr Ile Ala Tyr Ile Ala Gln Asn Tyr
1               5                   10                  15

Val Thr Asp Glu Val Ala Ser Trp Ala Gln Gly Val Leu Ser Asp Ser
            20                  25                  30

Ser Asp Ser Tyr Leu Ala Asn Ile Ala Ser Trp Ala Asp Ser Tyr Arg
        35                  40                  45

Thr Thr Thr Ala Gly Ala Trp Ser Ala Pro Leu His Phe Ile Asp Ala
```

```
    50                  55                  60

Glu Asp Ser Pro Pro Ser Asp Cys Asn Val Asp Tyr Asp Arg Asp Cys
65                  70                  75                  80

Gly Ser Thr Gly Cys Ser Val Ser Ala Ile Ala Asn Tyr Thr Gln Arg
                85                  90                  95

Val Gly Asp Gly Arg Leu Ser Ala Ala Asn Val Ala Glu Ala Leu Lys
            100                 105                 110

Phe Leu Val His Phe Thr Gly Asp Ile Thr Gln Pro Leu His Asp Glu
        115                 120                 125

Ala Tyr Glu Lys Gly Ala Asn Gly Val Asp Val Thr Tyr Gln Gly Tyr
    130                 135                 140

Ser Asp Asn Leu His Ala Asp Trp Asp Thr Tyr Leu Pro Ala Thr Leu
145                 150                 155                 160

Val Gly Gly Ser Thr Leu Ala Asp Ala Lys Ala Trp Ala Thr Asn Leu
                165                 170                 175

Thr Ala Glu Ile Asn Ser Gly Ile Tyr Lys Ser Gln Ala Ala Gly Trp
            180                 185                 190

Ile Ala Gly Asp Ser Leu Ser Glu Pro Ile Asp Thr Ala Met Ala Trp
        195                 200                 205

Ala Thr Asp Ala Asn Ala Tyr Val Cys Thr Val Val Met Pro Asn Gly
    210                 215                 220

Ala Ala Ala Leu Thr Ala Met Lys Asp Leu Tyr Pro Thr Tyr Tyr Glu
225                 230                 235                 240

Ser Val Ile Pro Thr Ile Glu Leu Gln Ile Ala Lys Gly Gly Tyr Arg
                245                 250                 255

Leu Gly Asn Trp Leu Asn Leu Ile Tyr Asn Ala Ser Ile Lys Arg Arg
            260                 265                 270

Asp Leu Val Ser Gly Glu Gly Ile Lys Arg Ala Glu Lys Lys Pro Leu
        275                 280                 285

Pro Asp Leu Met Gly Arg Asp Leu Leu Pro Ala Pro Arg Pro Leu Ser
    290                 295                 300

Lys Ala Lys Leu Ala Arg Ala Ala Phe Gly Tyr Gly Cys Asn His Glu
305                 310                 315                 320

His


<210> SEQ ID NO 19
<211> LENGTH: 1122
<212> TYPE: DNA
<213> ORGANISM: Cordyceps cardinalis
<220> FEATURE:
<221> NAME/KEY: CDS
<222> LOCATION: (1)..(131)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1119)
<220> FEATURE:
<221> NAME/KEY: CDS
<222> LOCATION: (249)..(1119)

<400> SEQUENCE: 19

atg gtc tct ttc ttc cac acc gct gtc gtg gcg gcc act gcc tcg cag       48
Met Val Ser Phe Phe His Thr Ala Val Val Ala Ala Thr Ala Ser Gln
-20                 -15                 -10                 -5

ggc gtg cat gct tgg ggt gtc ttg ggc cat gcc acg gtg gct tac att       96
Gly Val His Ala Trp Gly Val Leu Gly His Ala Thr Val Ala Tyr Ile
            -1  1               5                   10
```

```
gcc cag cat tac ctg act gct gat gct gcg act tg  gtgggttttc          141
Ala Gln His Tyr Leu Thr Ala Asp Ala Ala Thr Trp
        15                  20

atccaagacc aggaaaaaaa gggaaaaaat aaagaaaaaa aaaagaaaaa agagggagaa    201

aaaaccagct cttctttgtt tggctaacct ggaatttcat cacccag g gcg cag ggt    258
                                                      Ala Gln Gly
                                                      25

gtt cta ggc gac acc tca gac tcg tac ctc gcc aac atc gcc tcc tgg      306
Val Leu Gly Asp Thr Ser Asp Ser Tyr Leu Ala Asn Ile Ala Ser Trp
        30                  35                  40

gcc gac cat tac cgc tcc acc aag gcg ggc agg tgg tcc gcg ccg ctg      354
Ala Asp His Tyr Arg Ser Thr Lys Ala Gly Arg Trp Ser Ala Pro Leu
    45                  50                  55

cac ttc atc gac gcc gag gac agc ccg ccg tcg tcg tgc aac gtc gac      402
His Phe Ile Asp Ala Glu Asp Ser Pro Pro Ser Ser Cys Asn Val Asp
60                  65                  70                  75

tac gag cgc gac tgc ggc agc aag ggg tgc tcc gtc tcc gcc atc gcc      450
Tyr Glu Arg Asp Cys Gly Ser Lys Gly Cys Ser Val Ser Ala Ile Ala
                80                  85                  90

aac tac acg cag cgc gtg ggc gac ggg cgc acg agc gcc gcg cac gtc      498
Asn Tyr Thr Gln Arg Val Gly Asp Gly Arg Thr Ser Ala Ala His Val
            95                  100                 105

gcc gag gcg ctc aag ttc ctc gtg cac ttc ctc ggc gac gtc acg cag      546
Ala Glu Ala Leu Lys Phe Leu Val His Phe Leu Gly Asp Val Thr Gln
        110                 115                 120

ccg ctg cac gac gag gcg tac gag gtc ggc ggc aac gac atc aag gtc      594
Pro Leu His Asp Glu Ala Tyr Glu Val Gly Gly Asn Asp Ile Lys Val
    125                 130                 135

acc ttt gcg ggc tac agc gac aac ctg cac gcc gac tgg gac acg tac      642
Thr Phe Ala Gly Tyr Ser Asp Asn Leu His Ala Asp Trp Asp Thr Tyr
140                 145                 150                 155

atg ccc gag aag aag gtc ggc ggc ggc aag ctg acg gac gcg cag tcg      690
Met Pro Glu Lys Lys Val Gly Gly Gly Lys Leu Thr Asp Ala Gln Ser
                160                 165                 170

tgg gcg gcg gcg ctg att ggc gag atc gag tcg ggc cgc ttc gag ggc      738
Trp Ala Ala Ala Leu Ile Gly Glu Ile Glu Ser Gly Arg Phe Glu Gly
            175                 180                 185

cag gcg gcg ggc tgg att gcc ggc gat gat gtc ggt gac gcg att gcg      786
Gln Ala Ala Gly Trp Ile Ala Gly Asp Asp Val Gly Asp Ala Ile Ala
        190                 195                 200

tcg gcg acg cgc tgg gcg tcg gat gcg aat gcg tat gtg tgc agc gtc      834
Ser Ala Thr Arg Trp Ala Ser Asp Ala Asn Ala Tyr Val Cys Ser Val
    205                 210                 215

gtc atg ccc gat ggc gcg gac gcg ctg cag cag ggc gac ttg tac ccg      882
Val Met Pro Asp Gly Ala Asp Ala Leu Gln Gln Gly Asp Leu Tyr Pro
220                 225                 230                 235

gct tac tac aat tcg gtg att ggc acc atc gag ctg cag att gcc aag      930
Ala Tyr Tyr Asn Ser Val Ile Gly Thr Ile Glu Leu Gln Ile Ala Lys
                240                 245                 250

ggc ggc tac cgc ctc gga aac tgg ctc aac gcc atc tat agc ggt aag      978
Gly Gly Tyr Arg Leu Gly Asn Trp Leu Asn Ala Ile Tyr Ser Gly Lys
            255                 260                 265

att gcg tcg aag cgc agc gtc cat gac acc gcg ccg ctc ccg gac ctg     1026
Ile Ala Ser Lys Arg Ser Val His Asp Thr Ala Pro Leu Pro Asp Leu
        270                 275                 280

acg ggt cgc cat ctg ctg cct gcg tct cgc ccg ctg agc cgc gcg aag     1074
Thr Gly Arg His Leu Leu Pro Ala Ser Arg Pro Leu Ser Arg Ala Lys
    285                 290                 295
```

```
ctc gcg aga gag gcc att ggt gag tcg tgc tgt acg cac aac cac tga      1122
Leu Ala Arg Glu Ala Ile Gly Glu Ser Cys Cys Thr His Asn His
300                 305                 310
```

<210> SEQ ID NO 20
<211> LENGTH: 334
<212> TYPE: PRT
<213> ORGANISM: Cordyceps cardinalis

<400> SEQUENCE: 20

```
Met Val Ser Phe Phe His Thr Ala Val Val Ala Ala Thr Ala Ser Gln
-20                 -15                 -10                 -5

Gly Val His Ala Trp Gly Val Leu Gly His Ala Thr Val Ala Tyr Ile
            -1  1               5                   10

Ala Gln His Tyr Leu Thr Ala Asp Ala Ala Thr Trp Ala Gln Gly Val
        15                  20                  25

Leu Gly Asp Thr Ser Asp Ser Tyr Leu Ala Asn Ile Ala Ser Trp Ala
    30                  35                  40

Asp His Tyr Arg Ser Thr Lys Ala Gly Arg Trp Ser Ala Pro Leu His
45                  50                  55                  60

Phe Ile Asp Ala Glu Asp Ser Pro Pro Ser Ser Cys Asn Val Asp Tyr
                65                  70                  75

Glu Arg Asp Cys Gly Ser Lys Gly Cys Ser Val Ser Ala Ile Ala Asn
            80                  85                  90

Tyr Thr Gln Arg Val Gly Asp Gly Arg Thr Ser Ala Ala His Val Ala
        95                  100                 105

Glu Ala Leu Lys Phe Leu Val His Phe Leu Gly Asp Val Thr Gln Pro
    110                 115                 120

Leu His Asp Glu Ala Tyr Glu Val Gly Gly Asn Asp Ile Lys Val Thr
125                 130                 135                 140

Phe Ala Gly Tyr Ser Asp Asn Leu His Ala Asp Trp Asp Thr Tyr Met
                145                 150                 155

Pro Glu Lys Lys Val Gly Gly Gly Lys Leu Thr Asp Ala Gln Ser Trp
            160                 165                 170

Ala Ala Ala Leu Ile Gly Glu Ile Glu Ser Gly Arg Phe Glu Gly Gln
        175                 180                 185

Ala Ala Gly Trp Ile Ala Gly Asp Asp Val Gly Asp Ala Ile Ala Ser
    190                 195                 200

Ala Thr Arg Trp Ala Ser Asp Ala Asn Ala Tyr Val Cys Ser Val Val
205                 210                 215                 220

Met Pro Asp Gly Ala Asp Ala Leu Gln Gln Gly Asp Leu Tyr Pro Ala
                225                 230                 235

Tyr Tyr Asn Ser Val Ile Gly Thr Ile Glu Leu Gln Ile Ala Lys Gly
            240                 245                 250

Gly Tyr Arg Leu Gly Asn Trp Leu Asn Ala Ile Tyr Ser Gly Lys Ile
        255                 260                 265

Ala Ser Lys Arg Ser Val His Asp Thr Ala Pro Leu Pro Asp Leu Thr
    270                 275                 280

Gly Arg His Leu Leu Pro Ala Ser Arg Pro Leu Ser Arg Ala Lys Leu
285                 290                 295                 300

Ala Arg Glu Ala Ile Gly Glu Ser Cys Cys Thr His Asn His
                305                 310
```

<210> SEQ ID NO 21
<211> LENGTH: 314
<212> TYPE: PRT

<213> ORGANISM: Cordyceps cardinalis

<400> SEQUENCE: 21

```
Trp Gly Val Leu Gly His Ala Thr Val Ala Tyr Ile Ala Gln His Tyr
1               5                   10                  15

Leu Thr Ala Asp Ala Ala Thr Trp Ala Gln Gly Val Leu Gly Asp Thr
            20                  25                  30

Ser Asp Ser Tyr Leu Ala Asn Ile Ala Ser Trp Ala Asp His Tyr Arg
        35                  40                  45

Ser Thr Lys Ala Gly Arg Trp Ser Ala Pro Leu His Phe Ile Asp Ala
    50                  55                  60

Glu Asp Ser Pro Pro Ser Ser Cys Asn Val Asp Tyr Glu Arg Asp Cys
65                  70                  75                  80

Gly Ser Lys Gly Cys Ser Val Ser Ala Ile Ala Asn Tyr Thr Gln Arg
                85                  90                  95

Val Gly Asp Gly Arg Thr Ser Ala Ala His Val Ala Glu Ala Leu Lys
            100                 105                 110

Phe Leu Val His Phe Leu Gly Asp Val Thr Gln Pro Leu His Asp Glu
        115                 120                 125

Ala Tyr Glu Val Gly Gly Asn Asp Ile Lys Val Thr Phe Ala Gly Tyr
    130                 135                 140

Ser Asp Asn Leu His Ala Asp Trp Asp Thr Tyr Met Pro Glu Lys Lys
145                 150                 155                 160

Val Gly Gly Gly Lys Leu Thr Asp Ala Gln Ser Trp Ala Ala Ala Leu
                165                 170                 175

Ile Gly Glu Ile Glu Ser Gly Arg Phe Glu Gly Gln Ala Ala Gly Trp
            180                 185                 190

Ile Ala Gly Asp Asp Val Gly Asp Ala Ile Ala Ser Ala Thr Arg Trp
        195                 200                 205

Ala Ser Asp Ala Asn Ala Tyr Val Cys Ser Val Val Met Pro Asp Gly
    210                 215                 220

Ala Asp Ala Leu Gln Gln Gly Asp Leu Tyr Pro Ala Tyr Tyr Asn Ser
225                 230                 235                 240

Val Ile Gly Thr Ile Glu Leu Gln Ile Ala Lys Gly Gly Tyr Arg Leu
                245                 250                 255

Gly Asn Trp Leu Asn Ala Ile Tyr Ser Gly Lys Ile Ala Ser Lys Arg
            260                 265                 270

Ser Val His Asp Thr Ala Pro Leu Pro Asp Leu Thr Gly Arg His Leu
        275                 280                 285

Leu Pro Ala Ser Arg Pro Leu Ser Arg Ala Lys Leu Ala Arg Glu Ala
    290                 295                 300

Ile Gly Glu Ser Cys Cys Thr His Asn His
305                 310
```

<210> SEQ ID NO 22
<211> LENGTH: 1175
<212> TYPE: DNA
<213> ORGANISM: Phialophora geniculata
<220> FEATURE:
<221> NAME/KEY: CDS
<222> LOCATION: (1)..(70)
<220> FEATURE:
<221> NAME/KEY: sig_peptide
<222> LOCATION: (1)..(57)
<220> FEATURE:
<221> NAME/KEY: mat_peptide
<222> LOCATION: (58)..(634)
<220> FEATURE:

```
<221> NAME/KEY: CDS
<222> LOCATION: (159)..(634)
<220> FEATURE:
<221> NAME/KEY: CDS
<222> LOCATION: (756)..(1172)

<400> SEQUENCE: 22

atg cgt gtc aca act gtc gca gcc ctc gtg ggc atg gcc gcc gct ccg       48
Met Arg Val Thr Thr Val Ala Ala Leu Val Gly Met Ala Ala Ala Pro
                -15                 -10                 -5

gcc ctg gcc tgg aat acc gat g gtaagtggct accggcaaaa ttcacgcctc       100
Ala Leu Ala Trp Asn Thr Asp
        -1  1

ggtcaagagg atgaaaactg gaggccatgt tgaagctgac catcatactc ccctccag      158

tc  cac cag caa atc ggc tac gcg act gag gag ttc ctc acg gag gag     205
Val His Gln Gln Ile Gly Tyr Ala Thr Glu Glu Phe Leu Thr Glu Glu
5                   10                  15                  20

aca aag gag atc ctc gcc cag atc ctc gag ccc gag cat gag ggc agt     253
Thr Lys Glu Ile Leu Ala Gln Ile Leu Glu Pro Glu His Glu Gly Ser
                25                  30                  35

cta ggc cgc atc tcg gcc tgg gcg gac tcg cac cgc ggc acc gac gag     301
Leu Gly Arg Ile Ser Ala Trp Ala Asp Ser His Arg Gly Thr Asp Glu
            40                  45                  50

ggc agg cac acg acg acc tgg cac tgg atc aac ccg gct gac gag ccg     349
Gly Arg His Thr Thr Thr Trp His Trp Ile Asn Pro Ala Asp Glu Pro
        55                  60                  65

ccg agc ctg tgc aac ctc tac ttc aac cgc gac tgc acg ggc agc ggc     397
Pro Ser Leu Cys Asn Leu Tyr Phe Asn Arg Asp Cys Thr Gly Ser Gly
    70                  75                  80

tgc atc gtc agc gcc atc gcc aac gaa acg cag atc ctc aag ggc tgc     445
Cys Ile Val Ser Ala Ile Ala Asn Glu Thr Gln Ile Leu Lys Gly Cys
85                  90                  95                  100

atc cgg gac gcc aag ttt ggc cgt agg cag agc ggc aac ggg tct gac     493
Ile Arg Asp Ala Lys Phe Gly Arg Arg Gln Ser Gly Asn Gly Ser Asp
                105                 110                 115

gcg acc gcc tgc gcc aac gcc gtc aag ttc atc acg cac ttt acg cag     541
Ala Thr Ala Cys Ala Asn Ala Val Lys Phe Ile Thr His Phe Thr Gln
            120                 125                 130

gat ctg gcg cag ccc atg cac gtc act ggc gtt gcg agg ggt ggc aac     589
Asp Leu Ala Gln Pro Met His Val Thr Gly Val Ala Arg Gly Gly Asn
        135                 140                 145

gat att ccc gtc gtc ttt gac ggc gtc gac acg aac ctc cac gct         634
Asp Ile Pro Val Val Phe Asp Gly Val Asp Thr Asn Leu His Ala
    150                 155                 160

gtgagtttga cttccctgat atgcacaacg gatttctctt cctctgcaag agagaggggc    694

agagaagaag gcggtcgttc tgctggcaag gaatatcacc tcgactgacc tggcacgcta    754

g atc tgg gac ggc cgc atc gtc tac acc cta gcc aac aca acc cgc ttc   803
  Ile Trp Asp Gly Arg Ile Val Tyr Thr Leu Ala Asn Thr Thr Arg Phe
      165                 170                 175

ggt aac gaa tcg ctc gac ccc ttc ttc gcc gac atg gtc tcc cgc atc     851
Gly Asn Glu Ser Leu Asp Pro Phe Phe Ala Asp Met Val Ser Arg Ile
180                 185                 190                 195

aag gcc gac acc tac ttc acc cca acg gct gag tgg ctc gaa tgc acc     899
Lys Ala Asp Thr Tyr Phe Thr Pro Thr Ala Glu Trp Leu Glu Cys Thr
                200                 205                 210

agc ccc ggc acg ccg ctc gcg tgc ccc att gcc tgg gcc cgt gac acc     947
Ser Pro Gly Thr Pro Leu Ala Cys Pro Ile Ala Trp Ala Arg Asp Thr
            215                 220                 225

aac cag tgg aac tgc gac tac gcc ttc agc cag atc tac aac ggc acc     995
```

```
Asn Gln Trp Asn Cys Asp Tyr Ala Phe Ser Gln Ile Tyr Asn Gly Thr
        230                 235                 240

gac ctg cgc acc agc ggc tac gcg cag ggt gcc tgg ccc att gcc gag      1043
Asp Leu Arg Thr Ser Gly Tyr Ala Gln Gly Ala Trp Pro Ile Ala Glu
    245                 250                 255

atc cag atg gcc aag gct gtg ttg cgc acc gcc acc tgg ttc aac cgt      1091
Ile Gln Met Ala Lys Ala Val Leu Arg Thr Ala Thr Trp Phe Asn Arg
260                 265                 270                 275

ctc gtt gag aat tgc ttc cat gag cgt gag gtc att ctt gac ttg gtg      1139
Leu Val Glu Asn Cys Phe His Glu Arg Glu Val Ile Leu Asp Leu Val
                280                 285                 290

ccg agc tgg gtt ggt gga cct ggt ggc ggt aac taa                      1175
Pro Ser Trp Val Gly Gly Pro Gly Gly Gly Asn
            295                 300


<210> SEQ ID NO 23
<211> LENGTH: 321
<212> TYPE: PRT
<213> ORGANISM: Phialophora geniculata

<400> SEQUENCE: 23

Met Arg Val Thr Thr Val Ala Ala Leu Val Gly Met Ala Ala Ala Pro
                -15                 -10                 -5

Ala Leu Ala Trp Asn Thr Asp Val His Gln Gln Ile Gly Tyr Ala Thr
        -1  1               5                   10

Glu Glu Phe Leu Thr Glu Glu Thr Lys Glu Ile Leu Ala Gln Ile Leu
    15                  20                  25

Glu Pro Glu His Glu Gly Ser Leu Gly Arg Ile Ser Ala Trp Ala Asp
30                  35                  40                  45

Ser His Arg Gly Thr Asp Glu Gly Arg His Thr Thr Thr Trp His Trp
                50                  55                  60

Ile Asn Pro Ala Asp Glu Pro Pro Ser Leu Cys Asn Leu Tyr Phe Asn
            65                  70                  75

Arg Asp Cys Thr Gly Ser Gly Cys Ile Val Ser Ala Ile Ala Asn Glu
        80                  85                  90

Thr Gln Ile Leu Lys Gly Cys Ile Arg Asp Ala Lys Phe Gly Arg Arg
    95                  100                 105

Gln Ser Gly Asn Gly Ser Asp Ala Thr Ala Cys Ala Asn Ala Val Lys
110                 115                 120                 125

Phe Ile Thr His Phe Thr Gln Asp Leu Ala Gln Pro Met His Val Thr
                130                 135                 140

Gly Val Ala Arg Gly Gly Asn Asp Ile Pro Val Val Phe Asp Gly Val
            145                 150                 155

Asp Thr Asn Leu His Ala Ile Trp Asp Gly Arg Ile Val Tyr Thr Leu
        160                 165                 170

Ala Asn Thr Thr Arg Phe Gly Asn Glu Ser Leu Asp Pro Phe Phe Ala
    175                 180                 185

Asp Met Val Ser Arg Ile Lys Ala Asp Thr Tyr Phe Thr Pro Thr Ala
190                 195                 200                 205

Glu Trp Leu Glu Cys Thr Ser Pro Gly Thr Pro Leu Ala Cys Pro Ile
                210                 215                 220

Ala Trp Ala Arg Asp Thr Asn Gln Trp Asn Cys Asp Tyr Ala Phe Ser
            225                 230                 235

Gln Ile Tyr Asn Gly Thr Asp Leu Arg Thr Ser Gly Tyr Ala Gln Gly
        240                 245                 250

Ala Trp Pro Ile Ala Glu Ile Gln Met Ala Lys Ala Val Leu Arg Thr
```

```
    255                 260                 265

Ala Thr Trp Phe Asn Arg Leu Val Glu Asn Cys Phe His Glu Arg Glu
270                 275                 280                 285

Val Ile Leu Asp Leu Val Pro Ser Trp Val Gly Gly Pro Gly Gly Gly
                290                 295                 300

Asn


<210> SEQ ID NO 24
<211> LENGTH: 302
<212> TYPE: PRT
<213> ORGANISM: Phialophora geniculata

<400> SEQUENCE: 24

Trp Asn Thr Asp Val His Gln Gln Ile Gly Tyr Ala Thr Glu Glu Phe
1               5                   10                  15

Leu Thr Glu Glu Thr Lys Glu Ile Leu Ala Gln Ile Leu Glu Pro Glu
            20                  25                  30

His Glu Gly Ser Leu Gly Arg Ile Ser Ala Trp Ala Asp Ser His Arg
        35                  40                  45

Gly Thr Asp Glu Gly Arg His Thr Thr Thr Trp His Trp Ile Asn Pro
    50                  55                  60

Ala Asp Glu Pro Pro Ser Leu Cys Asn Leu Tyr Phe Asn Arg Asp Cys
65                  70                  75                  80

Thr Gly Ser Gly Cys Ile Val Ser Ala Ile Ala Asn Glu Thr Gln Ile
                85                  90                  95

Leu Lys Gly Cys Ile Arg Asp Ala Lys Phe Gly Arg Arg Gln Ser Gly
            100                 105                 110

Asn Gly Ser Asp Ala Thr Ala Cys Ala Asn Ala Val Lys Phe Ile Thr
        115                 120                 125

His Phe Thr Gln Asp Leu Ala Gln Pro Met His Val Thr Gly Val Ala
    130                 135                 140

Arg Gly Gly Asn Asp Ile Pro Val Val Phe Asp Gly Val Asp Thr Asn
145                 150                 155                 160

Leu His Ala Ile Trp Asp Gly Arg Ile Val Tyr Thr Leu Ala Asn Thr
                165                 170                 175

Thr Arg Phe Gly Asn Glu Ser Leu Asp Pro Phe Phe Ala Asp Met Val
            180                 185                 190

Ser Arg Ile Lys Ala Asp Thr Tyr Phe Thr Pro Thr Ala Glu Trp Leu
        195                 200                 205

Glu Cys Thr Ser Pro Gly Thr Pro Leu Ala Cys Pro Ile Ala Trp Ala
    210                 215                 220

Arg Asp Thr Asn Gln Trp Asn Cys Asp Tyr Ala Phe Ser Gln Ile Tyr
225                 230                 235                 240

Asn Gly Thr Asp Leu Arg Thr Ser Gly Tyr Ala Gln Gly Ala Trp Pro
                245                 250                 255

Ile Ala Glu Ile Gln Met Ala Lys Ala Val Leu Arg Thr Ala Thr Trp
            260                 265                 270

Phe Asn Arg Leu Val Glu Asn Cys Phe His Glu Arg Glu Val Ile Leu
        275                 280                 285

Asp Leu Val Pro Ser Trp Val Gly Gly Pro Gly Gly Gly Asn
    290                 295                 300


<210> SEQ ID NO 25
<211> LENGTH: 1168
<212> TYPE: DNA
```

```
<213> ORGANISM: Cadophora fastigiata
<220> FEATURE:
<221> NAME/KEY: CDS
<222> LOCATION: (1)..(339)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1165)
<220> FEATURE:
<221> NAME/KEY: CDS
<222> LOCATION: (392)..(448)
<220> FEATURE:
<221> NAME/KEY: CDS
<222> LOCATION: (499)..(510)
<220> FEATURE:
<221> NAME/KEY: CDS
<222> LOCATION: (567)..(992)
<220> FEATURE:
<221> NAME/KEY: CDS
<222> LOCATION: (1121)..(1165)

<400> SEQUENCE: 25

atg aga gtc acc tac ctc att cct ctc acc ctc ctt tcc tcc gtt ccg       48
Met Arg Val Thr Tyr Leu Ile Pro Leu Thr Leu Leu Ser Ser Val Pro
-20                 -15                 -10                 -5

agc aca ctc gcg tgg gga act ctt ggg cat acg aca gta gcc tac att       96
Ser Thr Leu Ala Trp Gly Thr Leu Gly His Thr Thr Val Ala Tyr Ile
            -1  1               5                   10

gcg agc aac ttc gtc caa ccc gag act cga gac ctt ttc caa aac atc      144
Ala Ser Asn Phe Val Gln Pro Glu Thr Arg Asp Leu Phe Gln Asn Ile
        15                  20                  25

ctg cac aat act tct gat gca tac cta gct ggc ata gcg aca tgg gct      192
Leu His Asn Thr Ser Asp Ala Tyr Leu Ala Gly Ile Ala Thr Trp Ala
    30                  35                  40

gat tcg ttt cgg tac acg gct gcg ggg aag ttt tct gcg ccg ttt cat      240
Asp Ser Phe Arg Tyr Thr Ala Ala Gly Lys Phe Ser Ala Pro Phe His
45                  50                  55                  60

ttc att gat gca gag gat agc ccg cca aat agt tgt gat gtg aag tat      288
Phe Ile Asp Ala Glu Asp Ser Pro Pro Asn Ser Cys Asp Val Lys Tyr
                65                  70                  75

gcg agg gat tgt ggg gag caa ggt tgt gtt gtt ggg gct att cag aat      336
Ala Arg Asp Cys Gly Glu Gln Gly Cys Val Val Gly Ala Ile Gln Asn
            80                  85                  90

tat gtgagttgaa tttgagcggt cgggtaggag gggcgactga tgatgggtgt ag aca    394
Tyr                                                             Thr

aga caa ctg ctt gat tct gag ctg aat gga gga ctc aga aat atg gct      442
Arg Gln Leu Leu Asp Ser Glu Leu Asn Gly Gly Leu Arg Asn Met Ala
95                  100                 105                 110

gct aag gtacgccttc caccttccta tatttgtcaa agtactaatg ctttgaatag       498
Ala Lys

ttc gtc gtc cac gtaagtatca gtcatattgt agctcaatat taaaaaccag          550
Phe Val Val His
        115

ctaataatgc ttcaag ctc atc ggg gac atc cac caa cct cta cat gtc gag    602
                  Leu Ile Gly Asp Ile His Gln Pro Leu His Val Glu
                              120                 125

aat tta gaa aag ggg ggc aac ggc ata caa gtc atc ttt ggc ggt gcc      650
Asn Leu Glu Lys Gly Gly Asn Gly Ile Gln Val Ile Phe Gly Gly Ala
    130                 135                 140

cat gtc aat ctc cac cac gtc tgg gat act agt att gca gag aag tta      698
His Val Asn Leu His His Val Trp Asp Thr Ser Ile Ala Glu Lys Leu
145                 150                 155                 160
```

```
gtt gga ggc tac gct ctt cct ttc gcc gaa gaa tgg gct aaa agt ctc      746
Val Gly Gly Tyr Ala Leu Pro Phe Ala Glu Glu Trp Ala Lys Ser Leu
                165                 170                 175

acc gag gcc atc aag gaa aac gag tac aag tct ctc gct cca tcg tgg      794
Thr Glu Ala Ile Lys Glu Asn Glu Tyr Lys Ser Leu Ala Pro Ser Trp
            180                 185                 190

ctg gaa ggc atc gat ttg agt gat ccg gtc aca act tcg ttg ggc tgg      842
Leu Glu Gly Ile Asp Leu Ser Asp Pro Val Thr Thr Ser Leu Gly Trp
        195                 200                 205

gca gag gaa acc aac aaa ctt gtt tgc acg gcg gtg ctc ccc gct ggc      890
Ala Glu Glu Thr Asn Lys Leu Val Cys Thr Ala Val Leu Pro Ala Gly
    210                 215                 220

cgt gag ggt gtc cag gac caa gag ttg agt ggg aag tat tac gaa aat      938
Arg Glu Gly Val Gln Asp Gln Glu Leu Ser Gly Lys Tyr Tyr Glu Asn
225                 230                 235                 240

gca gag cct gtt gtg aaa ctg cag gta gcc aag gct ggg tat aga ctt      986
Ala Glu Pro Val Val Lys Leu Gln Val Ala Lys Ala Gly Tyr Arg Leu
                245                 250                 255

gct aga gtaagtgggc cggggcaaat aattttctat tttctctatt tttctgttgc      1042
Ala Arg

aagtcatgta tttgtcctcc atgcaaccac tcctgagaga tttgaagaaa ggcatttact   1102

gactctgcga tcatctag tgg ttg gat ctg att gct caa gca cag gtc aag     1153
                    Trp Leu Asp Leu Ile Ala Gln Ala Gln Val Lys
                        260                 265

aag cca gag tta tga                                                 1168
Lys Pro Glu Leu
270


<210> SEQ ID NO 26
<211> LENGTH: 293
<212> TYPE: PRT
<213> ORGANISM: Cadophora fastigiata

<400> SEQUENCE: 26

Met Arg Val Thr Tyr Leu Ile Pro Leu Thr Leu Leu Ser Ser Val Pro
-20                 -15                 -10                 -5

Ser Thr Leu Ala Trp Gly Thr Leu Gly His Thr Thr Val Ala Tyr Ile
            -1  1               5                   10

Ala Ser Asn Phe Val Gln Pro Glu Thr Arg Asp Leu Phe Gln Asn Ile
        15                  20                  25

Leu His Asn Thr Ser Asp Ala Tyr Leu Ala Gly Ile Ala Thr Trp Ala
    30                  35                  40

Asp Ser Phe Arg Tyr Thr Ala Ala Gly Lys Phe Ser Ala Pro Phe His
45                  50                  55                  60

Phe Ile Asp Ala Glu Asp Ser Pro Pro Asn Ser Cys Asp Val Lys Tyr
                65                  70                  75

Ala Arg Asp Cys Gly Glu Gln Gly Cys Val Val Gly Ala Ile Gln Asn
            80                  85                  90

Tyr Thr Arg Gln Leu Leu Asp Ser Glu Leu Asn Gly Gly Leu Arg Asn
        95                  100                 105

Met Ala Ala Lys Phe Val Val His Leu Ile Gly Asp Ile His Gln Pro
    110                 115                 120

Leu His Val Glu Asn Leu Glu Lys Gly Gly Asn Gly Ile Gln Val Ile
125                 130                 135                 140

Phe Gly Gly Ala His Val Asn Leu His His Val Trp Asp Thr Ser Ile
                145                 150                 155

Ala Glu Lys Leu Val Gly Gly Tyr Ala Leu Pro Phe Ala Glu Glu Trp
```

```
            160                 165                 170

Ala Lys Ser Leu Thr Glu Ala Ile Lys Glu Asn Glu Tyr Lys Ser Leu
        175                 180                 185

Ala Pro Ser Trp Leu Glu Gly Ile Asp Leu Ser Asp Pro Val Thr Thr
    190                 195                 200

Ser Leu Gly Trp Ala Glu Glu Thr Asn Lys Leu Val Cys Thr Ala Val
205                 210                 215                 220

Leu Pro Ala Gly Arg Glu Gly Val Gln Asp Gln Glu Leu Ser Gly Lys
                225                 230                 235

Tyr Tyr Glu Asn Ala Glu Pro Val Val Lys Leu Gln Val Ala Lys Ala
            240                 245                 250

Gly Tyr Arg Leu Ala Arg Trp Leu Asp Leu Ile Ala Gln Ala Gln Val
        255                 260                 265

Lys Lys Pro Glu Leu
    270


<210> SEQ ID NO 27
<211> LENGTH: 273
<212> TYPE: PRT
<213> ORGANISM: Cadophora fastigiata

<400> SEQUENCE: 27

Trp Gly Thr Leu Gly His Thr Thr Val Ala Tyr Ile Ala Ser Asn Phe
1               5                   10                  15

Val Gln Pro Glu Thr Arg Asp Leu Phe Gln Asn Ile Leu His Asn Thr
            20                  25                  30

Ser Asp Ala Tyr Leu Ala Gly Ile Ala Thr Trp Ala Asp Ser Phe Arg
        35                  40                  45

Tyr Thr Ala Ala Gly Lys Phe Ser Ala Pro Phe His Phe Ile Asp Ala
    50                  55                  60

Glu Asp Ser Pro Pro Asn Ser Cys Asp Val Lys Tyr Ala Arg Asp Cys
65                  70                  75                  80

Gly Glu Gln Gly Cys Val Val Gly Ala Ile Gln Asn Tyr Thr Arg Gln
                85                  90                  95

Leu Leu Asp Ser Glu Leu Asn Gly Gly Leu Arg Asn Met Ala Ala Lys
            100                 105                 110

Phe Val Val His Leu Ile Gly Asp Ile His Gln Pro Leu His Val Glu
        115                 120                 125

Asn Leu Glu Lys Gly Gly Asn Gly Ile Gln Val Ile Phe Gly Gly Ala
    130                 135                 140

His Val Asn Leu His His Val Trp Asp Thr Ser Ile Ala Glu Lys Leu
145                 150                 155                 160

Val Gly Gly Tyr Ala Leu Pro Phe Ala Glu Glu Trp Ala Lys Ser Leu
                165                 170                 175

Thr Glu Ala Ile Lys Glu Asn Glu Tyr Lys Ser Leu Ala Pro Ser Trp
            180                 185                 190

Leu Glu Gly Ile Asp Leu Ser Asp Pro Val Thr Thr Ser Leu Gly Trp
        195                 200                 205

Ala Glu Glu Thr Asn Lys Leu Val Cys Thr Ala Val Leu Pro Ala Gly
    210                 215                 220

Arg Glu Gly Val Gln Asp Gln Glu Leu Ser Gly Lys Tyr Tyr Glu Asn
225                 230                 235                 240

Ala Glu Pro Val Val Lys Leu Gln Val Ala Lys Ala Gly Tyr Arg Leu
                245                 250                 255
```

```
Ala Arg Trp Leu Asp Leu Ile Ala Gln Ala Gln Val Lys Lys Pro Glu
            260                 265                 270

Leu


<210> SEQ ID NO 28
<211> LENGTH: 813
<212> TYPE: DNA
<213> ORGANISM: Unknown
<220> FEATURE:
<223> OTHER INFORMATION: Microbial metagenome enrichment
<220> FEATURE:
<221> NAME/KEY: CDS
<222> LOCATION: (1)..(810)
<220> FEATURE:
<221> NAME/KEY: sig_peptide
<222> LOCATION: (1)..(90)
<220> FEATURE:
<221> NAME/KEY: mat_peptide
<222> LOCATION: (91)..(810)

<400> SEQUENCE: 28

atg cct gaa gtt ttt tct tcc ccg gcc tca gta atc cgc cga atg gcc       48
Met Pro Glu Val Phe Ser Ser Pro Ala Ser Val Ile Arg Arg Met Ala
-30                 -25                 -20                 -15

ctc tta ctg ata gcc ttt tct tta agc gtt acc gcc ttc tgt tgg ggt       96
Leu Leu Leu Ile Ala Phe Ser Leu Ser Val Thr Ala Phe Cys Trp Gly
                -10                 -5                  -1  1

ctt acc gga cac cgg gta att ggc gaa ata gct gaa aac cat tta tcc      144
Leu Thr Gly His Arg Val Ile Gly Glu Ile Ala Glu Asn His Leu Ser
        5                   10                  15

aga aaa gca aaa aag gag ctg aaa aaa ctg att ggc cgc caa acg ctc      192
Arg Lys Ala Lys Lys Glu Leu Lys Lys Leu Ile Gly Arg Gln Thr Leu
    20                  25                  30

gcc tgg tgg tct aac tgg cct gat ttt atc aag tca gac act acc tgg      240
Ala Trp Trp Ser Asn Trp Pro Asp Phe Ile Lys Ser Asp Thr Thr Trp
35                  40                  45                  50

aat cat gct tcg ccc tgg cat tat gta aat gtg cag cct cac ctc tct      288
Asn His Ala Ser Pro Trp His Tyr Val Asn Val Gln Pro His Leu Ser
                55                  60                  65

aaa gaa gaa ttt gtg gag gca tta aaa aaa ctg ccg ggc aaa aac cta      336
Lys Glu Glu Phe Val Glu Ala Leu Lys Lys Leu Pro Gly Lys Asn Leu
            70                  75                  80

tat aca cag atc cag gaa acg atg agc cag ctt aaa gac cgg caa ttg      384
Tyr Thr Gln Ile Gln Glu Thr Met Ser Gln Leu Lys Asp Arg Gln Leu
        85                  90                  95

tcg ctg gag caa cgg caa ata gcc ctc cgg ttt ctg gta cac ctg gta      432
Ser Leu Glu Gln Arg Gln Ile Ala Leu Arg Phe Leu Val His Leu Val
    100                 105                 110

ggt gat ctg cat cag ccc ctg cat gtg ggt cat gcc gat gac cag ggt      480
Gly Asp Leu His Gln Pro Leu His Val Gly His Ala Asp Asp Gln Gly
115                 120                 125                 130

gga aat aaa att gta gta tac tgg ttt gat cgg aag acc aac ctt cat      528
Gly Asn Lys Ile Val Val Tyr Trp Phe Asp Arg Lys Thr Asn Leu His
                135                 140                 145

tct gtg tgg gat acc tgg ctt att gat gaa cag aaa tac agc tat tcc      576
Ser Val Trp Asp Thr Trp Leu Ile Asp Glu Gln Lys Tyr Ser Tyr Ser
            150                 155                 160

gaa tat gcc cgc ctg ctt gat atc act ccc aaa gaa cag gta gag gcc      624
Glu Tyr Ala Arg Leu Leu Asp Ile Thr Pro Lys Glu Gln Val Glu Ala
        165                 170                 175

tgg caa tct tcg tca ctc gag gat tgg ttt tat gaa tct tac cag ctg      672
Trp Gln Ser Ser Ser Leu Glu Asp Trp Phe Tyr Glu Ser Tyr Gln Leu
    180                 185                 190
```

```
gca gaa aaa atc tat gct tcg gta cag ccc gaa gac aaa ctt agt tat      720
Ala Glu Lys Ile Tyr Ala Ser Val Gln Pro Glu Asp Lys Leu Ser Tyr
195                 200                 205                 210

cgt tac aat tac ctg ttt cag tcg ttc atg gat gag caa ctg gta aaa      768
Arg Tyr Asn Tyr Leu Phe Gln Ser Phe Met Asp Glu Gln Leu Val Lys
                215                 220                 225

ggt ggt gta cgc ctg gct gcc ctc ctc aat aac agc ctc gaa taa          813
Gly Gly Val Arg Leu Ala Ala Leu Leu Asn Asn Ser Leu Glu
            230                 235                 240


<210> SEQ ID NO 29
<211> LENGTH: 270
<212> TYPE: PRT
<213> ORGANISM: Unknown
<220> FEATURE:
<223> OTHER INFORMATION: Synthetic Construct

<400> SEQUENCE: 29

Met Pro Glu Val Phe Ser Ser Pro Ala Ser Val Ile Arg Arg Met Ala
-30                 -25                 -20                 -15

Leu Leu Leu Ile Ala Phe Ser Leu Ser Val Thr Ala Phe Cys Trp Gly
                -10                 -5                  -1  1

Leu Thr Gly His Arg Val Ile Gly Glu Ile Ala Glu Asn His Leu Ser
        5                   10                  15

Arg Lys Ala Lys Lys Glu Leu Lys Lys Leu Ile Gly Arg Gln Thr Leu
    20                  25                  30

Ala Trp Trp Ser Asn Trp Pro Asp Phe Ile Lys Ser Asp Thr Thr Trp
35                  40                  45                  50

Asn His Ala Ser Pro Trp His Tyr Val Asn Val Gln Pro His Leu Ser
                55                  60                  65

Lys Glu Glu Phe Val Glu Ala Leu Lys Lys Leu Pro Gly Lys Asn Leu
            70                  75                  80

Tyr Thr Gln Ile Gln Glu Thr Met Ser Gln Leu Lys Asp Arg Gln Leu
        85                  90                  95

Ser Leu Glu Gln Arg Gln Ile Ala Leu Arg Phe Leu Val His Leu Val
    100                 105                 110

Gly Asp Leu His Gln Pro Leu His Val Gly His Ala Asp Asp Gln Gly
115                 120                 125                 130

Gly Asn Lys Ile Val Val Tyr Trp Phe Asp Arg Lys Thr Asn Leu His
                135                 140                 145

Ser Val Trp Asp Thr Trp Leu Ile Asp Glu Gln Lys Tyr Ser Tyr Ser
            150                 155                 160

Glu Tyr Ala Arg Leu Leu Asp Ile Thr Pro Lys Glu Gln Val Glu Ala
        165                 170                 175

Trp Gln Ser Ser Ser Leu Glu Asp Trp Phe Tyr Glu Ser Tyr Gln Leu
    180                 185                 190

Ala Glu Lys Ile Tyr Ala Ser Val Gln Pro Glu Asp Lys Leu Ser Tyr
195                 200                 205                 210

Arg Tyr Asn Tyr Leu Phe Gln Ser Phe Met Asp Glu Gln Leu Val Lys
                215                 220                 225

Gly Gly Val Arg Leu Ala Ala Leu Leu Asn Asn Ser Leu Glu
            230                 235                 240


<210> SEQ ID NO 30
<211> LENGTH: 240
<212> TYPE: PRT
<213> ORGANISM: Unknown
```

```
<220> FEATURE:
<223> OTHER INFORMATION: Microbial enrichment

<400> SEQUENCE: 30

Trp Gly Leu Thr Gly His Arg Val Ile Gly Glu Ile Ala Glu Asn His
1               5                   10                  15

Leu Ser Arg Lys Ala Lys Lys Glu Leu Lys Lys Leu Ile Gly Arg Gln
            20                  25                  30

Thr Leu Ala Trp Trp Ser Asn Trp Pro Asp Phe Ile Lys Ser Asp Thr
        35                  40                  45

Thr Trp Asn His Ala Ser Pro Trp His Tyr Val Asn Val Gln Pro His
    50                  55                  60

Leu Ser Lys Glu Glu Phe Val Glu Ala Leu Lys Lys Leu Pro Gly Lys
65                  70                  75                  80

Asn Leu Tyr Thr Gln Ile Gln Glu Thr Met Ser Gln Leu Lys Asp Arg
                85                  90                  95

Gln Leu Ser Leu Glu Gln Arg Gln Ile Ala Leu Arg Phe Leu Val His
            100                 105                 110

Leu Val Gly Asp Leu His Gln Pro Leu His Val Gly His Ala Asp Asp
        115                 120                 125

Gln Gly Gly Asn Lys Ile Val Val Tyr Trp Phe Asp Arg Lys Thr Asn
    130                 135                 140

Leu His Ser Val Trp Asp Thr Trp Leu Ile Asp Glu Gln Lys Tyr Ser
145                 150                 155                 160

Tyr Ser Glu Tyr Ala Arg Leu Leu Asp Ile Thr Pro Lys Glu Gln Val
                165                 170                 175

Glu Ala Trp Gln Ser Ser Ser Leu Glu Asp Trp Phe Tyr Glu Ser Tyr
            180                 185                 190

Gln Leu Ala Glu Lys Ile Tyr Ala Ser Val Gln Pro Glu Asp Lys Leu
        195                 200                 205

Ser Tyr Arg Tyr Asn Tyr Leu Phe Gln Ser Phe Met Asp Glu Gln Leu
    210                 215                 220

Val Lys Gly Gly Val Arg Leu Ala Ala Leu Leu Asn Asn Ser Leu Glu
225                 230                 235                 240


<210> SEQ ID NO 31
<211> LENGTH: 861
<212> TYPE: DNA
<213> ORGANISM: Lysobacter enzymogenes
<220> FEATURE:
<221> NAME/KEY: CDS
<222> LOCATION: (1)..(858)
<220> FEATURE:
<221> NAME/KEY: sig_peptide
<222> LOCATION: (1)..(102)
<220> FEATURE:
<221> NAME/KEY: mat_peptide
<222> LOCATION: (103)..(858)

<400> SEQUENCE: 31

atg atc gaa ccg cgc acc cgc ccc cgc ttc gcc cgc cgc ctg ctc gac       48
Met Ile Glu Pro Arg Thr Arg Pro Arg Phe Ala Arg Arg Leu Leu Asp
                -30                 -25                 -20

gcc gcc gtc gtg ctc gcc gtc gtg tcc gcc gcc ctg ccg ctg ccg gcc       96
Ala Ala Val Val Leu Ala Val Val Ser Ala Ala Leu Pro Leu Pro Ala
            -15                 -10                 -5

ctg gcc tgg ggc cgc caa ggc cat cga ctg gtc gcc gag ctg gcc tgg      144
Leu Ala Trp Gly Arg Gln Gly His Arg Leu Val Ala Glu Leu Ala Trp
    -1  1               5                   10
```

```
gac gaa atg tcc cca gcc gcg cgc gcc gaa gcg caa aag ctg ctc gcc      192
Asp Glu Met Ser Pro Ala Ala Arg Ala Glu Ala Gln Lys Leu Leu Ala
15                  20                  25                  30

ggc gaa ccc gac ccg acc ctg ccc ggc atc gcc aac tgg gcc gac ctg      240
Gly Glu Pro Asp Pro Thr Leu Pro Gly Ile Ala Asn Trp Ala Asp Leu
                35                  40                  45

ctg cgc gac gag aag ccg gaa ctg ggc aag cgc agc gcc aag tgg cat      288
Leu Arg Asp Glu Lys Pro Glu Leu Gly Lys Arg Ser Ala Lys Trp His
            50                  55                  60

tac atc gac ctg ccc gaa gac ggc gac tgc cag tac gac gcc gcc cgc      336
Tyr Ile Asp Leu Pro Glu Asp Gly Asp Cys Gln Tyr Asp Ala Ala Arg
        65                  70                  75

gat tgc ccc gac ggc aac tgt gcg gtc gcc gcg atc ctc gcc cag acc      384
Asp Cys Pro Asp Gly Asn Cys Ala Val Ala Ala Ile Leu Ala Gln Thr
    80                  85                  90

gcg atc ctg gcc gac cgc agc aag ccc aag gcc gaa cgc ctg gag gcg      432
Ala Ile Leu Ala Asp Arg Ser Lys Pro Lys Ala Glu Arg Leu Glu Ala
95                  100                 105                 110

ctg aaa ttc gtc gtc cac ctg gtc ggc gac gtg cac cag ccg ctg cac      480
Leu Lys Phe Val Val His Leu Val Gly Asp Val His Gln Pro Leu His
                115                 120                 125

gtc ggc tac gcc cgc gac aag ggc ggc aat agc ttc cag ctc gcc atc      528
Val Gly Tyr Ala Arg Asp Lys Gly Gly Asn Ser Phe Gln Leu Ala Ile
            130                 135                 140

ccc ggc gag cgt ccc ggc ggc tac ggc ggc aac ctg cat tcg ctg tgg      576
Pro Gly Glu Arg Pro Gly Gly Tyr Gly Gly Asn Leu His Ser Leu Trp
        145                 150                 155

gac agc ggc atg ccc aac atg agc aag ctc gat gac gat aag tac ctg      624
Asp Ser Gly Met Pro Asn Met Ser Lys Leu Asp Asp Asp Lys Tyr Leu
    160                 165                 170

gcc aaa ctc aag gac atc cag gtg ccc gcg gtc agc gcc ctg gcg ctg      672
Ala Lys Leu Lys Asp Ile Gln Val Pro Ala Val Ser Ala Leu Ala Leu
175                 180                 185                 190

ccg ccg ccg gcc gcc gac tgg gcc gag gaa tcg tgc aaa ctg atg cgg      720
Pro Pro Pro Ala Ala Asp Trp Ala Glu Glu Ser Cys Lys Leu Met Arg
                195                 200                 205

caa ccg ggt ttc tac ccg ccc acg cac aag ctg gcc ccc gac tac gtc      768
Gln Pro Gly Phe Tyr Pro Pro Thr His Lys Leu Ala Pro Asp Tyr Val
            210                 215                 220

gcc acc tgg cgg ccg ctg gcc gaa acc caa ctg cgc ctg ggc ggc gaa      816
Ala Thr Trp Arg Pro Leu Ala Glu Thr Gln Leu Arg Leu Gly Gly Glu
        225                 230                 235

cac ctg gcc aag ctg ctc gac gcc gcc ctg gcg ccg ggc cgc tga          861
His Leu Ala Lys Leu Leu Asp Ala Ala Leu Ala Pro Gly Arg
    240                 245                 250
```

<210> SEQ ID NO 32
<211> LENGTH: 286
<212> TYPE: PRT
<213> ORGANISM: Lysobacter enzymogenes

<400> SEQUENCE: 32

```
Met Ile Glu Pro Arg Thr Arg Pro Arg Phe Ala Arg Arg Leu Leu Asp
                -30                 -25                 -20

Ala Ala Val Val Leu Ala Val Val Ser Ala Ala Leu Pro Leu Pro Ala
            -15                 -10                 -5

Leu Ala Trp Gly Arg Gln Gly His Arg Leu Val Ala Glu Leu Ala Trp
    -1  1               5                   10

Asp Glu Met Ser Pro Ala Ala Arg Ala Glu Ala Gln Lys Leu Leu Ala
15                  20                  25                  30
```

```
Gly Glu Pro Asp Pro Thr Leu Pro Gly Ile Ala Asn Trp Ala Asp Leu
                35                  40                  45

Leu Arg Asp Glu Lys Pro Glu Leu Gly Lys Arg Ser Ala Lys Trp His
            50                  55                  60

Tyr Ile Asp Leu Pro Glu Asp Gly Asp Cys Gln Tyr Asp Ala Ala Arg
        65                  70                  75

Asp Cys Pro Asp Gly Asn Cys Ala Val Ala Ala Ile Leu Ala Gln Thr
    80                  85                  90

Ala Ile Leu Ala Asp Arg Ser Lys Pro Lys Ala Glu Arg Leu Glu Ala
95                  100                 105                 110

Leu Lys Phe Val Val His Leu Val Gly Asp Val His Gln Pro Leu His
                115                 120                 125

Val Gly Tyr Ala Arg Asp Lys Gly Gly Asn Ser Phe Gln Leu Ala Ile
            130                 135                 140

Pro Gly Glu Arg Pro Gly Gly Tyr Gly Gly Asn Leu His Ser Leu Trp
        145                 150                 155

Asp Ser Gly Met Pro Asn Met Ser Lys Leu Asp Asp Asp Lys Tyr Leu
    160                 165                 170

Ala Lys Leu Lys Asp Ile Gln Val Pro Ala Val Ser Ala Leu Ala Leu
175                 180                 185                 190

Pro Pro Pro Ala Ala Asp Trp Ala Glu Glu Ser Cys Lys Leu Met Arg
                195                 200                 205

Gln Pro Gly Phe Tyr Pro Pro Thr His Lys Leu Ala Pro Asp Tyr Val
            210                 215                 220

Ala Thr Trp Arg Pro Leu Ala Glu Thr Gln Leu Arg Leu Gly Gly Glu
        225                 230                 235

His Leu Ala Lys Leu Leu Asp Ala Ala Leu Ala Pro Gly Arg
    240                 245                 250
```

<210> SEQ ID NO 33
<211> LENGTH: 252
<212> TYPE: PRT
<213> ORGANISM: Lysobacter enzymogenes

<400> SEQUENCE: 33

```
Trp Gly Arg Gln Gly His Arg Leu Val Ala Glu Leu Ala Trp Asp Glu
1               5                   10                  15

Met Ser Pro Ala Ala Arg Ala Glu Ala Gln Lys Leu Leu Ala Gly Glu
            20                  25                  30

Pro Asp Pro Thr Leu Pro Gly Ile Ala Asn Trp Ala Asp Leu Leu Arg
        35                  40                  45

Asp Glu Lys Pro Glu Leu Gly Lys Arg Ser Ala Lys Trp His Tyr Ile
    50                  55                  60

Asp Leu Pro Glu Asp Gly Asp Cys Gln Tyr Asp Ala Ala Arg Asp Cys
65                  70                  75                  80

Pro Asp Gly Asn Cys Ala Val Ala Ala Ile Leu Ala Gln Thr Ala Ile
                85                  90                  95

Leu Ala Asp Arg Ser Lys Pro Lys Ala Glu Arg Leu Glu Ala Leu Lys
            100                 105                 110

Phe Val Val His Leu Val Gly Asp Val His Gln Pro Leu His Val Gly
        115                 120                 125

Tyr Ala Arg Asp Lys Gly Gly Asn Ser Phe Gln Leu Ala Ile Pro Gly
    130                 135                 140

Glu Arg Pro Gly Gly Tyr Gly Gly Asn Leu His Ser Leu Trp Asp Ser
```

```
145                 150                 155                 160

Gly Met Pro Asn Met Ser Lys Leu Asp Asp Asp Lys Tyr Leu Ala Lys
                165                 170                 175

Leu Lys Asp Ile Gln Val Pro Ala Val Ser Ala Leu Ala Leu Pro Pro
            180                 185                 190

Pro Ala Ala Asp Trp Ala Glu Glu Ser Cys Lys Leu Met Arg Gln Pro
        195                 200                 205

Gly Phe Tyr Pro Pro Thr His Lys Leu Ala Pro Asp Tyr Val Ala Thr
    210                 215                 220

Trp Arg Pro Leu Ala Glu Thr Gln Leu Arg Leu Gly Gly Glu His Leu
225                 230                 235                 240

Ala Lys Leu Leu Asp Ala Ala Leu Ala Pro Gly Arg
                245                 250


<210> SEQ ID NO 34
<211> LENGTH: 855
<212> TYPE: DNA
<213> ORGANISM: Pseudoalteromonas nigrifaciens
<220> FEATURE:
<221> NAME/KEY: CDS
<222> LOCATION: (1)..(852)
<220> FEATURE:
<221> NAME/KEY: sig_peptide
<222> LOCATION: (1)..(78)
<220> FEATURE:
<221> NAME/KEY: mat_peptide
<222> LOCATION: (79)..(852)

<400> SEQUENCE: 34

atg tac aaa aat gta aaa tat tcg ctt tct tta aca ctt tta att agt       48
Met Tyr Lys Asn Val Lys Tyr Ser Leu Ser Leu Thr Leu Leu Ile Ser
    -25                 -20                 -15

gca ata ttt gca agc aca gat tgt aat gct tgg ggc caa aac ggg cat       96
Ala Ile Phe Ala Ser Thr Asp Cys Asn Ala Trp Gly Gln Asn Gly His
-10                 -5              -1  1               5

cgt gta gtg ggt aaa att gca gag tcg cac ata agc gaa act act aag      144
Arg Val Val Gly Lys Ile Ala Glu Ser His Ile Ser Glu Thr Thr Lys
            10                  15                  20

act gca ctt atc ccc tat ctc aac ggc gaa tct tta gct cag att tca      192
Thr Ala Leu Ile Pro Tyr Leu Asn Gly Glu Ser Leu Ala Gln Ile Ser
        25                  30                  35

aca tgg cct gac gaa atg cga tct gca cca ggt gac ttt tgg caa aaa      240
Thr Trp Pro Asp Glu Met Arg Ser Ala Pro Gly Asp Phe Trp Gln Lys
    40                  45                  50

aaa tca tct cgt tgg cat tac att aat gct gat gac aac gcg acc ttt      288
Lys Ser Ser Arg Trp His Tyr Ile Asn Ala Asp Asp Asn Ala Thr Phe
55                  60                  65                  70

agt ttt gac cac gac cac act aaa cac aaa gaa tca gta aca aac ata      336
Ser Phe Asp His Asp His Thr Lys His Lys Glu Ser Val Thr Asn Ile
                75                  80                  85

tta gaa ggc att cac tac tct atc cgc gtg ttg aaa gat gat aaa tca      384
Leu Glu Gly Ile His Tyr Ser Ile Arg Val Leu Lys Asp Asp Lys Ser
            90                  95                  100

agc ctt gcg gcc aaa cag ttt agc ttg cgt ttt ttg gtg cat tta gtg      432
Ser Leu Ala Ala Lys Gln Phe Ser Leu Arg Phe Leu Val His Leu Val
        105                 110                 115

ggt gac agc cat caa cca ttt cat gca gga aga gca gaa gat aga ggc      480
Gly Asp Ser His Gln Pro Phe His Ala Gly Arg Ala Glu Asp Arg Gly
    120                 125                 130

ggc aat cgc gtt aag gtt tct ttt ttt aac caa caa acc aat ctt cat      528
Gly Asn Arg Val Lys Val Ser Phe Phe Asn Gln Gln Thr Asn Leu His
```

```
135                 140                 145                 150

agc tta tgg gat acc aag tta gta gaa aac gaa aac tta tct ttt act      576
Ser Leu Trp Asp Thr Lys Leu Val Glu Asn Glu Asn Leu Ser Phe Thr
                155                 160                 165

gaa tac gct cag ttt ata aat acc aac aac agc gag cta att agt gaa      624
Glu Tyr Ala Gln Phe Ile Asn Thr Asn Asn Ser Glu Leu Ile Ser Glu
            170                 175                 180

tat tta caa agt aca cca aca agc tgg ctt gaa gag tcg cac aac tta      672
Tyr Leu Gln Ser Thr Pro Thr Ser Trp Leu Glu Glu Ser His Asn Leu
        185                 190                 195

gcc cta aaa ata tat gaa tca aca gaa gaa cag att agc tac gac tat      720
Ala Leu Lys Ile Tyr Glu Ser Thr Glu Glu Gln Ile Ser Tyr Asp Tyr
    200                 205                 210

atc tac aac aac acc cct att gtg aaa aca cgc ttg caa caa gcg gga      768
Ile Tyr Asn Asn Thr Pro Ile Val Lys Thr Arg Leu Gln Gln Ala Gly
215                 220                 225                 230

att cgc ttg gct gga ttg tta aat aca tta ttt gat cct gct aac acg      816
Ile Arg Leu Ala Gly Leu Leu Asn Thr Leu Phe Asp Pro Ala Asn Thr
                235                 240                 245

caa tca aaa atg gcc tta aca cag caa aca caa aaa taa                  855
Gln Ser Lys Met Ala Leu Thr Gln Gln Thr Gln Lys
            250                 255


<210> SEQ ID NO 35
<211> LENGTH: 284
<212> TYPE: PRT
<213> ORGANISM: Pseudoalteromonas nigrifaciens

<400> SEQUENCE: 35

Met Tyr Lys Asn Val Lys Tyr Ser Leu Ser Leu Thr Leu Leu Ile Ser
    -25                 -20                 -15

Ala Ile Phe Ala Ser Thr Asp Cys Asn Ala Trp Gly Gln Asn Gly His
-10                 -5                  -1  1               5

Arg Val Val Gly Lys Ile Ala Glu Ser His Ile Ser Glu Thr Thr Lys
            10                  15                  20

Thr Ala Leu Ile Pro Tyr Leu Asn Gly Glu Ser Leu Ala Gln Ile Ser
        25                  30                  35

Thr Trp Pro Asp Glu Met Arg Ser Ala Pro Gly Asp Phe Trp Gln Lys
    40                  45                  50

Lys Ser Ser Arg Trp His Tyr Ile Asn Ala Asp Asp Asn Ala Thr Phe
55                  60                  65                  70

Ser Phe Asp His Asp His Thr Lys His Lys Glu Ser Val Thr Asn Ile
                75                  80                  85

Leu Glu Gly Ile His Tyr Ser Ile Arg Val Leu Lys Asp Asp Lys Ser
            90                  95                  100

Ser Leu Ala Ala Lys Gln Phe Ser Leu Arg Phe Leu Val His Leu Val
        105                 110                 115

Gly Asp Ser His Gln Pro Phe His Ala Gly Arg Ala Glu Asp Arg Gly
    120                 125                 130

Gly Asn Arg Val Lys Val Ser Phe Phe Asn Gln Gln Thr Asn Leu His
135                 140                 145                 150

Ser Leu Trp Asp Thr Lys Leu Val Glu Asn Glu Asn Leu Ser Phe Thr
                155                 160                 165

Glu Tyr Ala Gln Phe Ile Asn Thr Asn Asn Ser Glu Leu Ile Ser Glu
            170                 175                 180

Tyr Leu Gln Ser Thr Pro Thr Ser Trp Leu Glu Glu Ser His Asn Leu
        185                 190                 195
```

```
Ala Leu Lys Ile Tyr Glu Ser Thr Glu Glu Gln Ile Ser Tyr Asp Tyr
    200                 205                 210

Ile Tyr Asn Asn Thr Pro Ile Val Lys Thr Arg Leu Gln Gln Ala Gly
215                 220                 225                 230

Ile Arg Leu Ala Gly Leu Leu Asn Thr Leu Phe Asp Pro Ala Asn Thr
                235                 240                 245

Gln Ser Lys Met Ala Leu Thr Gln Gln Thr Gln Lys
            250                 255


<210> SEQ ID NO 36
<211> LENGTH: 258
<212> TYPE: PRT
<213> ORGANISM: Pseudoalteromonas nigrifaciens

<400> SEQUENCE: 36

Trp Gly Gln Asn Gly His Arg Val Val Gly Lys Ile Ala Glu Ser His
1               5                   10                  15

Ile Ser Glu Thr Thr Lys Thr Ala Leu Ile Pro Tyr Leu Asn Gly Glu
            20                  25                  30

Ser Leu Ala Gln Ile Ser Thr Trp Pro Asp Glu Met Arg Ser Ala Pro
        35                  40                  45

Gly Asp Phe Trp Gln Lys Lys Ser Ser Arg Trp His Tyr Ile Asn Ala
    50                  55                  60

Asp Asp Asn Ala Thr Phe Ser Phe Asp His Asp His Thr Lys His Lys
65                  70                  75                  80

Glu Ser Val Thr Asn Ile Leu Glu Gly Ile His Tyr Ser Ile Arg Val
                85                  90                  95

Leu Lys Asp Asp Lys Ser Ser Leu Ala Ala Lys Gln Phe Ser Leu Arg
            100                 105                 110

Phe Leu Val His Leu Val Gly Asp Ser His Gln Pro Phe His Ala Gly
        115                 120                 125

Arg Ala Glu Asp Arg Gly Gly Asn Arg Val Lys Val Ser Phe Phe Asn
    130                 135                 140

Gln Gln Thr Asn Leu His Ser Leu Trp Asp Thr Lys Leu Val Glu Asn
145                 150                 155                 160

Glu Asn Leu Ser Phe Thr Glu Tyr Ala Gln Phe Ile Asn Thr Asn Asn
                165                 170                 175

Ser Glu Leu Ile Ser Glu Tyr Leu Gln Ser Thr Pro Thr Ser Trp Leu
            180                 185                 190

Glu Glu Ser His Asn Leu Ala Leu Lys Ile Tyr Glu Ser Thr Glu Glu
        195                 200                 205

Gln Ile Ser Tyr Asp Tyr Ile Tyr Asn Asn Thr Pro Ile Val Lys Thr
    210                 215                 220

Arg Leu Gln Gln Ala Gly Ile Arg Leu Ala Gly Leu Leu Asn Thr Leu
225                 230                 235                 240

Phe Asp Pro Ala Asn Thr Gln Ser Lys Met Ala Leu Thr Gln Gln Thr
                245                 250                 255

Gln Lys


<210> SEQ ID NO 37
<211> LENGTH: 825
<212> TYPE: DNA
<213> ORGANISM: Vibrio sp-63684
<220> FEATURE:
<221> NAME/KEY: CDS
<222> LOCATION: (1)..(822)
```

```
<220> FEATURE:
<221> NAME/KEY: sig_peptide
<222> LOCATION: (1)..(69)
<220> FEATURE:
<221> NAME/KEY: mat_peptide
<222> LOCATION: (70)..(822)

<400> SEQUENCE: 37

atg gca gcc atg aac aga atc ctg ctg ctc gcc gcc ctg ctg ttg ctg      48
Met Ala Ala Met Asn Arg Ile Leu Leu Leu Ala Ala Leu Leu Leu Leu
            -20                 -15                 -10

atc gcc gcc ccc gcc cac gcc tgg ggc ccg cgc ggc cac cgc ctg gtg      96
Ile Ala Ala Pro Ala His Ala Trp Gly Pro Arg Gly His Arg Leu Val
        -5              -1  1               5

gga cat gtc gcc gaa tcc gaa ctc acg ccc gcc gcc cgc atc cag gtc     144
Gly His Val Ala Glu Ser Glu Leu Thr Pro Ala Ala Arg Ile Gln Val
10                  15                  20                  25

gat gcg ctg ctg gcc ggg gtg gaa gat ccg cat gac cgc tcg ctg gcg     192
Asp Ala Leu Leu Ala Gly Val Glu Asp Pro His Asp Arg Ser Leu Ala
                30                  35                  40

ggc att gcc acc tgg gct gac gag ctt cgc ggc tcc gac ccg gag ctg     240
Gly Ile Ala Thr Trp Ala Asp Glu Leu Arg Gly Ser Asp Pro Glu Leu
            45                  50                  55

ggc cgg aaa agc gcg cgc tgg cac ttc gtg aac atc ggc gag aac ggc     288
Gly Arg Lys Ser Ala Arg Trp His Phe Val Asn Ile Gly Glu Asn Gly
        60                  65                  70

tgc cgc tac cag cgc gag cgc gac tgc ccg gac ggc gcc aac tgc gtg     336
Cys Arg Tyr Gln Arg Glu Arg Asp Cys Pro Asp Gly Ala Asn Cys Val
    75                  80                  85

gtc gag gcg atc aac gac cag gcc gcg atc ctc ggt gac cgc acg cgc     384
Val Glu Ala Ile Asn Asp Gln Ala Ala Ile Leu Gly Asp Arg Thr Arg
90                  95                  100                 105

agc gag gcc gaa cgg ctg cag gcg ctg aag ttc gtg gtc cac ttc gtc     432
Ser Glu Ala Glu Arg Leu Gln Ala Leu Lys Phe Val Val His Phe Val
                110                 115                 120

ggc gac gta cac cag ccg atg cac gcc ggc tac gcc cac gac cgc ggc     480
Gly Asp Val His Gln Pro Met His Ala Gly Tyr Ala His Asp Arg Gly
            125                 130                 135

ggc aac aca ttc cag gtc aac ctg cgc gat ggc acc cgc gac ggg cgc     528
Gly Asn Thr Phe Gln Val Asn Leu Arg Asp Gly Thr Arg Asp Gly Arg
        140                 145                 150

ggc acc aac ctg cac gcg ctg tgg gac agc ggc ctg ttc tac ggt ctt     576
Gly Thr Asn Leu His Ala Leu Trp Asp Ser Gly Leu Phe Tyr Gly Leu
    155                 160                 165

cgc gag tcg gaa gag cgg cat ctg gcc gcc ttg cgc gag ctg ccg gac     624
Arg Glu Ser Glu Glu Arg His Leu Ala Ala Leu Arg Glu Leu Pro Asp
170                 175                 180                 185

gac gcg ccg gct ggc ggc agc ccg gcc acc tgg gcc gaa gag tcc tgc     672
Asp Ala Pro Ala Gly Gly Ser Pro Ala Thr Trp Ala Glu Glu Ser Cys
                190                 195                 200

gcc gtg gcg ctg cag gac ggc gta tat ccg cca cac gcc gtc atc gga     720
Ala Val Ala Leu Gln Asp Gly Val Tyr Pro Pro His Ala Val Ile Gly
            205                 210                 215

cag gac tac gtg gac cag tgg cgg ccg gtc gcc gag cag cgc atc gtt     768
Gln Asp Tyr Val Asp Gln Trp Arg Pro Val Ala Glu Gln Arg Ile Val
        220                 225                 230

gcc ggt ggc aag cgc ctg gcg cgg ctg ctc aac cag ata ctc gac ccc     816
Ala Gly Gly Lys Arg Leu Ala Arg Leu Leu Asn Gln Ile Leu Asp Pro
    235                 240                 245

gtc cgc tga                                                         825
Val Arg
```

250

<210> SEQ ID NO 38
<211> LENGTH: 274
<212> TYPE: PRT
<213> ORGANISM: Vibrio sp-63684

<400> SEQUENCE: 38

```
Met Ala Ala Met Asn Arg Ile Leu Leu Leu Ala Ala Leu Leu Leu Leu
            -20                 -15                 -10

Ile Ala Ala Pro Ala His Ala Trp Gly Pro Arg Gly His Arg Leu Val
        -5              -1  1               5

Gly His Val Ala Glu Ser Glu Leu Thr Pro Ala Ala Arg Ile Gln Val
10                  15                  20                  25

Asp Ala Leu Leu Ala Gly Val Glu Asp Pro His Asp Arg Ser Leu Ala
                30                  35                  40

Gly Ile Ala Thr Trp Ala Asp Glu Leu Arg Gly Ser Asp Pro Glu Leu
            45                  50                  55

Gly Arg Lys Ser Ala Arg Trp His Phe Val Asn Ile Gly Glu Asn Gly
        60                  65                  70

Cys Arg Tyr Gln Arg Glu Arg Asp Cys Pro Asp Gly Ala Asn Cys Val
    75                  80                  85

Val Glu Ala Ile Asn Asp Gln Ala Ala Ile Leu Gly Asp Arg Thr Arg
90                  95                  100                 105

Ser Glu Ala Glu Arg Leu Gln Ala Leu Lys Phe Val Val His Phe Val
                110                 115                 120

Gly Asp Val His Gln Pro Met His Ala Gly Tyr Ala His Asp Arg Gly
            125                 130                 135

Gly Asn Thr Phe Gln Val Asn Leu Arg Asp Gly Thr Arg Asp Gly Arg
        140                 145                 150

Gly Thr Asn Leu His Ala Leu Trp Asp Ser Gly Leu Phe Tyr Gly Leu
    155                 160                 165

Arg Glu Ser Glu Glu Arg His Leu Ala Ala Leu Arg Glu Leu Pro Asp
170                 175                 180                 185

Asp Ala Pro Ala Gly Gly Ser Pro Ala Thr Trp Ala Glu Glu Ser Cys
                190                 195                 200

Ala Val Ala Leu Gln Asp Gly Val Tyr Pro Pro His Ala Val Ile Gly
            205                 210                 215

Gln Asp Tyr Val Asp Gln Trp Arg Pro Val Ala Glu Gln Arg Ile Val
        220                 225                 230

Ala Gly Gly Lys Arg Leu Ala Arg Leu Leu Asn Gln Ile Leu Asp Pro
    235                 240                 245

Val Arg
250
```

<210> SEQ ID NO 39
<211> LENGTH: 251
<212> TYPE: PRT
<213> ORGANISM: Vibrio sp-63684

<400> SEQUENCE: 39

```
Trp Gly Pro Arg Gly His Arg Leu Val Gly His Val Ala Glu Ser Glu
1               5                   10                  15

Leu Thr Pro Ala Ala Arg Ile Gln Val Asp Ala Leu Leu Ala Gly Val
            20                  25                  30

Glu Asp Pro His Asp Arg Ser Leu Ala Gly Ile Ala Thr Trp Ala Asp
```

```
        35                  40                  45

Glu Leu Arg Gly Ser Asp Pro Glu Leu Gly Arg Lys Ser Ala Arg Trp
    50                  55                  60

His Phe Val Asn Ile Gly Glu Asn Gly Cys Arg Tyr Gln Arg Glu Arg
65                  70                  75                  80

Asp Cys Pro Asp Gly Ala Asn Cys Val Val Glu Ala Ile Asn Asp Gln
                85                  90                  95

Ala Ala Ile Leu Gly Asp Arg Thr Arg Ser Glu Ala Glu Arg Leu Gln
            100                 105                 110

Ala Leu Lys Phe Val Val His Phe Val Gly Asp Val His Gln Pro Met
        115                 120                 125

His Ala Gly Tyr Ala His Asp Arg Gly Gly Asn Thr Phe Gln Val Asn
    130                 135                 140

Leu Arg Asp Gly Thr Arg Asp Gly Arg Gly Thr Asn Leu His Ala Leu
145                 150                 155                 160

Trp Asp Ser Gly Leu Phe Tyr Gly Leu Arg Glu Ser Glu Glu Arg His
                165                 170                 175

Leu Ala Ala Leu Arg Glu Leu Pro Asp Asp Ala Pro Ala Gly Gly Ser
            180                 185                 190

Pro Ala Thr Trp Ala Glu Glu Ser Cys Ala Val Ala Leu Gln Asp Gly
        195                 200                 205

Val Tyr Pro Pro His Ala Val Ile Gly Gln Asp Tyr Val Asp Gln Trp
    210                 215                 220

Arg Pro Val Ala Glu Gln Arg Ile Val Ala Gly Gly Lys Arg Leu Ala
225                 230                 235                 240

Arg Leu Leu Asn Gln Ile Leu Asp Pro Val Arg
                245                 250


<210> SEQ ID NO 40
<211> LENGTH: 1038
<212> TYPE: DNA
<213> ORGANISM: Janthinobacterium agaricidamnosum
<220> FEATURE:
<221> NAME/KEY: CDS
<222> LOCATION: (1)..(1035)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1035)

<400> SEQUENCE: 40

atg aag aag ctc gta tgt att ctg gcg ttg agc agc gcc ttt gtt tcg       48
Met Lys Lys Leu Val Cys Ile Leu Ala Leu Ser Ser Ala Phe Val Ser
    -20                 -15                 -10

ttt aac gcc cac gca tgg ggc aac gat ggc cac cgc gcg gtg ggc gcg       96
Phe Asn Ala His Ala Trp Gly Asn Asp Gly His Arg Ala Val Gly Ala
-5                  -1  1               5                   10

atc gcc gat caa ctg atc aaa ggc agc aac gcc gaa cag cag gtg caa      144
Ile Ala Asp Gln Leu Ile Lys Gly Ser Asn Ala Glu Gln Gln Val Gln
            15                  20                  25

gcc ttg ctg ctg ccg ggc gaa agc ctg gcc ggc atc gcc tcg tgg gcg      192
Ala Leu Leu Leu Pro Gly Glu Ser Leu Ala Gly Ile Ala Ser Trp Ala
        30                  35                  40

gac tgc gtg aag ggc act tac tgc ggt ccg caa acg ccg gag atg gtg      240
Asp Cys Val Lys Gly Thr Tyr Cys Gly Pro Gln Thr Pro Glu Met Val
    45                  50                  55

gct tac acc acg gcc aat ccg aag cac agc gaa tat cac tac acc gat      288
```

```
Ala Tyr Thr Thr Ala Asn Pro Lys His Ser Glu Tyr His Tyr Thr Asp
60                  65                  70                  75

gtg ccg ttc cag ctg tcg cac tat gaa gac ggc ggc gtt ggc acc cac      336
Val Pro Phe Gln Leu Ser His Tyr Glu Asp Gly Gly Val Gly Thr His
                80                  85                  90

ggt cac gat atc gtg cag acg ctg aag cag tgc atc gcg gtg ctg caa      384
Gly His Asp Ile Val Gln Thr Leu Lys Gln Cys Ile Ala Val Leu Gln
            95                  100                 105

ggg aaa ggc gat gcg acc acc aat cca cac aac ttc acg ccg cgc cag      432
Gly Lys Gly Asp Ala Thr Thr Asn Pro His Asn Phe Thr Pro Arg Gln
        110                 115                 120

gct ttg ctg atg ctg acg cac ctg act ggc gac atc gcg cag ccg ctg      480
Ala Leu Leu Met Leu Thr His Leu Thr Gly Asp Ile Ala Gln Pro Leu
    125                 130                 135

cat gtg ggc gaa ggc tat gtc ggc aag agc ggc ggc ttt gtg ctg ccg      528
His Val Gly Glu Gly Tyr Val Gly Lys Ser Gly Gly Phe Val Leu Pro
140                 145                 150                 155

acg cag aag cag ttg gac aac aag gaa gcc ttc ccg tcc acc ggt ggc      576
Thr Gln Lys Gln Leu Asp Asn Lys Glu Ala Phe Pro Ser Thr Gly Gly
                160                 165                 170

aac aac ctg caa ctg gac gac gcc aag ttg acc act agc agc gcg cag      624
Asn Asn Leu Gln Leu Asp Asp Ala Lys Leu Thr Thr Ser Ser Ala Gln
            175                 180                 185

ctg att ccg gcc gat gac aaa ccg gcc aag ccg cag gcc acg cgc gcc      672
Leu Ile Pro Ala Asp Asp Lys Pro Ala Lys Pro Gln Ala Thr Arg Ala
        190                 195                 200

ttc cac tcg tac tgg gat acc acg gtg gtc aac tac gcc ttc cgc cgc      720
Phe His Ser Tyr Trp Asp Thr Thr Val Val Asn Tyr Ala Phe Arg Arg
    205                 210                 215

atc ggc gcg cgc acg ccg gag cag ttt gcg cag atg gtg att gct gat      768
Ile Gly Ala Arg Thr Pro Glu Gln Phe Ala Gln Met Val Ile Ala Asp
220                 225                 230                 235

ggt ccg gtg gtg gcg ccg agc agc ggc gac ccg gta acg tgg ccg tac      816
Gly Pro Val Val Ala Pro Ser Ser Gly Asp Pro Val Thr Trp Pro Tyr
                240                 245                 250

cag tgg gcc gac cag gcg ctg gtg gtg gcg aag ctc gcc tat acc gac      864
Gln Trp Ala Asp Gln Ala Leu Val Val Ala Lys Leu Ala Tyr Thr Asp
            255                 260                 265

gtg gtg ccc ggc ccg atg ggg cag cag acc agc aag agc agc ggt gag      912
Val Val Pro Gly Pro Met Gly Gln Gln Thr Ser Lys Ser Ser Gly Glu
        270                 275                 280

gtg tac aac gtg tgg ccg ctg gcg att ccg gac aac tat ccg gtg cca      960
Val Tyr Asn Val Trp Pro Leu Ala Ile Pro Asp Asn Tyr Pro Val Pro
    285                 290                 295

tcg tcg gct gcg gcc aag acg cag ctg atc cag ggc ggt tat cac ctg     1008
Ser Ser Ala Ala Ala Lys Thr Gln Leu Ile Gln Gly Gly Tyr His Leu
300                 305                 310                 315

gcg gcc gtg ctg aag gcc atc tgg ccg taa                             1038
Ala Ala Val Leu Lys Ala Ile Trp Pro
                320


<210> SEQ ID NO 41
<211> LENGTH: 345
<212> TYPE: PRT
<213> ORGANISM: Janthinobacterium agaricidamnosum

<400> SEQUENCE: 41

Met Lys Lys Leu Val Cys Ile Leu Ala Leu Ser Ser Ala Phe Val Ser
    -20                 -15                 -10

Phe Asn Ala His Ala Trp Gly Asn Asp Gly His Arg Ala Val Gly Ala
```

-continued

```
-5              -1  1               5                   10

Ile Ala Asp Gln Leu Ile Lys Gly Ser Asn Ala Glu Gln Gln Val Gln
            15                  20                  25

Ala Leu Leu Leu Pro Gly Glu Ser Leu Ala Gly Ile Ala Ser Trp Ala
        30                  35                  40

Asp Cys Val Lys Gly Thr Tyr Cys Gly Pro Gln Thr Pro Glu Met Val
    45                  50                  55

Ala Tyr Thr Thr Ala Asn Pro Lys His Ser Glu Tyr His Tyr Thr Asp
60                  65                  70                  75

Val Pro Phe Gln Leu Ser His Tyr Glu Asp Gly Gly Val Gly Thr His
                80                  85                  90

Gly His Asp Ile Val Gln Thr Leu Lys Gln Cys Ile Ala Val Leu Gln
            95                  100                 105

Gly Lys Gly Asp Ala Thr Thr Asn Pro His Asn Phe Thr Pro Arg Gln
        110                 115                 120

Ala Leu Leu Met Leu Thr His Leu Thr Gly Asp Ile Ala Gln Pro Leu
    125                 130                 135

His Val Gly Glu Gly Tyr Val Gly Lys Ser Gly Gly Phe Val Leu Pro
140                 145                 150                 155

Thr Gln Lys Gln Leu Asp Asn Lys Glu Ala Phe Pro Ser Thr Gly Gly
                160                 165                 170

Asn Asn Leu Gln Leu Asp Asp Ala Lys Leu Thr Thr Ser Ser Ala Gln
            175                 180                 185

Leu Ile Pro Ala Asp Asp Lys Pro Ala Lys Pro Gln Ala Thr Arg Ala
        190                 195                 200

Phe His Ser Tyr Trp Asp Thr Thr Val Val Asn Tyr Ala Phe Arg Arg
    205                 210                 215

Ile Gly Ala Arg Thr Pro Glu Gln Phe Ala Gln Met Val Ile Ala Asp
220                 225                 230                 235

Gly Pro Val Val Ala Pro Ser Ser Gly Asp Pro Val Thr Trp Pro Tyr
                240                 245                 250

Gln Trp Ala Asp Gln Ala Leu Val Val Ala Lys Leu Ala Tyr Thr Asp
            255                 260                 265

Val Val Pro Gly Pro Met Gly Gln Gln Thr Ser Lys Ser Ser Gly Glu
        270                 275                 280

Val Tyr Asn Val Trp Pro Leu Ala Ile Pro Asp Asn Tyr Pro Val Pro
    285                 290                 295

Ser Ser Ala Ala Ala Lys Thr Gln Leu Ile Gln Gly Gly Tyr His Leu
300                 305                 310                 315

Ala Ala Val Leu Lys Ala Ile Trp Pro
                320


<210> SEQ ID NO 42
<211> LENGTH: 324
<212> TYPE: PRT
<213> ORGANISM: Janthinobacterium agaricidamnosum

<400> SEQUENCE: 42

Trp Gly Asn Asp Gly His Arg Ala Val Gly Ala Ile Ala Asp Gln Leu
1               5                   10                  15

Ile Lys Gly Ser Asn Ala Glu Gln Gln Val Gln Ala Leu Leu Leu Pro
            20                  25                  30

Gly Glu Ser Leu Ala Gly Ile Ala Ser Trp Ala Asp Cys Val Lys Gly
        35                  40                  45
```

```
Thr Tyr Cys Gly Pro Gln Thr Pro Glu Met Val Ala Tyr Thr Thr Ala
    50                  55                  60

Asn Pro Lys His Ser Glu Tyr His Tyr Thr Asp Val Pro Phe Gln Leu
65                  70                  75                  80

Ser His Tyr Glu Asp Gly Gly Val Gly Thr His Gly His Asp Ile Val
                85                  90                  95

Gln Thr Leu Lys Gln Cys Ile Ala Val Leu Gln Gly Lys Gly Asp Ala
            100                 105                 110

Thr Thr Asn Pro His Asn Phe Thr Pro Arg Gln Ala Leu Leu Met Leu
        115                 120                 125

Thr His Leu Thr Gly Asp Ile Ala Gln Pro Leu His Val Gly Glu Gly
    130                 135                 140

Tyr Val Gly Lys Ser Gly Gly Phe Val Leu Pro Thr Gln Lys Gln Leu
145                 150                 155                 160

Asp Asn Lys Glu Ala Phe Pro Ser Thr Gly Gly Asn Asn Leu Gln Leu
                165                 170                 175

Asp Asp Ala Lys Leu Thr Thr Ser Ser Ala Gln Leu Ile Pro Ala Asp
            180                 185                 190

Asp Lys Pro Ala Lys Pro Gln Ala Thr Arg Ala Phe His Ser Tyr Trp
        195                 200                 205

Asp Thr Thr Val Val Asn Tyr Ala Phe Arg Arg Ile Gly Ala Arg Thr
    210                 215                 220

Pro Glu Gln Phe Ala Gln Met Val Ile Ala Asp Gly Pro Val Val Ala
225                 230                 235                 240

Pro Ser Ser Gly Asp Pro Val Thr Trp Pro Tyr Gln Trp Ala Asp Gln
                245                 250                 255

Ala Leu Val Val Ala Lys Leu Ala Tyr Thr Asp Val Val Pro Gly Pro
            260                 265                 270

Met Gly Gln Gln Thr Ser Lys Ser Ser Gly Glu Val Tyr Asn Val Trp
        275                 280                 285

Pro Leu Ala Ile Pro Asp Asn Tyr Pro Val Pro Ser Ser Ala Ala Ala
    290                 295                 300

Lys Thr Gln Leu Ile Gln Gly Gly Tyr His Leu Ala Ala Val Leu Lys
305                 310                 315                 320

Ala Ile Trp Pro


<210> SEQ ID NO 43
<211> LENGTH: 1062
<212> TYPE: DNA
<213> ORGANISM: Massilia aerilata
<220> FEATURE:
<221> NAME/KEY: CDS
<222> LOCATION: (1)..(1059)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1059)

<400> SEQUENCE: 43

atg aaa aaa ctc gct tgt gta atc gcc ctg gcc ggc gcc ttc atg gcg      48
Met Lys Lys Leu Ala Cys Val Ile Ala Leu Ala Gly Ala Phe Met Ala
    -20                 -15                 -10

cag gac gct ttc gcc tgg ggc cac gac ggc cat gcc gcc gtg ggc gcc      96
Gln Asp Ala Phe Ala Trp Gly His Asp Gly His Ala Ala Val Gly Ala
-5              -1  1               5                   10

atc gcc gac aaa ctg atc aag ggc acc gac gcc gag aag cag gtc aag     144
```

```
Ile Ala Asp Lys Leu Ile Lys Gly Thr Asp Ala Glu Lys Gln Val Lys
            15                  20                  25

gcc ctg ctg ctg ccg ggc gag tcg ctc gaa tcg atc gcc aac tgg ccg      192
Ala Leu Leu Leu Pro Gly Glu Ser Leu Glu Ser Ile Ala Asn Trp Pro
        30                  35                  40

gac tgc gtg aag ggc aat tac tgc ggt ccg cag acc cag gaa atg atc      240
Asp Cys Val Lys Gly Asn Tyr Cys Gly Pro Gln Thr Gln Glu Met Ile
    45                  50                  55

gat tac gtg aac gcc aac ccg ctg cac agc gaa tac cac tac acc gac      288
Asp Tyr Val Asn Ala Asn Pro Leu His Ser Glu Tyr His Tyr Thr Asp
60                  65                  70                  75

gtg ccg ttc cag ctc gag cac tac cat gac ggc gaa gtc ggc acc acc      336
Val Pro Phe Gln Leu Glu His Tyr His Asp Gly Glu Val Gly Thr Thr
                80                  85                  90

gac gtc gac atc gtg cag acg ctg aag gaa gcg atc gcc gtc ctg cag      384
Asp Val Asp Ile Val Gln Thr Leu Lys Glu Ala Ile Ala Val Leu Gln
            95                  100                 105

ggc aag gac acg cct cag acc aat ccg cat cac ttc acc aag cgc cag      432
Gly Lys Asp Thr Pro Gln Thr Asn Pro His His Phe Thr Lys Arg Gln
        110                 115                 120

gcc ctg atc ctg atc acc cat ctg gtg ggc gac atc cac cag ccg ctg      480
Ala Leu Ile Leu Ile Thr His Leu Val Gly Asp Ile His Gln Pro Leu
    125                 130                 135

cac gtg ggc gcg gcc tat gtc gac aag gac ggc aag ttc atc gtg ccg      528
His Val Gly Ala Ala Tyr Val Asp Lys Asp Gly Lys Phe Ile Val Pro
140                 145                 150                 155

aag acc aag gcc gag atc gac gag acc gtg gtc ttc gat tcg cgc ggc      576
Lys Thr Lys Ala Glu Ile Asp Glu Thr Val Val Phe Asp Ser Arg Gly
                160                 165                 170

ggc aac aac ttc ctg atg aac gac gag aag atc gaa cag ttc gcg gcc      624
Gly Asn Asn Phe Leu Met Asn Asp Glu Lys Ile Glu Gln Phe Ala Ala
            175                 180                 185

aag gcg gcc gac gtg atc ccg ccg gcc gag cag gcc gaa ggc aag ccg      672
Lys Ala Ala Asp Val Ile Pro Pro Ala Glu Gln Ala Glu Gly Lys Pro
        190                 195                 200

ggc gtg ccg aag gcg cta acc aag cct ttc cac tcg tac tgg gac acg      720
Gly Val Pro Lys Ala Leu Thr Lys Pro Phe His Ser Tyr Trp Asp Thr
    205                 210                 215

acc gtg gtc aac tac gcc ttc cgc cgc gtg cgc acc aag acc ccg gag      768
Thr Val Val Asn Tyr Ala Phe Arg Arg Val Arg Thr Lys Thr Pro Glu
220                 225                 230                 235

cag ttc gcg cag gtg acc atc gac agc cat ccg gac gtc gtc aag aac      816
Gln Phe Ala Gln Val Thr Ile Asp Ser His Pro Asp Val Val Lys Asn
                240                 245                 250

agc ggc gac ccg gtg acc tgg cct tac cag tgg gcc gac gac gcc ctg      864
Ser Gly Asp Pro Val Thr Trp Pro Tyr Gln Trp Ala Asp Asp Ala Leu
            255                 260                 265

gtc gtg gcc aag cag gcc ttc gac ggt gtc cac gtc ggc cag atc acc      912
Val Val Ala Lys Gln Ala Phe Asp Gly Val His Val Gly Gln Ile Thr
        270                 275                 280

aag cag acc agc aag aaa ggc gac acc tac tac acc tgg agc ctg gaa      960
Lys Gln Thr Ser Lys Lys Gly Asp Thr Tyr Tyr Thr Trp Ser Leu Glu
    285                 290                 295

gtg ccg cag aac tac ccg gtg ccg agc tcg gcg atc gcc aag gcg cag     1008
Val Pro Gln Asn Tyr Pro Val Pro Ser Ser Ala Ile Ala Lys Ala Gln
300                 305                 310                 315

ctg gcc aag ggt ggt tat cac ctg gcg gag gtg ctg gaa gcg atc tgg     1056
Leu Ala Lys Gly Gly Tyr His Leu Ala Glu Val Leu Glu Ala Ile Trp
                320                 325                 330
```

```
ccg taa                                                              1062
Pro


<210> SEQ ID NO 44
<211> LENGTH: 353
<212> TYPE: PRT
<213> ORGANISM: Massilia aerilata

<400> SEQUENCE: 44

Met Lys Lys Leu Ala Cys Val Ile Ala Leu Ala Gly Ala Phe Met Ala
    -20                 -15                 -10

Gln Asp Ala Phe Ala Trp Gly His Asp Gly His Ala Ala Val Gly Ala
-5              -1  1               5                   10

Ile Ala Asp Lys Leu Ile Lys Gly Thr Asp Ala Glu Lys Gln Val Lys
            15                  20                  25

Ala Leu Leu Leu Pro Gly Glu Ser Leu Glu Ser Ile Ala Asn Trp Pro
        30                  35                  40

Asp Cys Val Lys Gly Asn Tyr Cys Gly Pro Gln Thr Gln Glu Met Ile
    45                  50                  55

Asp Tyr Val Asn Ala Asn Pro Leu His Ser Glu Tyr His Tyr Thr Asp
60                  65                  70                  75

Val Pro Phe Gln Leu Glu His Tyr His Asp Gly Glu Val Gly Thr Thr
                80                  85                  90

Asp Val Asp Ile Val Gln Thr Leu Lys Glu Ala Ile Ala Val Leu Gln
            95                  100                 105

Gly Lys Asp Thr Pro Gln Thr Asn Pro His His Phe Thr Lys Arg Gln
        110                 115                 120

Ala Leu Ile Leu Ile Thr His Leu Val Gly Asp Ile His Gln Pro Leu
    125                 130                 135

His Val Gly Ala Ala Tyr Val Asp Lys Asp Gly Lys Phe Ile Val Pro
140                 145                 150                 155

Lys Thr Lys Ala Glu Ile Asp Glu Thr Val Val Phe Asp Ser Arg Gly
                160                 165                 170

Gly Asn Asn Phe Leu Met Asn Asp Glu Lys Ile Glu Gln Phe Ala Ala
            175                 180                 185

Lys Ala Ala Asp Val Ile Pro Pro Ala Glu Gln Ala Glu Gly Lys Pro
        190                 195                 200

Gly Val Pro Lys Ala Leu Thr Lys Pro Phe His Ser Tyr Trp Asp Thr
    205                 210                 215

Thr Val Val Asn Tyr Ala Phe Arg Arg Val Arg Thr Lys Thr Pro Glu
220                 225                 230                 235

Gln Phe Ala Gln Val Thr Ile Asp Ser His Pro Asp Val Val Lys Asn
                240                 245                 250

Ser Gly Asp Pro Val Thr Trp Pro Tyr Gln Trp Ala Asp Asp Ala Leu
            255                 260                 265

Val Val Ala Lys Gln Ala Phe Asp Gly Val His Val Gly Gln Ile Thr
        270                 275                 280

Lys Gln Thr Ser Lys Lys Gly Asp Thr Tyr Tyr Thr Trp Ser Leu Glu
    285                 290                 295

Val Pro Gln Asn Tyr Pro Val Pro Ser Ser Ala Ile Ala Lys Ala Gln
300                 305                 310                 315

Leu Ala Lys Gly Gly Tyr His Leu Ala Glu Val Leu Glu Ala Ile Trp
                320                 325                 330

Pro
```

```
<210> SEQ ID NO 45
<211> LENGTH: 332
<212> TYPE: PRT
<213> ORGANISM: Massilia aerilata

<400> SEQUENCE: 45

Trp Gly His Asp Gly His Ala Ala Val Gly Ala Ile Ala Asp Lys Leu
1               5                   10                  15

Ile Lys Gly Thr Asp Ala Glu Lys Gln Val Lys Ala Leu Leu Leu Pro
            20                  25                  30

Gly Glu Ser Leu Glu Ser Ile Ala Asn Trp Pro Asp Cys Val Lys Gly
        35                  40                  45

Asn Tyr Cys Gly Pro Gln Thr Gln Glu Met Ile Asp Tyr Val Asn Ala
    50                  55                  60

Asn Pro Leu His Ser Glu Tyr His Tyr Thr Asp Val Pro Phe Gln Leu
65                  70                  75                  80

Glu His Tyr His Asp Gly Glu Val Gly Thr Thr Asp Val Asp Ile Val
                85                  90                  95

Gln Thr Leu Lys Glu Ala Ile Ala Val Leu Gln Gly Lys Asp Thr Pro
            100                 105                 110

Gln Thr Asn Pro His His Phe Thr Lys Arg Gln Ala Leu Ile Leu Ile
        115                 120                 125

Thr His Leu Val Gly Asp Ile His Gln Pro Leu His Val Gly Ala Ala
    130                 135                 140

Tyr Val Asp Lys Asp Gly Lys Phe Ile Val Pro Lys Thr Lys Ala Glu
145                 150                 155                 160

Ile Asp Glu Thr Val Val Phe Asp Ser Arg Gly Gly Asn Asn Phe Leu
                165                 170                 175

Met Asn Asp Glu Lys Ile Glu Gln Phe Ala Ala Lys Ala Ala Asp Val
            180                 185                 190

Ile Pro Pro Ala Glu Gln Ala Glu Gly Lys Pro Gly Val Pro Lys Ala
        195                 200                 205

Leu Thr Lys Pro Phe His Ser Tyr Trp Asp Thr Thr Val Val Asn Tyr
    210                 215                 220

Ala Phe Arg Arg Val Arg Thr Lys Thr Pro Glu Gln Phe Ala Gln Val
225                 230                 235                 240

Thr Ile Asp Ser His Pro Asp Val Val Lys Asn Ser Gly Asp Pro Val
                245                 250                 255

Thr Trp Pro Tyr Gln Trp Ala Asp Asp Ala Leu Val Val Ala Lys Gln
            260                 265                 270

Ala Phe Asp Gly Val His Val Gly Gln Ile Thr Lys Gln Thr Ser Lys
        275                 280                 285

Lys Gly Asp Thr Tyr Tyr Thr Trp Ser Leu Glu Val Pro Gln Asn Tyr
    290                 295                 300

Pro Val Pro Ser Ser Ala Ile Ala Lys Ala Gln Leu Ala Lys Gly Gly
305                 310                 315                 320

Tyr His Leu Ala Glu Val Leu Glu Ala Ile Trp Pro
                325                 330


<210> SEQ ID NO 46
<211> LENGTH: 963
<212> TYPE: DNA
<213> ORGANISM: Aspergillus oryzae
<220> FEATURE:
<221> NAME/KEY: CDS
<222> LOCATION: (1)..(339)
```

```
<220> FEATURE:
<221> NAME/KEY: sig_peptide
<222> LOCATION: (1)..(60)
<220> FEATURE:
<221> NAME/KEY: mat_peptide
<222> LOCATION: (61)..(960)
<220> FEATURE:
<221> NAME/KEY: CDS
<222> LOCATION: (389)..(454)
<220> FEATURE:
<221> NAME/KEY: CDS
<222> LOCATION: (505)..(960)

<400> SEQUENCE: 46

atg ccg cgc tta ctc ccc att tcg gcg gct act ctg gcg ctg gcc caa       48
Met Pro Arg Leu Leu Pro Ile Ser Ala Ala Thr Leu Ala Leu Ala Gln
-20                 -15                 -10                 -5

ctc act tat ggt tgg ggc aac tta ggt cac gag acg gtt gcc tac att       96
Leu Thr Tyr Gly Trp Gly Asn Leu Gly His Glu Thr Val Ala Tyr Ile
            -1  1               5                   10

gcc cag agc ttc gtt gct tcg tca acc gaa tcc ttt tgt cag aat att      144
Ala Gln Ser Phe Val Ala Ser Ser Thr Glu Ser Phe Cys Gln Asn Ile
        15                  20                  25

ctg ggc gat gac tcc acc tcc tac ttg gcc aac gtc gcc aca tgg gcc      192
Leu Gly Asp Asp Ser Thr Ser Tyr Leu Ala Asn Val Ala Thr Trp Ala
    30                  35                  40

aat acg tac aag tac acc gac gcc gga gaa ttc tcc aag ccc tac cat      240
Asn Thr Tyr Lys Tyr Thr Asp Ala Gly Glu Phe Ser Lys Pro Tyr His
45                  50                  55                  60

ttt att gat gcg caa gac aac ccg ccg cag agc tgt gga gta gat tac      288
Phe Ile Asp Ala Gln Asp Asn Pro Pro Gln Ser Cys Gly Val Asp Tyr
                65                  70                  75

gat cgg gat tgt ggt agc gct ggg tgc agt atc agc gcg atc cag aac      336
Asp Arg Asp Cys Gly Ser Ala Gly Cys Ser Ile Ser Ala Ile Gln Asn
            80                  85                  90

tac gtgagttact ttagagttta taacgatata ggatgctcat cctacttag acc aat    394
Tyr                                                        Thr Asn
                                                                95

att ctc ttg gaa tct ccc aat ggc tcg gag gcg ttg aat gcc ctg aaa      442
Ile Leu Leu Glu Ser Pro Asn Gly Ser Glu Ala Leu Asn Ala Leu Lys
                100                 105                 110

ttc gtg gtt cat gttcgtcacg ttgcttgacc ggtttaatcc gatttcctaa          494
Phe Val Val His
            115

catgtcgcag atc atc gga gat att cac cag ccc tta cac gac gag aat      543
           Ile Ile Gly Asp Ile His Gln Pro Leu His Asp Glu Asn
                       120                 125

ctc gag gcc ggt ggt aac ggt att gat gtg acg tat gat gga gaa acc      591
Leu Glu Ala Gly Gly Asn Gly Ile Asp Val Thr Tyr Asp Gly Glu Thr
    130                 135                 140

acc aat ctc cat cat atc tgg gac acc aac atg ccc gag gaa gcc gca      639
Thr Asn Leu His His Ile Trp Asp Thr Asn Met Pro Glu Glu Ala Ala
145                 150                 155                 160

ggt ggc tac agt ctg tcg gtc gca aag acc tat gct gac ctt ctt act      687
Gly Gly Tyr Ser Leu Ser Val Ala Lys Thr Tyr Ala Asp Leu Leu Thr
                165                 170                 175

gag cgc atc aaa acc ggt acc tac tcg tct aag aag gac tca tgg aca      735
Glu Arg Ile Lys Thr Gly Thr Tyr Ser Ser Lys Lys Asp Ser Trp Thr
            180                 185                 190

gac gga att gat atc aaa gac cct gtg tcg acc tca atg atc tgg gcg      783
Asp Gly Ile Asp Ile Lys Asp Pro Val Ser Thr Ser Met Ile Trp Ala
        195                 200                 205
```

```
gcc gac gcc aat acc tac gtc tgc agt acg gtt ttg gat gac gga ctg      831
Ala Asp Ala Asn Thr Tyr Val Cys Ser Thr Val Leu Asp Asp Gly Leu
    210                 215                 220

gca tat att aac tcc aca gac ctg tct ggc gag tac tac gac aag tcc      879
Ala Tyr Ile Asn Ser Thr Asp Leu Ser Gly Glu Tyr Tyr Asp Lys Ser
225                 230                 235                 240

cag cca gtc ttt gag gaa ctc atc gcg aag gct ggg tat cgg ctg gcg      927
Gln Pro Val Phe Glu Glu Leu Ile Ala Lys Ala Gly Tyr Arg Leu Ala
                245                 250                 255

gct tgg ttg gat ctg att gcg agt cag ccc tct tga                      963
Ala Trp Leu Asp Leu Ile Ala Ser Gln Pro Ser
            260                 265


<210> SEQ ID NO 47
<211> LENGTH: 287
<212> TYPE: PRT
<213> ORGANISM: Aspergillus oryzae

<400> SEQUENCE: 47

Met Pro Arg Leu Leu Pro Ile Ser Ala Ala Thr Leu Ala Leu Ala Gln
-20                 -15                 -10                 -5

Leu Thr Tyr Gly Trp Gly Asn Leu Gly His Glu Thr Val Ala Tyr Ile
            -1  1               5                   10

Ala Gln Ser Phe Val Ala Ser Ser Thr Glu Ser Phe Cys Gln Asn Ile
        15                  20                  25

Leu Gly Asp Asp Ser Thr Ser Tyr Leu Ala Asn Val Ala Thr Trp Ala
    30                  35                  40

Asn Thr Tyr Lys Tyr Thr Asp Ala Gly Glu Phe Ser Lys Pro Tyr His
45                  50                  55                  60

Phe Ile Asp Ala Gln Asp Asn Pro Pro Gln Ser Cys Gly Val Asp Tyr
                65                  70                  75

Asp Arg Asp Cys Gly Ser Ala Gly Cys Ser Ile Ser Ala Ile Gln Asn
            80                  85                  90

Tyr Thr Asn Ile Leu Leu Glu Ser Pro Asn Gly Ser Glu Ala Leu Asn
        95                  100                 105

Ala Leu Lys Phe Val Val His Ile Ile Gly Asp Ile His Gln Pro Leu
    110                 115                 120

His Asp Glu Asn Leu Glu Ala Gly Gly Asn Gly Ile Asp Val Thr Tyr
125                 130                 135                 140

Asp Gly Glu Thr Thr Asn Leu His His Ile Trp Asp Thr Asn Met Pro
                145                 150                 155

Glu Glu Ala Ala Gly Gly Tyr Ser Leu Ser Val Ala Lys Thr Tyr Ala
            160                 165                 170

Asp Leu Leu Thr Glu Arg Ile Lys Thr Gly Thr Tyr Ser Ser Lys Lys
        175                 180                 185

Asp Ser Trp Thr Asp Gly Ile Asp Ile Lys Asp Pro Val Ser Thr Ser
    190                 195                 200

Met Ile Trp Ala Ala Asp Ala Asn Thr Tyr Val Cys Ser Thr Val Leu
205                 210                 215                 220

Asp Asp Gly Leu Ala Tyr Ile Asn Ser Thr Asp Leu Ser Gly Glu Tyr
                225                 230                 235

Tyr Asp Lys Ser Gln Pro Val Phe Glu Glu Leu Ile Ala Lys Ala Gly
            240                 245                 250

Tyr Arg Leu Ala Ala Trp Leu Asp Leu Ile Ala Ser Gln Pro Ser
        255                 260                 265
```

```
<210> SEQ ID NO 48
<211> LENGTH: 267
<212> TYPE: PRT
<213> ORGANISM: Aspergillus oryzae

<400> SEQUENCE: 48

Trp Gly Asn Leu Gly His Glu Thr Val Ala Tyr Ile Ala Gln Ser Phe
1               5                   10                  15

Val Ala Ser Ser Thr Glu Ser Phe Cys Gln Asn Ile Leu Gly Asp Asp
            20                  25                  30

Ser Thr Ser Tyr Leu Ala Asn Val Ala Thr Trp Ala Asn Thr Tyr Lys
        35                  40                  45

Tyr Thr Asp Ala Gly Glu Phe Ser Lys Pro Tyr His Phe Ile Asp Ala
    50                  55                  60

Gln Asp Asn Pro Pro Gln Ser Cys Gly Val Asp Tyr Asp Arg Asp Cys
65                  70                  75                  80

Gly Ser Ala Gly Cys Ser Ile Ser Ala Ile Gln Asn Tyr Thr Asn Ile
                85                  90                  95

Leu Leu Glu Ser Pro Asn Gly Ser Glu Ala Leu Asn Ala Leu Lys Phe
            100                 105                 110

Val Val His Ile Ile Gly Asp Ile His Gln Pro Leu His Asp Glu Asn
        115                 120                 125

Leu Glu Ala Gly Gly Asn Gly Ile Asp Val Thr Tyr Asp Gly Glu Thr
    130                 135                 140

Thr Asn Leu His His Ile Trp Asp Thr Asn Met Pro Glu Glu Ala Ala
145                 150                 155                 160

Gly Gly Tyr Ser Leu Ser Val Ala Lys Thr Tyr Ala Asp Leu Leu Thr
                165                 170                 175

Glu Arg Ile Lys Thr Gly Thr Tyr Ser Ser Lys Lys Asp Ser Trp Thr
            180                 185                 190

Asp Gly Ile Asp Ile Lys Asp Pro Val Ser Thr Ser Met Ile Trp Ala
        195                 200                 205

Ala Asp Ala Asn Thr Tyr Val Cys Ser Thr Val Leu Asp Asp Gly Leu
    210                 215                 220

Ala Tyr Ile Asn Ser Thr Asp Leu Ser Gly Glu Tyr Tyr Asp Lys Ser
225                 230                 235                 240

Gln Pro Val Phe Glu Glu Leu Ile Ala Lys Ala Gly Tyr Arg Leu Ala
                245                 250                 255

Ala Trp Leu Asp Leu Ile Ala Ser Gln Pro Ser
            260                 265


<210> SEQ ID NO 49
<211> LENGTH: 1102
<212> TYPE: DNA
<213> ORGANISM: Penicillium atramentosum
<220> FEATURE:
<221> NAME/KEY: CDS
<222> LOCATION: (1)..(128)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1099)
<220> FEATURE:
<221> NAME/KEY: CDS
<222> LOCATION: (199)..(1099)

<400> SEQUENCE: 49

atg gtg tct cta tct atc gct ctc gtg aca ctc ggg gtg gct cat ggg       48
```

```
Met Val Ser Leu Ser Ile Ala Leu Val Thr Leu Gly Val Ala His Gly
                -15                 -10                 -5

gca aat gca tgg ggt gta ttg ggc cat gcg gct gtt gcc tat gtc gca       96
Ala Asn Ala Trp Gly Val Leu Gly His Ala Ala Val Ala Tyr Val Ala
        -1  1               5                   10

caa agt tat gtt tgt cct gaa gcc gca tca tg  gtaagtgcct ccaaagagct    148
Gln Ser Tyr Val Cys Pro Glu Ala Ala Ser Trp
    15                  20

tgaactcagc aagagtatct ttctttcaat gctaaaacat tttttcaag g gca caa      205
                                                        Ala Gln
                                                        25

aaa gtt ctc aat gat tcc tct agc tca tac cta gca aac att gct tct      253
Lys Val Leu Asn Asp Ser Ser Ser Ser Tyr Leu Ala Asn Ile Ala Ser
            30                  35                  40

tgg gct gat cag tat cgc cta aca gat gct gga aaa tgg tca gcc cca      301
Trp Ala Asp Gln Tyr Arg Leu Thr Asp Ala Gly Lys Trp Ser Ala Pro
        45                  50                  55

ttg cat tac att gat gcc ttg gat gac ccc cca aaa agt tgc aac gtc      349
Leu His Tyr Ile Asp Ala Leu Asp Asp Pro Pro Lys Ser Cys Asn Val
    60                  65                  70

gac tac gag cgc gac tgt tct gat gaa ggc tgt tca atc tcc gcc att      397
Asp Tyr Glu Arg Asp Cys Ser Asp Glu Gly Cys Ser Ile Ser Ala Ile
75                  80                  85                  90

gcc aat tac act caa cgt gca ggc gac cgc cga ctt gac aat gtt cat      445
Ala Asn Tyr Thr Gln Arg Ala Gly Asp Arg Arg Leu Asp Asn Val His
                95                  100                 105

acc gca gaa gct ctc aga ttt ctg gtc cac ttt ctc ggc gat ctc acg      493
Thr Ala Glu Ala Leu Arg Phe Leu Val His Phe Leu Gly Asp Leu Thr
            110                 115                 120

cag cca ctg cat gat gag gcc tac gag att ggt ggc aat ggc atc aac      541
Gln Pro Leu His Asp Glu Ala Tyr Glu Ile Gly Gly Asn Gly Ile Asn
        125                 130                 135

gtc act ttt gac gga tat aat gac aac ctt cac gca gat tgg gat aca      589
Val Thr Phe Asp Gly Tyr Asn Asp Asn Leu His Ala Asp Trp Asp Thr
    140                 145                 150

tac atc ccc gtg aag ctg gtc ggc ggt agc tca ctc gcg gat gcg caa      637
Tyr Ile Pro Val Lys Leu Val Gly Gly Ser Ser Leu Ala Asp Ala Gln
155                 160                 165                 170

tca tgg gcc act agc ctg gtt aag gag atc acc tcc ggc agc ttc aaa      685
Ser Trp Ala Thr Ser Leu Val Lys Glu Ile Thr Ser Gly Ser Phe Lys
                175                 180                 185

tac aaa tct gcg aat tgg att aga ggc gac aat atc gat gat gtt atc      733
Tyr Lys Ser Ala Asn Trp Ile Arg Gly Asp Asn Ile Asp Asp Val Ile
            190                 195                 200

acc acg gcc acg aga tgg gcg aca gat gcc aac gcc tac atc tgt acc      781
Thr Thr Ala Thr Arg Trp Ala Thr Asp Ala Asn Ala Tyr Ile Cys Thr
        205                 210                 215

gtt gtt atg cca gat ggg gct gct gcc ttg caa act ggc gac ctc tat      829
Val Val Met Pro Asp Gly Ala Ala Ala Leu Gln Thr Gly Asp Leu Tyr
    220                 225                 230

cca act tac tac gag tct gcc atc ggc act atc gag ttg cag att gct      877
Pro Thr Tyr Tyr Glu Ser Ala Ile Gly Thr Ile Glu Leu Gln Ile Ala
235                 240                 245                 250

aaa gga ggc tac aga ctg ggc aac tgg atc aac ttg atc tat aga aat      925
Lys Gly Gly Tyr Arg Leu Gly Asn Trp Ile Asn Leu Ile Tyr Arg Asn
                255                 260                 265

aag atc gct aaa cat cgc ccc ggc aaa ccc gtt aaa gag cac cat gga      973
Lys Ile Ala Lys His Arg Pro Gly Lys Pro Val Lys Glu His His Gly
            270                 275                 280
```

```
cca ccc cct cac tca aac cat ggg gac gat att cgt cct cat cct cgt      1021
Pro Pro Pro His Ser Asn His Gly Asp Asp Ile Arg Pro His Pro Arg
        285                 290                 295

gga ccg agt cgc gca aat ttg gcc agg gcg gcc atg gga gga tcc tgc      1069
Gly Pro Ser Arg Ala Asn Leu Ala Arg Ala Ala Met Gly Gly Ser Cys
    300                 305                 310

tgt agc tct ggg gga cgt gaa cac gaa cac tga                          1102
Cys Ser Ser Gly Gly Arg Glu His Glu His
315                 320


<210> SEQ ID NO 50
<211> LENGTH: 343
<212> TYPE: PRT
<213> ORGANISM: Penicillium atramentosum

<400> SEQUENCE: 50

Met Val Ser Leu Ser Ile Ala Leu Val Thr Leu Gly Val Ala His Gly
                -15                 -10                 -5

Ala Asn Ala Trp Gly Val Leu Gly His Ala Ala Val Ala Tyr Val Ala
        -1  1               5                   10

Gln Ser Tyr Val Cys Pro Glu Ala Ala Ser Trp Ala Gln Lys Val Leu
    15                  20                  25

Asn Asp Ser Ser Ser Ser Tyr Leu Ala Asn Ile Ala Ser Trp Ala Asp
30                  35                  40                  45

Gln Tyr Arg Leu Thr Asp Ala Gly Lys Trp Ser Ala Pro Leu His Tyr
                50                  55                  60

Ile Asp Ala Leu Asp Asp Pro Pro Lys Ser Cys Asn Val Asp Tyr Glu
            65                  70                  75

Arg Asp Cys Ser Asp Glu Gly Cys Ser Ile Ser Ala Ile Ala Asn Tyr
        80                  85                  90

Thr Gln Arg Ala Gly Asp Arg Arg Leu Asp Asn Val His Thr Ala Glu
    95                  100                 105

Ala Leu Arg Phe Leu Val His Phe Leu Gly Asp Leu Thr Gln Pro Leu
110                 115                 120                 125

His Asp Glu Ala Tyr Glu Ile Gly Gly Asn Gly Ile Asn Val Thr Phe
                130                 135                 140

Asp Gly Tyr Asn Asp Asn Leu His Ala Asp Trp Asp Thr Tyr Ile Pro
            145                 150                 155

Val Lys Leu Val Gly Gly Ser Ser Leu Ala Asp Ala Gln Ser Trp Ala
        160                 165                 170

Thr Ser Leu Val Lys Glu Ile Thr Ser Gly Ser Phe Lys Tyr Lys Ser
    175                 180                 185

Ala Asn Trp Ile Arg Gly Asp Asn Ile Asp Asp Val Ile Thr Thr Ala
190                 195                 200                 205

Thr Arg Trp Ala Thr Asp Ala Asn Ala Tyr Ile Cys Thr Val Val Met
                210                 215                 220

Pro Asp Gly Ala Ala Ala Leu Gln Thr Gly Asp Leu Tyr Pro Thr Tyr
            225                 230                 235

Tyr Glu Ser Ala Ile Gly Thr Ile Glu Leu Gln Ile Ala Lys Gly Gly
        240                 245                 250

Tyr Arg Leu Gly Asn Trp Ile Asn Leu Ile Tyr Arg Asn Lys Ile Ala
    255                 260                 265

Lys His Arg Pro Gly Lys Pro Val Lys Glu His His Gly Pro Pro Pro
270                 275                 280                 285

His Ser Asn His Gly Asp Asp Ile Arg Pro His Pro Arg Gly Pro Ser
                290                 295                 300
```

```
Arg Ala Asn Leu Ala Arg Ala Ala Met Gly Gly Ser Cys Cys Ser Ser
            305                 310                 315

Gly Gly Arg Glu His Glu His
        320


<210> SEQ ID NO 51
<211> LENGTH: 324
<212> TYPE: PRT
<213> ORGANISM: Penicillium atramentosum

<400> SEQUENCE: 51

Trp Gly Val Leu Gly His Ala Ala Val Ala Tyr Val Ala Gln Ser Tyr
1               5                   10                  15

Val Cys Pro Glu Ala Ala Ser Trp Ala Gln Lys Val Leu Asn Asp Ser
            20                  25                  30

Ser Ser Ser Tyr Leu Ala Asn Ile Ala Ser Trp Ala Asp Gln Tyr Arg
        35                  40                  45

Leu Thr Asp Ala Gly Lys Trp Ser Ala Pro Leu His Tyr Ile Asp Ala
    50                  55                  60

Leu Asp Asp Pro Pro Lys Ser Cys Asn Val Asp Tyr Glu Arg Asp Cys
65                  70                  75                  80

Ser Asp Glu Gly Cys Ser Ile Ser Ala Ile Ala Asn Tyr Thr Gln Arg
                85                  90                  95

Ala Gly Asp Arg Arg Leu Asp Asn Val His Thr Ala Glu Ala Leu Arg
            100                 105                 110

Phe Leu Val His Phe Leu Gly Asp Leu Thr Gln Pro Leu His Asp Glu
        115                 120                 125

Ala Tyr Glu Ile Gly Gly Asn Gly Ile Asn Val Thr Phe Asp Gly Tyr
    130                 135                 140

Asn Asp Asn Leu His Ala Asp Trp Asp Thr Tyr Ile Pro Val Lys Leu
145                 150                 155                 160

Val Gly Gly Ser Ser Leu Ala Asp Ala Gln Ser Trp Ala Thr Ser Leu
                165                 170                 175

Val Lys Glu Ile Thr Ser Gly Ser Phe Lys Tyr Lys Ser Ala Asn Trp
            180                 185                 190

Ile Arg Gly Asp Asn Ile Asp Asp Val Ile Thr Thr Ala Thr Arg Trp
        195                 200                 205

Ala Thr Asp Ala Asn Ala Tyr Ile Cys Thr Val Val Met Pro Asp Gly
    210                 215                 220

Ala Ala Ala Leu Gln Thr Gly Asp Leu Tyr Pro Thr Tyr Tyr Glu Ser
225                 230                 235                 240

Ala Ile Gly Thr Ile Glu Leu Gln Ile Ala Lys Gly Gly Tyr Arg Leu
                245                 250                 255

Gly Asn Trp Ile Asn Leu Ile Tyr Arg Asn Lys Ile Ala Lys His Arg
            260                 265                 270

Pro Gly Lys Pro Val Lys Glu His His Gly Pro Pro Pro His Ser Asn
        275                 280                 285

His Gly Asp Asp Ile Arg Pro His Pro Arg Gly Pro Ser Arg Ala Asn
    290                 295                 300

Leu Ala Arg Ala Ala Met Gly Gly Ser Cys Cys Ser Ser Gly Gly Arg
305                 310                 315                 320

Glu His Glu His


<210> SEQ ID NO 52
```

```
<211> LENGTH: 955
<212> TYPE: DNA
<213> ORGANISM: Penicillium emersonii
<220> FEATURE:
<221> NAME/KEY: CDS
<222> LOCATION: (1)..(336)
<220> FEATURE:
<221> NAME/KEY: sig_peptide
<222> LOCATION: (1)..(57)
<220> FEATURE:
<221> NAME/KEY: mat_peptide
<222> LOCATION: (58)..(952)
<220> FEATURE:
<221> NAME/KEY: CDS
<222> LOCATION: (381)..(449)
<220> FEATURE:
<221> NAME/KEY: CDS
<222> LOCATION: (500)..(952)

<400> SEQUENCE: 52

atg ccc tcc cgc gcc tcc ctt ctc gcc ctc ctg gcc gcc ctc ccc cgc       48
Met Pro Ser Arg Ala Ser Leu Leu Ala Leu Leu Ala Ala Leu Pro Arg
                -15                 -10                 -5

agc tac gcc tgg ggc aat ctt ggc cac gag acg att gcc tac atc gcg       96
Ser Tyr Ala Trp Gly Asn Leu Gly His Glu Thr Ile Ala Tyr Ile Ala
        -1  1               5                   10

cag aac ttc atc gcc tcg tcg acg gcg tcc tac tgc cag gac gtc ctg      144
Gln Asn Phe Ile Ala Ser Ser Thr Ala Ser Tyr Cys Gln Asp Val Leu
    15                  20                  25

ggc gat acg tcc tcc tcg tat ctg gcc agc gta gcc acc tgg gcg gac      192
Gly Asp Thr Ser Ser Ser Tyr Leu Ala Ser Val Ala Thr Trp Ala Asp
30                  35                  40                  45

tcg tac cgc tac acg tcc gcc ggc cgc tgg tcc gag ccg ctg cac ttt      240
Ser Tyr Arg Tyr Thr Ser Ala Gly Arg Trp Ser Glu Pro Leu His Phe
                50                  55                  60

atc gat gcg cat gac gat ccc ccg acg agc tgc ggc gtc gac tat gag      288
Ile Asp Ala His Asp Asp Pro Pro Thr Ser Cys Gly Val Asp Tyr Glu
            65                  70                  75

agg gac tgc ggc gat aag gga tgc gtt gtg agc gcg atc aat aac tac      336
Arg Asp Cys Gly Asp Lys Gly Cys Val Val Ser Ala Ile Asn Asn Tyr
        80                  85                  90

gtaagctctc gatctacgtt aggaggttct ggctgacaat tcag acg acg caa tta     392
                                                 Thr Thr Gln Leu
                                                     95

ctg gac aaa tcg aca tcg agt tcc gaa gcg ttg gac gcg atg aaa ttc      440
Leu Asp Lys Ser Thr Ser Ser Ser Glu Ala Leu Asp Ala Met Lys Phe
        100                 105                 110

atc atc cac gttagtcgca cgtacacacc cttttcgtcg tgtttagcta              489
Ile Ile His
    115

acgaagccag ttc gtc ggt gac atc cac cag ccc ctt cac gac gag aac       538
           Phe Val Gly Asp Ile His Gln Pro Leu His Asp Glu Asn
                       120                 125

ctc gac gtg ggc ggc aac gac atc gac gtg acc ttc aac ggc acg aaa      586
Leu Asp Val Gly Gly Asn Asp Ile Asp Val Thr Phe Asn Gly Thr Lys
130                 135                 140                 145

acg aac ctg cac cac atc tgg gac acg aac atg ctg gaa gcc gac gcg      634
Thr Asn Leu His His Ile Trp Asp Thr Asn Met Leu Glu Ala Asp Ala
                150                 155                 160

ggg ggg tca tca ctg tcg acg gcc aag agc ttc gcg gcg acg ctg acc      682
Gly Gly Ser Ser Leu Ser Thr Ala Lys Ser Phe Ala Ala Thr Leu Thr
            165                 170                 175

acg cgc ctg cag agc ggc gag tac gcg tcg cag aag gcg tcg tgg atc      730
Thr Arg Leu Gln Ser Gly Glu Tyr Ala Ser Gln Lys Ala Ser Trp Ile
```

```
        180                 185                 190

tcg ggc atg aat atc agc gat ccg gtg gcc acg gcg atg ggc tgg gca      778
Ser Gly Met Asn Ile Ser Asp Pro Val Ala Thr Ala Met Gly Trp Ala
    195                 200                 205

agc gat gcc aac ggg tac gtc tgc agc acg gtg ctg aag ccg gga ctg      826
Ser Asp Ala Asn Gly Tyr Val Cys Ser Thr Val Leu Lys Pro Gly Leu
210                 215                 220                 225

tcg tat atc aag gac aac gat ctg tcg ggg aag tac tat gcc gac tgc      874
Ser Tyr Ile Lys Asp Asn Asp Leu Ser Gly Lys Tyr Tyr Ala Asp Cys
                230                 235                 240

aag ccg gtg ttt gag gag ctg ctt gcc cgg gca gga tac cgg ttg gcg      922
Lys Pro Val Phe Glu Glu Leu Leu Ala Arg Ala Gly Tyr Arg Leu Ala
            245                 250                 255

gcg tgg ttg gac ttg att gcg aag cag cag tag                          955
Ala Trp Leu Asp Leu Ile Ala Lys Gln Gln
        260                 265


<210> SEQ ID NO 53
<211> LENGTH: 286
<212> TYPE: PRT
<213> ORGANISM: Penicillium emersonii

<400> SEQUENCE: 53

Met Pro Ser Arg Ala Ser Leu Leu Ala Leu Leu Ala Ala Leu Pro Arg
                -15                 -10                 -5

Ser Tyr Ala Trp Gly Asn Leu Gly His Glu Thr Ile Ala Tyr Ile Ala
        -1  1               5                   10

Gln Asn Phe Ile Ala Ser Ser Thr Ala Ser Tyr Cys Gln Asp Val Leu
    15                  20                  25

Gly Asp Thr Ser Ser Ser Tyr Leu Ala Ser Val Ala Thr Trp Ala Asp
30                  35                  40                  45

Ser Tyr Arg Tyr Thr Ser Ala Gly Arg Trp Ser Glu Pro Leu His Phe
                50                  55                  60

Ile Asp Ala His Asp Asp Pro Pro Thr Ser Cys Gly Val Asp Tyr Glu
            65                  70                  75

Arg Asp Cys Gly Asp Lys Gly Cys Val Val Ser Ala Ile Asn Asn Tyr
        80                  85                  90

Thr Thr Gln Leu Leu Asp Lys Ser Thr Ser Ser Ser Glu Ala Leu Asp
    95                  100                 105

Ala Met Lys Phe Ile Ile His Phe Val Gly Asp Ile His Gln Pro Leu
110                 115                 120                 125

His Asp Glu Asn Leu Asp Val Gly Gly Asn Asp Ile Asp Val Thr Phe
                130                 135                 140

Asn Gly Thr Lys Thr Asn Leu His His Ile Trp Asp Thr Asn Met Leu
            145                 150                 155

Glu Ala Asp Ala Gly Gly Ser Ser Leu Ser Thr Ala Lys Ser Phe Ala
        160                 165                 170

Ala Thr Leu Thr Thr Arg Leu Gln Ser Gly Glu Tyr Ala Ser Gln Lys
    175                 180                 185

Ala Ser Trp Ile Ser Gly Met Asn Ile Ser Asp Pro Val Ala Thr Ala
190                 195                 200                 205

Met Gly Trp Ala Ser Asp Ala Asn Gly Tyr Val Cys Ser Thr Val Leu
                210                 215                 220

Lys Pro Gly Leu Ser Tyr Ile Lys Asp Asn Asp Leu Ser Gly Lys Tyr
            225                 230                 235

Tyr Ala Asp Cys Lys Pro Val Phe Glu Glu Leu Leu Ala Arg Ala Gly
```

```
        240                 245                 250

Tyr Arg Leu Ala Ala Trp Leu Asp Leu Ile Ala Lys Gln Gln
    255                 260                 265


<210> SEQ ID NO 54
<211> LENGTH: 267
<212> TYPE: PRT
<213> ORGANISM: Penicillium emersonii

<400> SEQUENCE: 54

Trp Gly Asn Leu Gly His Glu Thr Ile Ala Tyr Ile Ala Gln Asn Phe
1               5                   10                  15

Ile Ala Ser Ser Thr Ala Ser Tyr Cys Gln Asp Val Leu Gly Asp Thr
            20                  25                  30

Ser Ser Ser Tyr Leu Ala Ser Val Ala Thr Trp Ala Asp Ser Tyr Arg
        35                  40                  45

Tyr Thr Ser Ala Gly Arg Trp Ser Glu Pro Leu His Phe Ile Asp Ala
    50                  55                  60

His Asp Asp Pro Pro Thr Ser Cys Gly Val Asp Tyr Glu Arg Asp Cys
65                  70                  75                  80

Gly Asp Lys Gly Cys Val Val Ser Ala Ile Asn Asn Tyr Thr Thr Gln
                85                  90                  95

Leu Leu Asp Lys Ser Thr Ser Ser Ser Glu Ala Leu Asp Ala Met Lys
            100                 105                 110

Phe Ile Ile His Phe Val Gly Asp Ile His Gln Pro Leu His Asp Glu
        115                 120                 125

Asn Leu Asp Val Gly Gly Asn Asp Ile Asp Val Thr Phe Asn Gly Thr
    130                 135                 140

Lys Thr Asn Leu His His Ile Trp Asp Thr Asn Met Leu Glu Ala Asp
145                 150                 155                 160

Ala Gly Gly Ser Ser Leu Ser Thr Ala Lys Ser Phe Ala Ala Thr Leu
                165                 170                 175

Thr Thr Arg Leu Gln Ser Gly Glu Tyr Ala Ser Gln Lys Ala Ser Trp
            180                 185                 190

Ile Ser Gly Met Asn Ile Ser Asp Pro Val Ala Thr Ala Met Gly Trp
        195                 200                 205

Ala Ser Asp Ala Asn Gly Tyr Val Cys Ser Thr Val Leu Lys Pro Gly
    210                 215                 220

Leu Ser Tyr Ile Lys Asp Asn Asp Leu Ser Gly Lys Tyr Tyr Ala Asp
225                 230                 235                 240

Cys Lys Pro Val Phe Glu Glu Leu Leu Ala Arg Ala Gly Tyr Arg Leu
                245                 250                 255

Ala Ala Trp Leu Asp Leu Ile Ala Lys Gln Gln
            260                 265


<210> SEQ ID NO 55
<211> LENGTH: 1086
<212> TYPE: DNA
<213> ORGANISM: Ostropa Barbara
<220> FEATURE:
<221> NAME/KEY: CDS
<222> LOCATION: (1)..(336)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1083)
<220> FEATURE:
```

```
<221> NAME/KEY: CDS
<222> LOCATION: (403)..(459)
<220> FEATURE:
<221> NAME/KEY: CDS
<222> LOCATION: (507)..(518)
<220> FEATURE:
<221> NAME/KEY: CDS
<222> LOCATION: (569)..(984)
<220> FEATURE:
<221> NAME/KEY: CDS
<222> LOCATION: (1035)..(1083)

<400> SEQUENCE: 55

atg aaa tac aca acc ctc acc ctc acc ttc ctc tcc tcc ctc cct ttc       48
Met Lys Tyr Thr Thr Leu Thr Leu Thr Phe Leu Ser Ser Leu Pro Phe
                -15                 -10                 -5

tcc tat gcc tgg ggt tcc ctc ggc cat gaa acc gtc gct tac atc gcc       96
Ser Tyr Ala Trp Gly Ser Leu Gly His Glu Thr Val Ala Tyr Ile Ala
        -1  1               5                   10

tcc aac ttc gtc gcg ccc cca acg cgc acc ttc ttc cag tcc atc ctc      144
Ser Asn Phe Val Ala Pro Pro Thr Arg Thr Phe Phe Gln Ser Ile Leu
    15                  20                  25

cac aac acc agc gat tcc tat cta gcc agc gtg gcc acc tgg gct gat      192
His Asn Thr Ser Asp Ser Tyr Leu Ala Ser Val Ala Thr Trp Ala Asp
30                  35                  40                  45

tcc ttc aga tac aca gct gct ggg cgc ttc tcg gcg ccg ttc cat ttt      240
Ser Phe Arg Tyr Thr Ala Ala Gly Arg Phe Ser Ala Pro Phe His Phe
                50                  55                  60

att gat gca gag gat agc ccg ccg cat act tgt ggt gtg aag tat tcg      288
Ile Asp Ala Glu Asp Ser Pro Pro His Thr Cys Gly Val Lys Tyr Ser
            65                  70                  75

cgg gac tgt ggg gag cag ggg tgt gtg gtg ggg gct att tct aat tat      336
Arg Asp Cys Gly Glu Gln Gly Cys Val Val Gly Ala Ile Ser Asn Tyr
        80                  85                  90

gtgagttatt catgattttg tgatacggta ctcctggttt tgagagagga tggctaatgg    396

aagtag acg agt cag ttg ctg gat ccg gag ttg gat gct tgg aag agg       444
       Thr Ser Gln Leu Leu Asp Pro Glu Leu Asp Ala Trp Lys Arg
           95                  100                 105

acg atg gct gcc aag gtatgatttc cccggtattt tggatatcgg atactaacga      499
Thr Met Ala Ala Lys
        110

gaagtag ttt att gtt cat gtaaggaatc gaaagtcctt ttctgaaagc             548
        Phe Ile Val His
                115

agtcattaac agccagaaag ttc tta gga gat att cat caa cca ctc cac gat    601
                      Phe Leu Gly Asp Ile His Gln Pro Leu His Asp
                                  120                 125

gag aat ctc gac cgg ggt ggg aac tct att ccc gtg ctc ttc gac tcc      649
Glu Asn Leu Asp Arg Gly Gly Asn Ser Ile Pro Val Leu Phe Asp Ser
        130                 135                 140

gtt tcc acc aat tta cat cat ctt tgg gat agt aac ata ccc gaa aaa      697
Val Ser Thr Asn Leu His His Leu Trp Asp Ser Asn Ile Pro Glu Lys
    145                 150                 155

ctc atc gga ggc tac tca ctg cct gac gcc gag cgc tgg gct act gcg      745
Leu Ile Gly Gly Tyr Ser Leu Pro Asp Ala Glu Arg Trp Ala Thr Ala
160                 165                 170                 175

ctc act gcg gct atc aag acc ggc atc tat aag cca tta gca gcg gag      793
Leu Thr Ala Ala Ile Lys Thr Gly Ile Tyr Lys Pro Leu Ala Ala Glu
                180                 185                 190

tgg cta cat ggc atg gat ttg aaa gat ccg gta agt acg agc ttg aag      841
Trp Leu His Gly Met Asp Leu Lys Asp Pro Val Ser Thr Ser Leu Lys
            195                 200                 205
```

```
tgg gcg gag gaa gcg aat gct ttt gtg tgt tct act gtg ttg ccg gag      889
Trp Ala Glu Glu Ala Asn Ala Phe Val Cys Ser Thr Val Leu Pro Glu
        210                 215                 220

gga aaa gag ggt gta atg ggg aag gaa ctg aat ggg agt tac tat gag      937
Gly Lys Glu Gly Val Met Gly Lys Glu Leu Asn Gly Ser Tyr Tyr Glu
    225                 230                 235

aat gcg gtg cct gtg att cag ttg caa att gcg agg gcg ggg tat ag       984
Asn Ala Val Pro Val Ile Gln Leu Gln Ile Ala Arg Ala Gly Tyr Arg
240                 245                 250                 255

gtgagttgag attcttgttc ttggaaagaa gaaactaatc gtttgagtag a ctg gct    1041
                                                         Leu Ala

cgt tgg ttg gac ttg att gca gct gac ggt aaa acg gaa ttg taa         1086
Arg Trp Leu Asp Leu Ile Ala Ala Asp Gly Lys Thr Glu Leu
        260                 265                 270


<210> SEQ ID NO 56
<211> LENGTH: 290
<212> TYPE: PRT
<213> ORGANISM: Ostropa Barbara

<400> SEQUENCE: 56

Met Lys Tyr Thr Thr Leu Thr Leu Thr Phe Leu Ser Ser Leu Pro Phe
                -15                 -10                 -5

Ser Tyr Ala Trp Gly Ser Leu Gly His Glu Thr Val Ala Tyr Ile Ala
        -1  1               5                   10

Ser Asn Phe Val Ala Pro Pro Thr Arg Thr Phe Phe Gln Ser Ile Leu
    15                  20                  25

His Asn Thr Ser Asp Ser Tyr Leu Ala Ser Val Ala Thr Trp Ala Asp
30                  35                  40                  45

Ser Phe Arg Tyr Thr Ala Ala Gly Arg Phe Ser Ala Pro Phe His Phe
                50                  55                  60

Ile Asp Ala Glu Asp Ser Pro Pro His Thr Cys Gly Val Lys Tyr Ser
            65                  70                  75

Arg Asp Cys Gly Glu Gln Gly Cys Val Val Gly Ala Ile Ser Asn Tyr
        80                  85                  90

Thr Ser Gln Leu Leu Asp Pro Glu Leu Asp Ala Trp Lys Arg Thr Met
    95                  100                 105

Ala Ala Lys Phe Ile Val His Phe Leu Gly Asp Ile His Gln Pro Leu
110                 115                 120                 125

His Asp Glu Asn Leu Asp Arg Gly Gly Asn Ser Ile Pro Val Leu Phe
                130                 135                 140

Asp Ser Val Ser Thr Asn Leu His His Leu Trp Asp Ser Asn Ile Pro
            145                 150                 155

Glu Lys Leu Ile Gly Gly Tyr Ser Leu Pro Asp Ala Glu Arg Trp Ala
        160                 165                 170

Thr Ala Leu Thr Ala Ala Ile Lys Thr Gly Ile Tyr Lys Pro Leu Ala
    175                 180                 185

Ala Glu Trp Leu His Gly Met Asp Leu Lys Asp Pro Val Ser Thr Ser
190                 195                 200                 205

Leu Lys Trp Ala Glu Glu Ala Asn Ala Phe Val Cys Ser Thr Val Leu
                210                 215                 220

Pro Glu Gly Lys Glu Gly Val Met Gly Lys Glu Leu Asn Gly Ser Tyr
            225                 230                 235

Tyr Glu Asn Ala Val Pro Val Ile Gln Leu Gln Ile Ala Arg Ala Gly
        240                 245                 250
```

```
Tyr Arg Leu Ala Arg Trp Leu Asp Leu Ile Ala Ala Asp Gly Lys Thr
    255                 260                 265

Glu Leu
270


<210> SEQ ID NO 57
<211> LENGTH: 271
<212> TYPE: PRT
<213> ORGANISM: Ostropa Barbara

<400> SEQUENCE: 57

Trp Gly Ser Leu Gly His Glu Thr Val Ala Tyr Ile Ala Ser Asn Phe
1               5                   10                  15

Val Ala Pro Pro Thr Arg Thr Phe Phe Gln Ser Ile Leu His Asn Thr
            20                  25                  30

Ser Asp Ser Tyr Leu Ala Ser Val Ala Thr Trp Ala Asp Ser Phe Arg
        35                  40                  45

Tyr Thr Ala Ala Gly Arg Phe Ser Ala Pro Phe His Phe Ile Asp Ala
    50                  55                  60

Glu Asp Ser Pro Pro His Thr Cys Gly Val Lys Tyr Ser Arg Asp Cys
65                  70                  75                  80

Gly Glu Gln Gly Cys Val Val Gly Ala Ile Ser Asn Tyr Thr Ser Gln
                85                  90                  95

Leu Leu Asp Pro Glu Leu Asp Ala Trp Lys Arg Thr Met Ala Ala Lys
            100                 105                 110

Phe Ile Val His Phe Leu Gly Asp Ile His Gln Pro Leu His Asp Glu
        115                 120                 125

Asn Leu Asp Arg Gly Gly Asn Ser Ile Pro Val Leu Phe Asp Ser Val
    130                 135                 140

Ser Thr Asn Leu His His Leu Trp Asp Ser Asn Ile Pro Glu Lys Leu
145                 150                 155                 160

Ile Gly Gly Tyr Ser Leu Pro Asp Ala Glu Arg Trp Ala Thr Ala Leu
                165                 170                 175

Thr Ala Ala Ile Lys Thr Gly Ile Tyr Lys Pro Leu Ala Ala Glu Trp
            180                 185                 190

Leu His Gly Met Asp Leu Lys Asp Pro Val Ser Thr Ser Leu Lys Trp
        195                 200                 205

Ala Glu Glu Ala Asn Ala Phe Val Cys Ser Thr Val Leu Pro Glu Gly
    210                 215                 220

Lys Glu Gly Val Met Gly Lys Glu Leu Asn Gly Ser Tyr Tyr Glu Asn
225                 230                 235                 240

Ala Val Pro Val Ile Gln Leu Gln Ile Ala Arg Ala Gly Tyr Arg Leu
                245                 250                 255

Ala Arg Trp Leu Asp Leu Ile Ala Ala Asp Gly Lys Thr Glu Leu
            260                 265                 270


<210> SEQ ID NO 58
<211> LENGTH: 1047
<212> TYPE: DNA
<213> ORGANISM: Pyrenochaetopsis sp
<220> FEATURE:
<221> NAME/KEY: CDS
<222> LOCATION: (1)..(67)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1044)
```

```
<220> FEATURE:
<221> NAME/KEY: CDS
<222> LOCATION: (132)..(598)
<220> FEATURE:
<221> NAME/KEY: CDS
<222> LOCATION: (649)..(1044)

<400> SEQUENCE: 58

atg ctt ccc aga cac tcg ctc ctg agc gcc atc ctg gta gct tca gcc       48
Met Leu Pro Arg His Ser Leu Leu Ser Ala Ile Leu Val Ala Ser Ala
            -15                 -10                 -5

aca gca tgg aat atc gac g gtacgcgtac tcactccgac cgcagccctc            97
Thr Ala Trp Asn Ile Asp
    -1  1

caccacagta gctcgcaaca ctaaccgcat ccag tg  cac aac caa atc ggc ttc    151
                                      Val His Asn Gln Ile Gly Phe
                                      5                   10

atg gcc gaa aca ttc cta acg cct caa aca acc gct att ctc gcc gag      199
Met Ala Glu Thr Phe Leu Thr Pro Gln Thr Thr Ala Ile Leu Ala Glu
            15                  20                  25

ctg ctc gaa ccc cag tac aac agc tcc ata ggc cgc gcc gca gcg tgg      247
Leu Leu Glu Pro Gln Tyr Asn Ser Ser Ile Gly Arg Ala Ala Ala Trp
        30                  35                  40

gca gac gcc tac gcg cat acg cag gag ggc cgc ttc tcg tac caa tgg      295
Ala Asp Ala Tyr Ala His Thr Gln Glu Gly Arg Phe Ser Tyr Gln Trp
    45                  50                  55

cac tgg att gat acg cat gat agc gcg ccc gag tac tgc agc tta aat      343
His Trp Ile Asp Thr His Asp Ser Ala Pro Glu Tyr Cys Ser Leu Asn
60                  65                  70                  75

tat aca gcg gac tgt gca aaa ggc gga tgt gtt gtt agt gcg att gcg      391
Tyr Thr Ala Asp Cys Ala Lys Gly Gly Cys Val Val Ser Ala Ile Ala
                80                  85                  90

aat cag acg ggc ata cta aga gag tgc ata gag gat gtg aag gtt ggg      439
Asn Gln Thr Gly Ile Leu Arg Glu Cys Ile Glu Asp Val Lys Val Gly
            95                  100                 105

gtt gtg ggc ggt ggg agt aac ttg acg tgt tcg tat gcg ctg aag tgg      487
Val Val Gly Gly Gly Ser Asn Leu Thr Cys Ser Tyr Ala Leu Lys Trp
        110                 115                 120

gtt acg cat ttt ctg ggg gat gta cat cag ccg ctg cat gct aat ggg      535
Val Thr His Phe Leu Gly Asp Val His Gln Pro Leu His Ala Asn Gly
    125                 130                 135

aga gct gtg ggg ggg aat acg tat aaa gtc acg ttt ggc ggc gtg gct      583
Arg Ala Val Gly Gly Asn Thr Tyr Lys Val Thr Phe Gly Gly Val Ala
140                 145                 150                 155

acg cag ttg cat gct gtaaatacgc ccaaatcccg ctctctcgtg aaagtactaa      638
Thr Gln Leu His Ala
                160

cgtgcattag gtc tgg gac gga tat atc ccc tac ttc gca gcc agc gtc       687
           Val Trp Asp Gly Tyr Ile Pro Tyr Phe Ala Ala Ser Val
                           165                 170

agc aaa cca ttt tca aac cag tcc att gat cct ttc ttc act ggt ctg      735
Ser Lys Pro Phe Ser Asn Gln Ser Ile Asp Pro Phe Phe Thr Gly Leu
    175                 180                 185

gtg tct cgg atc cgc aat gat ggg ttc ttc tct gcg ccg tat atg tgg      783
Val Ser Arg Ile Arg Asn Asp Gly Phe Phe Ser Ala Pro Tyr Met Trp
190                 195                 200                 205

ttg gct tgc gtt gat cct tct acg gca gca gaa tgt gct acg agg tgg      831
Leu Ala Cys Val Asp Pro Ser Thr Ala Ala Glu Cys Ala Thr Arg Trp
                210                 215                 220

gca aag gag agt aat aag tgg gac tgc gat tat gtc tgg agc cgc gta      879
Ala Lys Glu Ser Asn Lys Trp Asp Cys Asp Tyr Val Trp Ser Arg Val
```

```
            225                 230                 235

cgg aat gac act gat ctg gga act aat ggg tat gcg gtc ggt gct gta      927
Arg Asn Asp Thr Asp Leu Gly Thr Asn Gly Tyr Ala Val Gly Ala Val
        240                 245                 250

cct att gtg gaa ttg caa atc agc aaa gct gcg ctc aga ttg ggt act      975
Pro Ile Val Glu Leu Gln Ile Ser Lys Ala Ala Leu Arg Leu Gly Thr
    255                 260                 265

tgg ctc aac agg ctt gtc gaa ggg gac aag tat gag tat gct tca cgc     1023
Trp Leu Asn Arg Leu Val Glu Gly Asp Lys Tyr Glu Tyr Ala Ser Arg
270                 275                 280                 285

aac caa gag gtc att gag ctt taa                                     1047
Asn Gln Glu Val Ile Glu Leu
                290


<210> SEQ ID NO 59
<211> LENGTH: 310
<212> TYPE: PRT
<213> ORGANISM: Pyrenochaetopsis sp

<400> SEQUENCE: 59

Met Leu Pro Arg His Ser Leu Leu Ser Ala Ile Leu Val Ala Ser Ala
            -15                 -10                 -5

Thr Ala Trp Asn Ile Asp Val His Asn Gln Ile Gly Phe Met Ala Glu
    -1  1               5                   10

Thr Phe Leu Thr Pro Gln Thr Thr Ala Ile Leu Ala Glu Leu Leu Glu
15                  20                  25                  30

Pro Gln Tyr Asn Ser Ser Ile Gly Arg Ala Ala Ala Trp Ala Asp Ala
                35                  40                  45

Tyr Ala His Thr Gln Glu Gly Arg Phe Ser Tyr Gln Trp His Trp Ile
            50                  55                  60

Asp Thr His Asp Ser Ala Pro Glu Tyr Cys Ser Leu Asn Tyr Thr Ala
        65                  70                  75

Asp Cys Ala Lys Gly Gly Cys Val Val Ser Ala Ile Ala Asn Gln Thr
    80                  85                  90

Gly Ile Leu Arg Glu Cys Ile Glu Asp Val Lys Val Gly Val Val Gly
95                  100                 105                 110

Gly Gly Ser Asn Leu Thr Cys Ser Tyr Ala Leu Lys Trp Val Thr His
                115                 120                 125

Phe Leu Gly Asp Val His Gln Pro Leu His Ala Asn Gly Arg Ala Val
            130                 135                 140

Gly Gly Asn Thr Tyr Lys Val Thr Phe Gly Gly Val Ala Thr Gln Leu
        145                 150                 155

His Ala Val Trp Asp Gly Tyr Ile Pro Tyr Phe Ala Ala Ser Val Ser
    160                 165                 170

Lys Pro Phe Ser Asn Gln Ser Ile Asp Pro Phe Phe Thr Gly Leu Val
175                 180                 185                 190

Ser Arg Ile Arg Asn Asp Gly Phe Phe Ser Ala Pro Tyr Met Trp Leu
                195                 200                 205

Ala Cys Val Asp Pro Ser Thr Ala Ala Glu Cys Ala Thr Arg Trp Ala
            210                 215                 220

Lys Glu Ser Asn Lys Trp Asp Cys Asp Tyr Val Trp Ser Arg Val Arg
        225                 230                 235

Asn Asp Thr Asp Leu Gly Thr Asn Gly Tyr Ala Val Gly Ala Val Pro
    240                 245                 250

Ile Val Glu Leu Gln Ile Ser Lys Ala Ala Leu Arg Leu Gly Thr Trp
255                 260                 265                 270
```

```
Leu Asn Arg Leu Val Glu Gly Asp Lys Tyr Glu Tyr Ala Ser Arg Asn
                275                 280                 285

Gln Glu Val Ile Glu Leu
            290


<210> SEQ ID NO 60
<211> LENGTH: 292
<212> TYPE: PRT
<213> ORGANISM: Pyrenochaetopsis sp

<400> SEQUENCE: 60

Trp Asn Ile Asp Val His Asn Gln Ile Gly Phe Met Ala Glu Thr Phe
1               5                   10                  15

Leu Thr Pro Gln Thr Thr Ala Ile Leu Ala Glu Leu Leu Glu Pro Gln
            20                  25                  30

Tyr Asn Ser Ser Ile Gly Arg Ala Ala Ala Trp Ala Asp Ala Tyr Ala
        35                  40                  45

His Thr Gln Glu Gly Arg Phe Ser Tyr Gln Trp His Trp Ile Asp Thr
    50                  55                  60

His Asp Ser Ala Pro Glu Tyr Cys Ser Leu Asn Tyr Thr Ala Asp Cys
65                  70                  75                  80

Ala Lys Gly Gly Cys Val Val Ser Ala Ile Ala Asn Gln Thr Gly Ile
                85                  90                  95

Leu Arg Glu Cys Ile Glu Asp Val Lys Val Gly Val Val Gly Gly Gly
            100                 105                 110

Ser Asn Leu Thr Cys Ser Tyr Ala Leu Lys Trp Val Thr His Phe Leu
        115                 120                 125

Gly Asp Val His Gln Pro Leu His Ala Asn Gly Arg Ala Val Gly Gly
    130                 135                 140

Asn Thr Tyr Lys Val Thr Phe Gly Gly Val Ala Thr Gln Leu His Ala
145                 150                 155                 160

Val Trp Asp Gly Tyr Ile Pro Tyr Phe Ala Ala Ser Val Ser Lys Pro
                165                 170                 175

Phe Ser Asn Gln Ser Ile Asp Pro Phe Phe Thr Gly Leu Val Ser Arg
            180                 185                 190

Ile Arg Asn Asp Gly Phe Phe Ser Ala Pro Tyr Met Trp Leu Ala Cys
        195                 200                 205

Val Asp Pro Ser Thr Ala Ala Glu Cys Ala Thr Arg Trp Ala Lys Glu
    210                 215                 220

Ser Asn Lys Trp Asp Cys Asp Tyr Val Trp Ser Arg Val Arg Asn Asp
225                 230                 235                 240

Thr Asp Leu Gly Thr Asn Gly Tyr Ala Val Gly Ala Val Pro Ile Val
                245                 250                 255

Glu Leu Gln Ile Ser Lys Ala Ala Leu Arg Leu Gly Thr Trp Leu Asn
            260                 265                 270

Arg Leu Val Glu Gly Asp Lys Tyr Glu Tyr Ala Ser Arg Asn Gln Glu
        275                 280                 285

Val Ile Glu Leu
    290


<210> SEQ ID NO 61
<211> LENGTH: 1448
<212> TYPE: DNA
<213> ORGANISM: Lachnellula sp
<220> FEATURE:
<221> NAME/KEY: CDS
```

```
<222> LOCATION: (1)..(112)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1445)
<220> FEATURE:
<221> NAME/KEY: CDS
<222> LOCATION: (190)..(269)
<220> FEATURE:
<221> NAME/KEY: CDS
<222> LOCATION: (322)..(471)
<220> FEATURE:
<221> NAME/KEY: CDS
<222> LOCATION: (523)..(579)
<220> FEATURE:
<221> NAME/KEY: CDS
<222> LOCATION: (626)..(637)
<220> FEATURE:
<221> NAME/KEY: CDS
<222> LOCATION: (831)..(935)
<220> FEATURE:
<221> NAME/KEY: CDS
<222> LOCATION: (1028)..(1338)
<220> FEATURE:
<221> NAME/KEY: CDS
<222> LOCATION: (1400)..(1445)

<400> SEQUENCE: 61

atg aag act caa gct gta gct tcc att ttc ttc ctc gcc acc tct ctt       48
Met Lys Thr Gln Ala Val Ala Ser Ile Phe Phe Leu Ala Thr Ser Leu
    -20                 -15                 -10

ccc tcc gct tta ggc tgg ggc act ctt ggt cat cag aca gta gct tat       96
Pro Ser Ala Leu Gly Trp Gly Thr Leu Gly His Gln Thr Val Ala Tyr
-5              -1  1               5                   10

atc gct aca aac ttt g gttaacagcc tagctttcaa cataaccgct gtttaaaatc    152
Ile Ala Thr Asn Phe
            15

gattgtgata gcatcatgtg ctgatatatc gaaatag tt  tca agt gcc acg aaa     206
                                         Val Ser Ser Ala Thr Lys
                                                     20

acc aaa ttc caa agc atc ttg gac gac aca agc acc gac tat ctt gcc      254
Thr Lys Phe Gln Ser Ile Leu Asp Asp Thr Ser Thr Asp Tyr Leu Ala
        25                  30                  35

tca gtt gca aca tgg gtaatagatc tgctaatcca ctttctcact tggtgctgat      309
Ser Val Ala Thr Trp
    40

gtcttcttgc ag gct gat act tat cgc tac acc gat gcc ggg acc tgg acg    360
              Ala Asp Thr Tyr Arg Tyr Thr Asp Ala Gly Thr Trp Thr
                  45                  50                  55

gcc ccg ttt cac ttc att gat gcc aat gac gat ccc cca tca agc tgc      408
Ala Pro Phe His Phe Ile Asp Ala Asn Asp Asp Pro Pro Ser Ser Cys
            60                  65                  70

agc gta gat tat tcc cgt gat tgt gga acg gga ggt tgt gtg att agc      456
Ser Val Asp Tyr Ser Arg Asp Cys Gly Thr Gly Gly Cys Val Ile Ser
        75                  80                  85

gct atc aat aat tat gtacgctgca aggaattgat gatactggat ttggtctaat      511
Ala Ile Asn Asn Tyr
    90

gagtaaaaca g acc tcg cgt att cag agt acc acc ttg agc gac gca gag     561
             Thr Ser Arg Ile Gln Ser Thr Thr Leu Ser Asp Ala Glu
                 95                  100                 105

gtg aag act gct gca aag gtaaggacga gcaaaccctg gttgcttgaa             609
Val Lys Thr Ala Ala Lys
            110
```

```
tactaacagc ctccag ttc atc gtc cat gtaagttgtg aatcctttga          657
                  Phe Ile Val His
                          115

gcagaagttc gcggatctat tctcgagtca gcggcaatca gatgccctca gtcatcgcgg    717

aggcacgtgg actatggcag ccagaaatct tctcttgacc ttgtctctcc cttcatggtc    777

atggaaacgt gctatctagt tgcgcactgt acttatccga tgactctatt cag ttt       833
                                                           Phe

att gga gac att cac cag cct ctt cat gac gag ggc ctc gac ttg gga      881
Ile Gly Asp Ile His Gln Pro Leu His Asp Glu Gly Leu Asp Leu Gly
        120                 125                 130

gga aac gaa atc gat gta acc ttt gac ggg gaa tcc acc aat ctc cac      929
Gly Asn Glu Ile Asp Val Thr Phe Asp Gly Glu Ser Thr Asn Leu His
    135                 140                 145

cac atc gttagtgcca ccattctcac ttacacccgt catacatcaa cacccgaacc       985
His Ile
150

cacctcccta tccccaaaaa ccatcttcta aattaatagc ag tgg gac acc aac      1039
                                               Trp Asp Thr Asn
                                                           155

atc ccc gag aaa tat gtc gga ggg tac gcg ctc tcc gac gcc aag tcc     1087
Ile Pro Glu Lys Tyr Val Gly Gly Tyr Ala Leu Ser Asp Ala Lys Ser
                160                 165                 170

ttc gcc gcg acc ctc acg acc tcg atc aaa aac gga tcc tat aaa tcc     1135
Phe Ala Ala Thr Leu Thr Thr Ser Ile Lys Asn Gly Ser Tyr Lys Ser
            175                 180                 185

ctc aaa gcg tcc tgg ctc gac ggc atc gac ata tcc gac ccc gtc agc     1183
Leu Lys Ala Ser Trp Leu Asp Gly Ile Asp Ile Ser Asp Pro Val Ser
        190                 195                 200

tcg gcc acg gat tgg gct tcg gac gcc aat gct tat gtc tgc agc acg     1231
Ser Ala Thr Asp Trp Ala Ser Asp Ala Asn Ala Tyr Val Cys Ser Thr
    205                 210                 215

gtc ctg ccc aat ggt att tca gcg gtc gaa aat acg gat ctg tca ggt     1279
Val Leu Pro Asn Gly Ile Ser Ala Val Glu Asn Thr Asp Leu Ser Gly
220                 225                 230                 235

gcg tac tat acg aag gct att ccg gtt gtg gag ttg cag atc gcc aaa     1327
Ala Tyr Tyr Thr Lys Ala Ile Pro Val Val Glu Leu Gln Ile Ala Lys
                240                 245                 250

gcg ggg tat ag  gtatgtctga ttagattttc ttggtgtttt ccaaaggggg         1378
Ala Gly Tyr Arg
            255

tatacctgct aatgtctgca g g ttg gcg gct tgg ttg gat ctc att gct act   1430
                          Leu Ala Ala Trp Leu Asp Leu Ile Ala Thr
                                          260                 265

ggt agt act aga ctt taa                                             1448
Gly Ser Thr Arg Leu
                270


<210> SEQ ID NO 62
<211> LENGTH: 291
<212> TYPE: PRT
<213> ORGANISM: Lachnellula sp

<400> SEQUENCE: 62

Met Lys Thr Gln Ala Val Ala Ser Ile Phe Phe Leu Ala Thr Ser Leu
    -20                 -15                 -10

Pro Ser Ala Leu Gly Trp Gly Thr Leu Gly His Gln Thr Val Ala Tyr
-5              -1  1               5                   10

Ile Ala Thr Asn Phe Val Ser Ser Ala Thr Lys Thr Lys Phe Gln Ser
            15                  20                  25
```

Ile Leu Asp Asp Thr Ser Thr Asp Tyr Leu Ala Ser Val Ala Thr Trp
30 35 40

Ala Asp Thr Tyr Arg Tyr Thr Asp Ala Gly Thr Trp Thr Ala Pro Phe
45 50 55

His Phe Ile Asp Ala Asn Asp Asp Pro Pro Ser Ser Cys Ser Val Asp
60 65 70 75

Tyr Ser Arg Asp Cys Gly Thr Gly Gly Cys Val Ile Ser Ala Ile Asn
80 85 90

Asn Tyr Thr Ser Arg Ile Gln Ser Thr Thr Leu Ser Asp Ala Glu Val
95 100 105

Lys Thr Ala Ala Lys Phe Ile Val His Phe Ile Gly Asp Ile His Gln
110 115 120

Pro Leu His Asp Glu Gly Leu Asp Leu Gly Gly Asn Glu Ile Asp Val
125 130 135

Thr Phe Asp Gly Glu Ser Thr Asn Leu His His Ile Trp Asp Thr Asn
140 145 150 155

Ile Pro Glu Lys Tyr Val Gly Gly Tyr Ala Leu Ser Asp Ala Lys Ser
160 165 170

Phe Ala Ala Thr Leu Thr Thr Ser Ile Lys Asn Gly Ser Tyr Lys Ser
175 180 185

Leu Lys Ala Ser Trp Leu Asp Gly Ile Asp Ile Ser Asp Pro Val Ser
190 195 200

Ser Ala Thr Asp Trp Ala Ser Asp Ala Asn Ala Tyr Val Cys Ser Thr
205 210 215

Val Leu Pro Asn Gly Ile Ser Ala Val Glu Asn Thr Asp Leu Ser Gly
220 225 230 235

Ala Tyr Tyr Thr Lys Ala Ile Pro Val Val Glu Leu Gln Ile Ala Lys
240 245 250

Ala Gly Tyr Arg Leu Ala Ala Trp Leu Asp Leu Ile Ala Thr Gly Ser
255 260 265

Thr Arg Leu
270

<210> SEQ ID NO 63
<211> LENGTH: 270
<212> TYPE: PRT
<213> ORGANISM: Lachnellula sp

<400> SEQUENCE: 63

Trp Gly Thr Leu Gly His Gln Thr Val Ala Tyr Ile Ala Thr Asn Phe
1 5 10 15

Val Ser Ser Ala Thr Lys Thr Lys Phe Gln Ser Ile Leu Asp Asp Thr
20 25 30

Ser Thr Asp Tyr Leu Ala Ser Val Ala Thr Trp Ala Asp Thr Tyr Arg
35 40 45

Tyr Thr Asp Ala Gly Thr Trp Thr Ala Pro Phe His Phe Ile Asp Ala
50 55 60

Asn Asp Asp Pro Pro Ser Ser Cys Ser Val Asp Tyr Ser Arg Asp Cys
65 70 75 80

Gly Thr Gly Gly Cys Val Ile Ser Ala Ile Asn Asn Tyr Thr Ser Arg
85 90 95

Ile Gln Ser Thr Thr Leu Ser Asp Ala Glu Val Lys Thr Ala Ala Lys
100 105 110

Phe Ile Val His Phe Ile Gly Asp Ile His Gln Pro Leu His Asp Glu

```
        115                 120                 125

Gly Leu Asp Leu Gly Gly Asn Glu Ile Asp Val Thr Phe Asp Gly Glu
    130                 135                 140

Ser Thr Asn Leu His His Ile Trp Asp Thr Asn Ile Pro Glu Lys Tyr
145                 150                 155                 160

Val Gly Gly Tyr Ala Leu Ser Asp Ala Lys Ser Phe Ala Ala Thr Leu
                165                 170                 175

Thr Thr Ser Ile Lys Asn Gly Ser Tyr Lys Ser Leu Lys Ala Ser Trp
            180                 185                 190

Leu Asp Gly Ile Asp Ile Ser Asp Pro Val Ser Ser Ala Thr Asp Trp
        195                 200                 205

Ala Ser Asp Ala Asn Ala Tyr Val Cys Ser Thr Val Leu Pro Asn Gly
    210                 215                 220

Ile Ser Ala Val Glu Asn Thr Asp Leu Ser Gly Ala Tyr Tyr Thr Lys
225                 230                 235                 240

Ala Ile Pro Val Val Glu Leu Gln Ile Ala Lys Ala Gly Tyr Arg Leu
                245                 250                 255

Ala Ala Trp Leu Asp Leu Ile Ala Thr Gly Ser Thr Arg Leu
            260                 265                 270


<210> SEQ ID NO 64
<211> LENGTH: 1119
<212> TYPE: DNA
<213> ORGANISM: Trichoderma reesei
<220> FEATURE:
<221> NAME/KEY: CDS
<222> LOCATION: (1)..(64)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1116)
<220> FEATURE:
<221> NAME/KEY: CDS
<222> LOCATION: (145)..(798)
<220> FEATURE:
<221> NAME/KEY: CDS
<222> LOCATION: (854)..(1116)

<400> SEQUENCE: 64

atg aag ctc tca aat gcc gtc gcc ttc agc ctc gtc tcc ctg ccg ggg       48
Met Lys Leu Ser Asn Ala Val Ala Phe Ser Leu Val Ser Leu Pro Gly
                -15                 -10                 -5

gct atg gcc tgg gga g gtgtgtatcg tctttccccc ccgtgacaca cattgtcaac    104
Ala Met Ala Trp Gly
        -1  1

accatcaacg ctagtctaac actcgtcttc ctcgcatcag gt  ctc ggc cac atc      158
                                            Gly Leu Gly His Ile
                                                    5

acg acc gcc tac att gcc agc aac ttc gtc tcc aac tcg acc gag gcc      206
Thr Thr Ala Tyr Ile Ala Ser Asn Phe Val Ser Asn Ser Thr Glu Ala
        10                  15                  20

tac ctg aag cag ctc ctg cgc agc aat gag tcc gac tac atg gcc aag      254
Tyr Leu Lys Gln Leu Leu Arg Ser Asn Glu Ser Asp Tyr Met Ala Lys
    25                  30                  35

gta gcc agc tgg gcc gat tcg atc cga tac acg aaa tgg ggc agg ttc      302
Val Ala Ser Trp Ala Asp Ser Ile Arg Tyr Thr Lys Trp Gly Arg Phe
40                  45                  50                  55

acg agc acg ttc cac ttc atc gac gcg cac gac aac ccg ccc gag tcg      350
Thr Ser Thr Phe His Phe Ile Asp Ala His Asp Asn Pro Pro Glu Ser
                60                  65                  70
```

```
tgc aac gtc gac ttt gag cgc gac tgc aag gag acg ggc tgc gtc atc      398
Cys Asn Val Asp Phe Glu Arg Asp Cys Lys Glu Thr Gly Cys Val Ile
            75                  80                  85

acc gcg ctg gcc aac tac acc gag cag tcg ctc gat ccc gcg ctg ccg      446
Thr Ala Leu Ala Asn Tyr Thr Glu Gln Ser Leu Asp Pro Ala Leu Pro
        90                  95                  100

gcg tgg cgg cgc gcc cag gcg gcc aag ttc gtc atc cac ttc gtc ggc      494
Ala Trp Arg Arg Ala Gln Ala Ala Lys Phe Val Ile His Phe Val Gly
    105                 110                 115

gac ctg cac cag ccg ctg cac aac gag gac gtt tcg agg ggc gga aac      542
Asp Leu His Gln Pro Leu His Asn Glu Asp Val Ser Arg Gly Gly Asn
120                 125                 130                 135

ggc atc cac gtc aag tgg gat gga cga gac tac aac ctg cac cac gtc      590
Gly Ile His Val Lys Trp Asp Gly Arg Asp Tyr Asn Leu His His Val
                140                 145                 150

tgg gac agc tcc att gcg gag aag ctg att ggg cgc ggg aag ccg tat      638
Trp Asp Ser Ser Ile Ala Glu Lys Leu Ile Gly Arg Gly Lys Pro Tyr
            155                 160                 165

ctc gtg gcg cag aag tgg tct gct gcc ctc acc gag aaa att act ggc      686
Leu Val Ala Gln Lys Trp Ser Ala Ala Leu Thr Glu Lys Ile Thr Gly
        170                 175                 180

ggc gcg tat gcc gac gag aag gag act tgg ctg gca gac ttg gat ttt      734
Gly Ala Tyr Ala Asp Glu Lys Glu Thr Trp Leu Ala Asp Leu Asp Phe
    185                 190                 195

ggc gac ttt gag gct acg gca atg gcc tgg tcg cgg gaa tgc aac agc      782
Gly Asp Phe Glu Ala Thr Ala Met Ala Trp Ser Arg Glu Cys Asn Ser
200                 205                 210                 215

ctc gta tgc gaa tat g gtaagctcta ccttgagtat gcttcaaact gcaaagttat    838
Leu Val Cys Glu Tyr
                220

cttaccagct tttag tc  ttc ccc gag ggc ccc aaa gcc atc gtc ggc cag      888
                 Val Phe Pro Glu Gly Pro Lys Ala Ile Val Gly Gln
                                 225                 230

gaa cta agc ggc gag tat tat gaa aag gcg gct cct atc ctc gag aag      936
Glu Leu Ser Gly Glu Tyr Tyr Glu Lys Ala Ala Pro Ile Leu Glu Lys
        235                 240                 245

cag gtc gcc cgc gca ggt tat cga atg gct gca tgg ctc gat cgc att      984
Gln Val Ala Arg Ala Gly Tyr Arg Met Ala Ala Trp Leu Asp Arg Ile
    250                 255                 260

gtg gat gag tac aag aag aga gag gcc agc tat acc ggc gaa ttg ccc     1032
Val Asp Glu Tyr Lys Lys Arg Glu Ala Ser Tyr Thr Gly Glu Leu Pro
265                 270                 275                 280

acg gac gac tat gcc gag gag cct ctt gat gag ttt gac ctc gag ctt     1080
Thr Asp Asp Tyr Ala Glu Glu Pro Leu Asp Glu Phe Asp Leu Glu Leu
                285                 290                 295

cta gac gag acg gag aag ccc ttt gtt gga gag ttg taa                 1119
Leu Asp Glu Thr Glu Lys Pro Phe Val Gly Glu Leu
            300                 305
```

<210> SEQ ID NO 65
<211> LENGTH: 327
<212> TYPE: PRT
<213> ORGANISM: Trichoderma reesei

<400> SEQUENCE: 65

```
Met Lys Leu Ser Asn Ala Val Ala Phe Ser Leu Val Ser Leu Pro Gly
                -15                 -10                 -5

Ala Met Ala Trp Gly Gly Leu Gly His Ile Thr Thr Ala Tyr Ile Ala
        -1  1               5                   10
```

```
Ser Asn Phe Val Ser Asn Ser Thr Glu Ala Tyr Leu Lys Gln Leu Leu
    15                  20                  25

Arg Ser Asn Glu Ser Asp Tyr Met Ala Lys Val Ala Ser Trp Ala Asp
30                  35                  40                  45

Ser Ile Arg Tyr Thr Lys Trp Gly Arg Phe Thr Ser Thr Phe His Phe
                50                  55                  60

Ile Asp Ala His Asp Asn Pro Pro Glu Ser Cys Asn Val Asp Phe Glu
            65                  70                  75

Arg Asp Cys Lys Glu Thr Gly Cys Val Ile Thr Ala Leu Ala Asn Tyr
        80                  85                  90

Thr Glu Gln Ser Leu Asp Pro Ala Leu Pro Ala Trp Arg Arg Ala Gln
    95                  100                 105

Ala Ala Lys Phe Val Ile His Phe Val Gly Asp Leu His Gln Pro Leu
110                 115                 120                 125

His Asn Glu Asp Val Ser Arg Gly Gly Asn Gly Ile His Val Lys Trp
                130                 135                 140

Asp Gly Arg Asp Tyr Asn Leu His His Val Trp Asp Ser Ser Ile Ala
            145                 150                 155

Glu Lys Leu Ile Gly Arg Gly Lys Pro Tyr Leu Val Ala Gln Lys Trp
        160                 165                 170

Ser Ala Ala Leu Thr Glu Lys Ile Thr Gly Gly Ala Tyr Ala Asp Glu
    175                 180                 185

Lys Glu Thr Trp Leu Ala Asp Leu Asp Phe Gly Asp Phe Glu Ala Thr
190                 195                 200                 205

Ala Met Ala Trp Ser Arg Glu Cys Asn Ser Leu Val Cys Glu Tyr Val
                210                 215                 220

Phe Pro Glu Gly Pro Lys Ala Ile Val Gly Gln Glu Leu Ser Gly Glu
            225                 230                 235

Tyr Tyr Glu Lys Ala Ala Pro Ile Leu Glu Lys Gln Val Ala Arg Ala
        240                 245                 250

Gly Tyr Arg Met Ala Ala Trp Leu Asp Arg Ile Val Asp Glu Tyr Lys
    255                 260                 265

Lys Arg Glu Ala Ser Tyr Thr Gly Glu Leu Pro Thr Asp Asp Tyr Ala
270                 275                 280                 285

Glu Glu Pro Leu Asp Glu Phe Asp Leu Glu Leu Leu Asp Glu Thr Glu
                290                 295                 300

Lys Pro Phe Val Gly Glu Leu
            305
```

<210> SEQ ID NO 66
<211> LENGTH: 308
<212> TYPE: PRT
<213> ORGANISM: Trichoderma reesei

<400> SEQUENCE: 66

```
Trp Gly Gly Leu Gly His Ile Thr Thr Ala Tyr Ile Ala Ser Asn Phe
1               5                   10                  15

Val Ser Asn Ser Thr Glu Ala Tyr Leu Lys Gln Leu Leu Arg Ser Asn
            20                  25                  30

Glu Ser Asp Tyr Met Ala Lys Val Ala Ser Trp Ala Asp Ser Ile Arg
        35                  40                  45

Tyr Thr Lys Trp Gly Arg Phe Thr Ser Thr Phe His Phe Ile Asp Ala
    50                  55                  60

His Asp Asn Pro Pro Glu Ser Cys Asn Val Asp Phe Glu Arg Asp Cys
65                  70                  75                  80
```

```
Lys Glu Thr Gly Cys Val Ile Thr Ala Leu Ala Asn Tyr Thr Glu Gln
                85                  90                  95

Ser Leu Asp Pro Ala Leu Pro Ala Trp Arg Arg Ala Gln Ala Ala Lys
            100                 105                 110

Phe Val Ile His Phe Val Gly Asp Leu His Gln Pro Leu His Asn Glu
        115                 120                 125

Asp Val Ser Arg Gly Gly Asn Gly Ile His Val Lys Trp Asp Gly Arg
    130                 135                 140

Asp Tyr Asn Leu His His Val Trp Asp Ser Ser Ile Ala Glu Lys Leu
145                 150                 155                 160

Ile Gly Arg Gly Lys Pro Tyr Leu Val Ala Gln Lys Trp Ser Ala Ala
                165                 170                 175

Leu Thr Glu Lys Ile Thr Gly Gly Ala Tyr Ala Asp Glu Lys Glu Thr
            180                 185                 190

Trp Leu Ala Asp Leu Asp Phe Gly Asp Phe Glu Ala Thr Ala Met Ala
        195                 200                 205

Trp Ser Arg Glu Cys Asn Ser Leu Val Cys Glu Tyr Val Phe Pro Glu
    210                 215                 220

Gly Pro Lys Ala Ile Val Gly Gln Glu Leu Ser Gly Glu Tyr Tyr Glu
225                 230                 235                 240

Lys Ala Ala Pro Ile Leu Glu Lys Gln Val Ala Arg Ala Gly Tyr Arg
                245                 250                 255

Met Ala Ala Trp Leu Asp Arg Ile Val Asp Glu Tyr Lys Lys Arg Glu
            260                 265                 270

Ala Ser Tyr Thr Gly Glu Leu Pro Thr Asp Asp Tyr Ala Glu Glu Pro
        275                 280                 285

Leu Asp Glu Phe Asp Leu Glu Leu Leu Asp Glu Thr Glu Lys Pro Phe
    290                 295                 300

Val Gly Glu Leu
305


<210> SEQ ID NO 67
<211> LENGTH: 1067
<212> TYPE: DNA
<213> ORGANISM: Cordyceps cardinalis
<220> FEATURE:
<221> NAME/KEY: CDS
<222> LOCATION: (1)..(64)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1064)
<220> FEATURE:
<221> NAME/KEY: CDS
<222> LOCATION: (134)..(793)
<220> FEATURE:
<221> NAME/KEY: CDS
<222> LOCATION: (868)..(1064)

<400> SEQUENCE: 67

atg aga ttc acc gcc gct gcc tca tat ggc ctc ctc tcg ctc cct gca       48
Met Arg Phe Thr Ala Ala Ala Ser Tyr Gly Leu Leu Ser Leu Pro Ala
                -15                 -10                 -5

gcc tct gcc tgg gga a gtacgttgtc gaccccgcgg aaatatgatg gcaacacgtc    104
Ala Ser Ala Trp Gly
        -1  1

atgccgaaaa ttgctaacat gctcattag gt  ctt ggg cac att acc acc gcg      156
                                Ser Leu Gly His Ile Thr Thr Ala
```

```
                                5                   10

tac ata gcc agc aac ttt gtc tcc aac acc act gaa gcc tat ctc aag      204
Tyr Ile Ala Ser Asn Phe Val Ser Asn Thr Thr Glu Ala Tyr Leu Lys
                15                  20                  25

gac att ctc atg cgc aat gac gag gac tat cta tct tct ata gcc agc      252
Asp Ile Leu Met Arg Asn Asp Glu Asp Tyr Leu Ser Ser Ile Ala Ser
            30                  35                  40

tgg gct gat tcc ata cgg tac acc aaa tgg ggc cgc ttc acc agc acc      300
Trp Ala Asp Ser Ile Arg Tyr Thr Lys Trp Gly Arg Phe Thr Ser Thr
        45                  50                  55

ttt cac ttc atc gac tcc cac gac aac ccc cct cac tcg tgc acc gtg      348
Phe His Phe Ile Asp Ser His Asp Asn Pro Pro His Ser Cys Thr Val
    60                  65                  70

gac ctt gag cgc gac tgc aag gag aca ggc tgc gtc atc tcg gcc ctc      396
Asp Leu Glu Arg Asp Cys Lys Glu Thr Gly Cys Val Ile Ser Ala Leu
75                  80                  85                  90

gcc aac tat acc gag cag gtc tac gac cac gcg ctg ccc gcc tgg cgc      444
Ala Asn Tyr Thr Glu Gln Val Tyr Asp His Ala Leu Pro Ala Trp Arg
                95                  100                 105

cgc gcg cag gcc gcc aag ttc gtc gtg cac ttt gtc ggc gac ctg cac      492
Arg Ala Gln Ala Ala Lys Phe Val Val His Phe Val Gly Asp Leu His
            110                 115                 120

cag ccg ctg cac aac gag gac gtc gcc aag ggc ggc aac ggc atc cac      540
Gln Pro Leu His Asn Glu Asp Val Ala Lys Gly Gly Asn Gly Ile His
        125                 130                 135

gtc ctc tgg gac ggc cgc ggc tac aac ctg cac cac gtc tgg gat agc      588
Val Leu Trp Asp Gly Arg Gly Tyr Asn Leu His His Val Trp Asp Ser
    140                 145                 150

tcc atc ctg gag aag tgg ctg ggc ggc ctg cgc ggc aag ccc tac gcg      636
Ser Ile Leu Glu Lys Trp Leu Gly Gly Leu Arg Gly Lys Pro Tyr Ala
155                 160                 165                 170

ctg gcc aag cgg tgg gcg gcg cag ctc acg gaa gaa atc acc gac ggc      684
Leu Ala Lys Arg Trp Ala Ala Gln Leu Thr Glu Glu Ile Thr Asp Gly
                175                 180                 185

aag tgg gcg cga gag aag gac ggc tgg ctg aag gac gtc agg ttg gat      732
Lys Trp Ala Arg Glu Lys Asp Gly Trp Leu Lys Asp Val Arg Leu Asp
            190                 195                 200

aat gca aac ggt acg gcg ctg gcg tgg tcg cgc gag acg aat gcc att      780
Asn Ala Asn Gly Thr Ala Leu Ala Trp Ser Arg Glu Thr Asn Ala Ile
        205                 210                 215

gtc tgt tca cat g gtgagttgct ccttttgtct tgagtaccgc ggggcttcgt        833
Val Cys Ser His
    220

ttggggggcg gacgatttcg gctaacggaa ccag tg  ttt ccc cag ggt cca gag    887
                                       Val Phe Pro Gln Gly Pro Glu
                                               225

gcc ata agg ggc caa gag ctg gga ggc aaa tac tat gaa gaa gca gca      935
Ala Ile Arg Gly Gln Glu Leu Gly Gly Lys Tyr Tyr Glu Glu Ala Ala
230                 235                 240                 245

cct gtt ttg gaa agg cag gtc gct cgg gct gga tat aga atg gct gct      983
Pro Val Leu Glu Arg Gln Val Ala Arg Ala Gly Tyr Arg Met Ala Ala
                250                 255                 260

tgg ctt gac gag att gcc aat gag tat cac ggc cag agg agt atc gcc     1031
Trp Leu Asp Glu Ile Ala Asn Glu Tyr His Gly Gln Arg Ser Ile Ala
            265                 270                 275

aag gtc gac gcg gag ctg gcc caa cta gaa ttg tga                     1067
Lys Val Asp Ala Glu Leu Ala Gln Leu Glu Leu
        280                 285
```

```
<210> SEQ ID NO 68
<211> LENGTH: 307
<212> TYPE: PRT
<213> ORGANISM: Cordyceps cardinalis

<400> SEQUENCE: 68

Met Arg Phe Thr Ala Ala Ala Ser Tyr Gly Leu Leu Ser Leu Pro Ala
                -15                 -10                 -5

Ala Ser Ala Trp Gly Ser Leu Gly His Ile Thr Thr Ala Tyr Ile Ala
        -1  1               5                   10

Ser Asn Phe Val Ser Asn Thr Thr Glu Ala Tyr Leu Lys Asp Ile Leu
    15                  20                  25

Met Arg Asn Asp Glu Asp Tyr Leu Ser Ser Ile Ala Ser Trp Ala Asp
30                  35                  40                  45

Ser Ile Arg Tyr Thr Lys Trp Gly Arg Phe Thr Ser Thr Phe His Phe
                50                  55                  60

Ile Asp Ser His Asp Asn Pro Pro His Ser Cys Thr Val Asp Leu Glu
            65                  70                  75

Arg Asp Cys Lys Glu Thr Gly Cys Val Ile Ser Ala Leu Ala Asn Tyr
        80                  85                  90

Thr Glu Gln Val Tyr Asp His Ala Leu Pro Ala Trp Arg Arg Ala Gln
    95                  100                 105

Ala Ala Lys Phe Val Val His Phe Val Gly Asp Leu His Gln Pro Leu
110                 115                 120                 125

His Asn Glu Asp Val Ala Lys Gly Gly Asn Gly Ile His Val Leu Trp
                130                 135                 140

Asp Gly Arg Gly Tyr Asn Leu His His Val Trp Asp Ser Ser Ile Leu
            145                 150                 155

Glu Lys Trp Leu Gly Gly Leu Arg Gly Lys Pro Tyr Ala Leu Ala Lys
        160                 165                 170

Arg Trp Ala Ala Gln Leu Thr Glu Glu Ile Thr Asp Gly Lys Trp Ala
    175                 180                 185

Arg Glu Lys Asp Gly Trp Leu Lys Asp Val Arg Leu Asp Asn Ala Asn
190                 195                 200                 205

Gly Thr Ala Leu Ala Trp Ser Arg Glu Thr Asn Ala Ile Val Cys Ser
                210                 215                 220

His Val Phe Pro Gln Gly Pro Glu Ala Ile Arg Gly Gln Glu Leu Gly
            225                 230                 235

Gly Lys Tyr Tyr Glu Glu Ala Ala Pro Val Leu Glu Arg Gln Val Ala
        240                 245                 250

Arg Ala Gly Tyr Arg Met Ala Ala Trp Leu Asp Glu Ile Ala Asn Glu
    255                 260                 265

Tyr His Gly Gln Arg Ser Ile Ala Lys Val Asp Ala Glu Leu Ala Gln
270                 275                 280                 285

Leu Glu Leu


<210> SEQ ID NO 69
<211> LENGTH: 288
<212> TYPE: PRT
<213> ORGANISM: Cordyceps cardinalis

<400> SEQUENCE: 69

Trp Gly Ser Leu Gly His Ile Thr Thr Ala Tyr Ile Ala Ser Asn Phe
1               5                   10                  15

Val Ser Asn Thr Thr Glu Ala Tyr Leu Lys Asp Ile Leu Met Arg Asn
            20                  25                  30
```

```
Asp Glu Asp Tyr Leu Ser Ser Ile Ala Ser Trp Ala Asp Ser Ile Arg
        35                  40                  45

Tyr Thr Lys Trp Gly Arg Phe Thr Ser Thr Phe His Phe Ile Asp Ser
    50                  55                  60

His Asp Asn Pro Pro His Ser Cys Thr Val Asp Leu Glu Arg Asp Cys
65                  70                  75                  80

Lys Glu Thr Gly Cys Val Ile Ser Ala Leu Ala Asn Tyr Thr Glu Gln
                85                  90                  95

Val Tyr Asp His Ala Leu Pro Ala Trp Arg Arg Ala Gln Ala Ala Lys
            100                 105                 110

Phe Val Val His Phe Val Gly Asp Leu His Gln Pro Leu His Asn Glu
        115                 120                 125

Asp Val Ala Lys Gly Gly Asn Gly Ile His Val Leu Trp Asp Gly Arg
    130                 135                 140

Gly Tyr Asn Leu His His Val Trp Asp Ser Ser Ile Leu Glu Lys Trp
145                 150                 155                 160

Leu Gly Gly Leu Arg Gly Lys Pro Tyr Ala Leu Ala Lys Arg Trp Ala
                165                 170                 175

Ala Gln Leu Thr Glu Glu Ile Thr Asp Gly Lys Trp Ala Arg Glu Lys
            180                 185                 190

Asp Gly Trp Leu Lys Asp Val Arg Leu Asp Asn Ala Asn Gly Thr Ala
        195                 200                 205

Leu Ala Trp Ser Arg Glu Thr Asn Ala Ile Val Cys Ser His Val Phe
    210                 215                 220

Pro Gln Gly Pro Glu Ala Ile Arg Gly Gln Glu Leu Gly Gly Lys Tyr
225                 230                 235                 240

Tyr Glu Glu Ala Ala Pro Val Leu Glu Arg Gln Val Ala Arg Ala Gly
                245                 250                 255

Tyr Arg Met Ala Ala Trp Leu Asp Glu Ile Ala Asn Glu Tyr His Gly
            260                 265                 270

Gln Arg Ser Ile Ala Lys Val Asp Ala Glu Leu Ala Gln Leu Glu Leu
        275                 280                 285


<210> SEQ ID NO 70
<211> LENGTH: 1103
<212> TYPE: DNA
<213> ORGANISM: Acremonium alcalophilum
<220> FEATURE:
<221> NAME/KEY: CDS
<222> LOCATION: (1)..(64)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1100)
<220> FEATURE:
<221> NAME/KEY: CDS
<222> LOCATION: (129)..(788)
<220> FEATURE:
<221> NAME/KEY: CDS
<222> LOCATION: (913)..(1100)

<400> SEQUENCE: 70

atg agg ttc ctc tcg ata tta acg gta ctc ggc gca tcg gcc tac gga       48
Met Arg Phe Leu Ser Ile Leu Thr Val Leu Gly Ala Ser Ala Tyr Gly
                -15                 -10                 -5

gct tta gca tgg gga a gtgagtgatc cgcagccgct acgccgatcc gtcgaaaaca    104
Ala Leu Ala Trp Gly
        -1  1
```

```
ctgctcacaa acgcgtacca tcag gt  ctc ggt cac gtc acg aca gct tac       154
                              Ser Leu Gly His Val Thr Thr Ala Tyr
                                      5                   10

cta gcc agt cac ctc gtc tcc aac tcg acc gaa gcg ttc ttt cag aat      202
Leu Ala Ser His Leu Val Ser Asn Ser Thr Glu Ala Phe Phe Gln Asn
            15                  20                  25

ctc ctg cgc gac gaa acg agc gat tac ctc ggc aaa gtg gcc acg tgg      250
Leu Leu Arg Asp Glu Thr Ser Asp Tyr Leu Gly Lys Val Ala Thr Trp
        30                  35                  40

gcc gac acc atc cgc tac acg cgc tgg ggc cgg ttc acg agc gtc ttc      298
Ala Asp Thr Ile Arg Tyr Thr Arg Trp Gly Arg Phe Thr Ser Val Phe
    45                  50                  55

cac ttc atc gac gcc aag gac gag ccc cct acg tac tgc ggc gtc gaa      346
His Phe Ile Asp Ala Lys Asp Glu Pro Pro Thr Tyr Cys Gly Val Glu
60                  65                  70                  75

ctc gcc cgc gac tgc aag ccc gag ggc tgc gtc gtc acg gcc cta gcg      394
Leu Ala Arg Asp Cys Lys Pro Glu Gly Cys Val Val Thr Ala Leu Ala
                80                  85                  90

aac tat acg gcc cgg ctc ctc gac ccg gag ctg ccg gct tgg gag cgc      442
Asn Tyr Thr Ala Arg Leu Leu Asp Pro Glu Leu Pro Ala Trp Glu Arg
            95                  100                 105

aac cag gcc gcc cgc ttc gtt gtc cac ttt gtc ggc gac atc cac cag      490
Asn Gln Ala Ala Arg Phe Val Val His Phe Val Gly Asp Ile His Gln
        110                 115                 120

ccg ttg cac gat gag aac gtg gcc cgt ggc ggg aac ggc atc tac gtg      538
Pro Leu His Asp Glu Asn Val Ala Arg Gly Gly Asn Gly Ile Tyr Val
    125                 130                 135

ctg tgg cag ggc cgc cga ttc aac ctc cat tat gtc tgg gat agc gcc      586
Leu Trp Gln Gly Arg Arg Phe Asn Leu His Tyr Val Trp Asp Ser Ala
140                 145                 150                 155

att gcc gag cgg ctg att ggg cgg aat cgc cgg aag ccg tat gac aat      634
Ile Ala Glu Arg Leu Ile Gly Arg Asn Arg Arg Lys Pro Tyr Asp Asn
                160                 165                 170

gcg aag tgg tgg gcg gaa gag ctt gcc gtc cag atc cgg gag ggc aag      682
Ala Lys Trp Trp Ala Glu Glu Leu Ala Val Gln Ile Arg Glu Gly Lys
            175                 180                 185

ttt gtc gag gag aag gag ggt tgg ttg aag gat gtt gac att gat gat      730
Phe Val Glu Glu Lys Glu Gly Trp Leu Lys Asp Val Asp Ile Asp Asp
        190                 195                 200

gcg act gcg acg gcg ctg gca tgg gct cgg gaa ggc aac gcc tat gtc      778
Ala Thr Ala Thr Ala Leu Ala Trp Ala Arg Glu Gly Asn Ala Tyr Val
    205                 210                 215

tgt tcg cac g gtgagtattt tttctttctt cgttctttct gtcttttctg            828
Cys Ser His
220

atgctgctga gcttgatgga atacttatcc tccccccttc tgccgtgtga cgttgacaac    888

agctgatcgt cctgcgtttc gtag tg  ttg cca gaa ggc cct ctt gcc atc       938
                              Val Leu Pro Glu Gly Pro Leu Ala Ile
                                      225                 230

gag gga cag gaa ctc agc gga gag tac tat gat aag gcg gcc ccc gtt      986
Glu Gly Gln Glu Leu Ser Gly Glu Tyr Tyr Asp Lys Ala Ala Pro Val
            235                 240                 245

gtt gag ttg cag att gcc cgt gcc ggg tac cgg atg gct gcc tgg cta     1034
Val Glu Leu Gln Ile Ala Arg Ala Gly Tyr Arg Met Ala Ala Trp Leu
        250                 255                 260

gat ctc att gcg agg cgg ttc cag gag caa gga gcc gag agg gag gaa     1082
Asp Leu Ile Ala Arg Arg Phe Gln Glu Gln Gly Ala Glu Arg Glu Glu
    265                 270                 275
```

```
gat ctt tgg gag gag cta taa                                          1103
Asp Leu Trp Glu Glu Leu
280                 285


<210> SEQ ID NO 71
<211> LENGTH: 304
<212> TYPE: PRT
<213> ORGANISM: Acremonium alcalophilum

<400> SEQUENCE: 71

Met Arg Phe Leu Ser Ile Leu Thr Val Leu Gly Ala Ser Ala Tyr Gly
                -15                 -10                 -5

Ala Leu Ala Trp Gly Ser Leu Gly His Val Thr Thr Ala Tyr Leu Ala
        -1  1               5                   10

Ser His Leu Val Ser Asn Ser Thr Glu Ala Phe Phe Gln Asn Leu Leu
    15                  20                  25

Arg Asp Glu Thr Ser Asp Tyr Leu Gly Lys Val Ala Thr Trp Ala Asp
30                  35                  40                  45

Thr Ile Arg Tyr Thr Arg Trp Gly Arg Phe Thr Ser Val Phe His Phe
                50                  55                  60

Ile Asp Ala Lys Asp Glu Pro Pro Thr Tyr Cys Gly Val Glu Leu Ala
            65                  70                  75

Arg Asp Cys Lys Pro Glu Gly Cys Val Val Thr Ala Leu Ala Asn Tyr
        80                  85                  90

Thr Ala Arg Leu Leu Asp Pro Glu Leu Pro Ala Trp Glu Arg Asn Gln
    95                  100                 105

Ala Ala Arg Phe Val Val His Phe Val Gly Asp Ile His Gln Pro Leu
110                 115                 120                 125

His Asp Glu Asn Val Ala Arg Gly Gly Asn Gly Ile Tyr Val Leu Trp
                130                 135                 140

Gln Gly Arg Arg Phe Asn Leu His Tyr Val Trp Asp Ser Ala Ile Ala
            145                 150                 155

Glu Arg Leu Ile Gly Arg Asn Arg Arg Lys Pro Tyr Asp Asn Ala Lys
        160                 165                 170

Trp Trp Ala Glu Glu Leu Ala Val Gln Ile Arg Glu Gly Lys Phe Val
    175                 180                 185

Glu Glu Lys Glu Gly Trp Leu Lys Asp Val Asp Ile Asp Asp Ala Thr
190                 195                 200                 205

Ala Thr Ala Leu Ala Trp Ala Arg Glu Gly Asn Ala Tyr Val Cys Ser
                210                 215                 220

His Val Leu Pro Glu Gly Pro Leu Ala Ile Glu Gly Gln Glu Leu Ser
            225                 230                 235

Gly Glu Tyr Tyr Asp Lys Ala Ala Pro Val Val Glu Leu Gln Ile Ala
        240                 245                 250

Arg Ala Gly Tyr Arg Met Ala Ala Trp Leu Asp Leu Ile Ala Arg Arg
    255                 260                 265

Phe Gln Glu Gln Gly Ala Glu Arg Glu Glu Asp Leu Trp Glu Glu Leu
270                 275                 280                 285


<210> SEQ ID NO 72
<211> LENGTH: 285
<212> TYPE: PRT
<213> ORGANISM: Acremonium alcalophilum

<400> SEQUENCE: 72

Trp Gly Ser Leu Gly His Val Thr Thr Ala Tyr Leu Ala Ser His Leu
1               5                   10                  15
```

```
Val Ser Asn Ser Thr Glu Ala Phe Phe Gln Asn Leu Leu Arg Asp Glu
            20                  25                  30

Thr Ser Asp Tyr Leu Gly Lys Val Ala Thr Trp Ala Asp Thr Ile Arg
        35                  40                  45

Tyr Thr Arg Trp Gly Arg Phe Thr Ser Val Phe His Phe Ile Asp Ala
    50                  55                  60

Lys Asp Glu Pro Pro Thr Tyr Cys Gly Val Glu Leu Ala Arg Asp Cys
65                  70                  75                  80

Lys Pro Glu Gly Cys Val Val Thr Ala Leu Ala Asn Tyr Thr Ala Arg
                85                  90                  95

Leu Leu Asp Pro Glu Leu Pro Ala Trp Glu Arg Asn Gln Ala Ala Arg
            100                 105                 110

Phe Val Val His Phe Val Gly Asp Ile His Gln Pro Leu His Asp Glu
        115                 120                 125

Asn Val Ala Arg Gly Gly Asn Gly Ile Tyr Val Leu Trp Gln Gly Arg
    130                 135                 140

Arg Phe Asn Leu His Tyr Val Trp Asp Ser Ala Ile Ala Glu Arg Leu
145                 150                 155                 160

Ile Gly Arg Asn Arg Arg Lys Pro Tyr Asp Asn Ala Lys Trp Trp Ala
                165                 170                 175

Glu Glu Leu Ala Val Gln Ile Arg Glu Gly Lys Phe Val Glu Glu Lys
            180                 185                 190

Glu Gly Trp Leu Lys Asp Val Asp Ile Asp Asp Ala Thr Ala Thr Ala
        195                 200                 205

Leu Ala Trp Ala Arg Glu Gly Asn Ala Tyr Val Cys Ser His Val Leu
    210                 215                 220

Pro Glu Gly Pro Leu Ala Ile Glu Gly Gln Glu Leu Ser Gly Glu Tyr
225                 230                 235                 240

Tyr Asp Lys Ala Ala Pro Val Val Glu Leu Gln Ile Ala Arg Ala Gly
                245                 250                 255

Tyr Arg Met Ala Ala Trp Leu Asp Leu Ile Ala Arg Arg Phe Gln Glu
            260                 265                 270

Gln Gly Ala Glu Arg Glu Glu Asp Leu Trp Glu Glu Leu
        275                 280                 285
```

<210> SEQ ID NO 73
<211> LENGTH: 1057
<212> TYPE: DNA
<213> ORGANISM: Microdochium phragmitis
<220> FEATURE:
<221> NAME/KEY: CDS
<222> LOCATION: (1)..(73)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1054)
<220> FEATURE:
<221> NAME/KEY: CDS
<222> LOCATION: (144)..(1054)

<400> SEQUENCE: 73

```
atg cgt act gcc cac gtc gct gcc gtc gcg gcc ggc ctt ctg gcc agc       48
Met Arg Thr Ala His Val Ala Ala Val Ala Ala Gly Leu Leu Ala Ser
-20                 -15                 -10                 -5

cca gcc atg tcc tgg aat acg gat g gtcagcatac tctctcctat               93
Pro Ala Met Ser Trp Asn Thr Asp
            -1  1
```

```
cccacaaaac cctaatcata aagtaccttt gctaacatat caactcatag tg  cac        148
                                                          Val His
                                                          5

caa caa atc gcc tac gct gcc gac gag ctc cta acc ccc tac acc aaa      196
Gln Gln Ile Ala Tyr Ala Ala Asp Glu Leu Leu Thr Pro Tyr Thr Lys
            10                  15                  20

caa atc atc cgc cag ctc ctc gag ccc tcc gct cag ggc tcc ctg ggg      244
Gln Ile Ile Arg Gln Leu Leu Glu Pro Ser Ala Gln Gly Ser Leu Gly
        25                  30                  35

cgc gtc ggc gcc tgg gcc gac ggc tac cgc aag acc ccc gag ggc gcc      292
Arg Val Gly Ala Trp Ala Asp Gly Tyr Arg Lys Thr Pro Glu Gly Ala
    40                  45                  50

tac acg gat aca tgg cac tac atc gac ccg gct gac aac ccg ccc tcc      340
Tyr Thr Asp Thr Trp His Tyr Ile Asp Pro Ala Asp Asn Pro Pro Ser
55                  60                  65                  70

ttc tgc aat gtg cac ttc aac cgc gac tgc tcc aag aag ggc tgc atc      388
Phe Cys Asn Val His Phe Asn Arg Asp Cys Ser Lys Lys Gly Cys Ile
                75                  80                  85

gtc tcc gcc ctg acg aac cag acc gag atc gcc aag ggc tgc atc acc      436
Val Ser Ala Leu Thr Asn Gln Thr Glu Ile Ala Lys Gly Cys Ile Thr
            90                  95                  100

cgc gcg aaa cac ggc cag atc cgc aac ggc gag gac gcc acc tgc gcc      484
Arg Ala Lys His Gly Gln Ile Arg Asn Gly Glu Asp Ala Thr Cys Ala
        105                 110                 115

aac gcg atc aaa ttc att gcg cat ttc acg ggt gat gcc acg cag cct      532
Asn Ala Ile Lys Phe Ile Ala His Phe Thr Gly Asp Ala Thr Gln Pro
    120                 125                 130

tta cac gtc tcc ggc atc gcg gcc ggt gga aac ggg ttc aac gtt act      580
Leu His Val Ser Gly Ile Ala Ala Gly Gly Asn Gly Phe Asn Val Thr
135                 140                 145                 150

ttc gcg ggc aaa gcc acc aat ctc cac tcc gtc tgg gac ggc gcc atc      628
Phe Ala Gly Lys Ala Thr Asn Leu His Ser Val Trp Asp Gly Ala Ile
                155                 160                 165

atc tac aaa ttc gcc aac gtc tcc ggt gac ccg acc caa aac atc ccc      676
Ile Tyr Lys Phe Ala Asn Val Ser Gly Asp Pro Thr Gln Asn Ile Pro
            170                 175                 180

gcc gga ttc aaa aac gat aca ctc cag cca ttt ttc aaa aac acc atc      724
Ala Gly Phe Lys Asn Asp Thr Leu Gln Pro Phe Phe Lys Asn Thr Ile
        185                 190                 195

aag cgt ctc cgg agc gat agt ttc atc acc ccc gtt gcg gat atg att      772
Lys Arg Leu Arg Ser Asp Ser Phe Ile Thr Pro Val Ala Asp Met Ile
    200                 205                 210

tcc tgc acg gac ccg ggg aca ccg cag aag tgt gcg atg gag tgg gcc      820
Ser Cys Thr Asp Pro Gly Thr Pro Gln Lys Cys Ala Met Glu Trp Ala
215                 220                 225                 230

aag gat acg aac gag tgg acg tgt gat tat gtg tat agt cag ctt ttc      868
Lys Asp Thr Asn Glu Trp Thr Cys Asp Tyr Val Tyr Ser Gln Leu Phe
                235                 240                 245

aat ggg acg gat ttg gcg gat agt ggg tat gct aaa gga gct ggg tat      916
Asn Gly Thr Asp Leu Ala Asp Ser Gly Tyr Ala Lys Gly Ala Gly Tyr
            250                 255                 260

att gtt gat gtg cag act gcg aaa gcg gcg gtg agg atg gcg acg tgg      964
Ile Val Asp Val Gln Thr Ala Lys Ala Ala Val Arg Met Ala Thr Trp
        265                 270                 275

ttc aac agg ctt gtg gag gga cgg tat ggg cag agg gag gtg cat ttg     1012
Phe Asn Arg Leu Val Glu Gly Arg Tyr Gly Gln Arg Glu Val His Leu
    280                 285                 290

gat ttg gtg ccg agc tgg gtt ttt ggg cct gtt aag ggt gct taa         1057
Asp Leu Val Pro Ser Trp Val Phe Gly Pro Val Lys Gly Ala
```

295 300 305

<210> SEQ ID NO 74
<211> LENGTH: 328
<212> TYPE: PRT
<213> ORGANISM: Microdochium phragmitis

<400> SEQUENCE: 74

```
Met Arg Thr Ala His Val Ala Ala Val Ala Ala Gly Leu Leu Ala Ser
-20                 -15                 -10                 -5

Pro Ala Met Ser Trp Asn Thr Asp Val His Gln Gln Ile Ala Tyr Ala
            -1  1               5                   10

Ala Asp Glu Leu Leu Thr Pro Tyr Thr Lys Gln Ile Ile Arg Gln Leu
        15                  20                  25

Leu Glu Pro Ser Ala Gln Gly Ser Leu Gly Arg Val Gly Ala Trp Ala
    30                  35                  40

Asp Gly Tyr Arg Lys Thr Pro Glu Gly Ala Tyr Thr Asp Thr Trp His
45                  50                  55                  60

Tyr Ile Asp Pro Ala Asp Asn Pro Pro Ser Phe Cys Asn Val His Phe
                65                  70                  75

Asn Arg Asp Cys Ser Lys Lys Gly Cys Ile Val Ser Ala Leu Thr Asn
            80                  85                  90

Gln Thr Glu Ile Ala Lys Gly Cys Ile Thr Arg Ala Lys His Gly Gln
        95                  100                 105

Ile Arg Asn Gly Glu Asp Ala Thr Cys Ala Asn Ala Ile Lys Phe Ile
    110                 115                 120

Ala His Phe Thr Gly Asp Ala Thr Gln Pro Leu His Val Ser Gly Ile
125                 130                 135                 140

Ala Ala Gly Gly Asn Gly Phe Asn Val Thr Phe Ala Gly Lys Ala Thr
                145                 150                 155

Asn Leu His Ser Val Trp Asp Gly Ala Ile Ile Tyr Lys Phe Ala Asn
            160                 165                 170

Val Ser Gly Asp Pro Thr Gln Asn Ile Pro Ala Gly Phe Lys Asn Asp
        175                 180                 185

Thr Leu Gln Pro Phe Phe Lys Asn Thr Ile Lys Arg Leu Arg Ser Asp
    190                 195                 200

Ser Phe Ile Thr Pro Val Ala Asp Met Ile Ser Cys Thr Asp Pro Gly
205                 210                 215                 220

Thr Pro Gln Lys Cys Ala Met Glu Trp Ala Lys Asp Thr Asn Glu Trp
                225                 230                 235

Thr Cys Asp Tyr Val Tyr Ser Gln Leu Phe Asn Gly Thr Asp Leu Ala
            240                 245                 250

Asp Ser Gly Tyr Ala Lys Gly Ala Gly Tyr Ile Val Asp Val Gln Thr
        255                 260                 265

Ala Lys Ala Ala Val Arg Met Ala Thr Trp Phe Asn Arg Leu Val Glu
    270                 275                 280

Gly Arg Tyr Gly Gln Arg Glu Val His Leu Asp Leu Val Pro Ser Trp
285                 290                 295                 300

Val Phe Gly Pro Val Lys Gly Ala
                305
```

<210> SEQ ID NO 75
<211> LENGTH: 308
<212> TYPE: PRT
<213> ORGANISM: Microdochium phragmitis

<400> SEQUENCE: 75

```
Trp Asn Thr Asp Val His Gln Gln Ile Ala Tyr Ala Ala Asp Glu Leu
1               5                   10                  15

Leu Thr Pro Tyr Thr Lys Gln Ile Ile Arg Gln Leu Leu Glu Pro Ser
            20                  25                  30

Ala Gln Gly Ser Leu Gly Arg Val Gly Ala Trp Ala Asp Gly Tyr Arg
        35                  40                  45

Lys Thr Pro Glu Gly Ala Tyr Thr Asp Thr Trp His Tyr Ile Asp Pro
    50                  55                  60

Ala Asp Asn Pro Pro Ser Phe Cys Asn Val His Phe Asn Arg Asp Cys
65                  70                  75                  80

Ser Lys Lys Gly Cys Ile Val Ser Ala Leu Thr Asn Gln Thr Glu Ile
                85                  90                  95

Ala Lys Gly Cys Ile Thr Arg Ala Lys His Gly Gln Ile Arg Asn Gly
            100                 105                 110

Glu Asp Ala Thr Cys Ala Asn Ala Ile Lys Phe Ile Ala His Phe Thr
        115                 120                 125

Gly Asp Ala Thr Gln Pro Leu His Val Ser Gly Ile Ala Ala Gly Gly
    130                 135                 140

Asn Gly Phe Asn Val Thr Phe Ala Gly Lys Ala Thr Asn Leu His Ser
145                 150                 155                 160

Val Trp Asp Gly Ala Ile Ile Tyr Lys Phe Ala Asn Val Ser Gly Asp
                165                 170                 175

Pro Thr Gln Asn Ile Pro Ala Gly Phe Lys Asn Asp Thr Leu Gln Pro
            180                 185                 190

Phe Phe Lys Asn Thr Ile Lys Arg Leu Arg Ser Asp Ser Phe Ile Thr
        195                 200                 205

Pro Val Ala Asp Met Ile Ser Cys Thr Asp Pro Gly Thr Pro Gln Lys
    210                 215                 220

Cys Ala Met Glu Trp Ala Lys Asp Thr Asn Glu Trp Thr Cys Asp Tyr
225                 230                 235                 240

Val Tyr Ser Gln Leu Phe Asn Gly Thr Asp Leu Ala Asp Ser Gly Tyr
                245                 250                 255

Ala Lys Gly Ala Gly Tyr Ile Val Asp Val Gln Thr Ala Lys Ala Ala
            260                 265                 270

Val Arg Met Ala Thr Trp Phe Asn Arg Leu Val Glu Gly Arg Tyr Gly
        275                 280                 285

Gln Arg Glu Val His Leu Asp Leu Val Pro Ser Trp Val Phe Gly Pro
    290                 295                 300

Val Lys Gly Ala
305
```

<210> SEQ ID NO 76
<211> LENGTH: 1200
<212> TYPE: DNA
<213> ORGANISM: Bacillus deramificans
<220> FEATURE:
<221> NAME/KEY: CDS
<222> LOCATION: (1)..(1197)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1197)

<400> SEQUENCE: 76

```
atg aaa ctg aca aaa aaa ata tct ttt gct tta tta gtt act ttt ttg       48
Met Lys Leu Thr Lys Lys Ile Ser Phe Ala Leu Leu Val Thr Phe Leu
            -25                 -20                 -15

ttt tca atg gtt agt gct tgc agt gat gtg agt agc cag tca caa cca       96
Phe Ser Met Val Ser Ala Cys Ser Asp Val Ser Ser Gln Ser Gln Pro
        -10                 -5              -1  1

act aaa aat aac caa gta gcc att aca aaa aca aat gtt aaa tca gac      144
Thr Lys Asn Asn Gln Val Ala Ile Thr Lys Thr Asn Val Lys Ser Asp
5                   10                  15                  20

att acg caa agc aaa aaa gcg aca gat aaa agt tcg aca act agt agt      192
Ile Thr Gln Ser Lys Lys Ala Thr Asp Lys Ser Ser Thr Thr Ser Ser
                25                  30                  35

tct act caa aag tct act act cat tca aca aat gta aaa aag gat tca      240
Ser Thr Gln Lys Ser Thr Thr His Ser Thr Asn Val Lys Lys Asp Ser
            40                  45                  50

gct aca acc aat aat tct aat tca gaa gat caa tat aaa aca ctt gcg      288
Ala Thr Thr Asn Asn Ser Asn Ser Glu Asp Gln Tyr Lys Thr Leu Ala
        55                  60                  65

gac tta gat ttt aag ggg aaa caa gtt att ata ttg aat aat aat cat      336
Asp Leu Asp Phe Lys Gly Lys Gln Val Ile Ile Leu Asn Asn Asn His
    70                  75                  80

gct gtt ttt tct aaa aat gac tta agt tta gct aaa gga agc tgg caa      384
Ala Val Phe Ser Lys Asn Asp Leu Ser Leu Ala Lys Gly Ser Trp Gln
85                  90                  95                  100

tct ttt tct aat tta gat tct tta aat cgt gtc ggt gca gca agt gcc      432
Ser Phe Ser Asn Leu Asp Ser Leu Asn Arg Val Gly Ala Ala Ser Ala
                105                 110                 115

atg tta tcg aag tct cta atg cct act gca gaa cgt gag cca ctt tat      480
Met Leu Ser Lys Ser Leu Met Pro Thr Ala Glu Arg Glu Pro Leu Tyr
            120                 125                 130

gtc gat cct aca ggt tgg aag aat aaa aaa atc att gtt aat ggt aaa      528
Val Asp Pro Thr Gly Trp Lys Asn Lys Lys Ile Ile Val Asn Gly Lys
        135                 140                 145

tcg gaa tgg ctt tat aat cgt tct cac ctt att ggt tat caa ttt aca      576
Ser Glu Trp Leu Tyr Asn Arg Ser His Leu Ile Gly Tyr Gln Phe Thr
    150                 155                 160

ggc gaa aat aac aat cct aaa aat tta atg aca gga aca aga agt ctt      624
Gly Glu Asn Asn Asn Pro Lys Asn Leu Met Thr Gly Thr Arg Ser Leu
165                 170                 175                 180

aat gac ccc gat atg ctt aaa tat gaa gac gaa gtg gcc tct tat tta      672
Asn Asp Pro Asp Met Leu Lys Tyr Glu Asp Glu Val Ala Ser Tyr Leu
                185                 190                 195

aga aca acc aat cac cat gtc cgt tac caa gta gaa cct ata ttt aga      720
Arg Thr Thr Asn His His Val Arg Tyr Gln Val Glu Pro Ile Phe Arg
            200                 205                 210

ggg gat gaa ttg gta gct aga ggc gtt cat atg caa gcc aaa agt ata      768
Gly Asp Glu Leu Val Ala Arg Gly Val His Met Gln Ala Lys Ser Ile
        215                 220                 225

gaa gat aat aaa att gat ttt aat gtt tat att ttt aat gtc gaa caa      816
Glu Asp Asn Lys Ile Asp Phe Asn Val Tyr Ile Phe Asn Val Glu Gln
    230                 235                 240

ggt gta acc atc aat tac gct gat ggt tct tct aga gtg caa tct ggt      864
Gly Val Thr Ile Asn Tyr Ala Asp Gly Ser Ser Arg Val Gln Ser Gly
245                 250                 255                 260

gca aca ata aat aat aat aca tct tct act aca acg aag aaa agc act      912
Ala Thr Ile Asn Asn Asn Thr Ser Ser Thr Thr Thr Lys Lys Ser Thr
                265                 270                 275

agc aac tcc aat gcg agc tct aca agt gtt tct acg agt gaa tta acg      960
Ser Asn Ser Asn Ala Ser Ser Thr Ser Val Ser Thr Ser Glu Leu Thr
            280                 285                 290
```

```
gta aat gat ggg gat caa gca acc gtg tca gtt aaa aca aaa cca aat     1008
Val Asn Asp Gly Asp Gln Ala Thr Val Ser Val Lys Thr Lys Pro Asn
        295                 300                 305

gtg caa gga act ata gaa gta gat tat tct tct ggt cct agc cat gca     1056
Val Gln Gly Thr Ile Glu Val Asp Tyr Ser Ser Gly Pro Ser His Ala
    310                 315                 320

tcc ggc tta gga cct aag aca tct gat cgt agc ggt aat ata agt tgg     1104
Ser Gly Leu Gly Pro Lys Thr Ser Asp Arg Ser Gly Asn Ile Ser Trp
325                 330                 335                 340

act tgg gca gtt ggt aca agg aca aaa cca gga act tat aat gta atc     1152
Thr Trp Ala Val Gly Thr Arg Thr Lys Pro Gly Thr Tyr Asn Val Ile
                345                 350                 355

att aca gtc aat gga caa acc atc aca aaa cat tta gtt gta aaa tga     1200
Ile Thr Val Asn Gly Gln Thr Ile Thr Lys His Leu Val Val Lys
            360                 365                 370


<210> SEQ ID NO 77
<211> LENGTH: 399
<212> TYPE: PRT
<213> ORGANISM: Bacillus deramificans

<400> SEQUENCE: 77

Met Lys Leu Thr Lys Lys Ile Ser Phe Ala Leu Leu Val Thr Phe Leu
            -25                 -20                 -15

Phe Ser Met Val Ser Ala Cys Ser Asp Val Ser Ser Gln Ser Gln Pro
        -10                 -5                  -1  1

Thr Lys Asn Asn Gln Val Ala Ile Thr Lys Thr Asn Val Lys Ser Asp
5                   10                  15                  20

Ile Thr Gln Ser Lys Lys Ala Thr Asp Lys Ser Ser Thr Thr Ser Ser
                25                  30                  35

Ser Thr Gln Lys Ser Thr Thr His Ser Thr Asn Val Lys Lys Asp Ser
            40                  45                  50

Ala Thr Thr Asn Asn Ser Asn Ser Glu Asp Gln Tyr Lys Thr Leu Ala
        55                  60                  65

Asp Leu Asp Phe Lys Gly Lys Gln Val Ile Ile Leu Asn Asn Asn His
    70                  75                  80

Ala Val Phe Ser Lys Asn Asp Leu Ser Leu Ala Lys Gly Ser Trp Gln
85                  90                  95                  100

Ser Phe Ser Asn Leu Asp Ser Leu Asn Arg Val Gly Ala Ala Ser Ala
                105                 110                 115

Met Leu Ser Lys Ser Leu Met Pro Thr Ala Glu Arg Glu Pro Leu Tyr
            120                 125                 130

Val Asp Pro Thr Gly Trp Lys Asn Lys Lys Ile Ile Val Asn Gly Lys
        135                 140                 145

Ser Glu Trp Leu Tyr Asn Arg Ser His Leu Ile Gly Tyr Gln Phe Thr
    150                 155                 160

Gly Glu Asn Asn Asn Pro Lys Asn Leu Met Thr Gly Thr Arg Ser Leu
165                 170                 175                 180

Asn Asp Pro Asp Met Leu Lys Tyr Glu Asp Glu Val Ala Ser Tyr Leu
                185                 190                 195

Arg Thr Thr Asn His His Val Arg Tyr Gln Val Glu Pro Ile Phe Arg
            200                 205                 210

Gly Asp Glu Leu Val Ala Arg Gly Val His Met Gln Ala Lys Ser Ile
        215                 220                 225

Glu Asp Asn Lys Ile Asp Phe Asn Val Tyr Ile Phe Asn Val Glu Gln
    230                 235                 240
```

Gly Val Thr Ile Asn Tyr Ala Asp Gly Ser Ser Arg Val Gln Ser Gly
245 250 255 260

Ala Thr Ile Asn Asn Asn Thr Ser Ser Thr Thr Thr Lys Lys Ser Thr
265 270 275

Ser Asn Ser Asn Ala Ser Ser Thr Ser Val Ser Thr Ser Glu Leu Thr
280 285 290

Val Asn Asp Gly Asp Gln Ala Thr Val Ser Val Lys Thr Lys Pro Asn
295 300 305

Val Gln Gly Thr Ile Glu Val Asp Tyr Ser Ser Gly Pro Ser His Ala
310 315 320

Ser Gly Leu Gly Pro Lys Thr Ser Asp Arg Ser Gly Asn Ile Ser Trp
325 330 335 340

Thr Trp Ala Val Gly Thr Arg Thr Lys Pro Gly Thr Tyr Asn Val Ile
345 350 355

Ile Thr Val Asn Gly Gln Thr Ile Thr Lys His Leu Val Val Lys
360 365 370

<210> SEQ ID NO 78
<211> LENGTH: 371
<212> TYPE: PRT
<213> ORGANISM: Bacillus deramificans

<400> SEQUENCE: 78

Gln Ser Gln Pro Thr Lys Asn Asn Gln Val Ala Ile Thr Lys Thr Asn
1 5 10 15

Val Lys Ser Asp Ile Thr Gln Ser Lys Lys Ala Thr Asp Lys Ser Ser
20 25 30

Thr Thr Ser Ser Ser Thr Gln Lys Ser Thr Thr His Ser Thr Asn Val
35 40 45

Lys Lys Asp Ser Ala Thr Thr Asn Asn Ser Asn Ser Glu Asp Gln Tyr
50 55 60

Lys Thr Leu Ala Asp Leu Asp Phe Lys Gly Lys Gln Val Ile Ile Leu
65 70 75 80

Asn Asn Asn His Ala Val Phe Ser Lys Asn Asp Leu Ser Leu Ala Lys
85 90 95

Gly Ser Trp Gln Ser Phe Ser Asn Leu Asp Ser Leu Asn Arg Val Gly
100 105 110

Ala Ala Ser Ala Met Leu Ser Lys Ser Leu Met Pro Thr Ala Glu Arg
115 120 125

Glu Pro Leu Tyr Val Asp Pro Thr Gly Trp Lys Asn Lys Lys Ile Ile
130 135 140

Val Asn Gly Lys Ser Glu Trp Leu Tyr Asn Arg Ser His Leu Ile Gly
145 150 155 160

Tyr Gln Phe Thr Gly Glu Asn Asn Asn Pro Lys Asn Leu Met Thr Gly
165 170 175

Thr Arg Ser Leu Asn Asp Pro Asp Met Leu Lys Tyr Glu Asp Glu Val
180 185 190

Ala Ser Tyr Leu Arg Thr Thr Asn His His Val Arg Tyr Gln Val Glu
195 200 205

Pro Ile Phe Arg Gly Asp Glu Leu Val Ala Arg Gly Val His Met Gln
210 215 220

Ala Lys Ser Ile Glu Asp Asn Lys Ile Asp Phe Asn Val Tyr Ile Phe
225 230 235 240

Asn Val Glu Gln Gly Val Thr Ile Asn Tyr Ala Asp Gly Ser Ser Arg

```
                245                 250                 255

Val Gln Ser Gly Ala Thr Ile Asn Asn Asn Thr Ser Ser Thr Thr Thr
            260                 265                 270

Lys Lys Ser Thr Ser Asn Ser Asn Ala Ser Ser Thr Ser Val Ser Thr
        275                 280                 285

Ser Glu Leu Thr Val Asn Asp Gly Asp Gln Ala Thr Val Ser Val Lys
    290                 295                 300

Thr Lys Pro Asn Val Gln Gly Thr Ile Glu Val Asp Tyr Ser Ser Gly
305                 310                 315                 320

Pro Ser His Ala Ser Gly Leu Gly Pro Lys Thr Ser Asp Arg Ser Gly
                325                 330                 335

Asn Ile Ser Trp Thr Trp Ala Val Gly Thr Arg Thr Lys Pro Gly Thr
            340                 345                 350

Tyr Asn Val Ile Ile Thr Val Asn Gly Gln Thr Ile Thr Lys His Leu
        355                 360                 365

Val Val Lys
    370


<210> SEQ ID NO 79
<211> LENGTH: 783
<212> TYPE: DNA
<213> ORGANISM: Bacillus thuringiensis
<220> FEATURE:
<221> NAME/KEY: CDS
<222> LOCATION: (1)..(780)
<220> FEATURE:
<221> NAME/KEY: sig_peptide
<222> LOCATION: (1)..(75)
<220> FEATURE:
<221> NAME/KEY: mat_peptide
<222> LOCATION: (76)..(780)

<400> SEQUENCE: 79

atg ttt aaa agt aaa gta tta aac agt aaa cta gta aaa aca tta gcc       48
Met Phe Lys Ser Lys Val Leu Asn Ser Lys Leu Val Lys Thr Leu Ala
-25                 -20                 -15                 -10

tta act aca ggg att tta gga ttt gca act ggt tgt gat aac tta gta       96
Leu Thr Thr Gly Ile Leu Gly Phe Ala Thr Gly Cys Asp Asn Leu Val
                -5                  -1  1               5

gac caa gct act caa aca ttt aaa gcc gac cac gga gtt aaa aca gaa      144
Asp Gln Ala Thr Gln Thr Phe Lys Ala Asp His Gly Val Lys Thr Glu
        10                  15                  20

gag gta gca caa gcg aag aaa cca aaa gtt aca gat tta aag aaa atc      192
Glu Val Ala Gln Ala Lys Lys Pro Lys Val Thr Asp Leu Lys Lys Ile
    25                  30                  35

gca acg agt tac aac ggt gaa aag gta gta aca gtt aac aac aat aaa      240
Ala Thr Ser Tyr Asn Gly Glu Lys Val Val Thr Val Asn Asn Asn Lys
40                  45                  50                  55

gca gac ttt aca caa gac caa tta gat aag gta aga tta act caa act      288
Ala Asp Phe Thr Gln Asp Gln Leu Asp Lys Val Arg Leu Thr Gln Thr
                60                  65                  70

gac cct aca tgg caa gaa tac tcg aat tta gat aat atg aat aga gta      336
Asp Pro Thr Trp Gln Glu Tyr Ser Asn Leu Asp Asn Met Asn Arg Val
            75                  80                  85

ggg gta gca acg gca tta ctt gga atg cag aat caa ccg aag gaa aag      384
Gly Val Ala Thr Ala Leu Leu Gly Met Gln Asn Gln Pro Lys Glu Lys
        90                  95                  100

cgt gac gat aga tta aat aca aaa cct aca ggt tgg cat caa aag aaa      432
Arg Asp Asp Arg Leu Asn Thr Lys Pro Thr Gly Trp His Gln Lys Lys
    105                 110                 115
```

```
cta agt gat ggt agc tac ttg tat gat aga agt cat cta att gga ttc      480
Leu Ser Asp Gly Ser Tyr Leu Tyr Asp Arg Ser His Leu Ile Gly Phe
120                 125                 130                 135

cag tta tca gga caa aac gat aac ccg aaa aac ctt atg aca ggt aca      528
Gln Leu Ser Gly Gln Asn Asp Asn Pro Lys Asn Leu Met Thr Gly Thr
                140                 145                 150

aaa gac ttt aat cgt aag agc atg tta aaa tat gag aac atg gta gac      576
Lys Asp Phe Asn Arg Lys Ser Met Leu Lys Tyr Glu Asn Met Val Asp
            155                 160                 165

aaa gaa gta gaa aaa gga agc tac gtc tta tat gaa gta aaa ccc gta      624
Lys Glu Val Glu Lys Gly Ser Tyr Val Leu Tyr Glu Val Lys Pro Val
        170                 175                 180

ttc att gga agt gaa aag gtt gct cgt ggt gta aac atg aaa gca aaa      672
Phe Ile Gly Ser Glu Lys Val Ala Arg Gly Val Asn Met Lys Ala Lys
    185                 190                 195

tca atg aac aat caa aat tta gaa ttc aac gta ttt tgt cat aat gta      720
Ser Met Asn Asn Gln Asn Leu Glu Phe Asn Val Phe Cys His Asn Val
200                 205                 210                 215

caa gat ggg gta gaa ata aac tac gaa gac gga act tct aaa cta aca      768
Gln Asp Gly Val Glu Ile Asn Tyr Glu Asp Gly Thr Ser Lys Leu Thr
                220                 225                 230

ggt aag ttg aaa taa                                                  783
Gly Lys Leu Lys
            235


<210> SEQ ID NO 80
<211> LENGTH: 260
<212> TYPE: PRT
<213> ORGANISM: Bacillus thuringiensis

<400> SEQUENCE: 80

Met Phe Lys Ser Lys Val Leu Asn Ser Lys Leu Val Lys Thr Leu Ala
-25                 -20                 -15                 -10

Leu Thr Thr Gly Ile Leu Gly Phe Ala Thr Gly Cys Asp Asn Leu Val
                -5                  -1  1               5

Asp Gln Ala Thr Gln Thr Phe Lys Ala Asp His Gly Val Lys Thr Glu
        10                  15                  20

Glu Val Ala Gln Ala Lys Lys Pro Lys Val Thr Asp Leu Lys Lys Ile
    25                  30                  35

Ala Thr Ser Tyr Asn Gly Glu Lys Val Val Thr Val Asn Asn Asn Lys
40                  45                  50                  55

Ala Asp Phe Thr Gln Asp Gln Leu Asp Lys Val Arg Leu Thr Gln Thr
                60                  65                  70

Asp Pro Thr Trp Gln Glu Tyr Ser Asn Leu Asp Asn Met Asn Arg Val
            75                  80                  85

Gly Val Ala Thr Ala Leu Leu Gly Met Gln Asn Gln Pro Lys Glu Lys
        90                  95                  100

Arg Asp Asp Arg Leu Asn Thr Lys Pro Thr Gly Trp His Gln Lys Lys
    105                 110                 115

Leu Ser Asp Gly Ser Tyr Leu Tyr Asp Arg Ser His Leu Ile Gly Phe
120                 125                 130                 135

Gln Leu Ser Gly Gln Asn Asp Asn Pro Lys Asn Leu Met Thr Gly Thr
                140                 145                 150

Lys Asp Phe Asn Arg Lys Ser Met Leu Lys Tyr Glu Asn Met Val Asp
            155                 160                 165

Lys Glu Val Glu Lys Gly Ser Tyr Val Leu Tyr Glu Val Lys Pro Val
        170                 175                 180
```

```
Phe Ile Gly Ser Glu Lys Val Ala Arg Gly Val Asn Met Lys Ala Lys
    185                 190                 195

Ser Met Asn Asn Gln Asn Leu Glu Phe Asn Val Phe Cys His Asn Val
200                 205                 210                 215

Gln Asp Gly Val Glu Ile Asn Tyr Glu Asp Gly Thr Ser Lys Leu Thr
                220                 225                 230

Gly Lys Leu Lys
            235


<210> SEQ ID NO 81
<211> LENGTH: 235
<212> TYPE: PRT
<213> ORGANISM: Bacillus thuringiensis

<400> SEQUENCE: 81

Thr Gly Cys Asp Asn Leu Val Asp Gln Ala Thr Gln Thr Phe Lys Ala
1               5                   10                  15

Asp His Gly Val Lys Thr Glu Glu Val Ala Gln Ala Lys Lys Pro Lys
            20                  25                  30

Val Thr Asp Leu Lys Lys Ile Ala Thr Ser Tyr Asn Gly Glu Lys Val
        35                  40                  45

Val Thr Val Asn Asn Asn Lys Ala Asp Phe Thr Gln Asp Gln Leu Asp
    50                  55                  60

Lys Val Arg Leu Thr Gln Thr Asp Pro Thr Trp Gln Glu Tyr Ser Asn
65                  70                  75                  80

Leu Asp Asn Met Asn Arg Val Gly Val Ala Thr Ala Leu Leu Gly Met
                85                  90                  95

Gln Asn Gln Pro Lys Glu Lys Arg Asp Asp Arg Leu Asn Thr Lys Pro
            100                 105                 110

Thr Gly Trp His Gln Lys Lys Leu Ser Asp Gly Ser Tyr Leu Tyr Asp
        115                 120                 125

Arg Ser His Leu Ile Gly Phe Gln Leu Ser Gly Gln Asn Asp Asn Pro
    130                 135                 140

Lys Asn Leu Met Thr Gly Thr Lys Asp Phe Asn Arg Lys Ser Met Leu
145                 150                 155                 160

Lys Tyr Glu Asn Met Val Asp Lys Glu Val Glu Lys Gly Ser Tyr Val
                165                 170                 175

Leu Tyr Glu Val Lys Pro Val Phe Ile Gly Ser Glu Lys Val Ala Arg
            180                 185                 190

Gly Val Asn Met Lys Ala Lys Ser Met Asn Asn Gln Asn Leu Glu Phe
        195                 200                 205

Asn Val Phe Cys His Asn Val Gln Asp Gly Val Glu Ile Asn Tyr Glu
    210                 215                 220

Asp Gly Thr Ser Lys Leu Thr Gly Lys Leu Lys
225                 230                 235


<210> SEQ ID NO 82
<211> LENGTH: 975
<212> TYPE: DNA
<213> ORGANISM: Penicillium virgatum
<220> FEATURE:
<221> NAME/KEY: CDS
<222> LOCATION: (1)..(972)
<220> FEATURE:
<221> NAME/KEY: sig_peptide
<222> LOCATION: (1)..(66)
<220> FEATURE:
<221> NAME/KEY: mat_peptide
<222> LOCATION: (67)..(972)
```

```
<400> SEQUENCE: 82

atg tcc aaa gca acc ttg gcc gtc atc gcc gcc gcc agt gca gcc act       48
Met Ser Lys Ala Thr Leu Ala Val Ile Ala Ala Ala Ser Ala Ala Thr
        -20                 -15                 -10

ggt gct ggt gtc act gca ctc ctt tac tcc ggc aaa ccc tcc aag ccg       96
Gly Ala Gly Val Thr Ala Leu Leu Tyr Ser Gly Lys Pro Ser Lys Pro
    -5              -1  1               5                   10

cat caa cag caa caa ctt cca aca ccc act acc cca ggt gtc aaa gct      144
His Gln Gln Gln Gln Leu Pro Thr Pro Thr Thr Pro Gly Val Lys Ala
                15                  20                  25

ccc tca acc atc gca ccc cca acc cta gca gcc aaa gtc acc ggc ccc      192
Pro Ser Thr Ile Ala Pro Pro Thr Leu Ala Ala Lys Val Thr Gly Pro
            30                  35                  40

gtc gat cca gcc gga gtc ctc caa tat ggc ttc cca ggc cca atc gcc      240
Val Asp Pro Ala Gly Val Leu Gln Tyr Gly Phe Pro Gly Pro Ile Ala
        45                  50                  55

gac gag ctc tcc tcc ctc ccc cta cac ggt gct tat gac cgt cgc act      288
Asp Glu Leu Ser Ser Leu Pro Leu His Gly Ala Tyr Asp Arg Arg Thr
    60                  65                  70

cgc aat ccc tcc tgg gta gcc gag cac atc aca cca gca tcc ctg gca      336
Arg Asn Pro Ser Trp Val Ala Glu His Ile Thr Pro Ala Ser Leu Ala
75                  80                  85                  90

atc aac aac gca gac cga aag aag agc acc ttc ttc gaa gac acc acc      384
Ile Asn Asn Ala Asp Arg Lys Lys Ser Thr Phe Phe Glu Asp Thr Thr
                95                  100                 105

gtc cca gcc atg ttc cgc gcc aaa ctg tcc gat tac ttc cgc tct ggc      432
Val Pro Ala Met Phe Arg Ala Lys Leu Ser Asp Tyr Phe Arg Ser Gly
            110                 115                 120

tac gac cgc ggc cac cag gtt ccc gcg gca gac gca aaa tgg tcc cag      480
Tyr Asp Arg Gly His Gln Val Pro Ala Ala Asp Ala Lys Trp Ser Gln
        125                 130                 135

gat gcc atg gac ggt act ttc gcg ctc tca aac atg tgt ccc cag gtc      528
Asp Ala Met Asp Gly Thr Phe Ala Leu Ser Asn Met Cys Pro Gln Val
    140                 145                 150

gga gag ggc ttc aac cgc gac tac tgg gct cac ttt gag act ttc tgc      576
Gly Glu Gly Phe Asn Arg Asp Tyr Trp Ala His Phe Glu Thr Phe Cys
155                 160                 165                 170

cgg gat ctc acc aag acc tac cca tcc gtt cgc atc gtt acg ggc ccg      624
Arg Asp Leu Thr Lys Thr Tyr Pro Ser Val Arg Ile Val Thr Gly Pro
                175                 180                 185

ctg tac ctg cct cac cgt gac cct gat gga aag tgg cgt gtc aac tat      672
Leu Tyr Leu Pro His Arg Asp Pro Asp Gly Lys Trp Arg Val Asn Tyr
            190                 195                 200

gag gtt att ggc act ccg ccc aat gtc gct gtt ccc acg cat ttc tat      720
Glu Val Ile Gly Thr Pro Pro Asn Val Ala Val Pro Thr His Phe Tyr
        205                 210                 215

aag gtc atc tat gcc gag gac gga act aac tcg cct act gcc aag gtt      768
Lys Val Ile Tyr Ala Glu Asp Gly Thr Asn Ser Pro Thr Ala Lys Val
    220                 225                 230

gcg ctc ggt gct ttt gtt ctg ccc aat gct cgc att gcg aat gat aag      816
Ala Leu Gly Ala Phe Val Leu Pro Asn Ala Arg Ile Ala Asn Asp Lys
235                 240                 245                 250

cgt ctg acg gac ttt gag gtt cct ctt gag gct gtt gag cgt gct tct      864
Arg Leu Thr Asp Phe Glu Val Pro Leu Glu Ala Val Glu Arg Ala Ser
                255                 260                 265

ggt ttg cag ttt ggt tcg cag ttg gac ctc agc cgt cgt cgt cgc ctg      912
Gly Leu Gln Phe Gly Ser Gln Leu Asp Leu Ser Arg Arg Arg Arg Leu
            270                 275                 280
```

```
tgc cag gag gtt gct tgc gag gtt act gtc cgc gag ttc aac aat gct      960
Cys Gln Glu Val Ala Cys Glu Val Thr Val Arg Glu Phe Asn Asn Ala
        285                 290                 295

aag aag cgt tct tga                                                  975
Lys Lys Arg Ser
    300


<210> SEQ ID NO 83
<211> LENGTH: 324
<212> TYPE: PRT
<213> ORGANISM: Penicillium virgatum

<400> SEQUENCE: 83

Met Ser Lys Ala Thr Leu Ala Val Ile Ala Ala Ala Ser Ala Ala Thr
        -20                 -15                 -10

Gly Ala Gly Val Thr Ala Leu Leu Tyr Ser Gly Lys Pro Ser Lys Pro
    -5              -1  1               5                   10

His Gln Gln Gln Gln Leu Pro Thr Pro Thr Thr Pro Gly Val Lys Ala
                15                  20                  25

Pro Ser Thr Ile Ala Pro Pro Thr Leu Ala Ala Lys Val Thr Gly Pro
            30                  35                  40

Val Asp Pro Ala Gly Val Leu Gln Tyr Gly Phe Pro Gly Pro Ile Ala
        45                  50                  55

Asp Glu Leu Ser Ser Leu Pro Leu His Gly Ala Tyr Asp Arg Arg Thr
    60                  65                  70

Arg Asn Pro Ser Trp Val Ala Glu His Ile Thr Pro Ala Ser Leu Ala
75                  80                  85                  90

Ile Asn Asn Ala Asp Arg Lys Lys Ser Thr Phe Phe Glu Asp Thr Thr
                95                  100                 105

Val Pro Ala Met Phe Arg Ala Lys Leu Ser Asp Tyr Phe Arg Ser Gly
            110                 115                 120

Tyr Asp Arg Gly His Gln Val Pro Ala Ala Asp Ala Lys Trp Ser Gln
        125                 130                 135

Asp Ala Met Asp Gly Thr Phe Ala Leu Ser Asn Met Cys Pro Gln Val
    140                 145                 150

Gly Glu Gly Phe Asn Arg Asp Tyr Trp Ala His Phe Glu Thr Phe Cys
155                 160                 165                 170

Arg Asp Leu Thr Lys Thr Tyr Pro Ser Val Arg Ile Val Thr Gly Pro
                175                 180                 185

Leu Tyr Leu Pro His Arg Asp Pro Asp Gly Lys Trp Arg Val Asn Tyr
            190                 195                 200

Glu Val Ile Gly Thr Pro Pro Asn Val Ala Val Pro Thr His Phe Tyr
        205                 210                 215

Lys Val Ile Tyr Ala Glu Asp Gly Thr Asn Ser Pro Thr Ala Lys Val
    220                 225                 230

Ala Leu Gly Ala Phe Val Leu Pro Asn Ala Arg Ile Ala Asn Asp Lys
235                 240                 245                 250

Arg Leu Thr Asp Phe Glu Val Pro Leu Glu Ala Val Glu Arg Ala Ser
                255                 260                 265

Gly Leu Gln Phe Gly Ser Gln Leu Asp Leu Ser Arg Arg Arg Arg Leu
            270                 275                 280

Cys Gln Glu Val Ala Cys Glu Val Thr Val Arg Glu Phe Asn Asn Ala
        285                 290                 295

Lys Lys Arg Ser
    300
```

<210> SEQ ID NO 84
<211> LENGTH: 302
<212> TYPE: PRT
<213> ORGANISM: Penicillium virgatum

<400> SEQUENCE: 84

```
Leu Leu Tyr Ser Gly Lys Pro Ser Lys Pro His Gln Gln Gln Gln Leu
1               5                   10                  15

Pro Thr Pro Thr Thr Pro Gly Val Lys Ala Pro Ser Thr Ile Ala Pro
            20                  25                  30

Pro Thr Leu Ala Ala Lys Val Thr Gly Pro Val Asp Pro Ala Gly Val
        35                  40                  45

Leu Gln Tyr Gly Phe Pro Gly Pro Ile Ala Asp Glu Leu Ser Ser Leu
    50                  55                  60

Pro Leu His Gly Ala Tyr Asp Arg Arg Thr Arg Asn Pro Ser Trp Val
65                  70                  75                  80

Ala Glu His Ile Thr Pro Ala Ser Leu Ala Ile Asn Asn Ala Asp Arg
                85                  90                  95

Lys Lys Ser Thr Phe Phe Glu Asp Thr Thr Val Pro Ala Met Phe Arg
            100                 105                 110

Ala Lys Leu Ser Asp Tyr Phe Arg Ser Gly Tyr Asp Arg Gly His Gln
        115                 120                 125

Val Pro Ala Ala Asp Ala Lys Trp Ser Gln Asp Ala Met Asp Gly Thr
    130                 135                 140

Phe Ala Leu Ser Asn Met Cys Pro Gln Val Gly Glu Gly Phe Asn Arg
145                 150                 155                 160

Asp Tyr Trp Ala His Phe Glu Thr Phe Cys Arg Asp Leu Thr Lys Thr
                165                 170                 175

Tyr Pro Ser Val Arg Ile Val Thr Gly Pro Leu Tyr Leu Pro His Arg
            180                 185                 190

Asp Pro Asp Gly Lys Trp Arg Val Asn Tyr Glu Val Ile Gly Thr Pro
        195                 200                 205

Pro Asn Val Ala Val Pro Thr His Phe Tyr Lys Val Ile Tyr Ala Glu
    210                 215                 220

Asp Gly Thr Asn Ser Pro Thr Ala Lys Val Ala Leu Gly Ala Phe Val
225                 230                 235                 240

Leu Pro Asn Ala Arg Ile Ala Asn Asp Lys Arg Leu Thr Asp Phe Glu
                245                 250                 255

Val Pro Leu Glu Ala Val Glu Arg Ala Ser Gly Leu Gln Phe Gly Ser
            260                 265                 270

Gln Leu Asp Leu Ser Arg Arg Arg Arg Leu Cys Gln Glu Val Ala Cys
        275                 280                 285

Glu Val Thr Val Arg Glu Phe Asn Asn Ala Lys Lys Arg Ser
    290                 295                 300
```

<210> SEQ ID NO 85
<211> LENGTH: 825
<212> TYPE: DNA
<213> ORGANISM: Streptomyces cirratus
<220> FEATURE:
<221> NAME/KEY: CDS
<222> LOCATION: (1)..(822)
<220> FEATURE:
<221> NAME/KEY: sig_peptide
<222> LOCATION: (1)..(84)
<220> FEATURE:
<221> NAME/KEY: mat_peptide
<222> LOCATION: (85)..(822)

```
<400> SEQUENCE: 85

atg gat aaa aaa aca aaa cag aca ctg atc gga ctg cta gtg tta ttg       48
Met Asp Lys Lys Thr Lys Gln Thr Leu Ile Gly Leu Leu Val Leu Leu
            -25                 -20                 -15

ctt tta tct gcg gga agc tat tat atc aag cag atg cag tcg aca gct       96
Leu Leu Ser Ala Gly Ser Tyr Tyr Ile Lys Gln Met Gln Ser Thr Ala
        -10                 -5                  -1  1

aat agt ccc aac acc aag ctt agt cag aaa aaa caa gcg tct gaa gct      144
Asn Ser Pro Asn Thr Lys Leu Ser Gln Lys Lys Gln Ala Ser Glu Ala
5                   10                  15                  20

cct agt caa gca ttg gca gag agt gtc tta aca gac gca gtc aag agt      192
Pro Ser Gln Ala Leu Ala Glu Ser Val Leu Thr Asp Ala Val Lys Ser
                25                  30                  35

caa gta aaa ggg agt ctg gag tgg aat ggc tca ggt gct ttt atc att      240
Gln Val Lys Gly Ser Leu Glu Trp Asn Gly Ser Gly Ala Phe Ile Ile
            40                  45                  50

aat ggt aat aaa aca aat cta gat gcc aag gtt tca agt aag ccc tac      288
Asn Gly Asn Lys Thr Asn Leu Asp Ala Lys Val Ser Ser Lys Pro Tyr
        55                  60                  65

gct gat aat aaa aca aag aca gtg ggc aag gaa aca gtg cca acc gta      336
Ala Asp Asn Lys Thr Lys Thr Val Gly Lys Glu Thr Val Pro Thr Val
    70                  75                  80

gca aat gcc ctc ttg tct aag gct act cgc cag tac aag aat cgt gaa      384
Ala Asn Ala Leu Leu Ser Lys Ala Thr Arg Gln Tyr Lys Asn Arg Glu
85                  90                  95                  100

gaa act ggg aat ggt tcg act tca tgg act cct cca ggc tgg cat cag      432
Glu Thr Gly Asn Gly Ser Thr Ser Trp Thr Pro Pro Gly Trp His Gln
                105                 110                 115

gtt aag aat cta aag ggt act tat acc cat gcg gtc gat aga ggt cac      480
Val Lys Asn Leu Lys Gly Thr Tyr Thr His Ala Val Asp Arg Gly His
            120                 125                 130

ttg tta ggc tat gcc tta atc ggt ggc ttg gat ggt ttt gat gcc tcg      528
Leu Leu Gly Tyr Ala Leu Ile Gly Gly Leu Asp Gly Phe Asp Ala Ser
        135                 140                 145

aca agc aat cct aaa aac att gct gtt caa aca gcc tgg gca aat cag      576
Thr Ser Asn Pro Lys Asn Ile Ala Val Gln Thr Ala Trp Ala Asn Gln
    150                 155                 160

gcg caa gcc gag gat tcg act ggt caa aac tac tat gaa agc atg gta      624
Ala Gln Ala Glu Asp Ser Thr Gly Gln Asn Tyr Tyr Glu Ser Met Val
165                 170                 175                 180

cgt aag gcc ttg gac caa aac aag cgt gtc cgt tat cgt gta acc ctt      672
Arg Lys Ala Leu Asp Gln Asn Lys Arg Val Arg Tyr Arg Val Thr Leu
                185                 190                 195

tat tac gct tca aat gag gat tta gtt cct tca gct tca cag att gaa      720
Tyr Tyr Ala Ser Asn Glu Asp Leu Val Pro Ser Ala Ser Gln Ile Glu
            200                 205                 210

gcc aag tct tca gac gga gaa ttg gaa ttc aat gtt cta gtt ccc aat      768
Ala Lys Ser Ser Asp Gly Glu Leu Glu Phe Asn Val Leu Val Pro Asn
        215                 220                 225

gtt caa aag gga ctt caa ctg gat tac cga act gga gaa gta acg gta      816
Val Gln Lys Gly Leu Gln Leu Asp Tyr Arg Thr Gly Glu Val Thr Val
    230                 235                 240

act cag taa                                                          825
Thr Gln
245

<210> SEQ ID NO 86
<211> LENGTH: 274
<212> TYPE: PRT
```

```
<213> ORGANISM: Streptomyces cirratus

<400> SEQUENCE: 86

Met Asp Lys Lys Thr Lys Gln Thr Leu Ile Gly Leu Leu Val Leu Leu
            -25                 -20                 -15

Leu Leu Ser Ala Gly Ser Tyr Tyr Ile Lys Gln Met Gln Ser Thr Ala
        -10                 -5              -1  1

Asn Ser Pro Asn Thr Lys Leu Ser Gln Lys Lys Gln Ala Ser Glu Ala
5                   10                  15                  20

Pro Ser Gln Ala Leu Ala Glu Ser Val Leu Thr Asp Ala Val Lys Ser
                25                  30                  35

Gln Val Lys Gly Ser Leu Glu Trp Asn Gly Ser Gly Ala Phe Ile Ile
            40                  45                  50

Asn Gly Asn Lys Thr Asn Leu Asp Ala Lys Val Ser Ser Lys Pro Tyr
        55                  60                  65

Ala Asp Asn Lys Thr Lys Thr Val Gly Lys Glu Thr Val Pro Thr Val
    70                  75                  80

Ala Asn Ala Leu Leu Ser Lys Ala Thr Arg Gln Tyr Lys Asn Arg Glu
85                  90                  95                  100

Glu Thr Gly Asn Gly Ser Thr Ser Trp Thr Pro Pro Gly Trp His Gln
                105                 110                 115

Val Lys Asn Leu Lys Gly Thr Tyr Thr His Ala Val Asp Arg Gly His
            120                 125                 130

Leu Leu Gly Tyr Ala Leu Ile Gly Gly Leu Asp Gly Phe Asp Ala Ser
        135                 140                 145

Thr Ser Asn Pro Lys Asn Ile Ala Val Gln Thr Ala Trp Ala Asn Gln
    150                 155                 160

Ala Gln Ala Glu Asp Ser Thr Gly Gln Asn Tyr Tyr Glu Ser Met Val
165                 170                 175                 180

Arg Lys Ala Leu Asp Gln Asn Lys Arg Val Arg Tyr Arg Val Thr Leu
                185                 190                 195

Tyr Tyr Ala Ser Asn Glu Asp Leu Val Pro Ser Ala Ser Gln Ile Glu
            200                 205                 210

Ala Lys Ser Ser Asp Gly Glu Leu Glu Phe Asn Val Leu Val Pro Asn
        215                 220                 225

Val Gln Lys Gly Leu Gln Leu Asp Tyr Arg Thr Gly Glu Val Thr Val
    230                 235                 240

Thr Gln
245


<210> SEQ ID NO 87
<211> LENGTH: 246
<212> TYPE: PRT
<213> ORGANISM: Streptomyces cirratus

<400> SEQUENCE: 87

Gln Ser Thr Ala Asn Ser Pro Asn Thr Lys Leu Ser Gln Lys Lys Gln
1               5                   10                  15

Ala Ser Glu Ala Pro Ser Gln Ala Leu Ala Glu Ser Val Leu Thr Asp
            20                  25                  30

Ala Val Lys Ser Gln Val Lys Gly Ser Leu Glu Trp Asn Gly Ser Gly
        35                  40                  45

Ala Phe Ile Ile Asn Gly Asn Lys Thr Asn Leu Asp Ala Lys Val Ser
    50                  55                  60

Ser Lys Pro Tyr Ala Asp Asn Lys Thr Lys Thr Val Gly Lys Glu Thr
```

```
65                  70                  75                  80

Val Pro Thr Val Ala Asn Ala Leu Leu Ser Lys Ala Thr Arg Gln Tyr
                85                  90                  95

Lys Asn Arg Glu Glu Thr Gly Asn Gly Ser Thr Ser Trp Thr Pro Pro
            100                 105                 110

Gly Trp His Gln Val Lys Asn Leu Lys Gly Thr Tyr Thr His Ala Val
        115                 120                 125

Asp Arg Gly His Leu Leu Gly Tyr Ala Leu Ile Gly Gly Leu Asp Gly
    130                 135                 140

Phe Asp Ala Ser Thr Ser Asn Pro Lys Asn Ile Ala Val Gln Thr Ala
145                 150                 155                 160

Trp Ala Asn Gln Ala Gln Ala Glu Asp Ser Thr Gly Gln Asn Tyr Tyr
                165                 170                 175

Glu Ser Met Val Arg Lys Ala Leu Asp Gln Asn Lys Arg Val Arg Tyr
            180                 185                 190

Arg Val Thr Leu Tyr Tyr Ala Ser Asn Glu Asp Leu Val Pro Ser Ala
        195                 200                 205

Ser Gln Ile Glu Ala Lys Ser Ser Asp Gly Glu Leu Glu Phe Asn Val
    210                 215                 220

Leu Val Pro Asn Val Gln Lys Gly Leu Gln Leu Asp Tyr Arg Thr Gly
225                 230                 235                 240

Glu Val Thr Val Thr Gln
                245


<210> SEQ ID NO 88
<211> LENGTH: 1032
<212> TYPE: DNA
<213> ORGANISM: Acremonium sp. XZ1968
<220> FEATURE:
<221> NAME/KEY: CDS
<222> LOCATION: (1)..(1029)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1029)

<400> SEQUENCE: 88

atg tcg aaa acc tcc gcc gcc atc gcc ctc ctc ggt gcg gga gca ggc       48
Met Ser Lys Thr Ser Ala Ala Ile Ala Leu Leu Gly Ala Gly Ala Gly
    -20                 -15                 -10

gcc tcc atc acc gca gcc gtc ctc tcg ctc cgc tcc tca aac aac gct       96
Ala Ser Ile Thr Ala Ala Val Leu Ser Leu Arg Ser Ser Asn Asn Ala
-5              -1  1               5                   10

gcc aag ccc gag atc ccc atc gcc tcg caa aac acc aca gcc atg ccc      144
Ala Lys Pro Glu Ile Pro Ile Ala Ser Gln Asn Thr Thr Ala Met Pro
            15                  20                  25

ccg acc cca aca tta cca ccg acc cgc acg aca gtg ccg ccg ccc gcc      192
Pro Thr Pro Thr Leu Pro Pro Thr Arg Thr Thr Val Pro Pro Pro Ala
        30                  35                  40

ccc ctc cca ggc agc gca ccc ttc cct ccc acc tcc tcg acc gcc ccc      240
Pro Leu Pro Gly Ser Ala Pro Phe Pro Pro Thr Ser Ser Thr Ala Pro
    45                  50                  55

gtc gat ccc gcc ggc ctc ttc cag tac ggc ttc ccc ggc ccg gtc gcc      288
Val Asp Pro Ala Gly Leu Phe Gln Tyr Gly Phe Pro Gly Pro Val Ala
60                  65                  70                  75

gac ctc gcc acc cgc gac tcc ctc gtc tcc tcc tac gac cgc cgc ctc      336
Asp Leu Ala Thr Arg Asp Ser Leu Val Ser Ser Tyr Asp Arg Arg Leu
                80                  85                  90
```

```
cgc aac ccc cac tgg gtc gtc gag cac atc acc ccg gcc tcc ctc gcc      384
Arg Asn Pro His Trp Val Val Glu His Ile Thr Pro Ala Ser Leu Ala
            95                  100                 105

gcc cgc aac gcc gac cgc aaa aac tcc gtc ttc gcc gag gac ccc tcc      432
Ala Arg Asn Ala Asp Arg Lys Asn Ser Val Phe Ala Glu Asp Pro Ser
        110                 115                 120

gtc ccg ccc aag ttc cgc gcc ctc ctc aag gac tac ttc cgc tcc ggc      480
Val Pro Pro Lys Phe Arg Ala Leu Leu Lys Asp Tyr Phe Arg Ser Gly
    125                 130                 135

tac gac cgc ggc cac cag gtc ccc gcc gcc gac gcg aaa tgg tcc cag      528
Tyr Asp Arg Gly His Gln Val Pro Ala Ala Asp Ala Lys Trp Ser Gln
140                 145                 150                 155

cgc gcc atg gac gac acc ttc tac ctc tcc aac atg tgc ccc cag gtc      576
Arg Ala Met Asp Asp Thr Phe Tyr Leu Ser Asn Met Cys Pro Gln Val
                160                 165                 170

ggc gag ggc ttc aac cgc gac tac tgg gcg cac ttt gag gac ttt tgc      624
Gly Glu Gly Phe Asn Arg Asp Tyr Trp Ala His Phe Glu Asp Phe Cys
            175                 180                 185

cgc cgc ctc acc gtc cgc tac ccc tcc gtc cgc atc gtc acg gga ccc      672
Arg Arg Leu Thr Val Arg Tyr Pro Ser Val Arg Ile Val Thr Gly Pro
        190                 195                 200

ctc tac ctc ccc aag aag gac cca aca gac aac aag tgg tac gtc aag      720
Leu Tyr Leu Pro Lys Lys Asp Pro Thr Asp Asn Lys Trp Tyr Val Lys
    205                 210                 215

tac gag atg atc ggg aac ccg ccc tcc gtc gcc gtg ccg acg cac ttt      768
Tyr Glu Met Ile Gly Asn Pro Pro Ser Val Ala Val Pro Thr His Phe
220                 225                 230                 235

tac aag gtc atc ctc gcc gag gac ggc cgc ccg ggg ggc agc gtg gcc      816
Tyr Lys Val Ile Leu Ala Glu Asp Gly Arg Pro Gly Gly Ser Val Ala
                240                 245                 250

gtc ggc gcc ttc gtc ctg ccc aac gcc gtc atc gac aac agc aag ccc      864
Val Gly Ala Phe Val Leu Pro Asn Ala Val Ile Asp Asn Ser Lys Pro
            255                 260                 265

atc acc gac ttt gag gtc ccg ctc gag gcc gtc gag agg gcg agc ggg      912
Ile Thr Asp Phe Glu Val Pro Leu Glu Ala Val Glu Arg Ala Ser Gly
        270                 275                 280

ctc gag ttt gcg agc aag ctc gac gtg agc agg cgc aag agg ctg tgt      960
Leu Glu Phe Ala Ser Lys Leu Asp Val Ser Arg Arg Lys Arg Leu Cys
    285                 290                 295

acg gac acg acg tgt gcg ctg gtg atc aaa gac tat gct aag agg cag     1008
Thr Asp Thr Thr Cys Ala Leu Val Ile Lys Asp Tyr Ala Lys Arg Gln
300                 305                 310                 315

gag gct ttc ggg aag aag aac tga                                     1032
Glu Ala Phe Gly Lys Lys Asn
                320
```

```
<210> SEQ ID NO 89
<211> LENGTH: 343
<212> TYPE: PRT
<213> ORGANISM: Acremonium sp. XZ1968

<400> SEQUENCE: 89

Met Ser Lys Thr Ser Ala Ala Ile Ala Leu Leu Gly Ala Gly Ala Gly
    -20                 -15                 -10

Ala Ser Ile Thr Ala Ala Val Leu Ser Leu Arg Ser Ser Asn Asn Ala
-5              -1  1               5                   10

Ala Lys Pro Glu Ile Pro Ile Ala Ser Gln Asn Thr Thr Ala Met Pro
            15                  20                  25

Pro Thr Pro Thr Leu Pro Pro Thr Arg Thr Thr Val Pro Pro Pro Ala
```

```
        30                  35                  40

Pro Leu Pro Gly Ser Ala Pro Phe Pro Pro Thr Ser Ser Thr Ala Pro
    45                  50                  55

Val Asp Pro Ala Gly Leu Phe Gln Tyr Gly Phe Pro Gly Pro Val Ala
60                  65                  70                  75

Asp Leu Ala Thr Arg Asp Ser Leu Val Ser Ser Tyr Asp Arg Arg Leu
                80                  85                  90

Arg Asn Pro His Trp Val Val Glu His Ile Thr Pro Ala Ser Leu Ala
            95                  100                 105

Ala Arg Asn Ala Asp Arg Lys Asn Ser Val Phe Ala Glu Asp Pro Ser
        110                 115                 120

Val Pro Pro Lys Phe Arg Ala Leu Leu Lys Asp Tyr Phe Arg Ser Gly
    125                 130                 135

Tyr Asp Arg Gly His Gln Val Pro Ala Ala Asp Ala Lys Trp Ser Gln
140                 145                 150                 155

Arg Ala Met Asp Asp Thr Phe Tyr Leu Ser Asn Met Cys Pro Gln Val
                160                 165                 170

Gly Glu Gly Phe Asn Arg Asp Tyr Trp Ala His Phe Glu Asp Phe Cys
            175                 180                 185

Arg Arg Leu Thr Val Arg Tyr Pro Ser Val Arg Ile Val Thr Gly Pro
        190                 195                 200

Leu Tyr Leu Pro Lys Lys Asp Pro Thr Asp Asn Lys Trp Tyr Val Lys
    205                 210                 215

Tyr Glu Met Ile Gly Asn Pro Pro Ser Val Ala Val Pro Thr His Phe
220                 225                 230                 235

Tyr Lys Val Ile Leu Ala Glu Asp Gly Arg Pro Gly Gly Ser Val Ala
                240                 245                 250

Val Gly Ala Phe Val Leu Pro Asn Ala Val Ile Asp Asn Ser Lys Pro
            255                 260                 265

Ile Thr Asp Phe Glu Val Pro Leu Glu Ala Val Glu Arg Ala Ser Gly
        270                 275                 280

Leu Glu Phe Ala Ser Lys Leu Asp Val Ser Arg Arg Lys Arg Leu Cys
    285                 290                 295

Thr Asp Thr Thr Cys Ala Leu Val Ile Lys Asp Tyr Ala Lys Arg Gln
300                 305                 310                 315

Glu Ala Phe Gly Lys Lys Asn
                320
```

<210> SEQ ID NO 90
<211> LENGTH: 322
<212> TYPE: PRT
<213> ORGANISM: Acremonium sp. XZ1968

<400> SEQUENCE: 90

```
Ala Val Leu Ser Leu Arg Ser Ser Asn Asn Ala Ala Lys Pro Glu Ile
1               5                   10                  15

Pro Ile Ala Ser Gln Asn Thr Thr Ala Met Pro Pro Thr Pro Thr Leu
            20                  25                  30

Pro Pro Thr Arg Thr Thr Val Pro Pro Pro Ala Pro Leu Pro Gly Ser
        35                  40                  45

Ala Pro Phe Pro Pro Thr Ser Ser Thr Ala Pro Val Asp Pro Ala Gly
    50                  55                  60

Leu Phe Gln Tyr Gly Phe Pro Gly Pro Val Ala Asp Leu Ala Thr Arg
65                  70                  75                  80
```

```
Asp Ser Leu Val Ser Ser Tyr Asp Arg Arg Leu Arg Asn Pro His Trp
                85                  90                  95

Val Val Glu His Ile Thr Pro Ala Ser Leu Ala Ala Arg Asn Ala Asp
            100                 105                 110

Arg Lys Asn Ser Val Phe Ala Glu Asp Pro Ser Val Pro Pro Lys Phe
        115                 120                 125

Arg Ala Leu Leu Lys Asp Tyr Phe Arg Ser Gly Tyr Asp Arg Gly His
    130                 135                 140

Gln Val Pro Ala Ala Asp Ala Lys Trp Ser Gln Arg Ala Met Asp Asp
145                 150                 155                 160

Thr Phe Tyr Leu Ser Asn Met Cys Pro Gln Val Gly Glu Gly Phe Asn
                165                 170                 175

Arg Asp Tyr Trp Ala His Phe Glu Asp Phe Cys Arg Arg Leu Thr Val
            180                 185                 190

Arg Tyr Pro Ser Val Arg Ile Val Thr Gly Pro Leu Tyr Leu Pro Lys
        195                 200                 205

Lys Asp Pro Thr Asp Asn Lys Trp Tyr Val Lys Tyr Glu Met Ile Gly
    210                 215                 220

Asn Pro Pro Ser Val Ala Val Pro Thr His Phe Tyr Lys Val Ile Leu
225                 230                 235                 240

Ala Glu Asp Gly Arg Pro Gly Gly Ser Val Ala Val Gly Ala Phe Val
                245                 250                 255

Leu Pro Asn Ala Val Ile Asp Asn Ser Lys Pro Ile Thr Asp Phe Glu
            260                 265                 270

Val Pro Leu Glu Ala Val Glu Arg Ala Ser Gly Leu Glu Phe Ala Ser
        275                 280                 285

Lys Leu Asp Val Ser Arg Arg Lys Arg Leu Cys Thr Asp Thr Thr Cys
    290                 295                 300

Ala Leu Val Ile Lys Asp Tyr Ala Lys Arg Gln Glu Ala Phe Gly Lys
305                 310                 315                 320

Lys Asn


<210> SEQ ID NO 91
<211> LENGTH: 1092
<212> TYPE: DNA
<213> ORGANISM: Daldinia fissa
<220> FEATURE:
<221> NAME/KEY: CDS
<222> LOCATION: (1)..(1089)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1089)

<400> SEQUENCE: 91

atg tca aaa act acg tta gca gtt atc gca gcg gca agc gca gga gcc       48
Met Ser Lys Thr Thr Leu Ala Val Ile Ala Ala Ala Ser Ala Gly Ala
            -15                 -10                 -5

ggc gcc gcc atc aca gct act atg tac ggg tta cga tca gac cgt aat       96
Gly Ala Ala Ile Thr Ala Thr Met Tyr Gly Leu Arg Ser Asp Arg Asn
    -1  1               5                   10

ctc gaa agc aag act ata tcc tta acg acg act acc tcc tcg gcc tca      144
Leu Glu Ser Lys Thr Ile Ser Leu Thr Thr Thr Thr Ser Ser Ala Ser
15                  20                  25                  30

cct acg gcg gga ggc tcc gcg ccg atc ccc atc cca gct aaa cag ata      192
Pro Thr Ala Gly Gly Ser Ala Pro Ile Pro Ile Pro Ala Lys Gln Ile
                35                  40                  45
```

```
ttt act ccc ccg aac caa caa acc gcg cag acg ggc ctg tcg acc tcg      240
Phe Thr Pro Pro Asn Gln Gln Thr Ala Gln Thr Gly Leu Ser Thr Ser
            50                  55                  60

gcc ccc gcc gcc gtg aac ctt gga ccc gtc gac ccg gcc ggc ctc ttc      288
Ala Pro Ala Ala Val Asn Leu Gly Pro Val Asp Pro Ala Gly Leu Phe
        65                  70                  75

gaa tat ggc ttc ccg ggc ccg gta gcc gac atc gcg acg cgg caa gcg      336
Glu Tyr Gly Phe Pro Gly Pro Val Ala Asp Ile Ala Thr Arg Gln Ala
    80                  85                  90

ctg atc tct tcg ttc gac cgc cga ctg cgc aac ccg cac tgg gta gca      384
Leu Ile Ser Ser Phe Asp Arg Arg Leu Arg Asn Pro His Trp Val Ala
95                  100                 105                 110

gag cac atc acg cca gcg tcg cta gca att cgc gac ggc gac cgc aag      432
Glu His Ile Thr Pro Ala Ser Leu Ala Ile Arg Asp Gly Asp Arg Lys
                115                 120                 125

cac agc aca ttc cta gaa gac gag gcc gtg ccc gag aag ttc cgc gcg      480
His Ser Thr Phe Leu Glu Asp Glu Ala Val Pro Glu Lys Phe Arg Ala
            130                 135                 140

cgg cta aag gac tac ttc cgc tcg ggc tac gac cgg ggc cac caa gtc      528
Arg Leu Lys Asp Tyr Phe Arg Ser Gly Tyr Asp Arg Gly His Gln Val
        145                 150                 155

ccc gcg gcc gac gcg cgc tgg ggc caa gcc gcc atg gac gag acc ttc      576
Pro Ala Ala Asp Ala Arg Trp Gly Gln Ala Ala Met Asp Glu Thr Phe
    160                 165                 170

ttc ctg acc aac atg tgc ccg cag gtc ggc gag ggc ttc aac cgg gac      624
Phe Leu Thr Asn Met Cys Pro Gln Val Gly Glu Gly Phe Asn Arg Asp
175                 180                 185                 190

tac tgg gcg cac ttc gag gac ttc tgc cgg ggc ctg acg tcg cgg tat      672
Tyr Trp Ala His Phe Glu Asp Phe Cys Arg Gly Leu Thr Ser Arg Tyr
                195                 200                 205

ccc agc gtg cgc gtc gtc acg ggc ccg cta tac ctg ccc aag cgc gac      720
Pro Ser Val Arg Val Val Thr Gly Pro Leu Tyr Leu Pro Lys Arg Asp
            210                 215                 220

ccc aca gac aac aag tgg tac gtg cgg tac gaa gtc atc ggc aac ccg      768
Pro Thr Asp Asn Lys Trp Tyr Val Arg Tyr Glu Val Ile Gly Asn Pro
        225                 230                 235

ccc aac gtc gcc gtc ccc acg cac ttc tac aag gtc ata ttc gcc gaa      816
Pro Asn Val Ala Val Pro Thr His Phe Tyr Lys Val Ile Phe Ala Glu
    240                 245                 250

gac gga gcc gtc ggc ggc aac gta gcc ctc ggc gcc ttc gta ctg ccc      864
Asp Gly Ala Val Gly Gly Asn Val Ala Leu Gly Ala Phe Val Leu Pro
255                 260                 265                 270

aac gcc ccc atc ccc aac gac aag ccc ctg aca gac ttc gaa gtc ccc      912
Asn Ala Pro Ile Pro Asn Asp Lys Pro Leu Thr Asp Phe Glu Val Pro
                275                 280                 285

gtc gag gcc gtc gag cgc gcc agc ggc ctc gaa ttc gcc acc aag ctc      960
Val Glu Ala Val Glu Arg Ala Ser Gly Leu Glu Phe Ala Thr Lys Leu
            290                 295                 300

ccc gcc cag cgc cgc agg cgc ctc tgc acc gaa gcc ccc tgc gcc ctc     1008
Pro Ala Gln Arg Arg Arg Arg Leu Cys Thr Glu Ala Pro Cys Ala Leu
        305                 310                 315

gtc atc aaa gac tac gcc aac cgg caa aag gcg ttt gcg aag ccc cag     1056
Val Ile Lys Asp Tyr Ala Asn Arg Gln Lys Ala Phe Ala Lys Pro Gln
    320                 325                 330

cag ggc gct tct tct tcc gcc gtc gcg aag cgc tag                     1092
Gln Gly Ala Ser Ser Ser Ala Val Ala Lys Arg
335                 340                 345
```

<210> SEQ ID NO 92

```
<211> LENGTH: 363
<212> TYPE: PRT
<213> ORGANISM: Daldinia fissa

<400> SEQUENCE: 92

Met Ser Lys Thr Thr Leu Ala Val Ile Ala Ala Ala Ser Ala Gly Ala
            -15                 -10                 -5

Gly Ala Ala Ile Thr Ala Thr Met Tyr Gly Leu Arg Ser Asp Arg Asn
    -1  1               5                   10

Leu Glu Ser Lys Thr Ile Ser Leu Thr Thr Thr Thr Ser Ser Ala Ser
15                  20                  25                  30

Pro Thr Ala Gly Gly Ser Ala Pro Ile Pro Ile Pro Ala Lys Gln Ile
                35                  40                  45

Phe Thr Pro Pro Asn Gln Gln Thr Ala Gln Thr Gly Leu Ser Thr Ser
            50                  55                  60

Ala Pro Ala Ala Val Asn Leu Gly Pro Val Asp Pro Ala Gly Leu Phe
        65                  70                  75

Glu Tyr Gly Phe Pro Gly Pro Val Ala Asp Ile Ala Thr Arg Gln Ala
    80                  85                  90

Leu Ile Ser Ser Phe Asp Arg Arg Leu Arg Asn Pro His Trp Val Ala
95                  100                 105                 110

Glu His Ile Thr Pro Ala Ser Leu Ala Ile Arg Asp Gly Asp Arg Lys
                115                 120                 125

His Ser Thr Phe Leu Glu Asp Glu Ala Val Pro Glu Lys Phe Arg Ala
            130                 135                 140

Arg Leu Lys Asp Tyr Phe Arg Ser Gly Tyr Asp Arg Gly His Gln Val
        145                 150                 155

Pro Ala Ala Asp Ala Arg Trp Gly Gln Ala Ala Met Asp Glu Thr Phe
    160                 165                 170

Phe Leu Thr Asn Met Cys Pro Gln Val Gly Glu Gly Phe Asn Arg Asp
175                 180                 185                 190

Tyr Trp Ala His Phe Glu Asp Phe Cys Arg Gly Leu Thr Ser Arg Tyr
                195                 200                 205

Pro Ser Val Arg Val Val Thr Gly Pro Leu Tyr Leu Pro Lys Arg Asp
            210                 215                 220

Pro Thr Asp Asn Lys Trp Tyr Val Arg Tyr Glu Val Ile Gly Asn Pro
        225                 230                 235

Pro Asn Val Ala Val Pro Thr His Phe Tyr Lys Val Ile Phe Ala Glu
    240                 245                 250

Asp Gly Ala Val Gly Gly Asn Val Ala Leu Gly Ala Phe Val Leu Pro
255                 260                 265                 270

Asn Ala Pro Ile Pro Asn Asp Lys Pro Leu Thr Asp Phe Glu Val Pro
                275                 280                 285

Val Glu Ala Val Glu Arg Ala Ser Gly Leu Glu Phe Ala Thr Lys Leu
            290                 295                 300

Pro Ala Gln Arg Arg Arg Arg Leu Cys Thr Glu Ala Pro Cys Ala Leu
        305                 310                 315

Val Ile Lys Asp Tyr Ala Asn Arg Gln Lys Ala Phe Ala Lys Pro Gln
    320                 325                 330

Gln Gly Ala Ser Ser Ser Ala Val Ala Lys Arg
335                 340                 345


<210> SEQ ID NO 93
<211> LENGTH: 345
<212> TYPE: PRT
```

-continued

<213> ORGANISM: Daldinia fissa

<400> SEQUENCE: 93

```
Ala Ile Thr Ala Thr Met Tyr Gly Leu Arg Ser Asp Arg Asn Leu Glu
1               5                   10                  15

Ser Lys Thr Ile Ser Leu Thr Thr Thr Thr Ser Ser Ala Ser Pro Thr
            20                  25                  30

Ala Gly Gly Ser Ala Pro Ile Pro Ile Pro Ala Lys Gln Ile Phe Thr
        35                  40                  45

Pro Pro Asn Gln Gln Thr Ala Gln Thr Gly Leu Ser Thr Ser Ala Pro
    50                  55                  60

Ala Ala Val Asn Leu Gly Pro Val Asp Pro Ala Gly Leu Phe Glu Tyr
65                  70                  75                  80

Gly Phe Pro Gly Pro Val Ala Asp Ile Ala Thr Arg Gln Ala Leu Ile
                85                  90                  95

Ser Ser Phe Asp Arg Arg Leu Arg Asn Pro His Trp Val Ala Glu His
            100                 105                 110

Ile Thr Pro Ala Ser Leu Ala Ile Arg Asp Gly Asp Arg Lys His Ser
        115                 120                 125

Thr Phe Leu Glu Asp Glu Ala Val Pro Glu Lys Phe Arg Ala Arg Leu
    130                 135                 140

Lys Asp Tyr Phe Arg Ser Gly Tyr Asp Arg Gly His Gln Val Pro Ala
145                 150                 155                 160

Ala Asp Ala Arg Trp Gly Gln Ala Ala Met Asp Glu Thr Phe Phe Leu
                165                 170                 175

Thr Asn Met Cys Pro Gln Val Gly Glu Gly Phe Asn Arg Asp Tyr Trp
            180                 185                 190

Ala His Phe Glu Asp Phe Cys Arg Gly Leu Thr Ser Arg Tyr Pro Ser
        195                 200                 205

Val Arg Val Val Thr Gly Pro Leu Tyr Leu Pro Lys Arg Asp Pro Thr
    210                 215                 220

Asp Asn Lys Trp Tyr Val Arg Tyr Glu Val Ile Gly Asn Pro Pro Asn
225                 230                 235                 240

Val Ala Val Pro Thr His Phe Tyr Lys Val Ile Phe Ala Glu Asp Gly
                245                 250                 255

Ala Val Gly Gly Asn Val Ala Leu Gly Ala Phe Val Leu Pro Asn Ala
            260                 265                 270

Pro Ile Pro Asn Asp Lys Pro Leu Thr Asp Phe Glu Val Pro Val Glu
        275                 280                 285

Ala Val Glu Arg Ala Ser Gly Leu Glu Phe Ala Thr Lys Leu Pro Ala
    290                 295                 300

Gln Arg Arg Arg Arg Leu Cys Thr Glu Ala Pro Cys Ala Leu Val Ile
305                 310                 315                 320

Lys Asp Tyr Ala Asn Arg Gln Lys Ala Phe Ala Lys Pro Gln Gln Gly
                325                 330                 335

Ala Ser Ser Ser Ala Val Ala Lys Arg
            340                 345
```

<210> SEQ ID NO 94
<211> LENGTH: 976
<212> TYPE: DNA
<213> ORGANISM: Actinomucor elegans
<220> FEATURE:
<221> NAME/KEY: CDS
<222> LOCATION: (1)..(160)
<220> FEATURE:

```
<221> NAME/KEY: sig_peptide
<222> LOCATION: (1)..(75)
<220> FEATURE:
<221> NAME/KEY: mat_peptide
<222> LOCATION: (76)..(973)
<220> FEATURE:
<221> NAME/KEY: CDS
<222> LOCATION: (222)..(973)

<400> SEQUENCE: 94

atg gcg ata ccc ttg gca cat tac gtt tgg tta act agc ggc ttc ttt       48
Met Ala Ile Pro Leu Ala His Tyr Val Trp Leu Thr Ser Gly Phe Phe
-25                 -20                 -15                 -10

ttg ggc atg ttc ttc atg tac aat ctc gtg cca ttt cga gtg aat gag       96
Leu Gly Met Phe Phe Met Tyr Asn Leu Val Pro Phe Arg Val Asn Glu
                -5                  -1  1               5

cac cat gcc cac ttg caa ccc aga cag aaa cta gcc aac agc gta ctc      144
His His Ala His Leu Gln Pro Arg Gln Lys Leu Ala Asn Ser Val Leu
        10                  15                  20

aaa ttc gga aac cca g gtgagctgca tataggatac agcaaagacg cattaaaaat    200
Lys Phe Gly Asn Pro
    25

aatagtctaa cttgatgtta g gg  cct atc aat gac ttg ctc gaa aga acg      250
                        Gly Pro Ile Asn Asp Leu Leu Glu Arg Thr
                            30                  35

gct tac acc gct tcc tat aac cgc aaa gac cgt ata cct cat tgg gtc      298
Ala Tyr Thr Ala Ser Tyr Asn Arg Lys Asp Arg Ile Pro His Trp Val
    40                  45                  50

gga gaa cat ctt act gct gac agt cta gtt gct ggt gag ggt gtg aca      346
Gly Glu His Leu Thr Ala Asp Ser Leu Val Ala Gly Glu Gly Val Thr
55                  60                  65                  70

cgc gat aaa tct cgt ttt aaa gat gac ggc gct gtc cct gat ctt ttc      394
Arg Asp Lys Ser Arg Phe Lys Asp Asp Gly Ala Val Pro Asp Leu Phe
                75                  80                  85

aag gta ttt aca aaa gac tat acc aac agt ggc tat gac cgc ggt cat      442
Lys Val Phe Thr Lys Asp Tyr Thr Asn Ser Gly Tyr Asp Arg Gly His
            90                  95                  100

atg gct cct gct ggc gac gct gtt gct acc cag caa gcc atg gat gaa      490
Met Ala Pro Ala Gly Asp Ala Val Ala Thr Gln Gln Ala Met Asp Glu
        105                 110                 115

aca ttt ttg ttg acc aac att gca cca caa att ggc ccc gga ttc aat      538
Thr Phe Leu Leu Thr Asn Ile Ala Pro Gln Ile Gly Pro Gly Phe Asn
    120                 125                 130

cga caa tac tgg gct tat ctg gaa aaa ttc tgt cgt gag ttg acc aag      586
Arg Gln Tyr Trp Ala Tyr Leu Glu Lys Phe Cys Arg Glu Leu Thr Lys
135                 140                 145                 150

aac tat acg gac gtg tat gtc tat aca ggg cct ttg ttt ctg cct caa      634
Asn Tyr Thr Asp Val Tyr Val Tyr Thr Gly Pro Leu Phe Leu Pro Gln
                155                 160                 165

ctg caa gga caa agt gtc aag gtg gat ctt gaa gat gac aag gtg gcc      682
Leu Gln Gly Gln Ser Val Lys Val Asp Leu Glu Asp Asp Lys Val Ala
            170                 175                 180

gtg tca cag gca gct ggt aaa aaa tac aag atg cag tat gat atg att      730
Val Ser Gln Ala Ala Gly Lys Lys Tyr Lys Met Gln Tyr Asp Met Ile
        185                 190                 195

ggt agc gca ggc cct acg atc gcc gta cca acg cat tat ttc aag atc      778
Gly Ser Ala Gly Pro Thr Ile Ala Val Pro Thr His Tyr Phe Lys Ile
    200                 205                 210

ctg ctt gta aat cac gca gac gag ttt ata ttg gcg gct ttt gtg tta      826
Leu Leu Val Asn His Ala Asp Glu Phe Ile Leu Ala Ala Phe Val Leu
215                 220                 225                 230
```

```
ccg aat cag gct atc gat cat aag atc cca ttg tct cag ttt cag gtg      874
Pro Asn Gln Ala Ile Asp His Lys Ile Pro Leu Ser Gln Phe Gln Val
                235                 240                 245

ggt tta gag gct att gaa aag gct tct ggt cta gtg ttc ttt gat caa      922
Gly Leu Glu Ala Ile Glu Lys Ala Ser Gly Leu Val Phe Phe Asp Gln
            250                 255                 260

ttg gat cga acc aca ttc aaa aat ttg tgt gat caa gta caa tgc atc      970
Leu Asp Arg Thr Thr Phe Lys Asn Leu Cys Asp Gln Val Gln Cys Ile
        265                 270                 275

gtt taa                                                              976
Val


<210> SEQ ID NO 95
<211> LENGTH: 304
<212> TYPE: PRT
<213> ORGANISM: Actinomucor elegans

<400> SEQUENCE: 95

Met Ala Ile Pro Leu Ala His Tyr Val Trp Leu Thr Ser Gly Phe Phe
-25                 -20                 -15                 -10

Leu Gly Met Phe Phe Met Tyr Asn Leu Val Pro Phe Arg Val Asn Glu
                -5                  -1  1               5

His His Ala His Leu Gln Pro Arg Gln Lys Leu Ala Asn Ser Val Leu
        10                  15                  20

Lys Phe Gly Asn Pro Gly Pro Ile Asn Asp Leu Leu Glu Arg Thr Ala
    25                  30                  35

Tyr Thr Ala Ser Tyr Asn Arg Lys Asp Arg Ile Pro His Trp Val Gly
40                  45                  50                  55

Glu His Leu Thr Ala Asp Ser Leu Val Ala Gly Glu Gly Val Thr Arg
                60                  65                  70

Asp Lys Ser Arg Phe Lys Asp Asp Gly Ala Val Pro Asp Leu Phe Lys
            75                  80                  85

Val Phe Thr Lys Asp Tyr Thr Asn Ser Gly Tyr Asp Arg Gly His Met
        90                  95                  100

Ala Pro Ala Gly Asp Ala Val Ala Thr Gln Gln Ala Met Asp Glu Thr
    105                 110                 115

Phe Leu Leu Thr Asn Ile Ala Pro Gln Ile Gly Pro Gly Phe Asn Arg
120                 125                 130                 135

Gln Tyr Trp Ala Tyr Leu Glu Lys Phe Cys Arg Glu Leu Thr Lys Asn
                140                 145                 150

Tyr Thr Asp Val Tyr Val Tyr Thr Gly Pro Leu Phe Leu Pro Gln Leu
            155                 160                 165

Gln Gly Gln Ser Val Lys Val Asp Leu Glu Asp Asp Lys Val Ala Val
        170                 175                 180

Ser Gln Ala Ala Gly Lys Lys Tyr Lys Met Gln Tyr Asp Met Ile Gly
    185                 190                 195

Ser Ala Gly Pro Thr Ile Ala Val Pro Thr His Tyr Phe Lys Ile Leu
200                 205                 210                 215

Leu Val Asn His Ala Asp Glu Phe Ile Leu Ala Ala Phe Val Leu Pro
                220                 225                 230

Asn Gln Ala Ile Asp His Lys Ile Pro Leu Ser Gln Phe Gln Val Gly
            235                 240                 245

Leu Glu Ala Ile Glu Lys Ala Ser Gly Leu Val Phe Phe Asp Gln Leu
        250                 255                 260

Asp Arg Thr Thr Phe Lys Asn Leu Cys Asp Gln Val Gln Cys Ile Val
    265                 270                 275
```

<210> SEQ ID NO 96
<211> LENGTH: 279
<212> TYPE: PRT
<213> ORGANISM: Actinomucor elegans

<400> SEQUENCE: 96

```
Val Pro Phe Arg Val Asn Glu His His Ala His Leu Gln Pro Arg Gln
1               5                   10                  15

Lys Leu Ala Asn Ser Val Leu Lys Phe Gly Asn Pro Gly Pro Ile Asn
            20                  25                  30

Asp Leu Leu Glu Arg Thr Ala Tyr Thr Ala Ser Tyr Asn Arg Lys Asp
        35                  40                  45

Arg Ile Pro His Trp Val Gly Glu His Leu Thr Ala Asp Ser Leu Val
    50                  55                  60

Ala Gly Glu Gly Val Thr Arg Asp Lys Ser Arg Phe Lys Asp Asp Gly
65                  70                  75                  80

Ala Val Pro Asp Leu Phe Lys Val Phe Thr Lys Asp Tyr Thr Asn Ser
                85                  90                  95

Gly Tyr Asp Arg Gly His Met Ala Pro Ala Gly Asp Ala Val Ala Thr
            100                 105                 110

Gln Gln Ala Met Asp Glu Thr Phe Leu Leu Thr Asn Ile Ala Pro Gln
        115                 120                 125

Ile Gly Pro Gly Phe Asn Arg Gln Tyr Trp Ala Tyr Leu Glu Lys Phe
    130                 135                 140

Cys Arg Glu Leu Thr Lys Asn Tyr Thr Asp Val Tyr Val Tyr Thr Gly
145                 150                 155                 160

Pro Leu Phe Leu Pro Gln Leu Gln Gly Gln Ser Val Lys Val Asp Leu
                165                 170                 175

Glu Asp Asp Lys Val Ala Val Ser Gln Ala Ala Gly Lys Lys Tyr Lys
            180                 185                 190

Met Gln Tyr Asp Met Ile Gly Ser Ala Gly Pro Thr Ile Ala Val Pro
        195                 200                 205

Thr His Tyr Phe Lys Ile Leu Leu Val Asn His Ala Asp Glu Phe Ile
    210                 215                 220

Leu Ala Ala Phe Val Leu Pro Asn Gln Ala Ile Asp His Lys Ile Pro
225                 230                 235                 240

Leu Ser Gln Phe Gln Val Gly Leu Glu Ala Ile Glu Lys Ala Ser Gly
                245                 250                 255

Leu Val Phe Phe Asp Gln Leu Asp Arg Thr Thr Phe Lys Asn Leu Cys
            260                 265                 270

Asp Gln Val Gln Cys Ile Val
        275
```

<210> SEQ ID NO 97
<211> LENGTH: 1011
<212> TYPE: DNA
<213> ORGANISM: Talaromyces leycettanus
<220> FEATURE:
<221> NAME/KEY: CDS
<222> LOCATION: (1)..(1008)
<220> FEATURE:
<221> NAME/KEY: sig_peptide
<222> LOCATION: (1)..(51)
<220> FEATURE:
<221> NAME/KEY: mat_peptide
<222> LOCATION: (52)..(1008)

<400> SEQUENCE: 97

```
atg tca aag gcc acg ata gcg atc atc gct gca gcc agt gct gcc act       48
Met Ser Lys Ala Thr Ile Ala Ile Ile Ala Ala Ala Ser Ala Ala Thr
        -15                 -10                 -5

ggc gct ggt gtc acc gct ctt ctc tac tcc tcc aaa tcc tct cgc cag       96
Gly Ala Gly Val Thr Ala Leu Leu Tyr Ser Ser Lys Ser Ser Arg Gln
-1  1               5                   10                  15

cag tca gct cct gca gct ctt cct ccc ccc gct gcg ccc gct cct ctg      144
Gln Ser Ala Pro Ala Ala Leu Pro Pro Pro Ala Ala Pro Ala Pro Leu
                20                  25                  30

acc aag act gct gtt cct gtt ccc tcc gcc cat gtc cca gag ccg act      192
Thr Lys Thr Ala Val Pro Val Pro Ser Ala His Val Pro Glu Pro Thr
            35                  40                  45

ctt gct ccc aaa ccc tcc acc gct gct ccg gtc aat ccc tcg ggc atc      240
Leu Ala Pro Lys Pro Ser Thr Ala Ala Pro Val Asn Pro Ser Gly Ile
        50                  55                  60

ttc caa tac ggc ttt ccc ggc cct gta gct gac cct ctc aac tcc ctg      288
Phe Gln Tyr Gly Phe Pro Gly Pro Val Ala Asp Pro Leu Asn Ser Leu
    65                  70                  75

cct ttg acc gga gca tac gat cgt cgc act cgc aat ccg gcc tgg gtt      336
Pro Leu Thr Gly Ala Tyr Asp Arg Arg Thr Arg Asn Pro Ala Trp Val
80                  85                  90                  95

gcc gaa cac atc act ccc caa tcg ctc gct ctc ggc aac gcg gac cgc      384
Ala Glu His Ile Thr Pro Gln Ser Leu Ala Leu Gly Asn Ala Asp Arg
                100                 105                 110

aag aac agt gtg ttc ttt gag gat gtc act atc ccg gtc gcc ttc cgt      432
Lys Asn Ser Val Phe Phe Glu Asp Val Thr Ile Pro Val Ala Phe Arg
            115                 120                 125

gcc aag ttg gcc gac tac ttc cgc tcc ggt tat gat cgc ggc cat cag      480
Ala Lys Leu Ala Asp Tyr Phe Arg Ser Gly Tyr Asp Arg Gly His Gln
        130                 135                 140

gtg ccc gcc gcg gac gcc aaa tgg tcg cag gat gcg atg gac gcg acc      528
Val Pro Ala Ala Asp Ala Lys Trp Ser Gln Asp Ala Met Asp Ala Thr
    145                 150                 155

ttc gct ttg acc aac atg tgt ccg cag gtc gga gag gga ttc aac agg      576
Phe Ala Leu Thr Asn Met Cys Pro Gln Val Gly Glu Gly Phe Asn Arg
160                 165                 170                 175

gac tac tgg gcc cat ttt gaa gat ttc tgc cgc aac ctg gcc aag aag      624
Asp Tyr Trp Ala His Phe Glu Asp Phe Cys Arg Asn Leu Ala Lys Lys
                180                 185                 190

tat cct tcg gtt cgc att gtc acc ggt cct ctg tac ctg cct cac cgt      672
Tyr Pro Ser Val Arg Ile Val Thr Gly Pro Leu Tyr Leu Pro His Arg
            195                 200                 205

gac cct gac gga aaa tgg cgc gtg agc tac gaa gtg att ggc aac cca      720
Asp Pro Asp Gly Lys Trp Arg Val Ser Tyr Glu Val Ile Gly Asn Pro
        210                 215                 220

cct aac gtc gca gtc ccg acg cat ttc tac aag gtc atc tac ggt gaa      768
Pro Asn Val Ala Val Pro Thr His Phe Tyr Lys Val Ile Tyr Gly Glu
    225                 230                 235

gac ggt act ggc agc ccc aac agc agc gtc gca ttg ggt gcg ttt gtc      816
Asp Gly Thr Gly Ser Pro Asn Ser Ser Val Ala Leu Gly Ala Phe Val
240                 245                 250                 255

ctg ccc aat gcc gtc att ccg aat acc aag agc ttg gcc gat ttc gaa      864
Leu Pro Asn Ala Val Ile Pro Asn Thr Lys Ser Leu Ala Asp Phe Glu
                260                 265                 270

gtg cct ctg gaa gct gtg gag cgt gcc agc ggt ctg gaa ttt gcg tcc      912
Val Pro Leu Glu Ala Val Glu Arg Ala Ser Gly Leu Glu Phe Ala Ser
            275                 280                 285

aag ttg gat gtc agc cgc cgt aag cgc ctt tgc cag gag gtg aag tgc      960
Lys Leu Asp Val Ser Arg Arg Lys Arg Leu Cys Gln Glu Val Lys Cys
```

```
        290                 295                 300

gag att acg gtg cgc gag ttc aac aat acc aac aag aag ctc ctg aag      1008
Glu Ile Thr Val Arg Glu Phe Asn Asn Thr Asn Lys Lys Leu Leu Lys
    305                 310                 315

tga                                                                  1011


<210> SEQ ID NO 98
<211> LENGTH: 336
<212> TYPE: PRT
<213> ORGANISM: Talaromyces leycettanus

<400> SEQUENCE: 98

Met Ser Lys Ala Thr Ile Ala Ile Ile Ala Ala Ala Ser Ala Ala Thr
        -15                 -10                 -5

Gly Ala Gly Val Thr Ala Leu Leu Tyr Ser Ser Lys Ser Ser Arg Gln
-1  1               5                   10                  15

Gln Ser Ala Pro Ala Ala Leu Pro Pro Pro Ala Ala Pro Ala Pro Leu
                20                  25                  30

Thr Lys Thr Ala Val Pro Val Pro Ser Ala His Val Pro Glu Pro Thr
            35                  40                  45

Leu Ala Pro Lys Pro Ser Thr Ala Ala Pro Val Asn Pro Ser Gly Ile
        50                  55                  60

Phe Gln Tyr Gly Phe Pro Gly Pro Val Ala Asp Pro Leu Asn Ser Leu
    65                  70                  75

Pro Leu Thr Gly Ala Tyr Asp Arg Arg Thr Arg Asn Pro Ala Trp Val
80                  85                  90                  95

Ala Glu His Ile Thr Pro Gln Ser Leu Ala Leu Gly Asn Ala Asp Arg
                100                 105                 110

Lys Asn Ser Val Phe Phe Glu Asp Val Thr Ile Pro Val Ala Phe Arg
            115                 120                 125

Ala Lys Leu Ala Asp Tyr Phe Arg Ser Gly Tyr Asp Arg Gly His Gln
        130                 135                 140

Val Pro Ala Ala Asp Ala Lys Trp Ser Gln Asp Ala Met Asp Ala Thr
    145                 150                 155

Phe Ala Leu Thr Asn Met Cys Pro Gln Val Gly Glu Gly Phe Asn Arg
160                 165                 170                 175

Asp Tyr Trp Ala His Phe Glu Asp Phe Cys Arg Asn Leu Ala Lys Lys
                180                 185                 190

Tyr Pro Ser Val Arg Ile Val Thr Gly Pro Leu Tyr Leu Pro His Arg
            195                 200                 205

Asp Pro Asp Gly Lys Trp Arg Val Ser Tyr Glu Val Ile Gly Asn Pro
        210                 215                 220

Pro Asn Val Ala Val Pro Thr His Phe Tyr Lys Val Ile Tyr Gly Glu
    225                 230                 235

Asp Gly Thr Gly Ser Pro Asn Ser Ser Val Ala Leu Gly Ala Phe Val
240                 245                 250                 255

Leu Pro Asn Ala Val Ile Pro Asn Thr Lys Ser Leu Ala Asp Phe Glu
                260                 265                 270

Val Pro Leu Glu Ala Val Glu Arg Ala Ser Gly Leu Glu Phe Ala Ser
            275                 280                 285

Lys Leu Asp Val Ser Arg Arg Lys Arg Leu Cys Gln Glu Val Lys Cys
        290                 295                 300

Glu Ile Thr Val Arg Glu Phe Asn Asn Thr Asn Lys Lys Leu Leu Lys
    305                 310                 315
```

```
<210> SEQ ID NO 99
<211> LENGTH: 319
<212> TYPE: PRT
<213> ORGANISM: Talaromyces leycettanus

<400> SEQUENCE: 99

Ala Gly Val Thr Ala Leu Leu Tyr Ser Ser Lys Ser Ser Arg Gln Gln
1               5                   10                  15

Ser Ala Pro Ala Ala Leu Pro Pro Pro Ala Ala Pro Ala Pro Leu Thr
            20                  25                  30

Lys Thr Ala Val Pro Val Pro Ser Ala His Val Pro Glu Pro Thr Leu
        35                  40                  45

Ala Pro Lys Pro Ser Thr Ala Ala Pro Val Asn Pro Ser Gly Ile Phe
    50                  55                  60

Gln Tyr Gly Phe Pro Gly Pro Val Ala Asp Pro Leu Asn Ser Leu Pro
65                  70                  75                  80

Leu Thr Gly Ala Tyr Asp Arg Arg Thr Arg Asn Pro Ala Trp Val Ala
                85                  90                  95

Glu His Ile Thr Pro Gln Ser Leu Ala Leu Gly Asn Ala Asp Arg Lys
            100                 105                 110

Asn Ser Val Phe Phe Glu Asp Val Thr Ile Pro Val Ala Phe Arg Ala
        115                 120                 125

Lys Leu Ala Asp Tyr Phe Arg Ser Gly Tyr Asp Arg Gly His Gln Val
    130                 135                 140

Pro Ala Ala Asp Ala Lys Trp Ser Gln Asp Ala Met Asp Ala Thr Phe
145                 150                 155                 160

Ala Leu Thr Asn Met Cys Pro Gln Val Gly Glu Gly Phe Asn Arg Asp
                165                 170                 175

Tyr Trp Ala His Phe Glu Asp Phe Cys Arg Asn Leu Ala Lys Lys Tyr
            180                 185                 190

Pro Ser Val Arg Ile Val Thr Gly Pro Leu Tyr Leu Pro His Arg Asp
        195                 200                 205

Pro Asp Gly Lys Trp Arg Val Ser Tyr Glu Val Ile Gly Asn Pro Pro
    210                 215                 220

Asn Val Ala Val Pro Thr His Phe Tyr Lys Val Ile Tyr Gly Glu Asp
225                 230                 235                 240

Gly Thr Gly Ser Pro Asn Ser Ser Val Ala Leu Gly Ala Phe Val Leu
                245                 250                 255

Pro Asn Ala Val Ile Pro Asn Thr Lys Ser Leu Ala Asp Phe Glu Val
            260                 265                 270

Pro Leu Glu Ala Val Glu Arg Ala Ser Gly Leu Glu Phe Ala Ser Lys
        275                 280                 285

Leu Asp Val Ser Arg Arg Lys Arg Leu Cys Gln Glu Val Lys Cys Glu
    290                 295                 300

Ile Thr Val Arg Glu Phe Asn Asn Thr Asn Lys Lys Leu Leu Lys
305                 310                 315


<210> SEQ ID NO 100
<211> LENGTH: 31
<212> TYPE: DNA
<213> ORGANISM: Artificial Sequence
<220> FEATURE:
<223> OTHER INFORMATION: Cloning primer

<400> SEQUENCE: 100

gacgcggccg caccatgccg cgcttactcc c                                  31
```

```
<210> SEQ ID NO 101
<211> LENGTH: 28
<212> TYPE: DNA
<213> ORGANISM: Artificial Sequence
<220> FEATURE:
<223> OTHER INFORMATION: Cloning primer

<400> SEQUENCE: 101

gacgcgatcg ctcaagaggg ctgactcg                                         28


<210> SEQ ID NO 102
<211> LENGTH: 11
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = His(H) or GLN (Q)
<220> FEATURE:
<221> NAME/KEY: MISC_FEATURE
<222> LOCATION: (2)..(2)
<223> OTHER INFORMATION: Xaa = Phe(F) or I (Ile) or L (Leu) or V (Val)
      or Y (Tyr)
<220> FEATURE:
<221> NAME/KEY: MISC_FEATURE
<222> LOCATION: (3)..(3)
<223> OTHER INFORMATION: Xaa =any amino acid
<220> FEATURE:
<221> NAME/KEY: MISC_FEATURE
<222> LOCATION: (4)..(4)
<223> OTHER INFORMATION: Xaa =G (Gly) or A (Ala) or Q (Gln) or S (Ser)
<220> FEATURE:
<221> NAME/KEY: MISC_FEATURE
<222> LOCATION: (6)..(6)
<223> OTHER INFORMATION: Xaa =any amino acid
<220> FEATURE:
<221> NAME/KEY: MISC_FEATURE
<222> LOCATION: (7)..(7)
<223> OTHER INFORMATION: Xaa =H (His) or T (Thr) or G (Gly) or S (Ser)
      or A(Ala)
<220> FEATURE:
<221> NAME/KEY: MISC_FEATURE
<222> LOCATION: (8)..(8)
<223> OTHER INFORMATION: Xaa =Q (Gln) or V (Val) or M (Met)
<220> FEATURE:
<221> NAME/KEY: MISC_FEATURE
<222> LOCATION: (10)..(10)
<223> OTHER INFORMATION: Xaa =L (Leu) or F (Phe) or M (Met)

<400> SEQUENCE: 102

Xaa Xaa Xaa Xaa Asp Xaa Xaa Xaa Pro Xaa His
1               5                   10


<210> SEQ ID NO 103
<211> LENGTH: 7
<212> TYPE: PRT
<213> ORGANISM: Artificial
<220> FEATURE:
<223> OTHER INFORMATION: Motif 2
<220> FEATURE:
<221> NAME/KEY: MISC_FEATURE
<222> LOCATION: (2)..(2)
<223> OTHER INFORMATION: Xaa = G (Gly) or A (Ala)
<220> FEATURE:
<221> NAME/KEY: MISC_FEATURE
<222> LOCATION: (4)..(4)
<223> OTHER INFORMATION: Xaa = any natural amino acid
<220> FEATURE:
<221> NAME/KEY: MISC_FEATURE
<222> LOCATION: (5)..(5)
<223> OTHER INFORMATION: Xaa = V (Val) or I (Ile) or L (Leu) or F (Phe)
```

```
      or Y (Tyr)
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = V (Val) or L (Leu) or M (Met)

<400> SEQUENCE: 103

Gly Xaa Asn Xaa Xaa Xaa Xaa
1               5


<210> SEQ ID NO 104
<211> LENGTH: 4
<212> TYPE: PRT
<213> ORGANISM: Artificial
<220> FEATURE:
<223> OTHER INFORMATION: Motif 3
<220> FEATURE:
<221> NAME/KEY: MISC_FEATURE
<222> LOCATION: (1)..(1)
<223> OTHER INFORMATION: Xaa = S (Ser) or A (Ala) or D (Asp) or N (Asn)
<220> FEATURE:
<221> NAME/KEY: MISC_FEATURE
<222> LOCATION: (3)..(3)
<223> OTHER INFORMATION: Xaa = G (Gly) or S (Ser)

<400> SEQUENCE: 104

Xaa Arg Xaa His
1


<210> SEQ ID NO 105
<211> LENGTH: 27
<212> TYPE: PRT
<213> ORGANISM: Artificial
<220> FEATURE:
<223> OTHER INFORMATION: Signal peptide

<400> SEQUENCE: 105

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25


<210> SEQ ID NO 106
<211> LENGTH: 789
<212> TYPE: DNA
<213> ORGANISM: Bacillus sp.
<220> FEATURE:
<221> NAME/KEY: CDS
<222> LOCATION: (1)..(786)
<220> FEATURE:
<221> NAME/KEY: sig_peptide
<222> LOCATION: (1)..(93)
<220> FEATURE:
<221> NAME/KEY: mat_peptide
<222> LOCATION: (94)..(786)

<400> SEQUENCE: 106

atg aaa ctt aaa aca aca ctt ata aaa tcc att tca att atc gca gca       48
Met Lys Leu Lys Thr Thr Leu Ile Lys Ser Ile Ser Ile Ile Ala Ala
    -30                 -25                 -20

agt atg atg ctg gga gct tgt agt cct cct tct aat gct agt tcc agt       96
Ser Met Met Leu Gly Ala Cys Ser Pro Pro Ser Asn Ala Ser Ser Ser
-15                 -10                 -5              -1  1

acg aat aaa caa gaa cca tct caa gct acc acg aaa caa gaa tct aat      144
Thr Asn Lys Gln Glu Pro Ser Gln Ala Thr Thr Lys Gln Glu Ser Asn
```

```
            5                   10                  15

cag act caa aat aag act tct aac ggc caa caa cag tct tat aac ata      192
Gln Thr Gln Asn Lys Thr Ser Asn Gly Gln Gln Gln Ser Tyr Asn Ile
        20                  25                  30

gag gac att gca aag aac tac aaa ggt caa aaa gta gta gaa ata aac      240
Glu Asp Ile Ala Lys Asn Tyr Lys Gly Gln Lys Val Val Glu Ile Asn
    35                  40                  45

gga aat aaa gct gat ttt aca caa gat caa tta gat aaa gta cag ttg      288
Gly Asn Lys Ala Asp Phe Thr Gln Asp Gln Leu Asp Lys Val Gln Leu
50                  55                  60                  65

aag aat aca aat cct aca tgg caa gag ttc tct aac tta gat agt aag      336
Lys Asn Thr Asn Pro Thr Trp Gln Glu Phe Ser Asn Leu Asp Ser Lys
                70                  75                  80

aac aga gtt gga gta gca aca gca tta att ggt aaa gaa att caa cct      384
Asn Arg Val Gly Val Ala Thr Ala Leu Ile Gly Lys Glu Ile Gln Pro
            85                  90                  95

aaa gaa aaa cga gat gag aga ttg aat aca aaa cct act ggt tgg cat      432
Lys Glu Lys Arg Asp Glu Arg Leu Asn Thr Lys Pro Thr Gly Trp His
        100                 105                 110

caa aag aaa tta agt gat ggt agt aca ttg ttt gat aga agt cat tta      480
Gln Lys Lys Leu Ser Asp Gly Ser Thr Leu Phe Asp Arg Ser His Leu
    115                 120                 125

att gga tat caa cta act ggt caa aac gac aat ccc aag aat tta atg      528
Ile Gly Tyr Gln Leu Thr Gly Gln Asn Asp Asn Pro Lys Asn Leu Met
130                 135                 140                 145

act ggt aca aaa gat ttt aac cga cat agt atg tta aag tat gaa aac      576
Thr Gly Thr Lys Asp Phe Asn Arg His Ser Met Leu Lys Tyr Glu Asn
                150                 155                 160

atg gta gat aaa gag gtt gaa aaa gga agt tat gta ctt tac gaa gta      624
Met Val Asp Lys Glu Val Glu Lys Gly Ser Tyr Val Leu Tyr Glu Val
            165                 170                 175

aaa cca gta ttt atc ggt gac gag tta gtc gca aga ggt gta caa atg      672
Lys Pro Val Phe Ile Gly Asp Glu Leu Val Ala Arg Gly Val Gln Met
        180                 185                 190

aaa gcg aaa acg gtt aat aat aat cac tta gat ttc aac gta ttc tgt      720
Lys Ala Lys Thr Val Asn Asn Asn His Leu Asp Phe Asn Val Phe Cys
    195                 200                 205

ttt aat gtg caa gat ggt gta gag att gac tat aaa gat ggt act tct      768
Phe Asn Val Gln Asp Gly Val Glu Ile Asp Tyr Lys Asp Gly Thr Ser
210                 215                 220                 225

aaa cta gtt aat aaa caa taa                                          789
Lys Leu Val Asn Lys Gln
                230


<210> SEQ ID NO 107
<211> LENGTH: 262
<212> TYPE: PRT
<213> ORGANISM: Bacillus sp.

<400> SEQUENCE: 107

Met Lys Leu Lys Thr Thr Leu Ile Lys Ser Ile Ser Ile Ile Ala Ala
    -30                 -25                 -20

Ser Met Met Leu Gly Ala Cys Ser Pro Pro Ser Asn Ala Ser Ser Ser
-15                 -10                 -5              -1  1

Thr Asn Lys Gln Glu Pro Ser Gln Ala Thr Thr Lys Gln Glu Ser Asn
            5                   10                  15

Gln Thr Gln Asn Lys Thr Ser Asn Gly Gln Gln Gln Ser Tyr Asn Ile
        20                  25                  30

Glu Asp Ile Ala Lys Asn Tyr Lys Gly Gln Lys Val Val Glu Ile Asn
```

```
    35                  40                  45

Gly Asn Lys Ala Asp Phe Thr Gln Asp Gln Leu Asp Lys Val Gln Leu
50                  55                  60                  65

Lys Asn Thr Asn Pro Thr Trp Gln Glu Phe Ser Asn Leu Asp Ser Lys
                70                  75                  80

Asn Arg Val Gly Val Ala Thr Ala Leu Ile Gly Lys Glu Ile Gln Pro
            85                  90                  95

Lys Glu Lys Arg Asp Glu Arg Leu Asn Thr Lys Pro Thr Gly Trp His
        100                 105                 110

Gln Lys Lys Leu Ser Asp Gly Ser Thr Leu Phe Asp Arg Ser His Leu
    115                 120                 125

Ile Gly Tyr Gln Leu Thr Gly Gln Asn Asp Asn Pro Lys Asn Leu Met
130                 135                 140                 145

Thr Gly Thr Lys Asp Phe Asn Arg His Ser Met Leu Lys Tyr Glu Asn
                150                 155                 160

Met Val Asp Lys Glu Val Glu Lys Gly Ser Tyr Val Leu Tyr Glu Val
            165                 170                 175

Lys Pro Val Phe Ile Gly Asp Glu Leu Val Ala Arg Gly Val Gln Met
        180                 185                 190

Lys Ala Lys Thr Val Asn Asn Asn His Leu Asp Phe Asn Val Phe Cys
    195                 200                 205

Phe Asn Val Gln Asp Gly Val Glu Ile Asp Tyr Lys Asp Gly Thr Ser
210                 215                 220                 225

Lys Leu Val Asn Lys Gln
                230


<210> SEQ ID NO 108
<211> LENGTH: 231
<212> TYPE: PRT
<213> ORGANISM: Bacillus sp.

<400> SEQUENCE: 108

Ser Thr Asn Lys Gln Glu Pro Ser Gln Ala Thr Thr Lys Gln Glu Ser
1               5                   10                  15

Asn Gln Thr Gln Asn Lys Thr Ser Asn Gly Gln Gln Gln Ser Tyr Asn
            20                  25                  30

Ile Glu Asp Ile Ala Lys Asn Tyr Lys Gly Gln Lys Val Val Glu Ile
        35                  40                  45

Asn Gly Asn Lys Ala Asp Phe Thr Gln Asp Gln Leu Asp Lys Val Gln
    50                  55                  60

Leu Lys Asn Thr Asn Pro Thr Trp Gln Glu Phe Ser Asn Leu Asp Ser
65                  70                  75                  80

Lys Asn Arg Val Gly Val Ala Thr Ala Leu Ile Gly Lys Glu Ile Gln
                85                  90                  95

Pro Lys Glu Lys Arg Asp Glu Arg Leu Asn Thr Lys Pro Thr Gly Trp
            100                 105                 110

His Gln Lys Lys Leu Ser Asp Gly Ser Thr Leu Phe Asp Arg Ser His
        115                 120                 125

Leu Ile Gly Tyr Gln Leu Thr Gly Gln Asn Asp Asn Pro Lys Asn Leu
    130                 135                 140

Met Thr Gly Thr Lys Asp Phe Asn Arg His Ser Met Leu Lys Tyr Glu
145                 150                 155                 160

Asn Met Val Asp Lys Glu Val Glu Lys Gly Ser Tyr Val Leu Tyr Glu
                165                 170                 175
```

```
Val Lys Pro Val Phe Ile Gly Asp Glu Leu Val Ala Arg Gly Val Gln
            180                 185                 190

Met Lys Ala Lys Thr Val Asn Asn Asn His Leu Asp Phe Asn Val Phe
        195                 200                 205

Cys Phe Asn Val Gln Asp Gly Val Glu Ile Asp Tyr Lys Asp Gly Thr
    210                 215                 220

Ser Lys Leu Val Asn Lys Gln
225                 230


<210> SEQ ID NO 109
<211> LENGTH: 828
<212> TYPE: DNA
<213> ORGANISM: Streptococcus infantis
<220> FEATURE:
<221> NAME/KEY: CDS
<222> LOCATION: (1)..(825)
<220> FEATURE:
<221> NAME/KEY: sig_peptide
<222> LOCATION: (1)..(90)
<220> FEATURE:
<221> NAME/KEY: mat_peptide
<222> LOCATION: (91)..(825)

<400> SEQUENCE: 109

atg aat aaa aaa aca agg cag gca ctc ata ggt ctt ctg ctt ttc cta       48
Met Asn Lys Lys Thr Arg Gln Ala Leu Ile Gly Leu Leu Leu Phe Leu
-30                 -25                 -20                 -15

ctt ttg tcg gca gga agt tac tac ata aaa gaa atg cag gct tcc aat       96
Leu Leu Ser Ala Gly Ser Tyr Tyr Ile Lys Glu Met Gln Ala Ser Asn
                -10                 -5                  -1  1

gct aca ccg caa aca cag gtt aac cag aaa tcc cag tcg ctt gat act      144
Ala Thr Pro Gln Thr Gln Val Asn Gln Lys Ser Gln Ser Leu Asp Thr
        5                   10                  15

cca agt caa aaa ttg gcc gag agt gta ctg act gat tcg gta aaa aag      192
Pro Ser Gln Lys Leu Ala Glu Ser Val Leu Thr Asp Ser Val Lys Lys
    20                  25                  30

caa ata aag ggt act ctt gag tgg aat gga tca ggt gcc ttt atc gta      240
Gln Ile Lys Gly Thr Leu Glu Trp Asn Gly Ser Gly Ala Phe Ile Val
35                  40                  45                  50

aat ggg aac aaa acg aac tta gat gca aag gtt tca agt aaa ccc tat      288
Asn Gly Asn Lys Thr Asn Leu Asp Ala Lys Val Ser Ser Lys Pro Tyr
                55                  60                  65

gct gat aat aag aca aaa act gta ggt ggg gag acg gtt cca act gtg      336
Ala Asp Asn Lys Thr Lys Thr Val Gly Gly Glu Thr Val Pro Thr Val
            70                  75                  80

gct aac gcc ctc atg tca aaa gca aca aga cag tat aaa gac cgt gaa      384
Ala Asn Ala Leu Met Ser Lys Ala Thr Arg Gln Tyr Lys Asp Arg Glu
        85                  90                  95

gaa acc ggg aat ggt tca act tct tgg acc cca gca gga tgg cat caa      432
Glu Thr Gly Asn Gly Ser Thr Ser Trp Thr Pro Ala Gly Trp His Gln
    100                 105                 110

gtc aaa aac cta aaa ggg act tat aat cac gct gta gat aga gga cat      480
Val Lys Asn Leu Lys Gly Thr Tyr Asn His Ala Val Asp Arg Gly His
115                 120                 125                 130

tta tta ggc tat gcc ttg att ggt ggc tta gat ggt ttt gat gca tct      528
Leu Leu Gly Tyr Ala Leu Ile Gly Gly Leu Asp Gly Phe Asp Ala Ser
                135                 140                 145

act agc aat ccc aaa aat atc gct gta caa aca gcc tgg gcc aac caa      576
Thr Ser Asn Pro Lys Asn Ile Ala Val Gln Thr Ala Trp Ala Asn Gln
            150                 155                 160

gca cgc gca gaa gat tcg act gga caa aac tac tat gaa agt tta gtt      624
Ala Arg Ala Glu Asp Ser Thr Gly Gln Asn Tyr Tyr Glu Ser Leu Val
```

```
        165                 170                 175

cga aag gct ttg gat caa aat aag cgg gtg cgg tac cgt gtc aca tta      672
Arg Lys Ala Leu Asp Gln Asn Lys Arg Val Arg Tyr Arg Val Thr Leu
    180                 185                 190

ctc tac gct aca gaa gaa gat ttg gtt cct tct gca tct cag att gaa      720
Leu Tyr Ala Thr Glu Glu Asp Leu Val Pro Ser Ala Ser Gln Ile Glu
195                 200                 205                 210

gcc aaa tca tct gat ggt gaa ttg gag ttt aac gtt gta gtt cct aac      768
Ala Lys Ser Ser Asp Gly Glu Leu Glu Phe Asn Val Val Val Pro Asn
                215                 220                 225

gtt caa aag gga att cag tta gat tac cga aca gga aaa gta act gtt      816
Val Gln Lys Gly Ile Gln Leu Asp Tyr Arg Thr Gly Lys Val Thr Val
            230                 235                 240

aca aag aac taa                                                      828
Thr Lys Asn
        245


<210> SEQ ID NO 110
<211> LENGTH: 275
<212> TYPE: PRT
<213> ORGANISM: Streptococcus infantis

<400> SEQUENCE: 110

Met Asn Lys Lys Thr Arg Gln Ala Leu Ile Gly Leu Leu Leu Phe Leu
-30                 -25                 -20                 -15

Leu Leu Ser Ala Gly Ser Tyr Tyr Ile Lys Glu Met Gln Ala Ser Asn
                -10                 -5                  -1  1

Ala Thr Pro Gln Thr Gln Val Asn Gln Lys Ser Gln Ser Leu Asp Thr
        5                   10                  15

Pro Ser Gln Lys Leu Ala Glu Ser Val Leu Thr Asp Ser Val Lys Lys
    20                  25                  30

Gln Ile Lys Gly Thr Leu Glu Trp Asn Gly Ser Gly Ala Phe Ile Val
35                  40                  45                  50

Asn Gly Asn Lys Thr Asn Leu Asp Ala Lys Val Ser Ser Lys Pro Tyr
                55                  60                  65

Ala Asp Asn Lys Thr Lys Thr Val Gly Gly Glu Thr Val Pro Thr Val
            70                  75                  80

Ala Asn Ala Leu Met Ser Lys Ala Thr Arg Gln Tyr Lys Asp Arg Glu
        85                  90                  95

Glu Thr Gly Asn Gly Ser Thr Ser Trp Thr Pro Ala Gly Trp His Gln
    100                 105                 110

Val Lys Asn Leu Lys Gly Thr Tyr Asn His Ala Val Asp Arg Gly His
115                 120                 125                 130

Leu Leu Gly Tyr Ala Leu Ile Gly Gly Leu Asp Gly Phe Asp Ala Ser
                135                 140                 145

Thr Ser Asn Pro Lys Asn Ile Ala Val Gln Thr Ala Trp Ala Asn Gln
            150                 155                 160

Ala Arg Ala Glu Asp Ser Thr Gly Gln Asn Tyr Tyr Glu Ser Leu Val
        165                 170                 175

Arg Lys Ala Leu Asp Gln Asn Lys Arg Val Arg Tyr Arg Val Thr Leu
    180                 185                 190

Leu Tyr Ala Thr Glu Glu Asp Leu Val Pro Ser Ala Ser Gln Ile Glu
195                 200                 205                 210

Ala Lys Ser Ser Asp Gly Glu Leu Glu Phe Asn Val Val Val Pro Asn
                215                 220                 225

Val Gln Lys Gly Ile Gln Leu Asp Tyr Arg Thr Gly Lys Val Thr Val
```

```
            230                 235                 240

Thr Lys Asn
        245


<210> SEQ ID NO 111
<211> LENGTH: 245
<212> TYPE: PRT
<213> ORGANISM: Streptococcus infantis

<400> SEQUENCE: 111

Ser Asn Ala Thr Pro Gln Thr Gln Val Asn Gln Lys Ser Gln Ser Leu
1               5                   10                  15

Asp Thr Pro Ser Gln Lys Leu Ala Glu Ser Val Leu Thr Asp Ser Val
            20                  25                  30

Lys Lys Gln Ile Lys Gly Thr Leu Glu Trp Asn Gly Ser Gly Ala Phe
        35                  40                  45

Ile Val Asn Gly Asn Lys Thr Asn Leu Asp Ala Lys Val Ser Ser Lys
    50                  55                  60

Pro Tyr Ala Asp Asn Lys Thr Lys Thr Val Gly Gly Glu Thr Val Pro
65                  70                  75                  80

Thr Val Ala Asn Ala Leu Met Ser Lys Ala Thr Arg Gln Tyr Lys Asp
                85                  90                  95

Arg Glu Glu Thr Gly Asn Gly Ser Thr Ser Trp Thr Pro Ala Gly Trp
            100                 105                 110

His Gln Val Lys Asn Leu Lys Gly Thr Tyr Asn His Ala Val Asp Arg
        115                 120                 125

Gly His Leu Leu Gly Tyr Ala Leu Ile Gly Gly Leu Asp Gly Phe Asp
    130                 135                 140

Ala Ser Thr Ser Asn Pro Lys Asn Ile Ala Val Gln Thr Ala Trp Ala
145                 150                 155                 160

Asn Gln Ala Arg Ala Glu Asp Ser Thr Gly Gln Asn Tyr Tyr Glu Ser
                165                 170                 175

Leu Val Arg Lys Ala Leu Asp Gln Asn Lys Arg Val Arg Tyr Arg Val
            180                 185                 190

Thr Leu Leu Tyr Ala Thr Glu Glu Asp Leu Val Pro Ser Ala Ser Gln
        195                 200                 205

Ile Glu Ala Lys Ser Ser Asp Gly Glu Leu Glu Phe Asn Val Val Val
    210                 215                 220

Pro Asn Val Gln Lys Gly Ile Gln Leu Asp Tyr Arg Thr Gly Lys Val
225                 230                 235                 240

Thr Val Thr Lys Asn
                245


<210> SEQ ID NO 112
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = L (Leu) or M (Met)
<220> FEATURE:
<221> NAME/KEY: MISC_FEATURE
<222> LOCATION: (4)..(4)
<223> OTHER INFORMATION: Xaa = V (Val) or A (Ala)
<220> FEATURE:
<221> NAME/KEY: MISC_FEATURE
<222> LOCATION: (5)..(5)
```

<223> OTHER INFORMATION: Xaa = G (Gly) or A (Ala)

<400> SEQUENCE: 112

Pro Xaa His Xaa Xaa
1 5

<210> SEQ ID NO 113
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa = D (Asp) or N (Asn)

<400> SEQUENCE: 113

Pro Leu His Xaa Glu
1 5

<210> SEQ ID NO 114
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Y (Tyr) or V (Val)
<220> FEATURE:
<221> NAME/KEY: MISC_FEATURE
<222> LOCATION: (2)..(2)
<223> OTHER INFORMATION: Xaa = D (Asp) or N (Asn)

<400> SEQUENCE: 114

Xaa Xaa Arg Gly His
1 5

<210> SEQ ID NO 115
<211> LENGTH: 7
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (7)..(7)
<223> OTHER INFORMATION: Xaa = A (Ala) or V (Val)

<400> SEQUENCE: 115

Tyr Asp Arg Gly His Gln Xaa
1 5

<210> SEQ ID NO 116
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = D (Asp) or N (Asn) or A (Ala)
<220> FEATURE:
<221> NAME/KEY: MISC_FEATURE
<222> LOCATION: (3)..(3)
<223> OTHER INFORMATION: Xaa = G (Gly) or S (Ser) or C (Cys)
<220> FEATURE:
<221> NAME/KEY: MISC_FEATURE

```
<222> LOCATION: (5)..(5)
<223> OTHER INFORMATION: Xaa = L (Leu) or I (Ile)

<400> SEQUENCE: 116

Xaa Arg Xaa His Xaa
1               5


<210> SEQ ID NO 117
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = R (Arg) or I (Ile) or E (Glu) or N (Asn)
      or L (Leu) or G (Gly)
<220> FEATURE:
<221> NAME/KEY: MISC_FEATURE
<222> LOCATION: (2)..(2)
<223> OTHER INFORMATION: Xaa = Y (Tyr) or F (Phe)
<220> FEATURE:
<221> NAME/KEY: MISC_FEATURE
<222> LOCATION: (3)..(3)
<223> OTHER INFORMATION: Xaa = R (Arg) or H (His) or N (Asn)

<400> SEQUENCE: 117

Xaa Xaa Xaa Val
1
```

POLYPEPTIDES HAVING NUCLEASE ACTIVITY

CROSS-REFERENCE TO RELATED APPLICATIONS

This application is a 35 U.S.C. 371 national application of international application no. PCT/CN2019/109813 filed Oct. 3, 2019, which claims priority or the benefit under 35 U.S.C. 119 of International application no. PCT/CN2018/109243 filed Oct. 4, 2018. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention relates to polypeptides having nuclease activity, and polynucleotides encoding the polypeptides. The invention also relates to nucleic acid constructs, vectors, and recombinant host cells comprising the polynucleotides as well as methods of producing, recovering and using the polypeptides. The invention further relates to a detergent composition comprising one or more of the polypeptides having nuclease activity. It further concerns a laundering method and the use of the polypeptides having nuclease activity.

BACKGROUND OF THE INVENTION

When laundry items like T-shirts or sportswear are used, they are exposed to bacteria, body soil e.g. sweat, dead cells, skin debris, pollution etc. from the body of the user and from the rest of the environment in which they are used. Some of these body soils and pollution may adhere to the laundry item and may form a biofilm on the item. The presence of body soiling implies that the laundry items become sticky and therefore soil adheres to the sticky areas. This soil is difficult to remove using commercially available detergent compositions. Further, when very dirty laundry items are washed together with less dirty laundry items, dirt present in the wash liquor tends to stick to the body soil, such that laundry items can be more "soiled" after wash than before wash. Further, these body soils may be a source of bad odour, which develops after use of the laundry item. The bad odour is difficult to remove and may remain even after wash.

International patent application WO 2011/098579 concerns bacterial deoxyribonuclease compounds and methods for biofilm disruption and prevention.

SUMMARY OF THE INVENTION

The present invention provides polypeptides having nuclease activity; polynucleotides encoding the polypeptides; compositions comprising said polypeptides; methods and use of said polypeptides having nuclease activity.

One aspect of the invention relates to a cleaning composition comprising:

(a) at least 0.001 ppm of a polypeptide have nuclease activity, wherein the polypeptide comprises one or more of the motifs [HQ][FILVY]X[GAQS]DX[HTGSA][QVM]P[LFM]H (SEQ ID NO: 102), G[GA]NX[VILFY]X[VLM] (SEQ ID NO: 103) and/or [SADN]R[GS]H (SEQ ID NO: 104); wherein the polypeptide belongs to the Pfam family PF02265 (S1-P1_nuclease), PF01223 (Endonuclease_NS) or PF13930 (Endonuclea_NS_2); and (b) one or more surfactants.

Another aspect of the invention relates to a polypeptide having nuclease activity, as well as a cleaning composition comprising such as polypeptide, wherein the polypeptide is selected from a first group consisting of:

(a) a polypeptide having at least 99% sequence identity to the polypeptide of SEQ ID NO: 3;

(b) a polypeptide having at least 62% sequence identity to the polypeptide of SEQ ID NO: 6;

(c) a polypeptide having at least 97% sequence identity to the polypeptide of SEQ ID NO: 12; and (d) a polypeptide having at least 86% sequence identity to the polypeptide of SEQ ID NO: 21 or 27;

(e) a polypeptide having at least 98% sequence identity to the polypeptide of SEQ ID NO: 30;

(f) a polypeptide having 100% sequence identity to the polypeptide of SEQ ID NO: 33 or 48;

(g) a polypeptide having at least 76% sequence identity to the polypeptide of SEQ ID NO: 39 or 51;

(h) a polypeptide having at least 95% sequence identity to the polypeptide of SEQ ID NO: 42;

(i) a polypeptide having at least 79% sequence identity to the polypeptide of SEQ ID NO: 45 or 24;

(j) a polypeptide having at least 94% sequence identity to the polypeptide of SEQ ID NO: 54;

(k) a polypeptide having at least 72% sequence identity to the polypeptide of SEQ ID NO: 57;

(l) a polypeptide having at least 82% sequence identity to the polypeptide of SEQ ID NO: 60;

(m) a polypeptide having at least 75% sequence identity to the polypeptide of SEQ ID NO: 63;

(n) a polypeptide having at least 80% sequence identity to the polypeptide of SEQ ID NO: 69 or 75;

or is selected from a second group consisting of:

(o) a polypeptide having at least 77% sequence identity to the polypeptide of SEQ ID NO: 78;

(p) a polypeptide having at least 94% sequence identity to the polypeptide of SEQ ID NO: 84;

(q) a polypeptide having at least 99% sequence identity to the polypeptide of SEQ ID NO: 87;

(r) a polypeptide having at least 80% sequence identity to the polypeptide of SEQ ID NO: 90; and (s) a polypeptide having at least 90% sequence identity to the polypeptide of SEQ ID NO: 93;

or is a variant or fragment selected from:

(t) a variant of the polypeptide selected from said first group or said second group wherein the variant has nuclease activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions; and (u) a fragment of the polypeptide of (a), (b), (c), (d), (e), (f), (g), (h), (i), (j), (k), (l), (m), (n), (o), (p), (q), (r) and (s), wherein said fragment has nuclease activity.

One aspect of the invention relates to a polynucleotide encoding a polypeptide of the invention.

One aspect of the invention relates to a nucleic acid construct or an expression vector comprising a polynucleotide encoding a polypeptide of the invention wherein the polynucleotide is operably linked to one or more control sequences that direct the production of the polypeptide in an expression host.

One aspect of the invention relates to a recombinant host cell comprising a polynucleotide encoding a polypeptide of the invention operably linked to one or more control sequences that direct the production of the polypeptide.

One aspect of the invention relates to a method of producing the polypeptide of the invention, comprising cultivating a cell, which in its wild-type form produces the polypeptide, under conditions conducive for production of the polypeptide, and optionally recovering the polypeptide.

One aspect of the invention relates to a whole broth formulation or cell culture composition comprising a polypeptide of the invention.

One aspect of the invention relates to a cleaning composition comprising:

(a) at least 0.001 ppm of a polypeptide having nuclease activity; and (b) one or more surfactants;

wherein the polypeptide is selected from the group consisting of:

(i) a polypeptide having at least 80% sequence identity to the polypeptide of SEQ ID NO: 9;

(ii) a polypeptide having at least 80% sequence identity to the polypeptide of SEQ ID NO: 15;

(iii) a polypeptide having at least 80% sequence identity to the polypeptide of SEQ ID NO: 18;

(iv) a polypeptide having at least 80% sequence identity to the polypeptide of SEQ ID NO: 36;

(v) a polypeptide having at least 80% sequence identity to the polypeptide of SEQ ID NO: 66;

(vi) a polypeptide having at least 80% sequence identity to the polypeptide of SEQ ID NO: 72;

(vii) a polypeptide having at least 80% sequence identity to the polypeptide of SEQ ID NO: 81;

(viii) a polypeptide having at least 80% sequence identity to the polypeptide of SEQ ID NO: 96;

(ix) a polypeptide having at least 80% sequence identity to the polypeptide of SEQ ID NO: 99.

The cleaning compositions herein further preferably comprise, in addition to at least one surfactant, one or more cleaning composition components, preferably selected from surfactants, builders, bleach components, polymers, dispersing agents and additional enzymes.

One aspect relates to a laundering method for laundering an item comprising the steps of:

a) exposing an item to a wash liquor comprising a polypeptide of the invention or a cleaning composition comprising a polypeptide of the invention;

b) completing at least one wash cycle; and c) optionally rinsing the item, wherein the item is a textile.

One aspect of the invention relates to the use of a polypeptide according to the invention or a cleaning composition according to the invention for cleaning an item by:

(a) preventing, reducing or removing stickiness of the item;

(b) preventing, reducing or removing biofilm or biofilm components from the item;

(c) preventing, reducing or removing redeposition of soil during cleaning of the item;

(d) preventing, reducing or removing adherence of soil to the item;

(e) maintaining or improving whiteness of the item; or (f) preventing, reducing or removing malodor from the item, wherein the item is a textile.

OVERVIEW OF SEQUENCES

S1-P1 Nuclease Genes and their Encoded Polypeptides:

SEQ ID NO: 1: DNA encoding full length polypeptide from *Trichoderma hamatum*

SEQ ID NO: 2: polypeptide derived from SEQ ID NO: 1

SEQ ID NO: 3: mature polypeptide obtained from *Trichoderma hamatum*

SEQ ID NO: 4: DNA encoding full length polypeptide from *Morchella costata*

SEQ ID NO: 5: polypeptide derived from SEQ ID NO: 4

SEQ ID NO: 6: mature polypeptide obtained from *Morchella costata*

SEQ ID NO: 7: DNA encoding full length polypeptide from *Trichoderma reesei*

SEQ ID NO: 8: polypeptide derived from SEQ ID NO: 7

SEQ ID NO: 9: mature polypeptide obtained from *Trichoderma reesei*

SEQ ID NO: 10: DNA encoding full length polypeptide from *Penicillium cremeogriseum*

SEQ ID NO: 11: polypeptide derived from SEQ ID NO: 10

SEQ ID NO: 12: mature polypeptide obtained from *Penicillium cremeogriseum*

SEQ ID NO: 13: DNA encoding full length polypeptide from *Stenocarpella maydis*

SEQ ID NO: 14: polypeptide derived from SEQ ID NO: 13

SEQ ID NO: 15: mature polypeptide obtained from *Stenocarpella maydis*

SEQ ID NO: 16: DNA encoding full length polypeptide from *Stenocarpella maydis*

SEQ ID NO: 17: polypeptide derived from SEQ ID NO: 16

SEQ ID NO: 18: mature polypeptide obtained from *Stenocarpella maydis*

SEQ ID NO: 19: DNA encoding full length polypeptide from *Cordyceps cardinalis*

SEQ ID NO: 20: polypeptide derived from SEQ ID NO: 19

SEQ ID NO: 21: mature polypeptide obtained from *Cordyceps cardinalis*

SEQ ID NO: 22: DNA encoding full length polypeptide from *Phialophora geniculata*

SEQ ID NO: 23: polypeptide derived from SEQ ID NO: 22

SEQ ID NO: 24: mature polypeptide obtained from *Phialophora geniculata*

SEQ ID NO: 25: DNA encoding full length polypeptide from *Cadophora fastigiata*

SEQ ID NO: 26: polypeptide derived from SEQ ID NO: 25

SEQ ID NO: 27: mature polypeptide obtained from *Cadophora fastigiata*

SEQ ID NO: 28: DNA encoding full length polypeptide from Microbial enrichment A

SEQ ID NO: 29: polypeptide derived from SEQ ID NO: 28

SEQ ID NO: 30: mature polypeptide obtained from Microbial enrichment A.

SEQ ID NO: 31: DNA encoding full length polypeptide from *Lysobacter enzymogenes*

SEQ ID NO: 32: polypeptide derived from SEQ ID NO: 31

SEQ ID NO: 33: mature polypeptide obtained from *Lysobacter enzymogenes*

SEQ ID NO: 34: DNA encoding full length polypeptide from *Pseudoalteromonas nigrifaciens*

SEQ ID NO: 35: polypeptide derived from SEQ ID NO: 34

SEQ ID NO: 36: mature polypeptide obtained from *Pseudoalteromonas nigrifaciens*

SEQ ID NO: 37: DNA encoding full length polypeptide from *Vibrio* sp.

SEQ ID NO: 38: polypeptide derived from SEQ ID NO: 37

SEQ ID NO: 39: mature polypeptide obtained from *Vibrio* sp.

SEQ ID NO: 40: DNA encoding full length polypeptide from *Janthinobacterium agaricidamnosum*

SEQ ID NO: 41: polypeptide derived from SEQ ID NO: 40

SEQ ID NO: 42: mature polypeptide obtained from *Janthinobacterium agaricidamnosum*

SEQ ID NO: 43: DNA encoding full length polypeptide from *Massilia aerilata*

SEQ ID NO: 44: polypeptide derived from SEQ ID NO: 43

SEQ ID NO: 45: mature polypeptide obtained from *Massilia aerilata*

SEQ ID NO: 46: DNA encoding full length polypeptide from *Aspergillus oryzae*

SEQ ID NO: 47: polypeptide derived from SEQ ID NO: 46

SEQ ID NO: 48: mature polypeptide obtained from *Aspergillus oryzae*

SEQ ID NO: 49: DNA encoding full length polypeptide from *Penicillium atramentosum*

SEQ ID NO: 50: polypeptide derived from SEQ ID NO: 49

SEQ ID NO: 51: mature polypeptide obtained from *Penicillium atramentosum*

SEQ ID NO: 52: DNA encoding full length polypeptide from *Penicillium emersonii*

SEQ ID NO: 53: polypeptide derived from SEQ ID NO: 52

SEQ ID NO: 54: mature polypeptide obtained from *Penicillium emersonii*

SEQ ID NO: 55: DNA encoding full length polypeptide from *Ostropa barbara*

SEQ ID NO: 56: polypeptide derived from SEQ ID NO: 55

SEQ ID NO: 57: mature polypeptide obtained from *Ostropa barbara*

SEQ ID NO: 58: DNA encoding full length polypeptide from *Pyrenochaetopsis* sp.

SEQ ID NO: 59: polypeptide derived from SEQ ID NO: 58

SEQ ID NO: 60: mature polypeptide obtained from *Pyrenochaetopsis* sp.

SEQ ID NO: 61: DNA encoding full length polypeptide from *Lachnellula* sp.

SEQ ID NO: 62: polypeptide derived from SEQ ID NO: 61

SEQ ID NO: 63: mature polypeptide obtained from *Lachnellula* sp.

SEQ ID NO: 64: DNA encoding full length polypeptide from *Trichoderma reesei*

SEQ ID NO: 65: polypeptide derived from SEQ ID NO: 64

SEQ ID NO: 66: mature polypeptide obtained from *Trichoderma reesei*

SEQ ID NO: 67: DNA encoding full length polypeptide from *Cordyceps cardinalis*

SEQ ID NO: 68: polypeptide derived from SEQ ID NO: 67

SEQ ID NO: 69: mature polypeptide obtained from *Cordyceps cardinalis*

SEQ ID NO: 70: DNA encoding full length polypeptide from *Acremonium alcalophilum*

SEQ ID NO: 71: polypeptide derived from SEQ ID NO: 70

SEQ ID NO: 72: mature polypeptide obtained from *Acremonium alcalophilum*

SEQ ID NO: 73: DNA encoding full length polypeptide from *Microdochium phragmitis*

SEQ ID NO: 74: polypeptide derived from SEQ ID NO: 73

SEQ ID NO: 75: mature polypeptide obtained from *Microdochium phragmitis*

EN_NS Nuclease Genes and their Encoded Polypeptides:

SEQ ID NO: 76: DNA encoding full length polypeptide from *Bacillus deramificans*

SEQ ID NO: 77: polypeptide derived from SEQ ID NO: 76

SEQ ID NO: 78: mature polypeptide obtained from *Bacillus deramificans*

SEQ ID NO: 79: DNA encoding full length polypeptide from *Bacillus thuringiensis*

SEQ ID NO: 80: polypeptide derived from SEQ ID NO: 79

SEQ ID NO: 81: mature polypeptide obtained from *Bacillus thuringiensis*

SEQ ID NO: 82: DNA encoding full length polypeptide from *Penicillium virgatum*

SEQ ID NO: 83: polypeptide derived from SEQ ID NO: 82

SEQ ID NO: 84: mature polypeptide obtained from *Penicillium virgatum*

SEQ ID NO: 85: DNA encoding full length polypeptide from *Streptomyces cirratus*

SEQ ID NO: 86: polypeptide derived from SEQ ID NO: 85

SEQ ID NO: 87: mature polypeptide obtained from *Streptomyces cirratus*

SEQ ID NO: 88: DNA encoding full length polypeptide from *Acremonium* sp. XZ1968

SEQ ID NO: 89: polypeptide derived from SEQ ID NO: 88

SEQ ID NO: 90: mature polypeptide obtained from *Acremonium* sp. XZ1968

SEQ ID NO: 91: DNA encoding full length polypeptide from *Daldinia fissa*

SEQ ID NO: 92: polypeptide derived from SEQ ID NO: 91

SEQ ID NO: 93: mature polypeptide obtained from *Daldinia fissa*

SEQ ID NO: 94: DNA encoding full length polypeptide from *Actinomucor elegans*

SEQ ID NO: 95: polypeptide derived from SEQ ID NO: 94

SEQ ID NO: 96: mature polypeptide obtained from *Actinomucor elegans*

SEQ ID NO: 97: DNA encoding full length polypeptide from *Talaromyces leycettanus*

SEQ ID NO: 98: polypeptide derived from SEQ ID NO: 97

SEQ ID NO: 99: mature polypeptide obtained from *Talaromyces leycettanus*

Cloning Primers:

```
SEQ ID NO: 100:
5'-GACGCGGCCGCACCATGCCGCGCTTACTCCC

SEQ ID NO: 101:
5'-GACGCGATCGCTCAAGAGGGCTGACTCG
```

Motifs:

```
SEQ ID NO: 102:
[HQ][FILVY]X[GAQS]DX[HIGSA][QVM]P[LFM]H

SEQ ID NO: 103:
G[GA]NX[VILFY]X[VLM]

SEQ ID NO: 104:
[SADN]R[GS]H
```

Signal Peptide:

```
SEQ ID NO: 105:
MKKPLGKIVASTALLISVAFSSSIASA
```

Additional EN_NS Nuclease Genes and their Encoded Polypeptides:

SEQ ID NO: 106: DNA encoding full length polypeptide from *Bacillus* sp.

SEQ ID NO: 107: polypeptide derived from SEQ ID NO: 106

SEQ ID NO: 108: mature polypeptide obtained from *Bacillus* sp.

SEQ ID NO: 109: DNA encoding full length polypeptide from *Streptococcus infantis*

SEQ ID NO: 110: polypeptide derived from SEQ ID NO: 109

SEQ ID NO: 111: mature polypeptide obtained from *Streptococcus infantis*

Additional Motifs:

```
SEQ ID NO: 112:
P[LM]H[VA][GA]

SEQ ID NO: 113:
PLH[DN]E

SEQ ID NO: 114:
[YV][DN]RGH

SEQ ID NO: 115:
YDRGHQ[AV]

SEQ ID NO: 116:
[DNA]R[GSC]H[LI]

SEQ ID NO: 117:
[RIENLG][YF][RHN]V
```

Definitions

The term "nuclease" means a polypeptide having nuclease activity, and in the context of the present invention is used in relation to two groups of polypeptides. The first group of polypeptides are S1-P1 nucleases that cleave single-stranded DNA and RNA with no sequence specificity (EC:3.1.30.1), and may also introduce single-stranded breaks in double-stranded DNA or RNA, or DNA-RNA hybrids. Polypeptides of this first group comprise an S1-P1_nuclease domain (Pfam domain id PF02265, Pfam version 31.0 Finn (2016). Nucleic Acids Research, Database Issue 44:D279-D285).

The second group of polypeptides are classified as exonucleases or endonucleases (EN_NS nucleases), since they are characterized by having a functional Endonuclease_NS or an Endonuclea_NS_2 domain, identified as Pfam domain id PF01223 or PF13930 (Finn et al., (2016) Nucleic Acids Research, 44:D279-D285 and Pfam version 31.0). The Endonuclease_NS and the Endonuclea_NS_2 are functional domains providing catalytic activity to the polypeptide.

S1_P1-nucleases are non-specific nucleases that cleave DNA or RNA in single-stranded or double-stranded nucleic acids.

Endonuclease_NS nucleases are non-specific endo-nucleases that cleave DNA and RNA, cleaving double-stranded or single-stranded nucleic acids.

For purposes of the present invention, nuclease activity is determined according to the procedure described in the Examples. The first group of polypeptides of the present invention have at least 20%, e.g., at least 40%, at least 50%, at least 60%, at least 70%, at least 80%, at least 90%, at least 95%, or at least 100% of the nuclease activity of the mature polypeptide of SEQ ID NO: 3, 6, 9, 12, 15, 18, 21, 24, 27, 30, 33, 36, 39, 42, 45, 48, 51, 54, 57, 60, 63, 66, 69, 72 or 75, The second group of polypeptides of the present invention have at least 20%, e.g., at least 40%, at least 50%, at least 60%, at least 70%, at least 80%, at least 90%, at least 95%, or at least 100% of the nuclease activity of the mature polypeptide of SEQ ID NO: 78, 81, 84, 87, 90, 93, 96, 99, 108 or 111.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means a film produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among species including *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Micro-*

*bacterium* sp., *Micrococcus luteus, Pseudomonas* sp., *Staphylococcus epidermidis, Staphylococcus aureus* and *Stenotrophomonas* sp.

The term "catalytic domain" means the region of an enzyme containing the catalytic machinery of the enzyme.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "deep cleaning" means in this context disruption, reduction or removal of organic components such as polysaccharides, proteins, RNA, DNA, soil or other components present in organic matter such as biofilm.

The term "cleaning composition" includes "detergent composition" and refers to compositions that find use in the removal of undesired compounds from items to be cleaned, such as textiles, dishware and hard surfaces. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and include, but are not limited to, detergent compositions (e.g., liquid and/or solid laundry detergents and fine fabric detergents; fabric fresheners; fabric softeners; and textile and laundry pre-spotters/pretreatment).

In addition to containing the enzyme of the invention, the cleaning composition may contain one or more additional enzymes (such as DNases, proteases, amylases, lipases, cutinases, cellulases, endoglucanases, xyloglucanases, pectinases, pectin lyases, xanthanases, peroxidases, haloperoxygenases, catalases, galactanase, mannanases, or any mixture thereof), and/or cleaning components such as surfactants, builders, chelators or chelating agents, bleach system or bleach components, polymers, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

The term "fragment" means a polypeptide or a catalytic domain having one or more amino acids absent from the amino and/or carboxyl terminus of a mature polypeptide or domain; wherein the fragment has nuclease activity.

The term "His-tag" refers to a polyhistidine tag typically comprising at least 6 histidine residues, that may be added to the N- or C-terminal. His-tags are known in the art for use in e.g. protein purification, but may also be used for improving solubility at low pH values. Similarly, an "HQ-tag", i.e. a histidine-glutamine tag, may also be used for the purpose of purification as is known in the art.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "improved wash performance" is defined herein as an enzyme displaying an increased wash performance in a detergent composition relative to the wash performance of same detergent composition without the enzyme e.g. by increased stain removal or less re-deposition. The term "improved wash performance" includes wash performance in laundry, hard surface and dish washing.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell which may be produced by microorganisms and trapped within a biofilm or stick to the "glue" of a biofilm. Other examples of unpleasant smells are sweat or body odor adhered to an item which has been in contact with a human or animal. Other examples of malodor are odors from spices which stick to items, for example curry or other exotic spices with a strong smell.

The term "mature polypeptide" means a polypeptide in its mature form following N-terminal processing (e.g., removal of signal peptide).

In one aspect, the mature polypeptide is amino acids 1 to 302 of SEQ ID NO: 2. Amino acids −19 to −1 of SEQ ID NO: 2 is the signal peptide.

In one aspect, the mature polypeptide is amino acids 1 to 336 of SEQ ID NO: 5. Amino acids −21 to −1 of SEQ ID NO: 5 is the signal peptide.

In one aspect, the mature polypeptide is amino acids 1 to 324 of SEQ ID NO: 8. Amino acids −20 to −1 of SEQ ID NO: 8 is the signal peptide.

In one aspect, the mature polypeptide is amino acids 1 to 322 of SEQ ID NO: 11. Amino acids −20 to −1 of SEQ ID NO: 11 is the signal peptide.

In one aspect, the mature polypeptide is amino acids 1 to 276 of SEQ ID NO: 14. Amino acids −19 to −1 of SEQ ID NO: 14 is the signal peptide.

In one aspect, the mature polypeptide is amino acids 1 to 321 of SEQ ID NO: 17. Amino acids −17 to −1 of SEQ ID NO: 17 is the signal peptide.

In one aspect, the mature polypeptide is amino acids 1 to 314 of SEQ ID NO: 20. Amino acids −20 to −1 of SEQ ID NO: 20 is the signal peptide.

In one aspect, the mature polypeptide is amino acids 1 to 302 of SEQ ID NO: 23. Amino acids −19 to −1 of SEQ ID NO: 23 is the signal peptide.

In one aspect, the mature polypeptide is amino acids 1 to 273 of SEQ ID NO: 26. Amino acids −20 to −1 of SEQ ID NO: 26 is the signal peptide.

In one aspect, the mature polypeptide is amino acids 1 to 240 of SEQ ID NO: 29. Amino acids −30 to −1 of SEQ ID NO: 29 is the signal peptide.

In one aspect, the mature polypeptide is amino acids 1 to 252 of SEQ ID NO: 32. Amino acids −34 to −1 of SEQ ID NO: 32 is the signal peptide.

In one aspect, the mature polypeptide is amino acids 1 to 258 of SEQ ID NO: 35. Amino acids −26 to −1 of SEQ ID NO: 35 is the signal peptide.

In one aspect, the mature polypeptide is amino acids 1 to 251 of SEQ ID NO: 38. Amino acids −24 to −1 of SEQ ID NO: 38 is the signal peptide.

In one aspect, the mature polypeptide is amino acids 1 to 324 of SEQ ID NO: 41. Amino acids −21 to −1 of SEQ ID NO: 41 is the signal peptide.

In one aspect, the mature polypeptide is amino acids 1 to 332 of SEQ ID NO: 44. Amino acids −2 to −1 of SEQ ID NO: 44 is the signal peptide.

In one aspect, the mature polypeptide is amino acids 1 to 322 of SEQ ID NO: 47. Amino acids −20 to −1 of SEQ ID NO: 47 is the signal peptide.

In one aspect, the mature polypeptide is amino acids 1 to 324 of SEQ ID NO: 50. Amino acids −19 to −1 of SEQ ID NO: 50 is the signal peptide.

In one aspect, the mature polypeptide is amino acids 1 to 267 of SEQ ID NO: 53. Amino acids −19 to −1 of SEQ ID NO: 53 is the signal peptide.

In one aspect, the mature polypeptide is amino acids 1 to 271 of SEQ ID NO: 56. Amino acids −19 to −1 of SEQ ID NO: 56 is the signal peptide.

In one aspect, the mature polypeptide is amino acids 1 to 292 of SEQ ID NO: 59. Amino acids −18 to −1 of SEQ ID NO: 59 is the signal peptide.

In one aspect, the mature polypeptide is amino acids 1 to 270 of SEQ ID NO: 62. Amino acids −21 to −1 of SEQ ID NO: 62 is the signal peptide.

In one aspect, the mature polypeptide is amino acids 1 to 308 of SEQ ID NO: 65. Amino acids −19 to −1 of SEQ ID NO: 65 is the signal peptide.

In one aspect, the mature polypeptide is amino acids 1 to 288 of SEQ ID NO: 68. Amino acids −19 to −1 of SEQ ID NO: 68 is the signal peptide.

In one aspect, the mature polypeptide is amino acids 1 to 285 of SEQ ID NO: 71. Amino acids −19 to −1 of SEQ ID NO: 71 is the signal peptide.

In one aspect, the mature polypeptide is amino acids 1 to 308 of SEQ ID NO: 74. Amino acids −20 to −1 of SEQ ID NO: 74 is the signal peptide.

In one aspect, the mature polypeptide is amino acids 1 to 371 of SEQ ID NO: 77. Amino acids −28 to −1 of SEQ ID NO: 77 is the signal peptide.

In one aspect, the mature polypeptide is amino acids 1 to 235 of SEQ ID NO: 80. Amino acids −25 to −1 of SEQ ID NO: 80 is the signal peptide.

In one aspect, the mature polypeptide is amino acids 1 to 302 of SEQ ID NO: 83. Amino acids −22 to −1 of SEQ ID NO: 83 is the signal peptide.

In one aspect, the mature polypeptide is amino acids 1 to 246 of SEQ ID NO: 86. Amino acids −28 to −1 of SEQ ID NO: 86 is the signal peptide.

In one aspect, the mature polypeptide is amino acids 1 to 322 of SEQ ID NO: 89. Amino acids −21 to −1 of SEQ ID NO: 89 is the signal peptide.

In one aspect, the mature polypeptide is amino acids 1 to 345 of SEQ ID NO: 92. Amino acids −18 to −1 of SEQ ID NO: 92 is the signal peptide.

In one aspect, the mature polypeptide is amino acids 1 to 279 of SEQ ID NO: 95. Amino acids −25 to −1 of SEQ ID NO: 95 is the signal peptide.

In one aspect, the mature polypeptide is amino acids 1 to 319 of SEQ ID NO: 98. Amino acids −17 to −1 of SEQ ID NO: 98 is the signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having nuclease activity. In one aspect, the mature polypeptide coding sequence is nucleotides 58 to 1095 of SEQ ID NO: 1; and nucleotides 1 to 57 of SEQ ID NO: 1 encode a signal peptide.

In another aspect, the mature polypeptide coding sequence is nucleotides 64 to 1135 of SEQ ID NO: 4; and nucleotides 1 to 63 of SEQ ID NO: 4 encode a signal peptide.

In another aspect, the mature polypeptide coding sequence is nucleotides 61 to 1113 of SEQ ID NO: 7; and nucleotides 1 to 60 of SEQ ID NO: 7 encode a signal peptide.

In another aspect, the mature polypeptide coding sequence is nucleotides 61 to 1078 of SEQ ID NO: 10; and nucleotides 1 to 60 of SEQ ID NO: 10 encode a signal peptide.

In another aspect, the mature polypeptide coding sequence is nucleotides 58 to 1124 of SEQ ID NO: 13; and nucleotides 1 to 57 of SEQ ID NO: 13 encode a signal peptide.

In another aspect, the mature polypeptide coding sequence is nucleotides 52 to 1083 of SEQ ID NO: 16; and nucleotides 1 to 51 of SEQ ID NO: 16 encode a signal peptide In another aspect, the mature polypeptide coding sequence is nucleotides 61 to 1119 of SEQ ID NO: 19; and nucleotides 1 to 60 of SEQ ID NO: 19 encode a signal peptide.

In another aspect, the mature polypeptide coding sequence is nucleotides 58 to 634 of SEQ ID NO: 22; and nucleotides 1 to 57 of SEQ ID NO: 22 encode a signal peptide.

In another aspect, the mature polypeptide coding sequence is nucleotides 61 to 1165 of SEQ ID NO: 25; and nucleotides 1 to 60 of SEQ ID NO: 25 encode a signal peptide.

In another aspect, the mature polypeptide coding sequence is nucleotides 91 to 810 of SEQ ID NO: 28; and nucleotides 1 to 90 of SEQ ID NO: 28 encode a signal peptide.

In another aspect, the mature polypeptide coding sequence is nucleotides 103 to 858 of SEQ ID NO: 31; and nucleotides 1 to 102 of SEQ ID NO: 31 encode a signal peptide.

In another aspect, the mature polypeptide coding sequence is nucleotides 79 to 852 of SEQ ID NO: 34; and nucleotides 1 to 78 of SEQ ID NO: 34 encode a signal peptide.

In another aspect, the mature polypeptide coding sequence is nucleotides 70 to 822 of SEQ ID NO: 37; and nucleotides 1 to 69 of SEQ ID NO: 37 encode a signal peptide.

In another aspect, the mature polypeptide coding sequence is nucleotides 64 to 1035 of SEQ ID NO: 40; and nucleotides 1 to 57 of SEQ ID NO: 40 encode a signal peptide.

In another aspect, the mature polypeptide coding sequence is nucleotides 64 to 1059 of SEQ ID NO: 43; and nucleotides 1 to 63 of SEQ ID NO: 43 encode a signal peptide.

In another aspect, the mature polypeptide coding sequence is nucleotides 61 to 960 of SEQ ID NO: 46; and nucleotides 1 to 60 of SEQ ID NO: 46 encode a signal peptide.

In another aspect, the mature polypeptide coding sequence is nucleotides 58 to 1099 of SEQ ID NO: 49; and nucleotides 1 to 57 of SEQ ID NO: 49 encode a signal peptide.

In another aspect, the mature polypeptide coding sequence is nucleotides 58 to 952 of SEQ ID NO: 52; and nucleotides 1 to 57 of SEQ ID NO: 52 encode a signal peptide.

In another aspect, the mature polypeptide coding sequence is nucleotides 58 to 1083 of SEQ ID NO: 55; and nucleotides 1 to 57 of SEQ ID NO: 55 encode a signal peptide.

In another aspect, the mature polypeptide coding sequence is nucleotides 55 to 1044 of SEQ ID NO: 58; and nucleotides 1 to 54 of SEQ ID NO: 58 encode a signal peptide.

In another aspect, the mature polypeptide coding sequence is nucleotides 64 to 1445 of SEQ ID NO: 61; and nucleotides 1 to 63 of SEQ ID NO: 61 encode a signal peptide.

In another aspect, the mature polypeptide coding sequence is nucleotides 58 to 1116 of SEQ ID NO: 57; and nucleotides 1 to 57 of SEQ ID NO: 64 encode a signal peptide.

In another aspect, the mature polypeptide coding sequence is nucleotides 58 to 1064 of SEQ ID NO: 67; and nucleotides 1 to 57 of SEQ ID NO: 67 encode a signal peptide.

In another aspect, the mature polypeptide coding sequence is nucleotides 58 to 1100 of SEQ ID NO: 70; and nucleotides 1 to 57 of SEQ ID NO: 70 encode a signal peptide.

In another aspect, the mature polypeptide coding sequence is nucleotides 61 to 1054 of SEQ ID NO: 73; and nucleotides 1 to 60 of SEQ ID NO: 73 encode a signal peptide.

In another aspect, the mature polypeptide coding sequence is nucleotides 85 to 1197 of SEQ ID NO: 76; and nucleotides 1 to 84 of SEQ ID NO: 76 encode a signal peptide.

In another aspect, the mature polypeptide coding sequence is nucleotides 76 to 780 of SEQ ID NO: 79; and nucleotides 1 to 75 of SEQ ID NO: 79 encode a signal peptide.

In another aspect, the mature polypeptide coding sequence is nucleotides 67 to 972 of SEQ ID NO: 82; and nucleotides 1 to 66 of SEQ ID NO: 82 encode a signal peptide.

In another aspect, the mature polypeptide coding sequence is nucleotides 85 to 822 of SEQ ID NO: 85; and nucleotides 1 to 84 of SEQ ID NO: 85 encode a signal peptide.

In another aspect, the mature polypeptide coding sequence is nucleotides 64 to 1029 of SEQ ID NO: 88; and nucleotides 1 to 63 of SEQ ID NO: 88 encode a signal peptide.

In another aspect, the mature polypeptide coding sequence is nucleotides 55 to 1089 of SEQ ID NO: 91; and nucleotides 1 to 75 of SEQ ID NO: 91 encode a signal peptide.

In another aspect, the mature polypeptide coding sequence is nucleotides 76 to 973 of SEQ ID NO: 94; and nucleotides 1 to 75 of SEQ ID NO: 94 encode a signal peptide.

In another aspect, the mature polypeptide coding sequence is nucleotides 52 to 1008 of SEQ ID NO: 97; and nucleotides 1 to 51 of SEQ ID NO: 97 encode a signal peptide.

The term “nucleic acid construct” means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term “operably linked” means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment)

The term "subsequence" means a polynucleotide having one or more nucleotides absent from the 5' and/or 3' end of a mature polypeptide coding sequence; wherein the subsequence encodes a fragment having nuclease activity.

The term "variant" means a polypeptide having nuclease activity comprising an alteration, i.e., a substitution, insertion, and/or deletion, at one or more positions. A substitution means replacement of the amino acid occupying a position with a different amino acid; a deletion means removal of the amino acid occupying a position; and an insertion means adding an amino acid adjacent to and immediately following the amino acid occupying a position The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose-based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose-based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

The term "wash cycle" is defined herein as a washing operation wherein one or more items are exposed to a wash liquor, and the items and wash liquor are subjected to interaction e.g. by applying is mechanical action of some kind to the wash liquor and/or to the item, or by spraying the washing liquor on to the items, in order to release stains and to facilitate flow of wash liquor in or around the items, and finally the superfluous wash liquor is removed. After one or more wash cycles, the items are generally rinsed and dried. The term "wash liquor" is defined herein as the solution or mixture of water and a cleaning composition.

Nomenclature: For purposes of the present invention, the nomenclature [E/Q] or simply [EQ] means that the amino acid at this position may be a glutamic acid (Glu, E) or a glutamine (Gln, Q). Likewise, the nomenclature [V/G/A/I] or [VGAI] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Cleaning Compositions and Polypeptides Having Nuclease Activity

The present invention provides polypeptides having nuclease activity, whose members are characterized by having a functional nuclease domain conferring the catalytic activity of the polypeptide, as well as cleaning compositions comprising the polypeptides.

According to a first embodiment, a polypeptide having nuclease activity is an S1-P1 nuclease. S1-P1 nucleases cleave single stranded DNA and RNA with no sequence specificity, and may also introduce single-stranded breaks in double-stranded DNA or RNA, or DNA-RNA hybrids. The S1-P1 comprises an S1-P1_nuclease domain (Pfam domain id PF02265, Pfam version 31.0 Finn (2016). Nucleic Acids Research, Database Issue 44:D279-D285) which is a functional domain conferring hydrolytic activity to the polypeptide, classified as EC:3.1.30.1. In nature S1-P1 nucleases are secreted proteins.

According to a second embodiment, the polypeptides having nuclease activity are classified as exonucleases or endonucleases, since they are characterized by having a functional Endonuclease_NS or an Endonuclea_NS_2 domain, identified as Pfam domain id PF01223 and PF13930 (Finn et al., (2016) Nucleic Acids Research, 44:D279-D285 and Pfam version 31.0). The Endonuclease_NS and the Endonuclea_NS_2 is a functional domain providing catalytic activity to the polypeptide.

In one embodiment, the polypeptide is an S1-P1 nuclease that belongs to the Pfam family PF02265 (S1-P1 nuclease), and which comprises the motif [HQ][FILVY]X[GAQS]DX[HTGSA][QVM]P[LFM]H (SEQ ID NO: 102) and/or G[GA]NX[VILFY]X[VLM] (SEQ ID NO: 103).

In a particular embodiment, the polypeptide is an S1-P1 nuclease of bacterial origin and comprises the motif P[LM]H[VA][GA] (SEQ ID NO: 112).

In another particular embodiment, the polypeptide is an S1-P1 nuclease of fungal origin and comprises the motif PLH[DN]E (SEQ ID NO: 113).

In another embodiment, the polypeptide is an EN_NS nuclease that belongs to the Pfam family PF01223 (Endonuclease_NS) or PF13930 (Endonuclea_NS_2), and which comprises the motif [SADN]R[GS]H (SEQ ID NO: 104) and/or [YV][DN]RGH (SEQ ID NO: 114), preferably [YV][DN]RGH (SEQ ID NO: 114).

In one particular embodiment, the polypeptide is an EN_NS nuclease of fungal origin, in particular one that belongs to the Pfam family PF01223 (Endonuclease_NS), and which comprises the motif YDRGHQ[AV] (SEQ ID NO: 115).

In another particular embodiment, the polypeptide is an EN_NS nuclease of fungal origin, in particular one that belongs to the Pfam family PF01223 (Endonuclease_NS), and which comprises the motif [DNA]R[GSC]H[LI] (SEQ ID NO: 116) and/or [RIENLG][YF][RHN]V (SEQ ID NO: 117).

In a first aspect the invention concerns a polypeptide having nuclease activity, selected from a first group consisting of:

(a) a polypeptide having at least 99% sequence identity to the polypeptide of SEQ ID NO: 3;
(b) a polypeptide having at least 62% sequence identity to the polypeptide of SEQ ID NO: 6;
(c) a polypeptide having at least 97% sequence identity to the polypeptide of SEQ ID NO: 12; and
(d) a polypeptide having at least 86% sequence identity to the polypeptide of SEQ ID NO: 21 or 27;
(e) a polypeptide having at least 98% sequence identity to the polypeptide of SEQ ID NO: 30;
(f) a polypeptide having 100% sequence identity to the polypeptide of SEQ ID NO: 33 or 48;
(g) a polypeptide having at least 76% sequence identity to the polypeptide of SEQ ID NO: 39 or 51;
(h) a polypeptide having at least 95% sequence identity to the polypeptide of SEQ ID NO: 42;
(i) a polypeptide having at least 79% sequence identity to the polypeptide of SEQ ID NO: 45 or 24;
(j) a polypeptide having at least 94% sequence identity to the polypeptide of SEQ ID NO: 54;
(k) a polypeptide having at least 72% sequence identity to the polypeptide of SEQ ID NO: 57;
(l) a polypeptide having at least 82% sequence identity to the polypeptide of SEQ ID NO: 60;
(m) a polypeptide having at least 75% sequence identity to the polypeptide of SEQ ID NO: 63;
(n) a polypeptide having at least 80% sequence identity to the polypeptide of SEQ ID NO: 69 or 75;

or selected from a second group consisting of:

(o) a polypeptide having at least 77% sequence identity to the polypeptide of SEQ ID NO: 78;
(p) a polypeptide having at least 94% sequence identity to the polypeptide of SEQ ID NO: 84;
(q) a polypeptide having at least 99% sequence identity to the polypeptide of SEQ ID NO: 87;
(r) a polypeptide having at least 80% sequence identity to the polypeptide of SEQ ID NO: 90;
(s) a polypeptide having at least 90% sequence identity to the polypeptide of SEQ ID NO: 93;

or a variant or fragment selected from:

(t) a variant of the polypeptide selected from said first group or said second group wherein the variant has nuclease activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions; and
(u) a fragment of the polypeptide of (a), (b), (c), (d), (e), (f), (g), (h), (i), (j), (k), (l), (m), (n), (o), (p), (q), (r) and (s), wherein said fragment has nuclease activity.

The polypeptide having nuclease activity can be selected from said first group consisting of:

i. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of any one of SEQ ID NO: 6, 24, 39, 45, 51, 57, 63, 69 and 75; and
ii. a polypeptide having at least 95%, at least 96%, at least 97%, at least 98%, at least 99% or 100% sequence identity to the polypeptide of any one of SEQ ID NO: 21, 27, 42, 54 and 60.

In another embodiment of the invention the polypeptide having nuclease activity is selected from said second group consisting of:

iii. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 78 or 90; and
iv. a polypeptide having at least 95%, at least 96%, at least 97%, at least 98%, at least 99% or 100% sequence identity to the polypeptide of SEQ ID NO: 84 or 93.

In one embodiment of the invention the polypeptide having nuclease activity can be encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to:

v. the mature polypeptide coding sequence of any one of SEQ ID NO: 28, 31, 37, 40, 76, 82, 85, 88, and 91; or
vi. the mature polypeptide cDNA coding sequence of any one of SEQ ID NO: 1, 4, 10, 19, 22, 25, 43, 46, 49, 52, 55, 58, 61, 67 and 73.

In an embodiment of the invention the polypeptide having nuclease activity can be selected from the group consisting of polypeptides:

(a) comprising or consisting of SEQ ID NO: 3 or the mature polypeptide of SEQ ID NO: 2;
(b) comprising or consisting of SEQ ID NO: 6 or the mature polypeptide of SEQ ID NO: 5;
(c) comprising or consisting of SEQ ID NO: 12 or the mature polypeptide of SEQ ID NO: 11;
(d) comprising or consisting of SEQ ID NO: 21 or the mature polypeptide of SEQ ID NO: 20;
(e) comprising or consisting of SEQ ID NO: 24 or the mature polypeptide of SEQ ID NO: 23;
(f) comprising or consisting of SEQ ID NO: 27 or the mature polypeptide of SEQ ID NO: 26;
(g) comprising or consisting of SEQ ID NO: 30 or the mature polypeptide of SEQ ID NO: 29;
(h) comprising or consisting of SEQ ID NO: 33 or the mature polypeptide of SEQ ID NO: 32;
(i) comprising or consisting of SEQ ID NO: 39 or the mature polypeptide of SEQ ID NO: 38;
(j) comprising or consisting of SEQ ID NO: 42 or the mature polypeptide of SEQ ID NO: 41;
(k) comprising or consisting of SEQ ID NO: 45 or the mature polypeptide of SEQ ID NO: 44;
(l) comprising or consisting of SEQ ID NO: 48 or the mature polypeptide of SEQ ID NO: 47;

(m) comprising or consisting of SEQ ID NO: 51 or the mature polypeptide of SEQ ID NO: 50;
(n) comprising or consisting of SEQ ID NO: 54 or the mature polypeptide of SEQ ID NO: 53;
(o) comprising or consisting of SEQ ID NO: 57 or the mature polypeptide of SEQ ID NO: 56;
(p) comprising or consisting of SEQ ID NO: 60 or the mature polypeptide of SEQ ID NO: 59;
(q) comprising or consisting of SEQ ID NO: 63 or the mature polypeptide of SEQ ID NO: 62;
(r) comprising or consisting of SEQ ID NO: 69 or the mature polypeptide of SEQ ID NO: 68;
(s) comprising or consisting of SEQ ID NO: 75 or the mature polypeptide of SEQ ID NO: 74;
(t) comprising or consisting of SEQ ID NO: 78 or the mature polypeptide of SEQ ID NO: 77;
(u) comprising or consisting of SEQ ID NO: 84 or the mature polypeptide of SEQ ID NO: 83;
(v) comprising or consisting of SEQ ID NO: 87 or the mature polypeptide of SEQ ID NO: 86;
(w) comprising or consisting of SEQ ID NO: 90 or the mature polypeptide of SEQ ID NO: 89;
(x) comprising or consisting of SEQ ID NO: 93 or the mature polypeptide of SEQ ID NO: 92;
(y) comprising or consisting of SEQ ID NO: 96 or the mature polypeptide of SEQ ID NO: 95;
(z) comprising or consisting of SEQ ID NO: 99 or the mature polypeptide of SEQ ID NO: 98;
(æ) comprising or consisting of SEQ ID NO: 108 or the mature polypeptide of SEQ ID NO: 107; and
(ø) comprising or consisting of SEQ ID NO: 111 or the mature polypeptide of SEQ ID NO: 110.

In an embodiment, the present invention relates to polypeptides having a sequence identity to the mature polypeptide of SEQ ID NO: 3 of at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 70% of the nuclease activity of the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 75% of the nuclease activity of the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 80% of the nuclease activity of the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 85% of the nuclease activity of the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 90% of the nuclease activity of the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 95% of the nuclease activity of the mature polypeptide of SEQ ID NO: 3.

In a particular embodiment the invention relates to polypeptides having a sequence identity to the mature polypeptide of SEQ ID NO: 3 of at least 99%, or 100%, and wherein the polypeptide has at least at least 100% of the nuclease activity of the mature polypeptide of SEQ ID NO: 3.

In an embodiment, the polypeptide has been isolated. A polypeptide of the present invention preferably comprises or consists of the amino acid sequence of SEQ ID NO: 3 or an allelic variant thereof; or is a fragment thereof having nuclease activity. In another aspect, the polypeptide comprises or consists of the mature polypeptide of SEQ ID NO: 3.

In an embodiment, the present invention relates to polypeptides having a sequence identity to the mature polypeptide of SEQ ID NO: 6 of at least 62%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 6.

In a particular embodiment the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 6.

In an embodiment, the polypeptide has been isolated. A polypeptide of the present invention preferably comprises or consists of the amino acid sequence of SEQ ID NO: 6 or an allelic variant thereof; or is a fragment thereof having nuclease activity. In another aspect, the polypeptide comprises or consists of the mature polypeptide of SEQ ID NO: 6.

In an embodiment, the present invention relates to polypeptides having a sequence identity to the mature polypeptide of SEQ ID NO: 12 of at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 12.

In a particular embodiment the invention relates to polypeptides having a sequence identity to the mature polypeptide of SEQ ID NO: 12 at least 97%, at least 98%, at least 99%, or 100%, and wherein the polypeptide has at least at least 70% of the nuclease activity of the mature polypeptide of SEQ ID NO: 12.

In a particular embodiment the invention relates to polypeptides having a sequence identity to the mature polypeptide of SEQ ID NO: 12 of at least 97%, at least 98%, at least 99%, or 100%, and wherein the polypeptide has at least at least 75% of the nuclease activity of the mature polypeptide of SEQ ID NO: 12.

In a particular embodiment the invention relates to polypeptides having a sequence identity to the mature polypeptide of SEQ ID NO: 12 of at least 97%, at least 98%, at least 99%, or 100%, and wherein the polypeptide has at least at least 80% of the nuclease activity of the mature polypeptide of SEQ ID NO: 12.

In a particular embodiment the invention relates to polypeptides having a sequence identity to the mature polypeptide of SEQ ID NO: 12 of at least 97%, at least 98%, at least 99%, or 100%, and wherein the polypeptide has at least at least 85% of the nuclease activity of the mature polypeptide of SEQ ID NO: 12.

In a particular embodiment the invention relates to polypeptides having a sequence identity to the mature polypeptide of SEQ ID NO: 12 of at least 97%, at least 98%, at least 99%, or 100%, and wherein the polypeptide has at least at least 90% of the nuclease activity of the mature polypeptide of SEQ ID NO: 12.

In a particular embodiment the invention relates to polypeptides having a sequence identity to the mature polypeptide of SEQ ID NO: 12 of at least 97%, at least 98%, at least 99%, or 100%, and wherein the polypeptide has at least at least 95% of the nuclease activity of the mature polypeptide of SEQ ID NO: 12.

In a particular embodiment the invention relates to polypeptides having a sequence identity to the mature polypeptide of SEQ ID NO: 12 of at least 97%, at least 98%, at least 99%, or 100%, and wherein the polypeptide has at least at least 100% of the nuclease activity of the mature polypeptide of SEQ ID NO: 12.

In an embodiment, the polypeptide has been isolated. A polypeptide of the present invention preferably comprises or consists of the amino acid sequence of SEQ ID NO: 12 or an allelic variant thereof; or is a fragment thereof having nuclease activity. In another aspect, the polypeptide comprises or consists of the mature polypeptide of SEQ ID NO: 12.

In an embodiment, the present invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 86%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 21 or SEQ ID NO: 27.

In a particular embodiment the invention relates to polypeptides having a sequence identity to the mature polypeptide of SEQ ID NO: 21 or SEQ ID NO: 27 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 21 or SEQ ID NO: 27.

In an embodiment, the polypeptide has been isolated. A polypeptide of the present invention preferably comprises or consists of the amino acid sequence of SEQ ID NO: 21 or SEQ ID NO: 27 or an allelic variant thereof; or is a fragment thereof having nuclease activity. In another aspect, the polypeptide comprises or consists of the mature polypeptide of SEQ ID NO: 21 or SEQ ID NO: 27.

In an embodiment, the present invention relates to polypeptides having a sequence identity to the mature polypeptide of SEQ ID NO: 30 of at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 70% of the nuclease activity of the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 75% of the nuclease activity of the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 80% of the nuclease activity of the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 85% of the nuclease activity of the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 90% of the nuclease activity of the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 95% of the nuclease activity of the mature polypeptide of SEQ ID NO: 30.

In a particular embodiment the invention relates to polypeptides having a sequence identity to the mature polypeptide of SEQ ID NO: 30 of at least 98%, at least 99%, or 100%, and wherein the polypeptide has at least at least 100% of the nuclease activity of the mature polypeptide of SEQ ID NO: 30.

In an embodiment, the polypeptide has been isolated. A polypeptide of the present invention preferably comprises or consists of the amino acid sequence of SEQ ID NO: 30 or an allelic variant thereof; or is a fragment thereof having nuclease activity. In another aspect, the polypeptide comprises or consists of the mature polypeptide of SEQ ID NO: 30.

In an embodiment, the present invention relates to polypeptides having a sequence identity of 100% to the mature polypeptide of SEQ ID NO: 33 or SEQ ID NO: 48, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48, and wherein the polypeptide has at least at least 70% of the nuclease activity of the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48, and wherein the polypeptide has at least at least 75% of the nuclease activity of the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48, and wherein the polypeptide has at least at least 80% of the nuclease activity of the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48, and wherein the polypeptide has at least at least 85% of the nuclease activity of the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48 and wherein the polypeptide has at least at least 90% of the nuclease activity of the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48, and wherein the polypeptide has at least at least 95% of the nuclease activity of the mature polypeptide of SEQ ID NO: 33 or SEQ ID NO: 48.

In a particular embodiment the invention relates to polypeptides having a sequence identity of 100% to the mature polypeptide of SEQ ID NO: 33 or SEQ ID NO: 48, and wherein the polypeptide has at least at least 100% of the nuclease activity of the mature polypeptide of SEQ ID NO: 33 or SEQ ID NO: 48.

In an embodiment, the polypeptide has been isolated. A polypeptide of the present invention preferably comprises or consists of the amino acid sequence of SEQ ID NO: 33 or SEQ ID NO: 48 or an allelic variant thereof; or is a fragment thereof having nuclease activity. In another aspect, the polypeptide comprises or consists of the mature polypeptide of SEQ ID NO: 33 or SEQ ID NO: 48

In an embodiment, the present invention relates to polypeptides having a sequence identity to the mature polypeptide of SEQ ID NO: 39 of at least 76%, at least 80%, at least 85%, at least 90%, at least 91%, at least 92%, at least 93%, at least 94%, at least 95%, at least 96%, at least 97%, at least 98%, at least 99%, or 100%, which have nuclease activity.

In one aspect, the polypeptides differ by up to 10 amino acids, e.g., 1, 2, 3, 4, 5, 6, 7, 8, 9, or 10, from the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 39.

In a particular embodiment the invention relates to polypeptides having a sequence identity to the mature polypeptide of SEQ ID NO: 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 39.

In an embodiment, the polypeptide has been isolated. A polypeptide of the present invention preferably comprises or consists of the amino acid sequence of SEQ ID NO: 39 or an allelic variant thereof; or is a fragment thereof having nuclease activity. In another aspect, the polypeptide comprises or consists of the mature polypeptide of SEQ ID NO: 39.

In an embodiment, the present invention relates to polypeptides having a sequence identity to the mature polypeptide of SEQ ID NO: 42 of at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 42.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 42.

In an embodiment, the polypeptide has been isolated. A polypeptide of the present invention preferably comprises or consists of the amino acid sequence of SEQ ID NO: 42 or an allelic variant thereof; or is a fragment thereof having nuclease activity. In another aspect, the polypeptide comprises or consists of the mature polypeptide of SEQ ID NO: 42.

In an embodiment, the present invention relates to polypeptides having a sequence identity to the mature polypeptide of SEQ ID NO: 45 or SEQ ID NO: 24 of at least 69%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 45 or SEQ ID NO: 24.

In a particular embodiment the invention relates to polypeptides having a sequence identity to the mature polypeptide of SEQ ID NO: 45 or SEQ ID NO: 24 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 45 or SEQ ID NO: 24.

In an embodiment, the polypeptide has been isolated. A polypeptide of the present invention preferably comprises or consists of the amino acid sequence of SEQ ID NO: 45 or SEQ ID NO: 24 or an allelic variant thereof; or is a fragment thereof having nuclease activity. In another aspect, the polypeptide comprises or consists of the mature polypeptide of SEQ ID NO: 45 or SEQ ID NO: 24.

In an embodiment, the present invention relates to polypeptides having a sequence identity to the mature polypeptide of SEQ ID NO: 54 of at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 70% of the nuclease activity of the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 75% of the nuclease activity of the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 80% of the nuclease activity of the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 85% of the nuclease activity of the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 90% of the nuclease activity of the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 95% of the nuclease activity of the mature polypeptide of SEQ ID NO: 54.

In a particular embodiment the invention relates to polypeptides having a sequence identity to the mature polypeptide of SEQ ID NO: 54 of at least 94%, at least 95%, at least 96%, at least 97%, at least 98%, at least 99%, or 100%, and wherein the polypeptide has at least at least 100% of the nuclease activity of the mature polypeptide of SEQ ID NO: 54.

In an embodiment, the polypeptide has been isolated. A polypeptide of the present invention preferably comprises or consists of the amino acid sequence of SEQ ID NO: 54 or an allelic variant thereof; or is a fragment thereof having nuclease activity. In another aspect, the polypeptide comprises or consists of the mature polypeptide of SEQ ID NO: 54.

In an embodiment, the present invention relates to polypeptides having a sequence identity to the mature polypeptide of SEQ ID NO: 57 of at least 72%, at least 75%, at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 57.

In a particular embodiment the invention relates to polypeptides having a sequence identity to the mature polypeptide of SEQ ID NO: 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 57.

In an embodiment, the polypeptide has been isolated. A polypeptide of the present invention preferably comprises or consists of the amino acid sequence of SEQ ID NO: 57 or an allelic variant thereof; or is a fragment thereof having nuclease activity. In another aspect, the polypeptide comprises or consists of the mature polypeptide of SEQ ID NO: 57.

In an embodiment, the present invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 60.

In a particular embodiment the invention relates to polypeptides having a sequence identity to the mature polypeptide of SEQ ID NO: 60 of at least 82%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 60.

In an embodiment, the polypeptide has been isolated. A polypeptide of the present invention preferably comprises or consists of the amino acid sequence of SEQ ID NO: 60 or an allelic variant thereof; or is a fragment thereof having nuclease activity. In another aspect, the polypeptide comprises or consists of the mature polypeptide of SEQ ID NO: 60.

In an embodiment, the present invention relates to polypeptides having a sequence identity to the mature polypeptide of SEQ ID NO: 63 of at least 75%, at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 63.

In a particular embodiment the invention relates to polypeptides having a sequence identity to the mature polypeptide of SEQ ID NO: 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 63.

In an embodiment, the polypeptide has been isolated. A polypeptide of the present invention preferably comprises or consists of the amino acid sequence of SEQ ID NO: 63 or an allelic variant thereof; or is a fragment thereof having nuclease activity. In another aspect, the polypeptide comprises or consists of the mature polypeptide of SEQ ID NO: 63.

In an embodiment, the present invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 69 or SEQ ID NO: 75.

In a particular embodiment the invention relates to polypeptides having a sequence identity to the mature polypeptide of SEQ ID NO: 69 or SEQ ID NO: 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 69 or SEQ ID NO: 75.

In an embodiment, the polypeptide has been isolated. A polypeptide of the present invention preferably comprises or consists of the amino acid sequence of SEQ ID NO: 69 or SEQ ID NO: 75 or an allelic variant thereof; or is a fragment thereof having nuclease activity. In another aspect, the polypeptide comprises or consists of the mature polypeptide of SEQ ID NO: 69 or SEQ ID NO: 75.

In an embodiment, the present invention relates to polypeptides having a sequence identity to the mature polypeptide of SEQ ID NO: 78 of at least 77%, at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 78.

In a particular embodiment the invention relates to polypeptides having a sequence identity to the mature polypeptide of SEQ ID NO: 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 78.

In an embodiment, the polypeptide has been isolated. A polypeptide of the present invention preferably comprises or consists of the amino acid sequence of SEQ ID NO: 78 or an allelic variant thereof; or is a fragment thereof having nuclease activity. In another aspect, the polypeptide comprises or consists of the mature polypeptide of SEQ ID NO: 78.

In an embodiment, the present invention relates to polypeptides having a sequence identity to the mature polypeptide of SEQ ID NO: 84 of at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 84.

In a particular embodiment the invention relates to polypeptides having a sequence identity to the mature polypeptide of SEQ ID NO: 84 at least 94%, at least 95%, at least 96%, at least 97%, at least 98%, at least 99%, or 100%, and wherein the polypeptide has at least at least 70% of the nuclease activity of the mature polypeptide of SEQ ID NO: 84.

In a particular embodiment the invention relates to polypeptides having a sequence identity to the mature polypeptide of SEQ ID NO: 84 of at least 94%, at least 95%, at least 96%, at least 97%, at least 98%, at least 99%, or 100%, and wherein the polypeptide has at least at least 75% of the nuclease activity of the mature polypeptide of SEQ ID NO: 84.

In a particular embodiment the invention relates to polypeptides having a sequence identity to the mature polypeptide of SEQ ID NO: 84 of at least 94%, at least 95%, at least 96%, at least 97%, at least 98%, at least 99%, or 100%, and wherein the polypeptide has at least at least 80% of the nuclease activity of the mature polypeptide of SEQ ID NO: 84.

In a particular embodiment the invention relates to polypeptides having a sequence identity to the mature polypeptide of SEQ ID NO: 84 of at least 94%, at least 95%, at least 96%, at least 97%, at least 98%, at least 99%, or 100%, and wherein the polypeptide has at least at least 85% of the nuclease activity of the mature polypeptide of SEQ ID NO: 84.

In a particular embodiment the invention relates to polypeptides having a sequence identity to the mature polypeptide of SEQ ID NO: 84 of at least 94%, at least 95%, at least 96%, at least 97%, at least 98%, at least 99%, or 100%, and wherein the polypeptide has at least at least 90% of the nuclease activity of the mature polypeptide of SEQ ID NO: 84.

In a particular embodiment the invention relates to polypeptides having a sequence identity to the mature polypeptide of SEQ ID NO: 84 of at least 94%, at least 95%, at least 96%, at least 97%, at least 98%, at least 99%, or 100%, and wherein the polypeptide has at least at least 95% of the nuclease activity of the mature polypeptide of SEQ ID NO: 84.

In a particular embodiment the invention relates to polypeptides having a sequence identity to the mature polypeptide of SEQ ID NO: 84 of at least 94%, at least 95%, at least 96%, at least 97%, at least 98%, at least 99%, or 100%, and wherein the polypeptide has at least at least 100% of the nuclease activity of the mature polypeptide of SEQ ID NO: 84.

In an embodiment, the polypeptide has been isolated. A polypeptide of the present invention preferably comprises or consists of the amino acid sequence of SEQ ID NO: 84 or an allelic variant thereof; or is a fragment thereof having nuclease activity. In another aspect, the polypeptide comprises or consists of the mature polypeptide of SEQ ID NO: 84.

In an embodiment, the present invention relates to polypeptides having a sequence identity to the mature polypeptide of SEQ ID NO: 87 of at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 70% of the nuclease activity of the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 75% of the nuclease activity of the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 80% of the nuclease activity of the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 85% of the nuclease activity of the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 90% of the nuclease activity of the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 95% of the nuclease activity of the mature polypeptide of SEQ ID NO: 87.

In a particular embodiment the invention relates to polypeptides having a sequence identity to the mature polypeptide of SEQ ID NO: 87 of at least 99%, or 100%, and wherein the polypeptide has at least at least 100% of the nuclease activity of the mature polypeptide of SEQ ID NO: 87.

In an embodiment, the polypeptide has been isolated. A polypeptide of the present invention preferably comprises or consists of the amino acid sequence of SEQ ID NO: 87 or an allelic variant thereof; or is a fragment thereof having nuclease activity. In another aspect, the polypeptide comprises or consists of the mature polypeptide of SEQ ID NO: 87.

In an embodiment, the present invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 90.

In a particular embodiment the invention relates to polypeptides having a sequence identity to the mature polypeptide of SEQ ID NO: 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 90.

In an embodiment, the polypeptide has been isolated. A polypeptide of the present invention preferably comprises or consists of the amino acid sequence of SEQ ID NO: 90 or an allelic variant thereof; or is a fragment thereof having nuclease activity. In another aspect, the polypeptide comprises or consists of the mature polypeptide of SEQ ID NO: 90.

In an embodiment, the present invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 93.

In a particular embodiment the invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 93.

In a particular embodiment the invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 93.

In a particular embodiment the invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 93.

In a particular embodiment the invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 93.

In a particular embodiment the invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 93.

In a particular embodiment the invention relates to polypeptides having a sequence identity to the mature polypeptide of SEQ ID NO: 93 of at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 93.

In a particular embodiment the invention relates to polypeptides having a sequence identity to the mature polypeptide of SEQ ID NO: 93 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 93.

In an embodiment, the polypeptide has been isolated. A polypeptide of the present invention preferably comprises or consists of the amino acid sequence of SEQ ID NO: 93 or an allelic variant thereof; or is a fragment thereof having nuclease activity. In another aspect, the polypeptide comprises or consists of the mature polypeptide of SEQ ID NO: 93.

The polynucleotide of SEQ ID NO: 1, 4, 7, 10, 13, 16, 19, 22, 25, 28, 31, 34, 37, 40, 43, 46, 49, 52, 55, 76, 79, 82, 85, 88, 91, 94, or 97 or a subsequence thereof, as well as the polypeptide of SEQ ID NO: 2, 5, 8, 11, 14, 17, 20, 23, 26, 29, 32, 35, 38, 41, 44, 47, 50, 53, 56, 77, 80, 83, 86, 89, 92, 95, or 96 or a fragment thereof may be used to design nucleic acid probes to identify and clone DNA encoding polypeptides having nuclease activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having nuclease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

In another embodiment, the present invention relates to an polypeptide having nuclease activity encoded by a polynucleotide having a sequence identity to the mature polypeptide coding sequence of SEQ ID NO: 1, SEQ ID NO: 4, SEQ ID NO: 7, SEQ ID NO: 10, SEQ ID NO: 13, or SEQ ID NO: 16 SEQ ID NO: 19, SEQ ID NO: 22, SEQ ID NO: 25, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to an polypeptide having nuclease activity encoded by a polynucleotide having a sequence identity to the mature polypeptide coding sequence of SEQ ID NO: 28, SEQ ID NO: 31, SEQ ID NO: 34, SEQ ID NO: 37, SEQ ID NO: 40, SEQ ID NO: 43, SEQ ID NO: 76, SEQ ID NO: 79, SEQ ID NO: 82, SEQ ID NO: 85, SEQ ID NO: 88, SEQ ID NO: 91, SEQ ID NO: 94 or SEQ ID NO: 97 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94 or SEQ ID NO: 97 comprising a substitution, deletion, and/or insertion at one or more positions. In an embodiment, the number of amino acid substitutions, deletions and/or insertions introduced into the mature polypeptide of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 108 or SEQ ID NO: 111 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for nuclease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Nuclease Activity

A polypeptide having nuclease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect the polypeptide having nuclease activity may be obtained from *Bacillus, Penicillium, Streptomyces, Acremonium, Daldinia, Actinomucor, Talaromyces, Lysobacter, Pseudoalteromonas, Vibrio, Janthinobacterium, Massilia, Aspergillus, Pyrenochaetopsis Lachnellula, Trichoderma, Cordyceps, Acremonium, Microdochium, Morchella, Stenocarpella, Cordyceps, Phialophora*, or an *Adophora* cell.

In one aspect, the polypeptide having nuclease activity may be obtained from *Bacillus*, e.g. from *Bacillus* sp-62738, *Bacillus deramificans* or *Bacillus thuringiensis.*

In one aspect, the polypeptide having nuclease activity may be obtained from *Penicillium*, e.g. from *Penicillium virgatum, Penicillium atramentosum, Penicillium emersonii* or *Penicillium cremeogriseum.*

In one aspect, the polypeptide having nuclease activity may be obtained from *Streptomyces*, e.g. *Streptomyces cirratus.*

In one aspect, the polypeptide having nuclease activity may be obtained from *Acremonium*, e.g. *Acremonium* sp. XZ1968 or *Acremonium alcalophilum.*

In one aspect, the polypeptide having nuclease activity may be obtained from *Daldinia, e.g. Daldinia fissa.*

In one aspect, the polypeptide having nuclease activity may be obtained from *Actinomucor*, e.g. *Actinomucor elegans.*

In one aspect, the polypeptide having nuclease activity may be obtained from *Talaromyces*, e.g. *Talaromyces leycettanus.*

In one aspect, the polypeptide having nuclease activity may be obtained from *Lysobacter*, e.g. *Lysobacter enzymogenes.*

In one aspect, the polypeptide having nuclease activity may be obtained from *Pseudoalteromonas*, e.g. *Pseudoalteromonas nigrifaciens.*

In one aspect, the polypeptide having nuclease activity may be obtained from *Vibrio*, e.g. *Vibrio* sp-63684.

In one aspect, the polypeptide having nuclease activity may be obtained from *Janthinobacterium*, e.g. *Janthinobacterium agaricidamnosum.*

In one aspect, the polypeptide having nuclease activity may be obtained from *Massilia*, e.g. *Massilia aerilata.*

In one aspect, the polypeptide having nuclease activity may be obtained from *Aspergillus*, e.g. *Aspergillus oryzae.*

In one aspect, the polypeptide having nuclease activity may be obtained from *Ostropa, e.g. Ostropa barbara.*

In one aspect, the polypeptide having nuclease activity may be obtained from *Lachnellula*, e.g. *Pyrenochaetopsis* sp.

In one aspect, the polypeptide having nuclease activity may be obtained from *Pyrenochaetopsis*, e.g. *Lachnellula* sp.

In one aspect, the polypeptide having nuclease activity may be obtained from *Trichoderma*, e.g. *Trichoderma reesei* or *Trichoderma hamatum.*

In one aspect, the polypeptide having nuclease activity may be obtained from *Cordyceps*, e.g. *Cordyceps cardinalis.*

In one aspect, the polypeptide having nuclease activity may be obtained from *Microdochium*, e.g. *Microdochium phragmitis.*

In one aspect, the polypeptide having nuclease activity may be obtained from *Morchella*, e.g. *Morchella costata.*

In one aspect, the polypeptide having nuclease activity may be obtained from *Stenocarpella*, e.g. *Stenocarpella maydis.*

In one aspect, the polypeptide having nuclease activity may be obtained from *Phialophora*, e.g. *Phialophora geniculate.*

In one aspect, the polypeptide having nuclease activity may be obtained from *Cadophora*, e.g. *Cadophora fastigiata.*

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus, Penicillium, Streptomyces, Acremonium, Daldinia, Actinomucor, Talaromyces, Lysobacter, Pseudoalteromonas, Vibrio, Janthinobacterium, Massilia, Aspergillus, Pyrenochaetopsis Lachnellula, Trichoderma, Cordyceps, Acremonium, Microdochium, Morchella, Stenocarpella, Cordyceps, Phialophora, Adophora* or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma.*

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi,* 8th edition, 1995, CAB International, University Press, Cambridge, UK). The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Bacillus, Penicillium, Streptomyces, Acremonium, Daldinia, Actinomucor, Talaromyces, Lysobacter, Pseudoalteromonas, Vibrio, Janthinobacterium, Massilia, Aspergillus, Pyrenochaetopsis Lachnellula, Trichoderma, Cordyceps, Acremonium, Microdochium, Morchella, Stenocarpella, Cordyceps, Phialophora*, or an *Adophora* cell.

In another aspect, the cell is a *Bacillus* cell. In another aspect, the cell is *Bacillus* sp-62738, *Bacillus* deramificans or *Bacillus thuringiensis.*

In another aspect, the cell is a *Penicillium* cell. In another aspect, the cell is *Penicillium virgatum, Penicillium atramentosum, Penicillium emersonii* or *Penicillium cremeogriseum.*

In another aspect, the cell is a *Streptomyces* cell. In another aspect, the cell is *Streptomyces cirratus.*

In another aspect, the cell is a *Acremonium* cell. In another aspect, the cell is *Acremonium* sp. XZ1968 or *Acremonium alcalophilum.*

In another aspect, the cell is a *Daldinia* cell. In another aspect, the cell is *Daldinia fissa.*

In another aspect, the cell is a *Actinomucor* cell. In another aspect, the cell is *Actinomucor elegans.*

In another aspect, the cell is a *Talaromyces* cell. In another aspect, the cell is *Talaromyces leycettanus.*

In another aspect, the cell is a *Lysobacter* cell. In another aspect, the cell is *Lysobacter enzymogenes.*

In another aspect, the cell is a *Pseudoalteromonas* cell. In another aspect, the cell is *Pseudoalteromonas nigrifaciens.*

In another aspect, the cell is a *Vibrio* cell. In another aspect, the cell is *Vibrio* sp-63684.

In another aspect, the cell is a *Janthinobacterium* cell. In another aspect, the cell is *Janthinobacterium agaricidamnosum.*

In another aspect, the cell is a *Massilia* cell. In another aspect, the cell is *Massilia aerilata.*

In another aspect, the cell is a *Aspergillus* cell. In another aspect, the cell is *Aspergillus oryzae.*

In another aspect, the cell is a *Ostropa* cell. In another aspect, the cell is *Ostropa barbara.*

In another aspect, the cell is a *Lachnellula* cell. In another aspect, the cell is *Pyrenochaetopsis* sp.

In another aspect, the cell is a *Pyrenochaetopsis* cell. In another aspect, the cell is *Lachnellula* sp.

In another aspect, the cell is a *Trichoderma* cell. In another aspect, the cell is *Trichoderma reesei* or *Trichoderma hamatum.*

In another aspect, the cell is a *Cordyceps* cell. In another aspect, the cell is *Cordyceps cardinalis.*

In another aspect, the cell is a *Microdochium* cell. In another aspect, the cell is *Microdochium phragmitis.*

In another aspect, the cell is a *Morchella* cell. In another aspect, the cell is *Morchella costata.*

In another aspect, the cell is a *Stenocarpella* cell. In another aspect, the cell is *Stenocarpella maydis.*

In another aspect, the cell is a *Phialophora* cell. In another aspect, the cell is *Phialophora geniculate.*

In another aspect, the cell is a *Cadophora* cell. In another aspect, the cell is *Cadophora fastigiata.*

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having nuclease activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The invention further comprises a composition comprising a polypeptide of the invention. In one embodiment the composition comprises a polypeptide having nuclease activity, selected from a first group consisting of:

(a) a polypeptide having at least 99% sequence identity to the polypeptide of SEQ ID NO: 3;
(b) a polypeptide having at least 62% sequence identity to the polypeptide of SEQ ID NO: 6;
(c) a polypeptide having at least 97% sequence identity to the polypeptide of SEQ ID NO: 12; and
(d) a polypeptide having at least 86% sequence identity to the polypeptide of SEQ ID NO: 21 or 27;
(e) a polypeptide having at least 98% sequence identity to the polypeptide of SEQ ID NO: 30;
(f) a polypeptide having 100% sequence identity to the polypeptide of SEQ ID NO: 33 or 48;
(g) a polypeptide having at least 76% sequence identity to the polypeptide of SEQ ID NO: 39 or 51;
(h) a polypeptide having at least 95% sequence identity to the polypeptide of SEQ ID NO: 42;
(i) a polypeptide having at least 79% sequence identity to the polypeptide of SEQ ID NO: 45 or 24;
(j) a polypeptide having at least 94% sequence identity to the polypeptide of SEQ ID NO: 54;
(k) a polypeptide having at least 72% sequence identity to the polypeptide of SEQ ID NO: 57;
(l) a polypeptide having at least 82% sequence identity to the polypeptide of SEQ ID NO: 60;
(m) a polypeptide having at least 75% sequence identity to the polypeptide of SEQ ID NO: 63;
(n) a polypeptide having at least 80% sequence identity to the polypeptide of SEQ ID NO: 69 or 75;

or selected from a second group consisting of:

(o) a polypeptide having at least 77% sequence identity to the polypeptide of SEQ ID NO: 78;
(p) a polypeptide having at least 94% sequence identity to the polypeptide of SEQ ID NO: 84;
(q) a polypeptide having at least 99% sequence identity to the polypeptide of SEQ ID NO: 87;
(r) a polypeptide having at least 80% sequence identity to the polypeptide of SEQ ID NO: 90; and
(s) a polypeptide having at least 90% sequence identity to the polypeptide of SEQ ID NO: 93;

or a variant or fragment selected from:

(t) a variant of the polypeptide selected from said first group or said second group wherein the variant has nuclease activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(u) a fragment of the polypeptide of (a), (b), (c), (d), (e), (f), (g), (h), (i), (j), (k), (I), (m), (n), (o), (p), (q), (r) and (s), wherein said fragment has nuclease activity.

In one embodiment of the invention, the composition comprises a polypeptide selected from the group consisting of:

i. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of any one of SEQ ID NO: 6, 24, 39, 45, 51, 57, 63, 69 and 75; and
ii. a polypeptide having at least 95%, at least 96%, at least 97%, at least 98%, at least 99% or 100% sequence identity to the polypeptide of any one of SEQ ID NO: 21, 27, 42, 54 and 60.

In one embodiment of the invention, the composition comprises a polypeptide selected from the group consisting of:

i. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 78 or 90; and
ii. a polypeptide having at least 95%, at least 96%, at least 97%, at least 98%, at least 99% or 100% sequence identity to the polypeptide of SEQ ID NO: 84 or 93.

In one embodiment of the invention, the composition comprises a polypeptide which is encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to:
i. the mature polypeptide coding sequence of any one of SEQ ID NO: 28, 31, 37, 40, 76, 82, 85, 88, and 91; or
ii. the mature polypeptide cDNA coding sequence of any one of SEQ ID NO: 1, 4, 10, 19, 22, 25, 43, 46, 49, 52, 55, 58, 61, 67 and 73.

In one embodiment of the invention, the composition comprises a polypeptide selected from the group consisting of polypeptides:
(a) comprising or consisting of SEQ ID NO: 3 or the mature polypeptide of SEQ ID NO: 2;
(b) comprising or consisting of SEQ ID NO: 6 or the mature polypeptide of SEQ ID NO: 5;
(c) comprising or consisting of SEQ ID NO: 12 or the mature polypeptide of SEQ ID NO: 11;
(d) comprising or consisting of SEQ ID NO: 21 or the mature polypeptide of SEQ ID NO: 20;
(e) comprising or consisting of SEQ ID NO: 24 or the mature polypeptide of SEQ ID NO: 23;
(f) comprising or consisting of SEQ ID NO: 27 or the mature polypeptide of SEQ ID NO: 26;
(g) comprising or consisting of SEQ ID NO: 30 or the mature polypeptide of SEQ ID NO: 29;
(h) comprising or consisting of SEQ ID NO: 33 or the mature polypeptide of SEQ ID NO: 32;
(i) comprising or consisting of SEQ ID NO: 39 or the mature polypeptide of SEQ ID NO: 38;
(j) comprising or consisting of SEQ ID NO: 42 or the mature polypeptide of SEQ ID NO: 41;
(k) comprising or consisting of SEQ ID NO: 45 or the mature polypeptide of SEQ ID NO: 44;
(l) comprising or consisting of SEQ ID NO: 48 or the mature polypeptide of SEQ ID NO: 47;
(m) comprising or consisting of SEQ ID NO: 51 or the mature polypeptide of SEQ ID NO: 50;
(n) comprising or consisting of SEQ ID NO: 54 or the mature polypeptide of SEQ ID NO: 53;
(o) comprising or consisting of SEQ ID NO: 57 or the mature polypeptide of SEQ ID NO: 56;
(p) comprising or consisting of SEQ ID NO: 60 or the mature polypeptide of SEQ ID NO: 59;
(q) comprising or consisting of SEQ ID NO: 63 or the mature polypeptide of SEQ ID NO: 62;
(r) comprising or consisting of SEQ ID NO: 69 or the mature polypeptide of SEQ ID NO: 68;
(s) comprising or consisting of SEQ ID NO: 75 or the mature polypeptide of SEQ ID NO: 74;
(t) comprising or consisting of SEQ ID NO: 78 or the mature polypeptide of SEQ ID NO: 77;
(u) comprising or consisting of SEQ ID NO: 84 or the mature polypeptide of SEQ ID NO: 83;
(v) comprising or consisting of SEQ ID NO: 87 or the mature polypeptide of SEQ ID NO: 86;
(w) comprising or consisting of SEQ ID NO: 90 or the mature polypeptide of SEQ ID NO: 89;
(x) comprising or consisting of SEQ ID NO: 93 or the mature polypeptide of SEQ ID NO: 92;
(y) comprising or consisting of SEQ ID NO: 96 or the mature polypeptide of SEQ ID NO: 95;
(z) comprising or consisting of SEQ ID NO: 99 or the mature polypeptide of SEQ ID NO: 98;
(æ) comprising or consisting of SEQ ID NO: 108 or the mature polypeptide of SEQ ID NO: 107; and
(ø) comprising or consisting of SEQ ID NO: 111 or the mature polypeptide of SEQ ID NO: 110.

In one embodiment of the invention the composition is a cleaning composition.

In one embodiment of the invention the composition is a cleaning composition comprising
(a) at least 0.001 ppm of a polypeptide have nuclease activity
(b) one or more surfactants; and
(c) optionally one or more cleaning composition components, preferably selected from surfactants, builders, bleach components, polymers, dispersing agents and additional enzymes, wherein said polypeptide is selected from the group consisting of:
(a) a polypeptide having at least 99% sequence identity to the polypeptide of SEQ ID NO: 3;
(b) a polypeptide having at least 62% sequence identity to the polypeptide of SEQ ID NO: 6;
(c) a polypeptide having at least 97% sequence identity to the polypeptide of SEQ ID NO: 12; and
(d) a polypeptide having at least 86% sequence identity to the polypeptide of SEQ ID NO: 21 or 27
(e) a polypeptide having at least 98% sequence identity to the polypeptide of SEQ ID NO: 30;
(f) a polypeptide having 100% sequence identity to the polypeptide of SEQ ID NO: 33 or 48;
(g) a polypeptide having at least 76% sequence identity to the polypeptide of SEQ ID NO: 39 or 51;
(h) a polypeptide having at least 95% sequence identity to the polypeptide of SEQ ID NO: 42;
(i) a polypeptide having at least 79% sequence identity to the polypeptide of SEQ ID NO: 45 or 24;
(j) a polypeptide having at least 94% sequence identity to the polypeptide of SEQ ID NO: 54;
(k) a polypeptide having at least 72% sequence identity to the polypeptide of SEQ ID NO: 57;
(l) a polypeptide having at least 82% sequence identity to the polypeptide of SEQ ID NO: 60;
(m) a polypeptide having at least 75% sequence identity to the polypeptide of SEQ ID NO: 63;
(n) a polypeptide having at least 80% sequence identity to the polypeptide of SEQ ID NO: 69 or 75;

or selected from a second group consisting of:
(o) a polypeptide having at least 77% sequence identity to the polypeptide of SEQ ID NO: 78;
(p) a polypeptide having at least 94% sequence identity to the polypeptide of SEQ ID NO: 84;
(q) a polypeptide having at least 99% sequence identity to the polypeptide of SEQ ID NO: 87;
(r) a polypeptide having at least 80% sequence identity to the polypeptide of SEQ ID NO: 90; and
(5) a polypeptide having at least 90% sequence identity to the polypeptide of SEQ ID NO: 93;

or a variant or fragment selected from:
(t) a variant of the polypeptide selected from said first group or said second group wherein the variant has nuclease activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;

(u) a fragment of the polypeptide of (a), (b), (c), (d), (e), (f), (g), (h), (i), (j), (k), (l), (m), (n), (o), (p), (q), (r) and (s), wherein said fragment has nuclease activity.

(i) a polypeptide having at least 80% sequence identity to the polypeptide of SEQ ID NO: 36;

(ii) a polypeptide having at least 80% sequence identity to the polypeptide of SEQ ID NO: 66;

(iii) a polypeptide having at least 80% sequence identity to the polypeptide of SEQ ID NO: 72;

(iv) a polypeptide having at least 80% sequence identity to the polypeptide of SEQ ID NO: 9;

(v) a polypeptide having at least 80% sequence identity to the polypeptide of SEQ ID NO: 15;

(vi) a polypeptide having at least 80% sequence identity to the polypeptide of SEQ ID NO: 18;

(vii) a polypeptide having at least 80% sequence identity to the polypeptide of SEQ ID NO: 81;

(viii) a polypeptide having at least 80% sequence identity to the polypeptide of SEQ ID NO: 96;

(ix) a polypeptide having at least 80% sequence identity to the polypeptide of SEQ ID NO: 99; and (x) a polypeptide comprising the motif [HQ][FILVY]X[GAQS]DX[HTGSA][QVM]P[LFM]H (SEQ ID NO: 102) and/or the motif G[GA]NX[VILFY]X[VLM] (SEQ ID NO: 103).

In an embodiment of the invention the composition is a cleaning composition comprising;

(a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 36.

In a particular embodiment the composition comprises polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 36.

In a particular embodiment the composition comprises to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 36.

In a particular embodiment the composition comprises to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 36.

In a particular embodiment the composition comprises to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 36.

In a particular embodiment the composition comprises to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 36.

In a particular embodiment the composition comprises to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 36.

In a particular embodiment the composition comprises to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 36.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 66.

In a particular embodiment the composition comprises polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 66.

In a particular embodiment the composition comprises to polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 66.

In a particular embodiment the composition comprises to polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 66.

In a particular embodiment the composition comprises to polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 66.

In a particular embodiment the composition comprises to polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 66.

In a particular embodiment the composition comprises to polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 66.

In a particular embodiment the composition comprises to polypeptides having a sequence identity to the mature polypeptide of SEQ ID NO: 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 66.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 72.

In a particular embodiment the composition comprises polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 72.

In a particular embodiment the composition comprises to polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 72.

In a particular embodiment the composition comprises to polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 72.

In a particular embodiment the composition comprises to polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 72.

In a particular embodiment the composition comprises to polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 72.

In a particular embodiment the composition comprises to polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 72.

In a particular embodiment the composition comprises to polypeptides having a sequence identity to the mature polypeptide of SEQ ID NO: 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 72.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 9.

In a particular embodiment the composition comprises polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 9.

In a particular embodiment the composition comprises to polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 9.

In a particular embodiment the composition comprises to polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 9.

In a particular embodiment the composition comprises to polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 9.

In a particular embodiment the composition comprises to polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 9.

In a particular embodiment the composition comprises to polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 9.

In a particular embodiment the composition comprises to polypeptides having a sequence identity to the mature polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 9.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 15.

In a particular embodiment the composition comprises polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 15.

In a particular embodiment the composition comprises to polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 15.

In a particular embodiment the composition comprises to polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 15.

In a particular embodiment the composition comprises to polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 15.

In a particular embodiment the composition comprises to polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 15.

In a particular embodiment the composition comprises to polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 15.

In a particular embodiment the composition comprises to polypeptides having a sequence identity to the mature polypeptide of SEQ ID NO: 15 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 15.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 18.

In a particular embodiment the composition comprises polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 18.

In a particular embodiment the composition comprises to polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 18.

In a particular embodiment the composition comprises to polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 18.

In a particular embodiment the composition comprises to polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 18.

In a particular embodiment the composition comprises to polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 18.

In a particular embodiment the composition comprises to polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 18.

In a particular embodiment the composition comprises to polypeptides having a sequence identity to the mature polypeptide of SEQ ID NO: 18 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 18.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 81.

In a particular embodiment the composition comprises polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 81.

In a particular embodiment the composition comprises to polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 81.

In a particular embodiment the composition comprises to polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 81.

In a particular embodiment the composition comprises to polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 81.

In a particular embodiment the composition comprises to polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 81.

In a particular embodiment the composition comprises to polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 81.

In a particular embodiment the composition comprises to polypeptides having a sequence identity to the mature polypeptide of SEQ ID NO: 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 81.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 96.

In a particular embodiment the composition comprises polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 96.

In a particular embodiment the composition comprises to polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 96.

In a particular embodiment the composition comprises to polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 96.

In a particular embodiment the composition comprises to polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 96.

In a particular embodiment the composition comprises to polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 96.

In a particular embodiment the composition comprises to polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 96.

In a particular embodiment the composition comprises to polypeptides having a sequence identity to the mature polypeptide of SEQ ID NO: 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 96.

In an embodiment of the invention the composition is a cleaning composition comprising (a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein the polypeptide has a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 99.

In a particular embodiment the composition comprises polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the nuclease activity of the mature polypeptide of SEQ ID NO: 99.

In a particular embodiment the composition comprises to polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the nuclease activity of the mature polypeptide of SEQ ID NO: 99.

In a particular embodiment the composition comprises to polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the nuclease activity of the mature polypeptide of SEQ ID NO: 99.

In a particular embodiment the composition comprises to polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the nuclease activity of the mature polypeptide of SEQ ID NO: 99.

In a particular embodiment the composition comprises to polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the nuclease activity of the mature polypeptide of SEQ ID NO: 99.

In a particular embodiment the composition comprises to polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the nuclease activity of the mature polypeptide of SEQ ID NO: 99.

In a particular embodiment the composition comprises to polypeptides having a sequence identity to the mature polypeptide of SEQ ID NO: 99 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the nuclease activity of the mature polypeptide of SEQ ID NO: 99.

In a preferred embodiment of the invention the cleaning composition comprises one or more surfactants selected from anionic surfactants, nonionic surfactants, cationic surfactants, zwitterionic and mixtures thereof.

In one embodiment the surfactant is an anionic surfactant preferably selected from the group consisting of linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

In one embodiment of the invention, the one or more surfactant is a nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides (FAGA) and combinations thereof.

In one embodiment of the invention the cleaning comprises one or more anionic surfactants and one or more nonionic surfactants.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN® and TWEEN®, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis (methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEG L), N-methyliminodiacetic acid (MI DA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

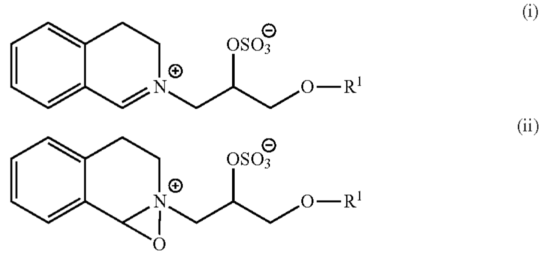

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.001 wt % to about 0.04 wt % fabric hueing agent. The composition may comprise from 0.001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as at least one lipase, cutinase, amylase, carbohydrase, cellulase, pectinase, mannanase, arabinase, galactanase, xylanase, oxidase, e.g., laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+1201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, 1203, S241, R458, T459, D460, G476 and G477. More preferred variants of SEQ ID NO: 1 are those having the substitution in one of more of the following positions: K176L, E187P, N192FYH, M199L, 1203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21 D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the 51 family, such as trypsin, or the S8 family such as subtilisin. A metalloprotease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and Subtilisin *lentus*, Subtilisin Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/Genencor Int.) such as those derived from *Bacillus amyloliquefaciens.*

Examples of useful proteases are the variants described in: WO89/06279 WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease shown in SEQ ID NO 1 of WO2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

Another suitable protease variant is one comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase®, Esperase®, Progress® Uno, Progress® In and Progress® Excel (Novozymes A/S), those sold under the tradename Maxatase®, Maxacal®, Maxapem®, Purafect Ox®, Purafect OxPe, Puramax®, FN2®, FN3®, FN4®, Excellase®, Excellenz P1000™, Excellenz P1250™, Eraser®, Preferenz P100™, Preferenz® P 300, Purafect Prime®, Preferenz P110™, Effectenz P1000™, Purafect®™, Effectenz P1050™, Purafect Ox®™ Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diary) pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

The compositions of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component.

The multi-enzyme co-granule may comprise polypeptide of the invention and (a) one or more enzymes selected from lipases, hemicellulases, proteases, amylases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The polypeptides having nuclease activity may be used for deep cleaning of an item, such as a textile. In one embodiment of the invention relates to the use of polypeptides having nuclease activity for prevention, reduction or removal of malodor. One embodiment of the invention relates to the use of polypeptides having nuclease activity for prevention or reduction of anti-redeposition and/or for improvement of whiteness of a textile subjected to multiple washes. When the biofilm components, e.g. RNA, of the extracellular biofilm matrix are removed or reduced the stickiness caused by biofilm is also reduced, whereby the adherence of soil to the item is prevented, reduced or removed. The polypeptides having nuclease activity therefore reduce the greyness of textiles when applied in the compositions of the invention to a cleaning process such as laundry. The polypeptides having nuclease activity may further be used for preventing, reducing or removing redeposition of soil during cleaning of the item One aspect of the invention relates to the use of a polypeptide having nuclease activity for cleaning an item by:

(a) preventing, reducing or removing stickiness of the item;
(b) preventing, reducing or removing biofilm or biofilm components from the item;
(c) preventing, reducing or removing redeposition of soil during cleaning of the item;
(d) preventing, reducing or removing adherence of soil to the item;
(e) maintaining or improving whiteness of the item; or
(f) preventing, reducing or removing malodor from the item, wherein the item is a textile, and wherein the polypeptide having nuclease activity selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 108 and SEQ ID NO: 111, and polypeptides having at least 80% sequence identity hereto:

Specific embodiments of the present invention are defined in the following paragraphs:

1. A polypeptide having nuclease activity, selected from a first group consisting of:

(a) a polypeptide having at least 99% sequence identity to the polypeptide of SEQ ID NO: 3;
(b) a polypeptide having at least 62% sequence identity to the polypeptide of SEQ ID NO: 6;
(c) a polypeptide having at least 97% sequence identity to the polypeptide of SEQ ID NO: 12; and
(d) a polypeptide having at least 86% sequence identity to the polypeptide of SEQ ID NO: 21 or 27;
(e) a polypeptide having at least 98% sequence identity to the polypeptide of SEQ ID NO: 30;
(f) a polypeptide having 100% sequence identity to the polypeptide of SEQ ID NO: 33 or 48;
(g) a polypeptide having at least 76% sequence identity to the polypeptide of SEQ ID NO: 39 or (h) a polypeptide having at least 95% sequence identity to the polypeptide of SEQ ID NO: 42;
(i) a polypeptide having at least 79% sequence identity to the polypeptide of SEQ ID NO: 45 or 24;
(j) a polypeptide having at least 94% sequence identity to the polypeptide of SEQ ID NO: 54;
(k) a polypeptide having at least 72% sequence identity to the polypeptide of SEQ ID NO: 57;
(l) a polypeptide having at least 82% sequence identity to the polypeptide of SEQ ID NO: 60;
(m) a polypeptide having at least 75% sequence identity to the polypeptide of SEQ ID NO: 63; and
(n) a polypeptide having at least 80% sequence identity to the polypeptide of SEQ ID NO: 69 or 75;

or selected from a second group consisting of:

(o) a polypeptide having at least 77% sequence identity to the polypeptide of SEQ ID NO: 78;
(p) a polypeptide having at least 94% sequence identity to the polypeptide of SEQ ID NO: 84;
(q) a polypeptide having at least 99% sequence identity to the polypeptide of SEQ ID NO: 87;
(r) a polypeptide having at least 80% sequence identity to the polypeptide of SEQ ID NO: 90; and
(s) a polypeptide having at least 90% sequence identity to the polypeptide of SEQ ID NO: 93; or a variant or fragment selected from:
(t) a variant of the polypeptide selected from said first group or said second group wherein the variant has nuclease activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions; and
(u) a fragment of the polypeptide of (a), (b), (c), (d), (e), (f), (g), (h), (i), (j), (k), (l), (m), (n), (o), (p), (q), (r) and (s), wherein said fragment has nuclease activity.

2. The polypeptide of paragraph 1, selected from said first group consisting of:

i. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of any of SEQ ID NO: 6, 24, 39, 45, 51, 57, 63, 69 and 75; and
ii. a polypeptide having at least 95%, at least 96%, at least 97%, at least 98%, at least 99% or 100% sequence identity to the polypeptide of any of SEQ ID NO: 42, 54, 60, 21 and 27.

3. The polypeptide of paragraph 1, selected from said second group consisting of:

i. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 78 or 90; and
ii. a polypeptide having at least 95%, at least 96%, at least 97%, at least 98%, at least 99% or 100% sequence identity to the polypeptide of SEQ ID NO: 84 or 93.

4. The polypeptide of any of paragraphs 1-3, which is encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to:

i. the mature polypeptide coding sequence of any of SEQ ID NO: 28, 31, 37, 40, 76, 82, 85, 88, and 91; or ii. the mature polypeptide cDNA coding sequence of any of SEQ ID NO: 1, 4, 10, 19, 22, 25, 43, 46, 49, 52, 55, 58, 61, 67 and 73.

5. The polypeptide of any of paragraphs 1-4, selected from the group consisting of polypeptides:

(a) comprising or consisting of SEQ ID NO: 3 or the mature polypeptide of SEQ ID NO: 2;

(b) comprising or consisting of SEQ ID NO: 6 or the mature polypeptide of SEQ ID NO: 5;

(c) comprising or consisting of SEQ ID NO: 12 or the mature polypeptide of SEQ ID NO: 11;

(d) comprising or consisting of SEQ ID NO: 21 or the mature polypeptide of SEQ ID NO: 20;

(e) comprising or consisting of SEQ ID NO: 24 or the mature polypeptide of SEQ ID NO: 23;

(f) comprising or consisting of SEQ ID NO: 27 or the mature polypeptide of SEQ ID NO: 26;

(g) comprising or consisting of SEQ ID NO: 30 or the mature polypeptide of SEQ ID NO: 29;

(h) comprising or consisting of SEQ ID NO: 33 or the mature polypeptide of SEQ ID NO: 32;

(i) comprising or consisting of SEQ ID NO: 39 or the mature polypeptide of SEQ ID NO: 38;

(j) comprising or consisting of SEQ ID NO: 42 or the mature polypeptide of SEQ ID NO: 41;

(k) comprising or consisting of SEQ ID NO: 45 or the mature polypeptide of SEQ ID NO: 44;

(l) comprising or consisting of SEQ ID NO: 48 or the mature polypeptide of SEQ ID NO: 47;

(m) comprising or consisting of SEQ ID NO: 51 or the mature polypeptide of SEQ ID NO: 50;

(n) comprising or consisting of SEQ ID NO: 54 or the mature polypeptide of SEQ ID NO: 53;

(o) comprising or consisting of SEQ ID NO: 57 or the mature polypeptide of SEQ ID NO: 56;

(p) comprising or consisting of SEQ ID NO: 60 or the mature polypeptide of SEQ ID NO: 59;

(q) comprising or consisting of SEQ ID NO: 63 or the mature polypeptide of SEQ ID NO: 62;

(r) comprising or consisting of SEQ ID NO: 69 or the mature polypeptide of SEQ ID NO: 68;

(s) comprising or consisting of SEQ ID NO: 75 or the mature polypeptide of SEQ ID NO: 74;

(t) comprising or consisting of SEQ ID NO: 78 or the mature polypeptide of SEQ ID NO: 77;

(u) comprising or consisting of SEQ ID NO: 84 or the mature polypeptide of SEQ ID NO: 83;

(v) comprising or consisting of SEQ ID NO: 87 or the mature polypeptide of SEQ ID NO: 86;

(w) comprising or consisting of SEQ ID NO: 90 or the mature polypeptide of SEQ ID NO: 89;

(x) comprising or consisting of SEQ ID NO: 93 or the mature polypeptide of SEQ ID NO: 92;

(y) comprising or consisting of SEQ ID NO: 96 or the mature polypeptide of SEQ ID NO: 95;

(z) comprising or consisting of SEQ ID NO: 99 or the mature polypeptide of SEQ ID NO: 98;

(æ) comprising or consisting of SEQ ID NO: 108 or the mature polypeptide of SEQ ID NO: 107; and (ø) comprising or consisting of SEQ ID NO: 111 or the mature polypeptide of SEQ ID NO: 110.

6. A polynucleotide encoding the polypeptide of any of paragraphs 1-5.

7. A nucleic acid construct or expression vector comprising the polynucleotide of paragraph 6 operably linked to one or more control sequences that direct the production of the polypeptide in an expression host.

8. A recombinant host cell comprising the polynucleotide of paragraph 6 operably linked to one or more control sequences that direct the production of the polypeptide.

9. A whole broth formulation or cell culture composition comprising the polypeptide of any of paragraphs 1-5.

10. A method of producing the polypeptide of any of paragraphs 1-5, comprising cultivating a cell, which in its wild-type form produces the polypeptide, under conditions conducive for production of the polypeptide, and optionally recovering the polypeptide.

11. A composition comprising the polypeptide of any of paragraphs 1-5.

12. A composition according to paragraph 11, wherein the composition is a cleaning composition.

13. The cleaning composition according to paragraph 12 comprising:

(a) at least 0.001 ppm of a polypeptide have nuclease activity (b) one or more surfactants; and (c) optionally one or more cleaning composition components, preferably selected from surfactants, builders, bleach components, polymers, dispersing agents and additional enzymes, wherein said polypeptide is a polypeptide of any of paragraphs 1-5, or said polypeptide is selected from the group consisting of:

(i) a polypeptide having at least 80% sequence identity to the polypeptide of SEQ ID NO: 9;

(ii) a polypeptide having at least 80% sequence identity to the polypeptide of SEQ ID NO: 15;

(iii) a polypeptide having at least 80% sequence identity to the polypeptide of SEQ ID NO: 18;

(iv) a polypeptide having at least 80% sequence identity to the polypeptide of SEQ ID NO: 36;

(v) a polypeptide having at least 80% sequence identity to the polypeptide of SEQ ID NO: 66;

(vi) a polypeptide having at least 80% sequence identity to the polypeptide of SEQ ID NO: 72;

(vii) a polypeptide having at least 80% sequence identity to the polypeptide of SEQ ID NO: 81;

(viii) a polypeptide having at least 80% sequence identity to the polypeptide of SEQ ID NO: 96; and (ix) a polypeptide having at least 80% sequence identity to the polypeptide of SEQ ID NO: 99;

(x) a polypeptide comprising one or more of the motifs [HQ][FILVY]X[GAQS]DX[HTGSA][QVM]P[LFM]H (SEQ ID NO: 102), G[GA]NX[VILFY]X[VLM] (SEQ ID NO: 103) and/or [SADN]R[GS]H (SEQ ID NO: 104), wherein the polypeptide belongs to the Pfam family PF02265 (S1-P1_nuclease), PF01223 (Endonuclease_NS) or PF13930 (Endonuclea_NS_2).

14. The cleaning composition according to paragraph 13, wherein the one or more surfactants are selected from anionic surfactants, nonionic surfactants, cationic surfactants, zwitterionic and mixtures thereof.

15. The cleaning composition according to any of paragraphs 13-14, wherein the one or more surfactant is a anionic surfactant preferably selected from the group consisting of linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

16. The cleaning composition according to any of paragraphs 13-15, wherein the one or more surfactant is a nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides (FAGA) and combinations thereof.

17. The cleaning composition according to any of paragraphs 15 or 16, wherein the composition comprises one or more anionic surfactants and one or more nonionic surfactants.

18. A method for laundering an item comprising the steps of:

(a) exposing an item to a wash liquor comprising the polypeptide according to any of paragraphs 1 to 5 or the composition according to paragraphs 11 to 17;
(b) completing at least one wash cycle; and
(c) optionally rinsing the item, wherein the item is a textile.

19. Use of a polypeptide according to any of paragraphs 1-5, or a cleaning composition according to paragraphs 11-17 for cleaning an item by:

(a) preventing, reducing or removing stickiness of the item;
(b) preventing, reducing or removing biofilm or biofilm components from the item;
(c) preventing, reducing or removing redeposition of soil during cleaning of the item;
(d) preventing, reducing or removing adherence of soil to the item;
(e) maintaining or improving whiteness of the item; or
(f) preventing, reducing or removing malodor from the item, wherein the item is a textile.

The present invention is further described by the following examples that should not be construed as limiting the scope of the invention.

EXAMPLES

Materials and Methods

Strain

*Escherichia coli* Top-10 strain purchased from TIANGEN (TIANGEN Biotech Co. Ltd., Beijing, China) was used to propagate our expression vector. *Aspergillus oryzae* MT3568 strain was used for heterologous expression of the gene encoding a polypeptide having homology with polypeptides with phospholipase activity. *A. oryzae* MT3568 is an amdS (acetamidase) disrupted gene derivative of *A. oryzae* JaL355 (WO02/40694) in which pyrG auxotrophy was restored by disrupting the *A. oryzae* acetamidase (amdS) gene with the pyrG gene.

Media

YPM medium was composed of 10 g yeast extract, 20 g Bacto-peptone, 20 g maltose, and deionised water to 1000 ml.

LB plates were composed of 10 g of Bacto-tryptone, 5 g of yeast extract, 10 g of sodium chloride, 15 g of Bacto-agar, and deionised water to 1000 ml.

LB medium was composed of 1 g of Bacto-tryptone, 5 g of yeast extract, and 10 g of sodium chloride, and deionised water to 1000 ml.

COVE sucrose plates were composed of 342 g of sucrose, 20 g of agar powder, 20 ml of COVE salt solution, and deionized water to 1 liter. The medium was sterilized by autoclaving at 15 psi for 15 minutes. The medium was cooled to 60° C. and 10 mM acetamide, 15 mM CsCl, Triton X-100 (50 μl/500 ml) were added.

COVE-2 plate/tube for isolation: 30 g/L sucrose, 20 ml/L COVE salt solution, 10 mM acetamide, 30 g/L noble agar (Difco, Cat #214220).

COVE salt solution was composed of 26 g of $MgSO_4 \cdot 7H_2O$, 26 g of KCL, 26 g of $KH_2PO_4$, 50 ml of COVE trace metal solution, and deionised water to 1000 ml.

COVE trace metal solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_4 \cdot 2H_2O$, 10 g of $ZnSO_4 \cdot 7H_2O$, and deionised water to 1000 ml.

Minimal medium with PNAG-extract (External Polymeric Substances from *Staphylococcus xylosus*) as carbon, nitrogen and energy source (CN-AG medium) was composed of magnesium sulfate ($MgSO_4$) 0.2 g, calcium chloride ($CaCl_2$)) 0.02 g, monopotassium phosphate ($KH_2PO_4$) 1.0 g, dipotassium phosphate ($K_2HPO_4$) 1.0 g, ferric chloride ($FeCl_3$) 0.05 g water to 1000 ml and PNAG-extracts.

Assays

Test for DNase Activity

Assay Principle: The experimental setup is based on separation of deoxyribonucleic acid (DNA) fragments by anion-exchange chromatography. Binding of DNA to the column is caused by phosphate groups in the backbone of the molecule, and separation of the fragments is induced by an elution step using a linear salt gradient. As a consequence, the order of elution is expected to approximately follow the size of the DNA pieces, the largest molecules being eluted last in the salt gradient due to the highest content of phosphate groups. The elution order from the anion-exchange column is monitored by absorption at 260 nm. Both double- and single-stranded DNA absorb at this wavelength. However, single-stranded DNA will display stronger absorption characteristics due to the hyperchromic effect.

Assay Execution: A suitable substrate for measuring DNase activity is deoxyribonucleic acid sodium salt from salmon testes (D1626 Sigma). This was dissolved at a concentration of 1 mg/mL in 20 mM Tris pH 8.5 buffer. The substrate solution is preferably prepared one day before use and left to condition overnight at 5° C. This ensures a homogenous solution, which is easy to handle and aspirate using pipettes. The candidate enzymes to be tested for activity were diluted to an appropriate concentration using 2 mM $MgCl_2$+0.01% Triton X-100, and mixed 1:1 with the substrate solution. Then the samples were incubated with shaking at 30° C. (500 rpm) on a thermomixer and the reaction mixture stopped by addition of 200 mM EDTA pH≈8 in a reaction mixture: EDTA ratio of 9:1. The resulting DNA degradation profile was analyzed using anion-exchange chromatography (e.g. TSKgel® DNA-STAT HPLC column (10×4.6, 5 μm, part #0021962) from Tosoh Bioscience). 10 μL of sample was injected onto a column equilibrated with 20 mM Tris pH 8.5 (Buffer A). The DNA fragments were separated using a flow rate of 0.5 mL/min. in a linear gradient (Buffer B: Buffer A+1 M NaCl): 0-60% B in 15 minutes; 60-100% B in 20 minutes; 100% B for 5 minutes; and finally, 0% B for 5 minutes. The separation of the DNA fragments was monitored at 260 nm using an Agilent 1100 series analytical HPLC equipped with a diode array detector. DNA, EDTA, and sample blanks were included in the setup.

The polypeptides showed DNase activity as shown below.

| Mature protein SEQ ID NO: | Nuclease family | Origin |
|---|---|---|
| 15 | S1-P1 | *Stenocarpella maydis* |
| 27 | S1-P1 | *Cadophora fastigiata* |
| 9 | S1-P1 | *Trichoderma reesei* |
| 3 | S1-P1 | *Trichoderma hamatum* |
| 6 | S1-P1 | *Morchella costata* |
| 72 | S1-P1 | *Acremonium alcalophilum* |

Example 1: Cloning, Expression and Fermentation of Bacterial S1-P1 or EN_NS Nucleases of the Invention Chromosomal DNA from pure cultures of individual bacterial strains listed in Table 1 and DNA extracted from a metagenome-enrichment of tap water source selected on a minimal medium with PNAG-extract (see Media) at pH7.5 and 30° C. was purified and subjected to full genome sequencing using Illumina sequencing technology. Coding sequences SEQ ID NOs: 28, 31, 34, 37, 40, 43, 76 and 79 encoding for the 51-P1 or EN_NS nucleases SEQ ID NOs: 30, 33, 36, 39, 42, 45, 78 and 81 were identified in those genome assemblies.

TABLE 1

| Strain | Origin | DNA SEQ ID NO* | Mature Protein SEQ ID NO |
|---|---|---|---|
| Microbial enrichment A | Denmark | SEQ ID NO: 28 | SEQ ID NO: 30 |
| *Lysobacter enzymogenes* | Canada | SEQ ID NO: 31 | SEQ ID NO: 33 |
| *Pseudoalteromonas nigrifaciens* | Denmark | SEQ ID NO: 34 | SEQ ID NO: 36 |
| *Vibrio* sp. | USA | SEQ ID NO: 37 | SEQ ID NO: 39 |
| *Janthinobacterium agaricidamnosum* | Sweden | SEQ ID NO: 40 | SEQ ID NO: 42 |
| *Massilia aerilata* | Sweden | SEQ ID NO: 43 | SEQ ID NO: 45 |
| *Bacillus deramificans* | Denmark | SEQ ID NO: 76 | SEQ ID NO: 78 |
| *Bacillus thuringiensis* | Denmark | SEQ ID NO: 79 | SEQ ID NO: 81 |

*Gene nucleotide sequence

The S1-P1 nuclease genes having DNA SEQ ID NO's: 28, 31, 34, 37, 40 and 43 and the EN_NS nuclease genes having DNA SEQ ID NO's: 76 and 79 were cloned and transformed in *Bacillus subtilis* and expressed as secreted enzymes. For each gene, the sequence encoding the native secretion signal peptide was replaced with a sequence encoding a *Bacillus clausii* secretion signal (with the following amino acid sequence: SEQ ID NO: 105: MKKPLGKIVASTALLISVAFSSSIASA). Additionally, the gene included a coding sequence for a 6×His tag fused on the carboxy-terminal amino acid residue of the encoded nuclease for purification.

For the purpose of heterologous expression, all S1-P1 nuclease and EN_NS nuclease gene constructs for expression of each of polypeptides having SEQ ID NOs: 30, 33, 36, 39, 42, 45, 78 and 81 were made as linear integration constructs, where the genes were fused by PCR between two *Bacillus subtilis* homologous chromosomal regions together with a strong promoter and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The SOE PCR method is also described in patent application WO 2003095658. The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The linear PCR constructs were transformed into *Bacillus subtilis*. Transformants were selected on LB plates supplemented with 6 μg of chloramphenicol per ml.

Recombinant *Bacillus subtilis* clones comprising an integrated expression construct encoding an S1-P1 nuclease of one of SEQ ID NOs: 30, 33, 36, 39, 42, 45, 78 and 81 were cultivated in 3 L flasks containing 500 ml yeast extract-based medium at 30° C. for 3 days with shaking at 250 rpm. Each of the culture broths was centrifuged at 20,000×g for 20 minutes and the supernatants were carefully decanted from the pelleted material. Each supernatant was filtered using a filtration and EN_NS nucleases were purified from the filtered supernatants as described below.

The filtered supernatants from each fermentation broth were pH adjusted to pH 7.5-8.0, samples were stirred for 30 minutes and filtrated through a 0.2 μm membrane, and the filtrate was applied to a 5 ml HisTrap™ excel column. Prior to loading the samples, the columns were equilibrated in 5 column volumes (CV) of 50 mM TRIS pH 8.0. To remove unbound material, columns were washed with 5 CV of 50 mM HEPES pH 7.0, and elution of bound expressed proteins was performed with 50 mM HEPES pH 7.0+0.75 M imidazole. The eluted proteins were desalted on a ~50 mL HiPrep™ 26/10 desalting column, equilibrated using 3 CV of 50 mM HEPES pH 7.0+100 mM NaCl. This buffer was also used for transferring the expressed proteins from the loop to the desalting column. The expressed proteins were eluted based on peak fractionation to obtain the sample in one tube. The flow rate was 10 ml/min. An estimate of protein concentration was obtained by absorbance maxima at 280 nm and purity of the samples was evaluated by SDS-PAGE analyses.

Example 2: Cloning, Expression and Fermentation of Fungal S1-P1 Nucleases of the Invention Eleven genes encoding nucleases belonging to the PFAM defined protein family designated "S1-P1_nuclease" and having reference number PF02265 (R. D. Finn, et al., Nucleic Acids Research (2016), D44:D279-D285) were cloned from a variety of fungal strains that were isolated from environmental samples or obtained from culture collections as described in Tables 2 and 3 below.

TABLE 2

| Strain | Origin | DNA SEQ ID NO: * | Mature protein SEQ ID NO |
|---|---|---|---|
| *Morchella costata* | Japan | 4 | 6 |
| *Penicillium cremeogriseum* | Japan | 10 | 12 |
| *Cadophora fasfigiata* | United Kingdom | 25 | 27 |

* Gene nucleotide sequence

TABLE 3

| Strain | Origin | DNA* SEQ ID NO | Mature protein SEQ ID NO |
|---|---|---|---|
| *Trichoderma reesei* | Solomon | 64 | 66 |
| | Islands | 7 | 9 |
| *Stenocarpella maydis* | USA | 13 | 15 |
| *Cordyceps* | USA | 67 | 69 |
| *cardinalis* | | 19 | 21 |
| *Phialophora geniculata* | Indonesia | 22 | 24 |
| *Ostropa barbara* | Switzerland | 55 | 57 |
| *Pyrenochaetopsis* sp. | Denmark | 58 | 60 |

*Gene nucleotide sequence

For most of the strains, chromosomal DNA was isolated and used for whole genome sequencing by standard methods known to the person skilled in the art. The whole genome sequences were assembled with either IDBA or SPAdes genome assemblers (Peng, Y., et al. Bioinformatics. (2012), 28: 1420-1428 and Bankevich, A. et al. J Comput Biol. (2012) 19(5):455-77), and genes were annotated on the genomes with the GeneMark 2.3c gene prediction software (Ter-Hovhannisyan V. et al. Genome Res. (2008) 18(12): 1979-90.). For *Trichoderma reesei*, the assembled genome sequence of RUT-C30 with accession number PRJNA207855 was downloaded from the NCBI genome database (National Center for Biotechnology Information, https://www.ncbi.nlm.nih.gov/) and annotated with GeneMark 2.3c. Chromosomal DNA was also isolated from RUT-C30 to enable subsequent cloning.

The set of protein sequences predicted from genes annotated on the whole genome sequences were searched for similarity to the PF02265 domain. Eleven proteins identified in this search are listed in the tables 2 and 3 above with their respective SEQ ID NOs for both the nucleotide and peptide sequences. The genes encoding these peptides were cloned by PCR amplification from genomic DNA using gene-specific primers that also append a Kozak translation initiation sequence “TCACC” immediately 5' of the start codon. The amplified DNA fragments were cloned into the *Aspergillus* expression vector pMStr57 (WO04/032648) that had been digested with BamHI and XhoI.

The cloned nuclease-encoding genes were sequenced and confirmed to be identical to the corresponding genes found in the genome sequence, and transformed into the *Aspergillus oryzae* strain (WO11/057140) by the methods described in Christensen et al., 1988, *Biotechnology* 6, 1419-1422 and WO04/032648. Transformants were selected during regeneration from protoplasts based on the ability, conferred by a selectable marker in the expression vector, to utilize acetamide as a nitrogen source, and were subsequently re-isolated twice under selection.

Production of the recombinant nucleases was evaluated by culturing transformants in 96-well deep-well microtiter plates for 4 days at 30° C. in 0.25 ml of YPG medium (WO05/066338) or DAP-4C-1 medium (WO12/103350) and monitoring recombinant expression by SDS-PAGE.

For larger-scale production of the recombinant S1-P1 nucleases, a single *Aspergillus* transformant was selected for each nuclease based on recombinant yield, and most of the transformants were cultured in 500 ml baffled flasks containing 150 ml of DAP-4C-1 medium. The cultures were shaken on a rotary table at 150 RPM at a temperature of 30° C. for 4 days. The recombinant transformant producing the 51-P1 nuclease from *Cordyceps cardinalis* with SEQ ID NO: 69 was instead cultured at 26° C., and the transformant producing the S1-P1 nuclease from *Ostropa barbara* was cultivated in DAP-2C-1 medium (WO 04/032648) at 26° C. Culture broth was separated from cellular material by passage through a 0.22 um filtration unit.

Chromatographic purification of recombinantly-expressed S1-P1 nucleases, originating from *Morchella costata, Penicillium cremeogriseum, Cadophora fastigiata, Trichoderma reesei, Stenocarpella maydis, Cordyceps cardinalis, Phialophora geniculata* and *Ostropa barbara*, was performed as follows:

The pH of each filtered sample, derived from the respective separated culture both, was adjusted to around pH 7.5 and 1.8M ammonium sulfate (AMS) was added. The samples were applied to a 5 ml HiTrap™ Phenyl (HS) column on an Äkta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target proteins were eluted from the column into a 10 ml loop using 50 mM HEPES+20% isopropanol pH 7. From the loop, the samples were loaded onto a desalting column (HiPrep™ 26/10 Desalting), which had been equilibrated with 3CV of 50 mM HEPES+100 mM NaCl pH 7.0. The target proteins were eluted with 50 mM HEPES+100 mM NaCl pH 7.0 and relevant fractions were selected and pooled based on the chromatograms. The flow rate was 5 ml/min. Protein concentration in the final samples was estimated by measuring absorption at 280 nm.

Example 3: Cloning, Expression and Fermentation of S1-P1 Fungal Nucleases of *Penicillium* and *Trichoderma* Origin The nucleases (S1-P1 nucleases) were derived from fungal strains isolated from environmental samples by standard microbiological isolation techniques. Strains were identified and taxonomy was assigned based on their internal transcribed spacer (ITS) sequences, (see Table 4).

TABLE 4

| Strain | Origin | DNA SEQ ID NO* | Mature Protein SEQ ID NO |
|---|---|---|---|
| *Penicillium emersonii* | China | 52 | 54 |
| *Trichoderma hamatum* | China | 1 | 3 |

*Gene nucleotide sequence

Chromosomal DNA from individual strains (Table 1) was isolated by QIAamp DNA Blood Mini Kit (Qiagen, Hilden, Germany). 5 μg of chromosomal DNA were sent for full genome sequencing using Illumina technology. Genome sequencing, the subsequent assembly of reads and the gene discovery (i.e. annotation of gene functions) is known to the person skilled in the art and the service can be purchased commercially. The genome sequences were analyzed for putative nucleases from the PFAM database families PF02265 (S1-P1_nuclease). This analysis identified 2 genes encoding putative nucleases, which were subsequently cloned and recombinantly expressed in *Aspergillus oryzae*. The 2 genes were amplified by PCR from above isolated fungal genomic DNA. The purified PCR product was cloned into the previously digested expression vector by ligation with an IN-FUSION™ CF Dry-down Cloning Kit (Clontech Laboratories, Inc., Mountain View, CA, USA) according to the manufacturer's instructions. The ligation mixture was used to transform *E. coli* TOP10 chemically competent cellsCorrect colonies containing SEQ ID NO: 52 and 1 were selected and verified by DNA sequencing (by SinoGenoMax Company Limited, Beijing, China). Colonies comprising SEQ ID NO: 52 and 1 were cultivated overnight in 3 ml of LB medium supplemented with 100 μg of ampicillin per ml. Plasmid DNA was purified using a Qiagen Spin Miniprep kit (Cat. 27106) (QIAGEN GmbH, Hilden, Germany) according to the manufacturer's instructions. Protoplasts of *Aspergillus oryzae* were prepared according to WO95/002043. 100 μl of protoplasts were respectively mixed with 2.5-10 μg of each *Aspergillus* expression vector comprising SEQ ID NO: 52 and 1 and 250 μl of 60% PEG 4000, 10 mM $CaCl_2$), and 10 mM Tris-HCl pH7.5 and gently mixed. The mixture was incubated at 37° C. for 30 minutes and the protoplasts were spread onto COVE sucrose plates for selection. After incubation for 4-7 days at 37° C. spores of 4 transformants were inoculated into 3 ml of YPM medium.

After 3 days of cultivation at 30° C., the culture broths were analyzed by SDS-PAGE using Novex® 4-20% Tris-Glycine Gel (Invitrogen Corporation, Carlsbad, CA, USA) to identify the transformants producing the largest amounts of recombinant nucleases.

Spores of the best transformants were spread on COVE-2 plates for re-isolation in order to isolate single colonies. Then a single colony was spread on a COVE-2 tube until sporulation.

Spores from the best expressed transformants were cultivated in 2400 ml of YPM medium in shake flasks for 3 days at a temperature of 30° C. with agitation at 80 rpm. Culture broth was harvested by filtration using a 0.2 μm filter device. The filtered fermentation broth was used for enzyme characterization.

Example 4: Cloning, Expression and Fermentation of S1-P1 Fungal Nucleases of *Aspergillus* Origin The wild type gene (*A. oryzae*) encoding an S1-P1 nuclease (Table 5) was cloned as follows:

TABLE 5

| Strain | DNA SEQ ID NO* | Mature Protein SEQ ID NO |
|---|---|---|
| *Aspergillus oryzae* | 46 | 48 |

*Gene nucleotide sequence

The wild type S1-P1_nuclease gene was amplified from DNA derived from *A. oryzae* strain (IFO4177) using primers 5'-GACGCGGCCGCACCATGCCGCGCTTACTCCC [SEQ ID NO: 100] and 5'-GACGCGATCGCTCAAGAGGGCTGACTCG [SEQ ID NO: 101] having overhangs with recognition for restriction endonuclease sites, NotI and SgfI, respectively. The amplified DNA (988 base pairs long) was digested with restriction endonucleases NotI and SgfI and the resulting 977-base-pair product was cloned into the corresponding restriction sites of the *Aspergillus* expression vector pCOIs1202 (described in patent WO15025055 example 2). The resulting vector, named pJaL1349, was transformed into the *Aspergillus oryzae* strain RUNG237 and expressed, as described.

Example 5: Cloning, Expression and Fermentation of EN_NS Fungal Nucleases of the Invention A gene encoding a nuclease belonging to the PFAM defined protein family designated "Endonuclease_NS" and having reference number PF01223 (R. D. Finn, et al., Nucleic Acids Research (2016), D44:D279-D285) was cloned from a strain of *Talaromyces leycettanus*, CBS398.68, that was originally isolated in England and obtained from CBS-KNAW (Fungal Biodiversity Centre, Utrecht, The Netherlands).

Chromosomal DNA was isolated from the *Talaromyces leycettanus* strain and the whole genome of this strain was sequenced and assembled by standard methods known to the person skilled in the art. The gene was annotated on the assembled genome sequences with the GeneMark 2.3c gene prediction software (Ter-Hovhannisyan V. et al. Genome Res. (2008) 18(12):1979-90.).

The predicted protein sequence, assigned SEQ ID NO: 99, based on annotation of the gene on the whole genome sequence, was searched for similarity to the PF01223 domain. The gene encoding this protein was cloned by PCR amplification from genomic DNA using gene-specific primers that also append a Kozak translation initiation sequence "TCACC" immediately 5' of the start codon. The amplified DNA fragments were cloned into the *Aspergillus* expression vector pMStr57 (WO 04/032648) that had been digested with BamHI and XhoI.

The cloned nuclease encoding gene was sequenced and confirmed to be identical to the corresponding gene found in the genome sequence, and was then transformed into the *Aspergillus oryzae* strain (WO 11/057140) by the methods described in Christensen et al., 1988, *Biotechnology* 6, 1419-1422 and WO 04/032648. Transformants were selected during regeneration from protoplasts based on the ability, conferred by a selectable marker in the expression vector, to utilize acetamide as a nitrogen source, and were subsequently re-isolated twice under selection.

Production of the recombinant Endonuclease_NS nuclease from *Talaromyces leycettanus* was evaluated by culturing transformants in a 96-well deep-well microtiter plate for 5 days at 30° C. in 0.25 ml of DAP-4C-1 medium (WO 12/103350) and monitoring recombinant expression by SDS-PAGE.

Example 6: Construction of Clades and Phylogenetic Trees

S1_P1_Nuclease Phylogenetic Tree

A phylogenetic tree was constructed from polypeptide sequences of the invention containing an S1-P1_nuclease domain, as defined in PFAM (PF02265, Pfam version 31.0 Finn (2016). Nucleic Acids Research, Database Issue 44: D279-D285). The phylogenetic tree was constructed from a multiple alignment of mature polypeptide sequences containing at least one S1-P1_nuclease domain. The sequences were aligned using the MUSCLE algorithm version 3.8.31 (Edgar, 2004. *Nucleic Acids Research* 32(5): 1792-1797), and the trees were constructed using FastTree version 2.1.8

(Price et al., 2010, *PloS one* 5(3)) and visualized using iTOL (Letunic & Bork, 2007. *Bioinformatics* 23(1): 127-128).

Polypeptides containing the S1-P1_nuclease domain comprise several conserved motifs. One example is [HQ][FILVY]X[GAQS]DX[HTGSA][QVM]P[LFM]H (SEQ ID NO: 102) situated in positions corresponding to positions 116 to 126 in *Trichoderma hamatum* (SEQ ID NO: 3), where H at position 116 and D at position 120 are involved in metal ion binding, and H at position 127 is involved in substrate binding.

Another motif contained in the S1_P1_nuclease domain polypeptides is G[GA]NX[VILFY]X[VLM] (SEQ ID NO: 103), located at positions 133 to 139 in SEQ ID NO: 3, where G at position 133 is involved in nucleoside binding.

The polypeptides comprising a S1-P1_nuclease domain can be further separated into multiple distinct sub-clusters, or clades, where we define the clades listed below.

The PLHVG Clade

Polypeptides containing a S1-P1_nuclease domain can be separated into distinct sub-clusters, where sub-clusters are defined by one or more short sequence motifs, as well as by containing an S1-P1_nuclease domain as defined in PFAM (PF02265, Pfam version 31.0 Finn (2016). Nucleic Acids Research, Database Issue 44: D279-D285).

We denoted one sub-cluster comprising the motif P[LM]H[VA][GA] (SEQ ID NO: 112) as the PLHVG clade. It is situated at positions 124 to 128 in *Lysobacter enzymogenes* (SEQ ID NO: 33). All polypeptide sequences of bacterial origin containing an S1-P1_nuclease domain as well as this motif will be denoted as belonging to the PLHVG clade.

Examples of polypeptides of the PLHVG clade include those with SEQ ID NO: 30, SEQ ID NO: 33, SEQ ID NO: 36, SEQ ID NO: 39, SEQ ID NO: 42 and SEQ ID NO: 45.

The PLHDE Clade

Another subcluster is defined from the polypeptides containing an S1-P1_nuclease domain. We denoted another sub-cluster comprising the motif PLH[DN]E (SEQ ID NO: 113) as the PLHDE clade. It is situated at positions 124 to 128 in *Trichoderma hamatum* (SEQ ID NO: 3), where H at position 126 is fully conserved in the clade and is involved in nucleoside binding. All polypeptide sequences of fungal origin containing an S1-P1_nuclease domain as well as this motif will be denoted as belonging to the PLHDE clade.

Examples of polypeptides of the PLHDE clade include those with SEQ ID NO: 3, SEQ ID NO: 9, SEQ ID NO: 12 SEQ ID NO: 15, SEQ ID NO: 18, SEQ ID NO: 21, SEQ ID NO: 48, SEQ ID NO: 51, SEQ ID NO: 54, SEQ ID NO: 60, SEQ ID NO: 66, SEQ ID NO: 69, SEQ ID NO: 72 and SEQ ID NO: 75.

Endonuclease_NS Phylogenetic Tree

A phylogenetic tree was constructed from polypeptide sequences of the invention containing an Endonuclease_NS domain, as defined in PFAM (PF01223, Pfam version 31.0 Finn (2016). Nucleic Acids Research, Database Issue 44: D279-D285). The phylogenetic tree was constructed from a multiple alignment of mature polypeptide sequences containing at least one Endonuclease_NS domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

Polypeptides containing the Endonuclease_NS domain comprise several conserved motifs. One example is [YV][DN]RGH (SEQ ID NO: 114), situated in positions corresponding to positions 123 to 127 in *Penicillium virgatum* (SEQ ID NO: 87), where the histidine at position 127 is fully conserved in the clade and putatively involved in substrate binding.

Another example is [SADN]R[GS]H (SEQ ID NO: 104), situated in positions corresponding to positions 154 to 157 in *Bacillus deramificans* (SEQ ID NO: 81).

The polypeptides comprising an Endonuclease_NS domain can be further separated into multiple distinct sub-clusters, or clades, where we define the clades listed below.

The YDRGH Clade

Polypeptides containing an Endonuclease_NS domain can be separated into distinct sub-clusters, where sub-clusters are defined by one or more short sequence motifs, as well as containing an Endonuclease_NS domain as defined in PFAM (PF01223, Pfam version 31.0 Finn (2016). Nucleic Acids Research, Database Issue 44: D279-D285).

We denoted one sub-cluster comprising the motif YDRGHQ[AV] (SEQ ID NO: 115) as the YDRGH clade. It is situated at positions 123 to 129 in *Penicillium virgatum* (SEQ ID NO: 87). All polypeptide sequences of fungal origin containing an Endonuclease_NS domain as well as the above motif will be denoted as belonging to the YDRGH clade.

Examples of polypeptides of the YDRGH clade include those with SEQ ID NO: 87, SEQ ID NO: 93, SEQ ID NO: 96 and SEQ ID NO: 102.

The DRHGL Clade

Another subcluster was defined from the polypeptides containing an Endonuclease_NS domain. We denoted a sub-cluster comprising the motif [DNA]R[GSC]H[LI] (SEQ ID NO: 116) as the DRHGL clade. It is situated at positions 129 to 133 in *Streptomyces cirratus* (SEQ ID NO: 90). All polypeptide sequences of bacterial origin containing an Endonuclease_NS domain as well as the motif [DNA]R[GSC]H[LI] (SEQ ID NO: 116) will be denoted as belonging to the DRHGL clade.

Another motif which may be identified in members of the DRHGL clade is [RIENLG][YF][RHN]V (SEQ ID NO: 117), situated in positions corresponding to positions 191 to 194 in *Streptomyces cirratus* (SEQ ID NO: 90).

Examples of polypeptides of the DRHGL clade include those with SEQ ID NO: 90, SEQ ID NO: 81, SEQ ID NO: 84, SEQ ID NO: 108 and SEQ ID NO: 111.

Example 7: DNase Activity of Polypeptides

The cloned and expressed polypeptides listed below were examined for DNase activity. DNase activity was determined by fluorescence using a fluorescence-quenched oligonucleotide probe (relative fluorescence units, RFU). This probe emits a signal after nuclease degradation (DNaseAlert™ kit, Integrated DNA Technologies, Inc., Coralville, Iowa, USA).

Briefly, DNase was diluted in 0.01% Triton solution in Milli-Q to 0.6 ppm and further diluted 1:1 with pH universal buffer (100 mM Acetic Acid, 100 mM MES, 100 mM HEPES, 100 mM Glycin, 2 mM CaCl2), 2 mM MgCl2), at pH 2, 3, 4, 5, 6, 7, 8, 9, 10 and 11. The reaction was started by adding 25 µl of the DNaseAlert™ substrate to 100 µl of 0.3 ppm DNase sample. A kinetic curve was measured for 15 min at 22° C. using a Synergy H1 microplate reader, BioTek (excitation 536 nm, emission at 590 nm).

Table 6 below shows the pH optima of the DNase activity, determined by fluorescence after 2 min (given as approximate pH optima, rounded to the nearest whole number pH value). Background in controls that contained DNaseAlert™ fluorescence-quenched oligonucleotide substrate with no enzyme was negligible at the given pH values.

TABLE 6

| SEQ ID NO. | Donor organism | pH optimum |
|---|---|---|
| 15 | *Stenocarpella maydis* | 6 |
| 21 | *Cordyceps cardinalis* | 5 |
| 57 | *Ostropa barbara* | 5 |
| 27 | *Cadophora fastigiata* | 5 |
| 9 | *Trichoderma reesei* | 4 |
| 24 | *Phialophora geniculata* | 5 |
| 18 | *Stenocarpella maydis* | 4 |
| 12 | *Penicillium cremeogriseum* | 4 |

Example 8: DNase Activity of Polypeptides

The cloned and expressed polypeptides listed below were examined for DNase activity. DNase activity was determined by fluorescence using a fluorescence-quenched oligonucleotide probe (relative fluorescence units, RFU). This probe emits a signal after nuclease degradation (DNaseAlert™ kit, Integrated DNA Technologies, Inc., Coralville, Iowa, USA).

Briefly, DNase was diluted in 2 mM MES pH 6.5+ 0.0025% Brij L23 to approx. 0.2-2 ppm. pH universal buffer (80 mM Acetate, 80 mM MES, 80 mM HEPES, 80 mM TRIS, 10 mM MgCl2, 0.0050% Brij L23) at pH 4, 5, 6, 7, 8 or 9 was mixed in a 5:3 ratio with the DNaseAlert™ substrate solution (1 vial dissolved in 15 mL Milli-Q water). The reaction was started by adding 20 µL of DNase sample to 80 µL substrate/buffer mixture. A kinetic curve was measured for 15 min at room temperature using a Varioskan® Flash plate reader, Thermo Scientific (excitation at 535 nm, emission at 556 nm).

Table 7 below shows the pH optimum of the DNase activity, given as approximate pH optima (rounded to the nearest whole number pH value). The background in controls that contained DNaseAlert™ fluorescence-quenched oligonucleotide substrate with no enzyme was negligible at the given pH values.

TABLE 7

| SEQ ID NO. | Donor organism | Origin | pH optimum |
|---|---|---|---|
| 108 | *Bacillus* sp. | Denmark | 7 |
| 111 | *Streptococcus infantis* | Sweden | 7 |

The invention claimed is:

1. A cleaning composition comprising:

(a) at least 0.001 ppm of a polypeptide have nuclease activity, wherein the polypeptide has at least 90% sequence identity to the polypeptide of SEQ ID NO: 96; and (b) one or more surfactants.

2. The cleaning composition of claim 1, wherein the polypeptide comprises one or more of the motifs [HQ][FILVY]X[GAQS]DX[HTGSA][QVM]P[LFM]H (SEQ ID NO: 102), G[GA]NX[VILFY]X[VLM] (SEQ ID NO: 103), [SADN]R[GS]H (SEQ ID NO: 104), P[LM]H[VA][GA] (SEQ ID NO: 112), PLH[DN]E/(SEQ ID NO: 113), [YV][DN]RGH (SEQ ID NO: 114), YDRGHQ[AV] (SEQ ID NO: 115), [DNA]R[GSC]H[LI] (SEQ ID NO: 116) and/or [RIENLG][YF][RHN]V (SEQ ID NO: 117); and the polypeptide belongs to the Pfam family PF02265 (S1-P1_nuclease), PF01223 (Endonuclease_NS) or PF13930 (Endonuclea_NS_2).

3. The cleaning composition of claim 2, wherein the polypeptide is an S1-P1 nuclease that belongs to the Pfam family PF02265 (S1-P1_nuclease), and which comprises the motif [HQ][FILVY]X[GAQS]DX[HTGSA][QVM]P[LFM]H (SEQ ID NO: 102) and/or G[GA]NX[VILFY]X[VLM] (SEQ ID NO: 103).

4. The cleaning composition of claim 2, wherein the polypeptide is of bacterial origin and comprises the motif P[LM]H[VA][GA] (SEQ ID NO: 112).

5. The cleaning composition of claim 2, wherein the polypeptide is of fungal origin and comprises the motif PLH[DN]E (SEQ ID NO: 113).

6. The cleaning composition of claim 1, wherein the polypeptide is an EN_NS nuclease that belongs to the Pfam family PF01223 (Endonuclease_NS) or PF13930 (Endonuclea_NS_2), and which comprises the motif [SADN]R[GS]H (SEQ ID NO: 104) and/or [YV][DN]RGH (SEQ ID NO: 114).

7. The cleaning composition of claim 6, wherein the polypeptide is of fungal origin and comprises the motif YDRGHQ[AV] (SEQ ID NO: 115).

8. The cleaning composition of claim 6, wherein the polypeptide is of bacterial origin and comprises the motif [DNA]R[GSC]H[LI] (SEQ ID NO: 116) and/or [RIENLG][YF][RHN]V (SEQ ID NO: 117).

9. The cleaning composition of claim 1, wherein the polypeptide has at least 95% sequence identity to the polypeptide of SEQ ID NO: 96.

10. The cleaning composition of claim 1, wherein the polypeptide comprises or consists of the amino acid sequence of SEQ ID NO: 96.

11. The cleaning composition of claim 1, wherein the one or more surfactants are selected from anionic surfactants, nonionic surfactants, cationic surfactants, zwitterionic and mixtures thereof.

12. A method for laundering a textile, comprising the steps of:

(a) exposing the textile to a wash liquor comprising the cleaning composition of claim 1;

(b) completing at least one wash cycle; and (c) optionally rinsing the textile.

13. An isolated polypeptide, which is (a) a variant of the polypeptide of SEQ ID NO: 96, wherein the variant has nuclease activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions and wherein the variant has at least 90% sequence identity to the polypeptide of SEQ ID NO: 96; or (b) a fragment of the polypeptide of SEQ ID NO:96, wherein the fragment has at least 90% sequence identity to the polypeptide of SEQ ID NO:96;

wherein the polypeptide has nuclease activity.

14. A recombinant host cell comprising a polynucleotide encoding the polypeptide of claim 13 operably linked to one or more control sequences that direct production of the polypeptide.

15. A method for producing a polypeptide having nuclease activity, comprising culturing the recombinant host cell of claim 14 under conditions for producing the polypeptide.

16. A recombinant host cell comprising a polynucleotide encoding a polypeptide having nuclease activity, wherein the polynucleotide is operably linked to one or more control sequences that direct production of the polypeptide and wherein the polypeptide has at least 90% sequence identity to the polypeptide of SEQ ID NO: 96.

17. A method for producing a polypeptide having nuclease activity, comprising culturing the recombinant host cell of claim 16 under conditions for producing the polypeptide.

18. The method of claim 17, wherein the polypeptide has at least 95% sequence identity to the polypeptide of SEQ ID NO: 96.

19. The polypeptide of claim 13, wherein the variant has at least 95% sequence identity to the polypeptide of SEQ ID NO: 96.

20. The polypeptide of claim 13, which is a fragment of the polypeptide of SEQ ID NO: 96.

* * * * *